US012668845B2

(12) United States Patent
Knudsen

(10) Patent No.: US 12,668,845 B2
(45) Date of Patent: Jun. 30, 2026

(54) METHODS FOR PREDICTING DRUG RESPONSIVENESS IN CANCER PATIENTS

(71) Applicant: Allarity Therapeutics Europe ApS, Hørsholm (DK)

(72) Inventor: Steen Knudsen, Scottsdale, AZ (US)

(73) Assignee: Allarity Therapeutics Europe ApS, Hørsholm (DK)

( * ) Notice: Subject to any disclaimer, the term of this patent is extended or adjusted under 35 U.S.C. 154(b) by 1075 days.

(21) Appl. No.: 17/055,342

(22) PCT Filed: May 15, 2019

(86) PCT No.: PCT/EP2019/062508
§ 371 (c)(1),
(2) Date: Nov. 13, 2020

(87) PCT Pub. No.: WO2019/219759
PCT Pub. Date: Nov. 21, 2019

(65) Prior Publication Data
US 2021/0222252 A1 Jul. 22, 2021

Related U.S. Application Data

(60) Provisional application No. 62/671,594, filed on May 15, 2018.

(51) Int. Cl.
| | |
|---|---|
| *C12Q 1/6886* | (2018.01) |
| *A61K 9/00* | (2006.01) |
| *A61K 31/519* | (2006.01) |
| *A61K 45/06* | (2006.01) |
| *A61P 35/00* | (2006.01) |

(52) U.S. Cl.
CPC .......... *C12Q 1/6886* (2013.01); *A61K 9/0053* (2013.01); *A61K 31/519* (2013.01); *A61K 45/06* (2013.01); *A61P 35/00* (2018.01); *C12Q 2600/106* (2013.01); *C12Q 2600/158* (2013.01)

(58) Field of Classification Search
CPC .................... C12Q 2600/106; C12Q 2600/158
See application file for complete search history.

(56) References Cited

U.S. PATENT DOCUMENTS

| | | | |
|---|---|---|---|
| 6,911,306 | B1 | 6/2005 | Vertino |
| 7,239,986 | B2 | 7/2007 | Golub et al. |
| 7,268,138 | B2 | 9/2007 | Kalish et al. |
| 7,709,616 | B2 | 5/2010 | Bentwich et al. |
| 8,236,802 | B2 | 8/2012 | Xu et al. |
| 8,445,198 | B2 | 5/2013 | Knudsen |
| 8,894,989 | B2 | 11/2014 | Xu et al. |
| 9,598,734 | B2 | 3/2017 | Knudsen |
| 9,725,769 | B1 | 8/2017 | Knudsen |
| 2001/0051344 | A1 | 12/2001 | Shalon et al. |
| 2002/0164663 | A1 | 11/2002 | Fuqua et al. |
| 2003/0073083 | A1 | 4/2003 | Tamayo et al. |
| 2004/0018525 | A1 | 1/2004 | Wirtz et al. |
| 2004/0072722 | A1 | 4/2004 | Kornblith et al. |
| 2005/0176669 | A1 | 8/2005 | Al-Murrani |
| 2005/0260586 | A1 | 11/2005 | Demuth et al. |
| 2005/0260646 | A1 | 11/2005 | Baker et al. |
| 2006/0105360 | A1 | 5/2006 | Croce et al. |
| 2006/0121511 | A1 | 6/2006 | Lee et al. |
| 2006/0142231 | A1 | 6/2006 | Ashworth et al. |
| 2007/0059720 | A9* | 3/2007 | Fuqua ................. C12Q 1/6886 435/6.16 |
| 2007/0172844 | A1 | 7/2007 | Lancaster et al. |
| 2008/0227663 | A1 | 9/2008 | Tisone et al. |
| 2008/0306006 | A1 | 12/2008 | Croce et al. |
| 2009/0023149 | A1 | 1/2009 | Knudsen |
| 2009/0221435 | A1 | 9/2009 | Baskerville et al. |
| 2009/0239223 | A1 | 9/2009 | Gehrmann et al. |
| 2010/0240043 | A1 | 9/2010 | Rotter et al. |
| 2011/0123990 | A1 | 5/2011 | Baker et al. |
| 2012/0046186 | A1 | 2/2012 | Pelham et al. |
| 2012/0177726 | A1 | 7/2012 | Petersen et al. |
| 2012/0214703 | A1 | 8/2012 | Croce et al. |
| 2012/0302626 | A1 | 11/2012 | Dave et al. |
| 2013/0053275 | A1 | 2/2013 | Knudsen |
| 2013/0059015 | A1 | 3/2013 | Lancaster et al. |
| 2014/0294730 | A1 | 10/2014 | Slack-Davis et al. |
| 2015/0141429 | A1 | 5/2015 | Xu et al. |

(Continued)

FOREIGN PATENT DOCUMENTS

| | | |
|---|---|---|
| CA | 2428112 A1 | 11/2003 |
| CN | 102002490 A | 4/2011 |

(Continued)

OTHER PUBLICATIONS

Michiels et al. Lancet. 2005. 365: 488-492. (Year: 2005).*
Slonim et al. Nature Genetics Supplement. 2002. 32: 502-508. (Year: 2002).*
Simon et al. Journal of Clinical Oncology. 2005. 23(29): 7332-7341. (Year: 2005).*
"Oncology Venture presents LiPlaCis on AACR in New Orleans," Press release issued by Oncology Venture Sweden AB, Hoersholm, Denmark, Mar. 4, 2016 (2 pages).

(Continued)

*Primary Examiner* — Joseph G. Dauner
(74) *Attorney, Agent, or Firm* — Clark & Elbing LLP

(57) ABSTRACT

The present invention features methods, devices, and kits for detecting gene expression in a patient with a cancer or determining responsive of a patient with a cancer to a treatment, such as treatment with 2X-121 or a pharmaceutically acceptable salt thereof. The invention further includes methods of treating a patient with a cancer by administering a treatment, e.g., treatment with 2X-121 or a pharmaceutically acceptable salt thereof, in particular when the patient is determined to be responsive to the treatment based on the expression of the biomarkers described herein.

38 Claims, 7 Drawing Sheets

Specification includes a Sequence Listing.

(56) References Cited

U.S. PATENT DOCUMENTS

| | | | | |
|---|---|---|---|---|
| 2015/0353928 A1 | 12/2015 | Weiner | | |
| 2016/0199399 A1 | 7/2016 | Knudsen | | |
| 2017/0100368 A1* | 4/2017 | Cox | .................... | A61K 31/357 |
| 2017/0283884 A1 | 10/2017 | Knudsen | | |
| 2018/0087113 A1 | 3/2018 | Knudsen | | |
| 2018/0202004 A1 | 7/2018 | Knudsen | | |

FOREIGN PATENT DOCUMENTS

| | | | |
|---|---|---|---|
| EP | 1550731 A1 | 7/2005 | |
| EP | 2081950 B1 | 3/2013 | |
| JP | 2001-17171 A | 1/2001 | |
| JP | 2002-531066 A | 9/2002 | |
| JP | 2004-43446 A | 2/2004 | |
| JP | 2005-530784 A | 10/2005 | |
| JP | 2009-513161 A | 4/2009 | |
| RU | 2528247 C2 | 9/2014 | |
| WO | WO-00/31930 A1 | 6/2000 | |
| WO | WO-00/35473 A2 | 6/2000 | |
| WO | WO-03/082078 A2 | 10/2003 | |
| WO | WO-2005/005601 A2 | 1/2005 | |
| WO | WO-2005/014856 A1 | 2/2005 | |
| WO | WO-2005/047534 A2 | 5/2005 | |
| WO | WO-2005/066371 A2 | 7/2005 | |
| WO | WO-2005/087948 A2 | 9/2005 | |
| WO | WO-2005/094863 A1 | 10/2005 | |
| WO | WO-2005/100606 A2 | 10/2005 | |
| WO | WO-2006078711 A2 | 7/2006 | |
| WO | WO-2007/053648 A2 | 5/2007 | |
| WO | WO-2007/072225 A2 | 6/2007 | |
| WO | WO-2008/073177 A2 | 6/2008 | |
| WO | WO-2008/073629 A2 | 6/2008 | |
| WO | WO-2008/112283 A2 | 9/2008 | |
| WO | WO-2008/138578 A2 | 11/2008 | |
| WO | WO-2009/036332 A1 | 3/2009 | |
| WO | WO-2009/046205 A1 | 4/2009 | |
| WO | WO-2009/080437 A1 | 7/2009 | |
| WO | WO-2009/100159 A2 | 8/2009 | |
| WO | WO-2009/141450 A2 | 11/2009 | |
| WO | WO-2011/032563 A1 | 3/2011 | |
| WO | WO-2011/047689 A2 | 4/2011 | |
| WO | WO-2011/058367 A2 | 5/2011 | |
| WO | WO-2011/098578 A2 | 8/2011 | |
| WO | WO-2011/135459 A2 | 11/2011 | |
| WO | WO-2012/024543 A1 | 2/2012 | |
| WO | WO-2012/106718 A2 | 8/2012 | |
| WO | WO-2012/109233 A2 | 8/2012 | |
| WO | WO-2012/163541 A1 | 12/2012 | |
| WO | WO-2013/130465 A2 | 9/2013 | |
| WO | WO-2013/133876 A1 | 9/2013 | |
| WO | WO-2014/195032 A1 | 12/2014 | |
| WO | WO-2014/205105 A1 | 12/2014 | |
| WO | WO-2015/135035 A2 | 9/2015 | |
| WO | WO-2015/184145 A1 | 12/2015 | |

OTHER PUBLICATIONS

Abba et al., "Gene expression signature of estrogen receptor alpha status in breast cancer," BMC Genomics. 6:37 (2005) (13 pages).

Affymetrix Expression Probeset Details for HG-U133_PLUS_ 2:209083_AT, <www.affymetrix.com/analysis/netaffx/fullrecord. affx?pk=HG-U133_PLUS_2:209083_AT>, retrieved Nov. 27, 2018 (4 pages).

Agrawal et al., "Long-term effect of fulvestrant on hormone receptors and proliferation marker in breast cancer," EJC Supplements. 8(3):111 (2010).

Arienti et al., "Activity of lipoplatin in tumor and in normal cells in vitro," Anti-Cancer Drugs. 19(10):983-990 (2008) (8 pages).

Baker, "The central role of receiver operating characteristic (ROC) curves in evaluating tests for the early detection of cancer," J Natl Cancer Inst. 95(7):511-5 (2003).

Bild et al., "Oncogenic pathway signatures in human cancers as a guide to targeted therapies," Nature. 439(7074):353-7 (2006).

Boulikas, "Clinical overview on Lipoplatin™: a successful liposomal formulation of cisplatin," Expert Opin Investig Drugs. 18(8):1197-218 (2009) (23 pages).

Buhl et al., "A genetic response profile to predict efficacy of adjuvant 5-FU in colon cancer," Ann Oncol. 25(Suppl. 4):iv167-209 (2014) (1 page).

Casagrande et al., "Preclinical Activity of the Liposomal Cisplatin Lipoplatin in Ovarian Cancer," Clin Cancer Res. 20(21):5496-5506 (12 pages).

Castelli et al., "In silico analysis of microRNAS targeting the HLA-G 3' untranslated region alleles and haplotypes," Hum Immunol. 70(12):1020-5 (2009).

Chow et al., "Increased expression of annexin I is associated with drug-resistance in nasopharyngeal carcinoma and other solid tumors," Proteomics Clin Appl. 3(6):654-62 (2009).

Dahlén et al., "Activation of the GLI oncogene through fusion with the beta-actin gene (ACTB) in a group of distinctive pericytic neoplasms: pericytoma with t(7;12)," Am J Pathol. 164(5):1645-53 (2004).

De Jonge et al., "Early cessation of the clinical development of LiPlaCis, a liposomal cisplatin formulation," Eur J Cancer. 46(16):3016-3021 (2010) (6 pages).

Di Lisio, "MicroRNA expression in B-cell lymphomas," Doctoral Thesis, Facultad de Ciencias, Departamento de Biología Molecular, Universidad Autónoma de Madrid (2012) (223 pages).

Elstrom et al., "Response to second-line therapy defines the potential for cure in patients with recurrent diffuse large B-cell lymphoma: implications for the development of novel therapeutic strategies," Clin Lymphoma Myeloma Leuk. 10(3):192-6 (2010).

Etter et al., "The combination of chemotherapy and intraperitoneal MegaFas Ligand improves treatment of ovarian carcinoma," Gynecol Oncol. 107(1):14-21 (2007).

Fournier et al., "Gene expression signature in organized and growth-arrested mammary acini predicts good outcome in breast cancer," Cancer Res. 66(14):7095-7102 (2006).

Friis-Hansen et al., "Mir-449 inhibits growth of gastric cancer cells partly by inhibiting the expression of met and amphiregulin," Gastroenterology. 136(5):A-165 (2009) (1 page).

Fumagalli et al., "Oral vinorelbine and capecitabine plus bevacizumab in recurrent inflammatory breast cancer: gene profiling and response to treatment," Thirty-Third Annual CTRC-AACR San Antonio Breast Cancer Symposium, Dec. 8-12, San Antonio, TX. Cancer Res. 70(24 Suppl.): Abstract P6-12-06 (2010) (4 pages).

Gallardo et al., "miR-34a as a prognostic marker of relapse in surgically resected non-small-cell lung cancer," Carcinogenesis. 30(11):1903-9 (2009).

Genbank Accession No. AY889152.1. Retrieved on Mar. 5, 2013 (2 pages).

GenBank Accession No. HC040507.1: Sequence 486 from Patent EP2112235 (1 page).

Gerspach et al., "Therapeutic targeting of CD95 and the TRAIL death receptors," Recent Pat Anticancer Drug Discov. 6(3):294-310 (2011).

Grimm et al., "Drugs interfering with apoptosis in breast cancer," Curr Pharm Des. 17(3):272-83 (2011).

International Preliminary Report on Patentability for International Application No. PCT/EP2019/062508, mailed Nov. 17, 2020 (10 pages).

International Search Report for International Patent Application No. PCT/EP2019/062508 mailed Oct. 14, 2019 (20 pages).

Juncker-Jensen et al., "Insulin-like growth factor binding protein 2 is a marker for antiestrogen resistant human breast cancer cell lines but is not a major growth regulator," Growth Horm IGF Res. 16(4):224-39 (2006).

Kinoshita et al. Inhibitor-induced structural change of the active site of human poly(ADP-ribose) polymerase. FEBS Letters,556(1-3):43-46, (2004).

Knudsen et al., "Development and validation of a gene expression score that predicts response to fulvestrant in breast cancer patients," PLoS One. 9(2):e87415 (2014) (12 pages).

(56) References Cited

OTHER PUBLICATIONS

Koeppel et al., "Irofulven cytotoxicity depends on transcription-coupled nucleotide excision repair and is correlated with XPG expression in solid tumor cells," Clin Cancer Res. 10(16):5604-13 (2004) (11 pages).

Kornmann et al., "Thymidylate synthase and dihydropyrimidine dehydrogenase mRNA expression levels: predictors for survival in colorectal cancer patients receiving adjuvant 5-fluorouracil," Clinical Cancer Res. 9(11):4116-4124 (2003).

Kuter et al., "Dose-dependent change in biomarkers during neoadjuvant endocrine therapy with fulvestrant: results from NEWEST, a randomized Phase II study," Breast Cancer Res Treat. 133(1):237-246 (2012).

Lee et al., "Cancer pharmacogenomics: powerful tools in cancer chemotherapy and drug development," Oncologist. 10(2):104-111 (2005) (9 pages).

Li et al., "Intronic microRNA: discovery and biological implications," DNA Cell Biol. 26(4):195-207 (2007).

Li et al., "Selection of optimal oligonucleotide probes for microarrays using multiple criteria, global alignment and parameter estimation," Nucleic Acids Res. 33(19):6114-6123 (2005).

Liang et al., "Caspase-mediated apoptosis and caspase-independent cell death induced by irofulven in prostate cancer cells," Mol Cancer Ther. 3(11):1385-1396 (2004) (13 pages).

Liang et al., "Characterization of microRNA expression profiles in normal human tissues," BMC Genomics. 8(166):1-20 (2007).

Liu et al., "Roles of USF, Ikaros and Sp proteins in the transcriptional regulation of the human reduced folate carrier B promoter," Biochem J. 383(Pt 2):249-257 (2004).

López et al., Chapter 11: MicroRNAs in Lymphoma, *MicroRNAs in Cancer Translational Research.* W.C.S. Cho (ed.), 239-267 (2011).

McCune et al., "Prognosis of hormone-dependent breast cancers: implications of the presence of dysfunctional transcriptional networks activated by insulin via the immune transcription factor T-bet," Cancer Res. 70(2):685-696 (2010).

Medinger et al., "Gene-expression Profiling in Patients with Plasma Cell Myeloma Treated with Novel Agents," Cancer Genomics Proteomics. 13(4):275-9 (2016).

Michels, "The promises and challenges of epigenetic epidemiology," Exp Gerontol. 45(4):297-301 (2010).

Mizutani et al., "Significance of orotate phosphoribosyltransferase activity in renal cell carcinoma," J Urol. 171(2 Pt 1):605-10 (2004).

Nair et al., "A simple practice guide for dose conversion between animals and human," J Basic Clin Pharm. 7(2):27-31 (2016).

Nakamura et al., "Search of a group of genes involved with sensitivity to anticancer agent Cisplatin (CDDP) using cDNA microarray," Chiba Med J. 80(2):88 (2004) (2 pages).

Narita et al., "Lower expression of activating transcription factors 3 and 4 correlates with shorter progression-free survival in multiple myeloma patients receiving bortezomib plus dexamethasone therapy," Blood Cancer J. 5:e373 (2015) (8 pages).

NCode™ Multi-Species miRNA Microarray Probe Set, Version 2.0 (Cat. # MIRMPS2-01 ), retrieved from <www.invitrogen.com/site/us/en/home/Products-and-Services/Applications/epigenetics-noncoding-rna-research/miRNA-Profiling-/miRNA-Probe-Set-Files.html> (2009) (21 pages).

Nielsen et al., "Design of oligonucleotides for microarrays and perspectives for design of multi- transcriptome arrays," Nucleic Acids Res. 31(13):3491-6 (2003).

NIH DailyMed for Fluorouracil Injection, USP, revised May 2010, retrieved Jan. 29, 2019 (2010) (8 pages).

Nikas et al., "Prognosis of treatment response (pathological complete response) in breast cancer," Biomark Insights. 7:59-70 (2012).

Ocio et al., "The Activation of Fas Receptor by APO010, a Recombinant Form of Fas Ligand, Induces In Vitro and In Vivo Antimyeloma Activity," Blood. 110(11):1515 (2007) (4 pages) (Abstract Only).

Okumura et al., "Correlation between chemosensitivity and mRNA expression level of 5-fluorouracil-related metabolic enzymes during liver metastasis of colorectal cancer," Oncol Rep. 15(4):875-82 (2006).

Ooyama et al., "Gene expression analysis using human cancer xenografts to identify novel predictive marker genes for the efficacy of 5-fluorouracil-based drugs," Cancer Sci. 97(6):510-22 (2006).

Oplustilova et al., "Evaluation of candidate biomarkers to predict cancer cell sensitivity or resistance to PARP-1 inhibitor treatment", Cell Cycle 11(20):3837-50 (2012).

Paul et al., "Impact of miRNA deregulation on mRNA expression profiles in response to environmental toxicant, nonylphenol," Mol Cell Toxicol. 7:259-69 (2011).

Pourhassan et al., "Revisiting the use of sPLA$_2$-sensitive liposomes in cancer therapy," J Control Release. 261:163-173 (2017).

Pradervand et al., "Concordance among digital gene expression, microarrays, and qPCR when measuring differential expression of microRNAs," Biotechniques. 48(3):219-222 (2010).

Reid et al., "Circulating microRNAs: Association with disease and potential use as biomarkers," Crit Rev Oncol Hematol. 80(2):193-208 (2011).

Rouillard et al., "OligoArray 2.0: design of oligonucleotide probes for DNA microarrays using a thermodynamic approach," Nucleic Acids Res. 31(12):3057-62 (2003).

Senzer et al., "Irofulven demonstrates clinical activity against metastatic hormone-refractory prostate cancer in a phase 2 single-agent trial," Am J Clin Oncol. 28(1):36-42 (2005).

Sezaki et al., "Over-expression of the dominant-negative isoform of Ikaros confers resistance to dexamethasone-induced and anti-IgM-induced apoptosis," Br J Haematol. 121(1):165-9 (2003) (Abstract only).

Slonim, "From patterns to pathways: gene expression data analysis comes of age," Nat Genet. 32 Suppl:502-8 (2002).

Suresh et al., "Resistance/response molecular signature for oral tongue squamous cell carcinoma," Dis Markers. 32(1):51-64 (2012).

The Japanese Journal of Urology, 94(2):159 (APP-105) (2003).

Van't Veer et al., "Gene expression profiling predicts clinical outcome of breast cancer," Nature. 415(6871):530-6 (2002).

Vangsted et al., "APO010 sensitivity in relapsed multiple myeloma patients," Annals of Oncol. 27(Supplement 6): vi15-vi42 (2016) (2 pages) (Abstract only).

Verbrugge et al., "Combining radiotherapy with APO010 in cancer treatment," Clin Cancer Res. 15(6):2031-8 (2009) (9 pages).

Wang et al., "Independent Validation of a Model Using Cell Line Chemosensitivity to Predict Response to Therapy," J Natl Cancer Inst. 105(17): 1284-91 (2013).

Woynarowska et al., "Changes in prostate-specific antigen (PSA) level correlate with growth inhibition of prostate cancer cells treated in vitro with a novel anticancer drug, irofulven," Invest New Drugs. 19(4):283-91 (2001).

Xu et al., "[Association of miRNAs expression profiles with prognosis and relapse in childhood acute lymphoblastic leukemia]," Zhonghua Xue Ye Xue Za Zhi. 32(3):178-81 (Abstract only) (2011).

Yang et al., "The role of microRNA in human lung squamous cell carcinoma," Cancer Genet Cytogenet. 200(2):127-33 (2010).

Yin, "Screening of laryngeal carcinoma multidrug resistance-associated genes and study on reversion by Chinese herbs," China Doctoral Dissertations Full-text Database, Division of Medical and Hygiene Technology. 8:E072-85 (2010) (3 pages) (Abstract only).

Zhang et al., "MicroRNA-650 targets ING4 to promote gastric cancer tumorigenicity," Biochem Biophys Res Commun. 395(2):275-280 (2010).

McGonigle et al., "E7449: A dual inhibitor of PARP1/2 and tankyrase1/2 inhibits growth of DNA repair deficient tumors and antagonizes Wnt signaling," Oncotarget. 6(38):41307-23 (Dec. 2015).

Knudsen et al., "A novel drug specific mRNA biomarker predictor for selection of patients responding to dovitinib treatment of advanced renal cell carcinoma and other solid tumors," PLOS ONE. 18(8):e0290681 (2023) (16 pages).

Plummer et al., "First-in-human study of the PARP/tankyrase inhibitor E7449 in patients with advanced solid tumours and evaluation of a novel drug-response predictor," Br J Cancer. 123(4):525-533 (2020) (9 pages).

(56)                    References Cited

OTHER PUBLICATIONS

Plummer et al., "First-in-human study of the PARP/tankyrase inhibitor E7449 in patients with advanced solid tumours and evaluation of a novel drug-response predictor," Br J Cancer. 123(4):525-533 (Jun. 2020) (9 pages).

* cited by examiner

METHODS FOR PREDICTING DRUG RESPONSIVENESS IN CANCER PATIENTS

FIELD OF THE INVENTION

The use of biomarkers to predict the responsiveness of a cancer in a subject to a cancer therapy.

BACKGROUND

DNA microarrays have been used to measure gene expression in tumor samples from patients and to facilitate diagnosis. Gene expression can reveal the presence of cancer in a patient in addition to the type, stage, and origin. Gene expression may even have a role in predicting the efficacy of cancer therapies. In recent decades, the National Cancer Institute (NCI) has tested cancer therapeutics for their effect in limiting the growth of 60 human cancer cell lines. The NCI has also measured gene expression in those 60 cancer cell lines using DNA microarrays. Various studies have explored the relationship between gene expression and therapeutic effect using the NCI datasets.

During cancer treatment, critical time is often lost due to a trial and error approach to finding an effective therapy. In addition, cancer cells often develop resistance to a previously effective therapy. In such situations, patient outcome would be greatly improved by early detection of such resistance.

Thus, there exists a need in the art for methods and devices that can predict the responsiveness of cancer patients to a medical treatment.

SUMMARY OF THE INVENTION

Featured are methods for detecting gene expression of a biomarker (e.g., one, two, three, four, five, ten, fifteen, twenty, twenty five, or all of the biomarkers shown in Tables 2 and/or 3, such as SRSF7 (SEQ ID NO: 1) and/or HLA-E (SEQ ID NO: 173 or 174 or 178)), respectively, in a patient, such as a patient with a cancer (e.g., a patient with breast cancer, ovarian cancer or pancreatic cancer, or a recurrence thereof), and for determining responsiveness of a cancer patient (e.g., a patient with breast cancer, ovarian cancer or pancreatic cancer, or a recurrence thereof) to treatment with 2X-121 or a pharmaceutically acceptable salt thereof. The invention also features methods of treating cancer in a patient in need thereof (e.g., a patient with breast cancer, ovarian cancer or pancreatic cancer, or a recurrence thereof) that include administering 2X-121 or a pharmaceutically acceptable salt thereof to the patient, in which the patient is or has been determined to be responsive to 2X-121 or a pharmaceutically acceptable salt thereof according to the diagnostic methods described herein.

Exemplary types of cancer that can be diagnosed or treated with the methods include, e.g., myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma, and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, or neoplasms of the central nervous system. For example, the cancer may be a solid tumor or a hematological cancer.

A first aspect features a method of determining responsiveness of a patient with a cancer (e.g., one of the cancers noted above, such as breast cancer, ovarian cancer or pancreatic cancer) to 2X-121 or a pharmaceutically acceptable salt thereof. In particular, the patient may have recurrence of cancer, such as recurrence of breast cancer, ovarian cancer or pancreatic cancer. The method includes: (a) contacting a sample (e.g., a tumor sample) from the patient including one or more nucleic acid molecules with a device (e.g., a microarray) including: (i) one or more single-stranded nucleic acid molecules capable of specifically hybridizing with the nucleotides of one or more biomarkers of sensitivity selected from the biomarkers of Table 2 (e.g., SRSF7 (SEQ ID NO: 1)); and/or (ii) one or more single-stranded nucleic acid molecules capable of specifically hybridizing with the nucleotides of one or more biomarkers of resistance selected from the biomarkers of Table 3 (e.g., HLA-E (SEQ ID NO: 173 or 174 or 178)); and (b) measuring hybridization between the one or more nucleic acid molecules from the patient and the single-stranded nucleic acid molecules of the device to detect a level of expression of the one or more biomarkers of sensitivity and/or the one or more biomarkers of resistance. The patient is determined to be responsive to 2X-121 or a pharmaceutically acceptable salt thereof if: (i) the level of expression of the biomarker(s) of sensitivity is substantially similar to the level of expression of the biomarker(s) of sensitivity (e.g., SRSF7 (SEQ ID NO: 1)) in a cell (e.g., a cancer cell) or tissue (e.g., a tumor tissue) known to be sensitive to 2X-121 or a pharmaceutically acceptable salt thereof; (ii) the level of expression of the biomarker(s)

of resistance (e.g., HLA-E (SEQ ID NO: 173 or 174 or 178)) is substantially similar to the level of expression of the biomarker(s) of resistance in a cell (e.g., a cancer cell) or tissue (e.g., a tumor tissue) known to be sensitive to 2X-121 or a pharmaceutically acceptable salt thereof; (iii) the level of expression of the biomarker(s) of sensitivity is substantially dissimilar to the level of expression of the biomarker(s) of sensitivity (e.g., SRSF7 (SEQ ID NO: 1)) in a cell (e.g., a cancer cell) or tissue (e.g., a tumor tissue) known to be resistant to 2X-121 or a pharmaceutically acceptable salt thereof; and/or (iv) the level of expression of the biomarker(s) of resistance (e.g., HLA-E (SEQ ID NO: 173 or 174 or 178)) is substantially dissimilar to the level of expression of the biomarker(s) of resistance in a cell (e.g., a cancer cell) or tissue (e.g., a tumor tissue) known to be resistant to 2X-121 or a pharmaceutically acceptable salt thereof.

The method of the first aspect can further include administering 2X-121 or a pharmaceutically acceptable salt thereof to the patient if: (i) the level of expression of the biomarker(s) of sensitivity is substantially similar to the level of expression of the biomarker(s) of sensitivity (e.g., SRSF7 (SEQ ID NO: 1)) in a cell (e.g., a cancer cell) or tissue (e.g., a tumor tissue) known to be sensitive to 2X-121 or a pharmaceutically acceptable salt thereof; (ii) the level of expression of the biomarker(s) of resistance (e.g., HLA-E (SEQ ID NO: 173 or 174 or 178)) is substantially similar to the level of expression of the biomarker(s) of resistance in a cell (e.g., a cancer cell) or tissue (e.g., a tumor tissue) known to be sensitive to 2X-121 or a pharmaceutically acceptable salt thereof; (iii) the level of expression of the biomarker(s) of sensitivity is substantially dissimilar to the level of expression of the biomarker(s) of sensitivity (e.g., SRSF7 (SEQ ID NO: 1)) in a cell (e.g., a cancer cell) or tissue (e.g., a tumor tissue) known to be resistant to 2X-121 or a pharmaceutically acceptable salt thereof; and/or (iv) the level of expression of the biomarker(s) of resistance (e.g., HLA-E (SEQ ID NO: 173 or 174 or 178)) is substantially dissimilar to the level of expression of the biomarker(s) of resistance in a cell (e.g., a cancer cell) or tissue (e.g., a tumor tissue) known to be resistant to 2X-121 or a pharmaceutically acceptable salt thereof. The method can further include administering one or more cancer therapies other than 2X-121 or a pharmaceutically acceptable salt thereof to the patient if: (i) the level of expression of the biomarker(s) of sensitivity is substantially dissimilar to the level of expression of the biomarker(s) of sensitivity (e.g., SRSF7 (SEQ ID NO: 1)) in a cell (e.g., a cancer cell) or tissue (e.g., a tumor tissue) known to be sensitive to 2X-121 or a pharmaceutically acceptable salt thereof; (ii) the level of expression of the biomarker(s) of resistance (e.g., HLA-E (SEQ ID NO: 173 or 174 or 178)) is substantially dissimilar to the level of expression of the biomarker(s) of resistance in a cell (e.g., a cancer cell) or tissue (e.g., a tumor tissue) known to be sensitive to 2X-121 or a pharmaceutically acceptable salt thereof; (iii) the level of expression of the biomarker(s) of sensitivity is substantially similar to the level of expression of the biomarker(s) of sensitivity (e.g., SRSF7 (SEQ ID NO: 1)) in a cell (e.g., a cancer cell) or tissue (e.g., a tumor tissue) known to be resistant to 2X-121 or a pharmaceutically acceptable salt thereof; and/or (iv) the level of expression of the biomarker(s) of resistance (e.g., HLA-E (SEQ ID NO: 173 or 174 or 178)) is substantially similar to the level of expression of the biomarker(s) of resistance in a cell (e.g., a cancer cell) or tissue (e.g., a tumor tissue) known to be resistant to 2X-121 or a pharmaceutically acceptable salt thereof. In particular, the one or more of the cancer therapies can include surgery, radiation, or a therapeutic agent, such as a histone deacetylase (HDAC) inhibitor, a PD1/PD-L1 inhibitor, ipilimumab, bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, fulvestrant, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, tamoxifen, floxuridine, thioguanine, PSC 833, herceptin, bevacizumab, celecoxib, iressa, anastrozole, letrozole, or rituximab.

Also featured is a method of treating cancer in a patient in need thereof (e.g., a patient with one of the cancers noted above, such as breast cancer, ovarian cancer or pancreatic cancer) that includes administering 2X-121 or a pharmaceutically acceptable salt thereof to the patient, in which the patient has been determined to be responsive to 2X-121 or a pharmaceutically acceptable salt thereof according to the method of the first aspect of the invention. In particular, the patient may have recurrence of cancer, such as recurrence of breast cancer, ovarian cancer or pancreatic cancer.

A second aspect features a method of treating a patient having cancer (e.g., one of the cancers noted above, such as breast cancer, ovarian cancer or pancreatic cancer). In particular, the patient may have recurrence of cancer, such as recurrence of breast cancer, ovarian cancer or pancreatic cancer. The method includes: (a) contacting a sample (e.g., a tumor sample) from the patient including one or more nucleic acid molecules with a device including: (i) one or more single-stranded nucleic acid molecules capable of specifically hybridizing with the nucleotides of one or more biomarkers of sensitivity selected from the biomarkers of Table 2 (e.g., SRSF7 (SEQ ID NO: 1)); and/or (ii) one or more single-stranded nucleic acid molecules capable of specifically hybridizing with the nucleotides of one or more biomarkers of resistance selected from the biomarkers of Table 3 (e.g., HLA-E (SEQ ID NO: 173 or 174 or 178)); (b) measuring hybridization between the one or more nucleic acid molecules from the patient and the single-stranded nucleic acid molecules of the device to detect a level of expression of the one or more biomarkers of sensitivity and/or the one or more biomarkers of resistance; and (c) administering 2X-121 or a pharmaceutically acceptable salt thereof to the patient. 2X-121 or a pharmaceutically acceptable salt thereof can be administered to the patient if: (i) the level of expression of the biomarker(s) of sensitivity is substantially similar to the level of expression of the biomarker(s) of sensitivity (e.g., SRSF7 (SEQ ID NO: 1)) in a cell (e.g., a cancer cell) or tissue (e.g., a tumor tissue) known to be sensitive to 2X-121 or a pharmaceutically acceptable salt thereof; (ii) the level of expression of the biomarker(s) of resistance (e.g., HLA-E (SEQ ID NO: 173 or 174 or 178)) is substantially similar to the level of expression of the biomarker(s) of resistance in a cell (e.g., a cancer cell) or tissue (e.g., a tumor tissue) known to be sensitive to 2X-121 or a pharmaceutically acceptable salt thereof; (iii) the level of expression of the biomarker(s) of sensitivity is substantially dissimilar to the level of expression of the biomarker(s) of sensitivity (e.g., SRSF7 (SEQ ID NO: 1)) in a cell (e.g., a cancer cell) or tissue (e.g., a tumor tissue) known to be resistant to 2X-121 or a pharmaceutically acceptable salt thereof; and/or (iv) the level of expression of the biomarker(s) of resistance (e.g., HLA-E (SEQ ID NO: 173 or 174 or 178)) is substantially dissimilar to the level of expression of the biomarker(s) of resistance in a cell (e.g., a cancer cell) or tissue (e.g., a tumor tissue) known to be resistant to 2X-121 or a pharmaceutically acceptable salt thereof.

Also featured is a composition containing 2X-121 or a pharmaceutically acceptable salt thereof for use in treating a cancer (e.g., one of the cancers noted above, such as breast cancer, ovarian cancer or pancreatic cancer, or a recurrence thereof) in a subject (e.g., a patient), wherein the subject has been determined to be responsive to 2X-121 or the pharmaceutically acceptable salt thereof by the methods of aforementioned aspects.

A third aspect features a composition containing 2X-121 or a pharmaceutically acceptable salt thereof for use in treating a cancer (e.g., one of the cancers noted above, such as breast cancer, ovarian cancer or pancreatic cancer, or a recurrence thereof) in a subject (e.g., a patient), wherein the subject has been determined to be responsive to 2X-121 or the pharmaceutically acceptable salt thereof by: (a) contacting a sample (e.g., a tumor sample) from the subject (e.g., patient) including one or more nucleic acid molecules with a device including: (i) one or more single-stranded nucleic acid molecules capable of specifically hybridizing with the nucleotides of one or more biomarkers of sensitivity selected from the biomarkers of Table 2 (e.g., SRSF7 (SEQ ID NO: 1)); and/or (ii) one or more single-stranded nucleic acid molecules capable of specifically hybridizing with the nucleotides of one or more biomarkers of resistance selected from the biomarkers of Table 3 (e.g., HLA-E (SEQ ID NO: 173 or 174 or 178)); and (b) measuring hybridization between the one or more nucleic acid molecules from the patient and the single-stranded nucleic acid molecules of the device to detect a level of expression of the one or more biomarkers of sensitivity and/or the one or more biomarkers of resistance. The composition containing 2X-121 or a pharmaceutically acceptable salt thereof can be administered to the patient if: (i) the level of expression of the biomarker(s) of sensitivity is substantially similar to the level of expression of the biomarker(s) of sensitivity (e.g., SRSF7 (SEQ ID NO: 1)) in a cell (e.g., a cancer cell) or tissue (e.g., a tumor tissue) known to be sensitive to 2X-121 or a pharmaceutically acceptable salt thereof; (ii) the level of expression of the biomarker(s) of resistance (e.g., HLA-E (SEQ ID NO: 173 or 174 or 178)) is substantially similar to the level of expression of the biomarker(s) of resistance in a cell (e.g., a cancer cell) or tissue (e.g., a tumor tissue) known to be sensitive to 2X-121 or a pharmaceutically acceptable salt thereof; (iii) the level of expression of the biomarker(s) of sensitivity is substantially dissimilar to the level of expression of the biomarker(s) of sensitivity (e.g., SRSF7 (SEQ ID NO: 1)) in a cell (e.g., a cancer cell) or tissue (e.g., a tumor tissue) known to be resistant to 2X-121 or a pharmaceutically acceptable salt thereof; and/or (iv) the level of expression of the biomarker(s) of resistance (e.g., HLA-E (SEQ ID NO: 173 or 174 or 178)) is substantially dissimilar to the level of expression of the biomarker(s) of resistance in a cell (e.g., a cancer cell) or tissue (e.g., a tumor tissue) known to be resistant to 2X-121 or a pharmaceutically acceptable salt thereof.

In any of the aforementioned aspects, one or more additional therapies (e.g., surgery, radiation, or a therapeutic agent) may be administered to the patient prior to, concurrently, or after administration of 2X-121 or a pharmaceutically acceptable salt thereof or a composition containing the same (e.g., a composition containing 2X-121 or a pharmaceutically acceptable salt thereof). In particular, the therapeutic agent may be selected from the group consisting of a histone deacetylase (HDAC) inhibitor, a PD1 or PD-L1 inhibitor, ipilimumab, bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, fulvestrant, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, tamoxifen, floxuridine, thioguanine, PSC 833, herceptin, bevacizumab, celecoxib, iressa, anastrozole, letrozole, and rituximab. The therapeutic agent can be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally, or topically.

In any of the aforementioned aspects, 2X-121 or a pharmaceutically acceptable salt thereof or a composition containing the same (e.g., a composition containing 2X-121 or a pharmaceutically acceptable salt thereof) may be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally (e.g., orally), or topically. Preferably, 2X-121 a pharmaceutically acceptable salt thereof or a composition containing the same (e.g., a composition containing 2X-121 or a pharmaceutically acceptable salt thereof) is administered orally. 2X-121 or a pharmaceutically acceptable salt thereof or a composition containing the same (e.g., a composition containing 2X-121 or a pharmaceutically acceptable salt thereof) may be administered to the patient two or more times, such as one or more times daily (e.g., once daily for up to six days), weekly, every two weeks, every three weeks, or monthly. Preferably, 2X-121 or a pharmaceutically acceptable salt thereof or a composition containing the same (e.g., a composition containing 2X-121 or a pharmaceutically acceptable salt thereof) is administered once daily. The method may further include administering a second dose of 2X-121 or a pharmaceutically acceptable salt thereof or a composition containing the same (e.g., a composition containing 2X-121 or a pharmaceutically acceptable salt thereof) to the patient one week, two weeks, three weeks, four weeks, or five weeks after administration of a first dose of 2X-121 or a pharmaceutically acceptable salt thereof or a composition containing the same (e.g., a composition containing 2X-121 or a pharmaceutically acceptable salt thereof). 2X-121 or a pharmaceutically acceptable salt thereof or a composition containing the same (e.g., a composition containing 2X-121 or a pharmaceutically acceptable salt thereof) may be administered in a particular dosage form (e.g., liquid, tablet, capsule, etc.) and it may be administered at a dose of about 5-5000 mg (e.g., about 50-800 mg). In particular, 2X-121 or a pharmaceutically acceptable salt thereof or a composition containing the same (e.g., a composition containing 2X-121 or a pharmaceutically acceptable salt thereof) may be administered at doses of about 10 mg, 50 mg, 200 mg, or 600 mg. Preferably, about 600 mg of 2X-121 or a pharmaceutically acceptable salt thereof or a composition containing the same (e.g., a composition containing 2X-121 or a pharmaceutically acceptable salt thereof) is administered daily. 2X-121 or a pharmaceutically acceptable salt thereof or a composition containing the same (e.g., a composition containing 2X-121 or a pharmaceutically acceptable salt thereof) can be administered in the form of hard gelatin capsules (e.g., hard gelatin capsules of 10 mg, 50 mg, or 200 mg) or film coated tablets (e.g., film coated tablets of 10 mg, 50 mg, or 200 mg). Preferably, 2X-121 or a pharmaceutically acceptable salt thereof or a composition containing the same (e.g., a composition containing 2X-121 or a pharmaceutically acceptable salt thereof) is administered in the form of hard gelatin capsules (e.g., hard gelatin capsules of 200 mg). In particular, the contacting step (a) and the measuring step (b) occur prior to, concurrent to, or after administration of 2X-121 or a pharmaceutically acceptable salt thereof or a composition containing the same (e.g., a composition containing 2X-121 or a pharmaceutically acceptable salt thereof) to the patient. Each of the contacting step (a) and the measuring step (b) may occur multiple times.

In any of the above aspects, the device can include at least two, at least three, at least four, at least five, at least six, at least seven, at least eight, at least nine, at least ten, or more single-stranded nucleic acid molecules capable of specifically hybridizing with the nucleotides of one or more biomarkers of sensitivity selected from the biomarkers of Table 2 (e.g., SRSF7 (SEQ ID NO: 1)); and/or at least two, at least three, at least four, at least five, at least six, at least seven, at least eight, at least nine, at least ten, or more single-stranded nucleic acid molecules capable of specifically hybridizing with the nucleotides of one or more biomarkers of resistance selected from the biomarkers of Table 3 (e.g., HLA-E (SEQ ID NO: 173 or 174 or 178)). In particular, one or more of the single-stranded nucleic acid molecules of the device have a length in the range of 10 to 100 nucleotides in length (e.g., a length in the range of 20 to 60 nucleotides).

In any of the aforementioned aspects, the sensitivity and/or resistance of a cell (e.g., a cancer cell) or tissue (e.g., a tumor tissue) known to be sensitive and/or resistant to 2X-121 or a pharmaceutically acceptable salt thereof is based on GI50 data of NCI60 cell lines.

In any of the above aspects, the method may include converting the level of expression of one or more of the biomarkers of sensitivity (e.g., one, two, three, four, five, ten, fifteen, twenty, twenty five, or all of the biomarkers shown in Table 2, such as SRSF7 (SEQ ID NO: 1)) and/or one or more of the biomarkers of resistance (e.g., one, two, three, four, five, ten, fifteen, twenty, twenty five, or all of the biomarkers shown in Table 3, such as HLA-E (SEQ ID NO: 173 or 174 or 178)) into a mean score, in which the mean score indicates the responsiveness of the patient to 2X-121 or a pharmaceutically acceptable salt thereof. The method can further include subtracting the mean score for one or more of the biomarkers of resistance (e.g., one, two, three, four, five, ten, fifteen, twenty, twenty five, or all of the biomarkers shown in Table 3, such as HLA-E (SEQ ID NO:

173 or 174 or 178)) from the mean score for one or more of the biomarkers of sensitivity (e.g., one, two, three, four, five, ten, fifteen, twenty, twenty five, or all of the biomarkers shown in Table 2, such as SRSF7 (SEQ ID NO: 1)) to obtain a difference score, in which the difference score indicates the responsiveness of the patient to 2X-121 or a pharmaceutically acceptable salt thereof. In particular, the mean score and/or the difference score above a cutoff value indicates that the patient is responsive to 2X-121 or a pharmaceutically acceptable salt thereof, such as if the cutoff value is about 0.3, about 0.35, about 0.4, about 0.45, about 0.5, about 0.6, about 0.7, about 0.8, about 0.9, or greater.

In any of the above aspects, the device can be a microarray, such as a deoxyribonucleic acid (DNA)-based platform. The expression level of the biomarkers of sensitivity (e.g., one, two, three, four, five, ten, fifteen, twenty, twenty five, or all of the biomarkers shown in Table 2, such as SRSF7 (SEQ ID NO: 1)) and/or the biomarkers of resistance (e.g., one, two, three, four, five, ten, fifteen, twenty, twenty five, or all of the biomarkers shown in Table 3, such as HLA-E (SEQ ID NO: 173 or 174 or 178)) can be measured using microarray analysis or nucleic acid amplification methods (e.g., reverse transcription quantitative real-time polymerase chain reaction (RT-qPCR)). In particular, the level of expression of the biomarkers of sensitivity and/or the biomarkers of resistance is determined by detecting the level of mRNA transcribed from a gene coding one or more of the biomarkers of Table(s) 2 and/or 3.

In any of the above aspects, the biomarker of sensitivity may be selected from one or more of SRSF7 (SEQ ID NO: 1), UCHL1 (SEQ ID NO: 2), MLLT11 (SEQ ID NO: 3), ADD2 (SEQ ID NO: 4 or 5), PRMT1 (SEQ ID NO: 6), SRSF3 (SEQ ID NO: 7), PRMT5 (SEQ ID NO: 8), COCH (SEQ ID NO: 9), RUVBL1 (SEQ ID NO: 10), MARCKSL1 (SEQ ID NO: 11), CHERP (SEQ ID NO: 12), MTSS1 (SEQ ID NO: 13), LSM4 (SEQ ID NO: 14), RAPGEF5 (SEQ ID NO: 15), PRPF4 (SEQ ID NO: 16), LSM4 (SEQ ID NO: 17), DESI2 (SEQ ID NO: 18), RNPS1 (SEQ ID NO: 19), SNX10 (SEQ ID NO: 20), CUL3 (SEQ ID NO: 21), CHD4 (SEQ ID NO: 22), MSH2 (SEQ ID NO: 23), HNRNPM (SEQ ID NO: 24), SRSF1 (SEQ ID NO: 25), NELL2 (SEQ ID NO: 26), PAICS (SEQ ID NO: 27), HOXA10 (SEQ ID NO: 28), BUB1B (SEQ ID NO: 29), E2F5 (SEQ ID NO: 30), MAGED4 MAGED4B SNORA11D SNORA11E (SEQ ID NO: 31), PRPF8 (SEQ ID NO: 32), SORD (SEQ ID NO: 33), HNRNPU (SEQ ID NO: 34), PEX5 (SEQ ID NO: 35), HYPK MIR1282 SERF2 SERF2-C15ORF63 (SEQ ID NO: 36), STRAP (SEQ ID NO: 37), NDUFAB1 (SEQ ID NO: 38), FARSA (SEQ ID NO: 39), STOML2 (SEQ ID NO: 40), ERH (SEQ ID NO: 41), HSBP1 (SEQ ID NO: 42), DDX39A (SEQ ID NO: 43), ODC1 (SEQ ID NO: 44), TAF5 (SEQ ID NO: 45), TBC1D31 (SEQ ID NO: 46), TRA2B (SEQ ID NO: 47), NUDC (SEQ ID NO: 48), DDX23 (SEQ ID NO: 49), PRPF31 (SEQ ID NO: 50), UBE2S (SEQ ID NO: 51), TCF4 (SEQ ID NO: 52), MLF2 (SEQ ID NO: 53), CCDC181 (SEQ ID NO: 54), TCF4 (SEQ ID NO: 55), DESI2 (SEQ ID NO: 56), RPF1 (SEQ ID NO: 57), PASK (SEQ ID NO: 58), NUP88 (SEQ ID NO: 59), RNASEH2A (SEQ ID NO: 60), FBL (SEQ ID NO: 61), LOC101928747 RBMX SNORD61 (SEQ ID NO: 62), NXF1 (SEQ ID NO: 63), PLEKHO1 (SEQ ID NO: 64), GAR1 (SEQ ID NO: 65), RPA1 (SEQ ID NO: 66), ZNF24 (SEQ ID NO: 67), BOP1 MIR7112 (SEQ ID NO: 68), RAB3B (SEQ ID NO: 69), SLC35G2 (SEQ ID NO: 70), TSPAN3 (SEQ ID NO: 71), DKC1 MIR664B SNORA56 (SEQ ID NO: 72), PSMC3IP (SEQ ID NO: 73), DNAJC7 (SEQ ID NO: 74), RRP1B (SEQ ID NO: 75), NME1 (SEQ ID NO: 76), SNRPA (SEQ ID NO: 77), DBN1 (SEQ ID NO: 78), KIAA0020 (SEQ ID NO: 79), SUPV3L1 (SEQ ID NO: 80), ZNF573 (SEQ ID NO: 81), FAM134B (SEQ ID NO: 82), TOX3 (SEQ ID NO: 83), HSPD1 (SEQ ID NO: 84), ACLY (SEQ ID NO: 85), TOX3 (SEQ ID NO: 86), MSANTD3-TMEFF1 TMEFF1 (SEQ ID NO: 87), AKIRIN1 (SEQ ID NO: 88), UBE2M (SEQ ID NO: 89), MTF2 (SEQ ID NO: 90), EWSR1 (SEQ ID NO: 91), FARSA (SEQ ID NO: 92), SKP2 (SEQ ID NO: 93), TMEM97 (SEQ ID NO: 94), HNRNPD (SEQ ID NO: 95), ILKAP (SEQ ID NO: 96), NASP (SEQ ID NO: 97), SNRPD1 (SEQ ID NO: 98), TIMM44 (SEQ ID NO: 99), PKN1 (SEQ ID NO: 100), STAU2 (SEQ ID NO: 101), DNAAF2 (SEQ ID NO: 102), SNRPD2 (SEQ ID NO: 103), FUS (SEQ ID NO: 104), PASK (SEQ ID NO: 105), ATP6V1G2-DDX39B DDX39B SNORD84 (SEQ ID NO: 106), PDSS1 (SEQ ID NO: 107), NUDC (SEQ ID NO: 108), TOX3 (SEQ ID NO: 109), TPGS2 (SEQ ID NO: 110), SLIRP (SEQ ID NO: 111), NCL (SEQ ID NO: 112), ANP32A (SEQ ID NO: 113), SAFB (SEQ ID NO: 114), STIP1 (SEQ ID NO: 115), CEP68 (SEQ ID NO: 116), STIP1 (SEQ ID NO: 117), C8orf33 (SEQ ID NO: 118), MRPL11 (SEQ ID NO: 119), POLR2I (SEQ ID NO: 120), FAM134B (SEQ ID NO: 121), MCAM MIR6756 (SEQ ID NO: 122), ECSIT (SEQ ID NO: 123), MDK (SEQ ID NO: 124), PUF60 (SEQ ID NO: 125), PFN2 (SEQ ID NO: 126), SYNCRIP (SEQ ID NO: 127), TSPAN3 (SEQ ID NO: 128), SLC16A1 (SEQ ID NO: 129), POLR2H (SEQ ID NO: 130), MAP3K7 (SEQ ID NO: 131), CSRP2 (SEQ ID NO: 132), BCL11A (SEQ ID NO: 133), PNKP (SEQ ID NO: 134), DNAJC6 (SEQ ID NO: 135), FDFT1 (SEQ ID NO: 136), FADS1 MIR1908 (SEQ ID NO: 137), RPARP-AS1 (SEQ ID NO: 138), DHRS7 (SEQ ID NO: 139), CCNB1IP1 (SEQ ID NO: 140), CCT3 LOC101927137 (SEQ ID NO: 141), DDX18 (SEQ ID NO: 142), AARSD1 PTGES3L PTGES3L-AARSD1 (SEQ ID NO: 143), HNRNPDL (SEQ ID NO: 144), ATXN7L3B (SEQ ID NO: 145), MRPS14 (SEQ ID NO: 146), SOX4 (SEQ ID NO: 147), ELOVL2 (SEQ ID NO: 148), KCNJ8 (SEQ ID NO: 149), TRIAP1 (SEQ ID NO: 150), EIF2B1 (SEQ ID NO: 151), FBXL14 (SEQ ID NO: 152), MAPRE2 (SEQ ID NO: 153), ORC4 (SEQ ID NO: 154), MDN1 (SEQ ID NO: 155), KNOP1 (SEQ ID NO: 156), KBTBD11 (SEQ ID NO: 157), FADS2 (SEQ ID NO: 158), RANBP1 (SEQ ID NO: 159), PLEKHB1 (SEQ ID NO: 160), HSPE1 (SEQ ID NO: 161), TMEM97 (SEQ ID NO: 162), ITFG2 LOC100507424 (SEQ ID NO: 163), SFPQ (SEQ ID NO: 164), RFC3 (SEQ ID NO: 165), SDR39U1 (SEQ ID NO: 166), PBK (SEQ ID NO: 167), PHB (SEQ ID NO: 168), KHDRBS1 (SEQ ID NO: 169), PDAP1 (SEQ ID NO: 170), SSRP1 (SEQ ID NO: 171), and B3GALT2 (SEQ ID NO: 172).

In any of the above aspects, the biomarker of resistance may be selected from one or more of HLA-E (SEQ ID NO: 173 or 174 or 178), GADD45B (SEQ ID NO: 175), CLIC1 (SEQ ID NO: 176), LASP1 (SEQ ID NO: 177), APOBEC3B (SEQ ID NO: 179), LGALS1 (SEQ ID NO: 180), TAPBP (SEQ ID NO: 181), AHNAK (SEQ ID NO: 182), BHLHE40 (SEQ ID NO: 183), S100A11 (SEQ ID NO: 184), LITAF (SEQ ID NO: 185), ZBTB38 (SEQ ID NO: 186), STAT1 (SEQ ID NO: 187), TCIRG1 (SEQ ID NO: 188), S100A11P1 (SEQ ID NO: 189), CTSA (SEQ ID NO: 190), VEGFA (SEQ ID NO: 191), STOM (SEQ ID NO: 192), P4HB (SEQ ID NO: 193), LITAF (SEQ ID NO: 194), FXYD5 (SEQ ID NO: 195), HLA-C(SEQ ID NO: 196), YPEL5 (SEQ ID NO: 197), HLA-C(SEQ ID NO: 198), HLA-C(SEQ ID NO: 199), STOM (SEQ ID NO: 200), PLIN3 (SEQ ID NO: 201), RRBP1 (SEQ ID NO: 202), IRF1 (SEQ ID NO: 203), LMNA (SEQ ID NO: 204), NPC2 (SEQ ID NO: 205), P4HB (SEQ ID NO: 206), KLF6 (SEQ ID NO: 207), HLA-B (SEQ ID NO: 208), RHOC (SEQ ID NO: 209), CD59 (SEQ ID NO: 210), SRGN (SEQ ID NO: 211), SRGN (SEQ ID NO: 212), STAT1 (SEQ ID NO: 213), TNFSF10 (SEQ ID NO: 214), HLA-B (SEQ ID NO: 215), PIEZO1 (SEQ ID NO: 216), LGALS3 (SEQ ID NO: 217), LDLRAP1 (SEQ ID NO: 218), CD97 (SEQ ID NO: 219), HLA-B (SEQ ID NO: 220), CFLAR (SEQ ID NO: 221), FNDC3B LOC101928615 (SEQ ID NO: 222), CKLF CKLF-CMTM1 (SEQ ID NO: 223), IFI35 (SEQ ID NO: 224), TIPARP (SEQ ID NO: 225), TAP1 (SEQ ID NO: 226), MICALL2 (SEQ ID NO: 227), RRBP1 (SEQ ID NO: 228), ZFP36 (SEQ ID NO: 229), HLA-G (SEQ ID NO: 230), TNIP1 (SEQ ID NO: 231), CD59 (SEQ ID NO: 232), VEGFA (SEQ ID NO: 233), LDLRAP1 (SEQ ID NO: 234), FLNB (SEQ ID NO: 235), PSG6 (SEQ ID NO: 236), CBX7 (SEQ ID NO: 237), RARRES3 (SEQ ID NO: 238), CFLAR (SEQ ID NO: 239), SUN2 (SEQ ID NO: 240), EHD2 (SEQ ID NO: 241), MAP3K5 (SEQ ID NO: 242), BTN3A2 (SEQ ID NO: 243), NOL12 TRIOBP (SEQ ID NO: 244), CKLF (SEQ ID NO: 245), ARPC1B (SEQ ID NO: 246), TNFSF10 (SEQ ID NO: 247), HLA-G (SEQ ID NO: 248), RP11-395B7.7 (SEQ ID NO: 249), EHD2 (SEQ ID NO: 250), LEPROT (SEQ ID NO: 251), BTN3A2 BTN3A3 (SEQ ID NO: 252), INPP4B (SEQ ID NO: 253), DUSP1 (SEQ ID NO: 254), EVI2A (SEQ ID NO: 255), TFPI (SEQ ID NO: 256), EHD1 (SEQ ID NO: 257), VEGFA (SEQ ID NO: 258), EPAS1 (SEQ ID NO: 259), IQGAP1 (SEQ ID NO: 260), IL6ST (SEQ ID NO: 261), CLIC3 (SEQ ID NO: 262), TFPI (SEQ ID NO: 263), NACC2 (SEQ ID NO: 264), TGFBI (SEQ ID NO: 265), IER3 (SEQ ID NO: 266), MICA (SEQ ID NO: 267), BTN3A2 (SEQ ID NO: 268), IQGAP1 (SEQ ID NO: 269), CNN2 (SEQ ID NO: 270), TNFAIP8 (SEQ ID NO: 271), VEGFA (SEQ ID NO: 272), MBNL1 (SEQ ID NO: 273), ISG15 (SEQ ID NO: 274), TNFAIP8 (SEQ ID NO: 275), COPG1 (SEQ ID NO: 276), CD99 (SEQ ID NO: 277), PSMB9 (SEQ ID NO: 278), ZFP36L1 (SEQ ID NO: 279), IL6ST (SEQ ID NO: 280), SHC1 (SEQ ID NO: 281), GSTK1 (SEQ ID NO: 282), CAV1 (SEQ ID NO: 283), HLA-F (SEQ ID NO: 284), KRT7 (SEQ ID NO: 285), TFPI (SEQ ID NO: 286), SPTBN1 (SEQ ID NO: 287), RHOG (SEQ ID NO: 288), CDH11 (SEQ ID NO: 289), ABCC3 (SEQ ID NO: 290), CAV1 (SEQ ID NO: 291), HLA-J (SEQ ID NO: 292), MYL12A (SEQ ID NO: 293), MRPS10 (SEQ ID NO: 294), RRAS (SEQ ID NO: 295), TMEM2 (SEQ ID NO: 296), SIDT2 (SEQ ID NO: 297), RAB11FIP1 (SEQ ID NO: 298), RTP4 (SEQ ID NO: 299), LOC101928916 NNMT (SEQ ID NO: 300), SPTBN1 (SEQ ID NO: 301), TMEM189 TMEM189-UBE2V1 UBE2V1 UBE2V2 (SEQ ID NO: 302), RPN2 (SEQ ID NO: 303), ITGA5 (SEQ ID NO: 304), CDC42EP1 (SEQ ID NO: 305), BTN3A3 (SEQ ID NO: 306), OSER1 (SEQ ID NO: 307), CHST15 (SEQ ID NO: 308), MDFIC (SEQ ID NO: 309), CAV2 (SEQ ID NO: 310), CARD10 (SEQ ID NO: 311), RAC2 (SEQ ID NO: 312), MLPH (SEQ ID NO: 313), F2R (SEQ ID NO: 314), ICAM3 (SEQ ID NO: 315), CRIM1 LOC101929500 (SEQ ID NO: 316), IFI16 (SEQ ID NO: 317), EVI2B (SEQ ID NO: 318), PFKFB3 (SEQ ID NO: 319), MIR6513 TMBIM1 (SEQ ID NO: 320), APOL3 (SEQ ID NO: 321), CD55 (SEQ ID NO: 322), TRAM2 (SEQ ID NO: 323), S100A4 (SEQ ID NO: 324), SERPINB1 (SEQ ID NO: 325), PIP4K2A (SEQ ID NO: 326), RPN2 (SEQ ID NO: 327), ALDOA (SEQ ID NO: 328), IFIT3 (SEQ ID NO: 329), PLAC8 (SEQ ID NO: 330), SDF4 (SEQ ID NO: 331), CAV2 (SEQ ID NO: 332), HLA-C(SEQ ID NO: 333), MVP (SEQ ID NO: 334), RNH1 (SEQ ID NO: 335), EIF1 (SEQ ID NO: 336), SERPINB1 (SEQ ID NO: 337), ASL (SEQ ID NO: 338), CD99 (SEQ ID NO: 339), USP4 (SEQ ID NO: 340), TACC1 (SEQ ID NO: 341), CD55 (SEQ ID NO: 342), PDXK (SEQ ID NO: 343), BST2 (SEQ ID NO: 344), LOC101928916 NNMT (SEQ ID NO: 345), DUSP5 (SEQ ID NO: 346), TNFSF13 (SEQ ID NO: 347), COMT (SEQ ID NO: 348), CYR61 (SEQ ID NO: 349), LY6E (SEQ ID NO: 350), ACSL5 (SEQ ID NO: 351), GBP2 (SEQ ID NO: 352), TNFRSF1B (SEQ ID NO: 353), PTRF (SEQ ID NO: 354), CYR61 (SEQ ID NO: 355), BTN3A1 (SEQ ID NO: 356), PLEC (SEQ ID NO: 357), CTNND1 TMX2-CTNND1 (SEQ ID NO: 358), TNFRSF14 (SEQ ID NO: 359), ABCC10 (SEQ ID NO: 360), SELPLG (SEQ ID NO: 361), GPX4 (SEQ ID NO: 362), EDEM1 (SEQ ID NO: 363), MIR6787 SLC16A3 (SEQ ID NO: 364), DMBT1 (SEQ ID NO: 365), PSMB8 (SEQ ID NO: 366), FN1 (SEQ ID NO: 367), COL1A1 (SEQ ID NO: 368), FOS (SEQ ID NO: 369), CYLD (SEQ ID NO: 370), ADAMTS1 (SEQ ID NO: 371), ALDOA (SEQ ID NO: 372), GATA6 (SEQ ID NO: 373), YWHAB (SEQ ID NO: 374), CIB1 (SEQ ID NO: 375), OPTN (SEQ ID NO: 376), IFI16 (SEQ ID NO: 377), CFLAR (SEQ ID NO: 378), PTGER4 (SEQ ID NO: 379), CCND1 (SEQ ID NO: 380), PDLIM5 (SEQ ID NO: 381), HLA-F (SEQ ID NO: 382), CYP1B1 (SEQ ID NO: 383), SVIL (SEQ ID NO: 384), RNASET2 (SEQ ID NO: 385), TAGLN2 (SEQ ID NO: 386), IFI27 (SEQ ID NO: 387), FLII (SEQ ID NO: 388), STAT6 (SEQ ID NO: 389), WWP2 (SEQ ID NO: 390), FLNC (SEQ ID NO: 391), PARP12 (SEQ ID NO: 392), VPS13D (SEQ ID NO: 393), IFITM2 (SEQ ID NO: 394), CTSZ (SEQ ID NO: 395), C19orf10 (SEQ ID NO: 396), DAPK1 (SEQ ID NO: 397), LOC101928189 RSRP1 (SEQ ID NO: 398), MYOF (SEQ ID NO: 399), ATP2B4 (SEQ ID NO: 400), AXL (SEQ ID NO: 401), MIR6787 SLC16A3 (SEQ ID NO: 402), LY96 (SEQ ID NO: 403), FN1 (SEQ ID NO: 404), CREB3L1 (SEQ ID NO: 405), TNFSF12-TNFSF13 TNFSF13 (SEQ ID NO: 406), POFUT2 (SEQ ID NO: 407), WDR1 (SEQ ID NO: 408), SLC7A7 (SEQ ID NO: 409), MICB (SEQ ID NO: 410), GATA3 (SEQ ID NO: 411), LRRFIP1 (SEQ ID NO: 412), RNASET2 (SEQ ID NO: 413), and ITM2A (SEQ ID NO: 414).

In particular embodiments, the biomarkers of sensitivity may include one or more of: (a) SEQ ID NOs: 1-25; (b) SEQ ID NOs: 26-50; (c) SEQ ID NOs: 51-75; (d) SEQ ID NOs: 76-100; (e) SEQ ID NOs: 101-125; (f) SEQ ID NOs: 126-150; and/or (g) SEQ ID NOs: 151-172. In more specific embodiments, the biomarker of sensitivity may be SRSF7 (SEQ ID NO: 1).

In particular embodiments, the biomarkers of resistance may include one or more of: (a) SEQ ID NOs: 173-200; (b) SEQ ID NOs: 201-225; (c) SEQ ID NOs: 226-250; (d) SEQ ID NOs: 251-275; (e) SEQ ID NOs: 276-300; (f) SEQ ID NOs: 301-325; (g) SEQ ID NOs: 326-350; (h) SEQ ID NOs: 351-375; (i) SEQ ID NOs: 376-400; and/or (j) SEQ ID NOs: 401-414. In more specific embodiments, the biomarker of resistance may be HLA-E (SEQ ID NO: 173 or 174 or 178).

In particular embodiments, the biomarkers of sensitivity may be selected from at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, or at least 172 of the biomarkers of Table 2. The biomarkers of resistance may be selected from at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, or at least 242 of the biomarkers of Table 3.

In any of the above aspects, the cancer is selected from a solid tumor cancer and a hematological cancer. For example, the cancer is, e.g., multiple myeloma, breast cancer, acute myelogenous leukemia (AML), acute lympho-blastic leukemia (ALL), chronic lymphocytic leukemia (CLL), myelo-dysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, estrogen receptor-positive (ERpos) breast cancer, lung cancer, non-small cell lung carcinoma (NSCLC), mesothelioma, intestinal cancer, colon cancer, bladder cancer, adrenal cancer, gallbladder cancer, and squamous cell carcinoma of the head and neck (SCCHN). In specific embodiments, the cancer is breast cancer (e.g., estrogen receptor-positive (ER pos) breast cancer, or a metastatic form of breast cancer). In other embodiments, the cancer is ovarian cancer. In another embodiment, the cancer is pancreatic cancer.

Definitions

As used herein, "a" or "an" means "at least one" or "one or more" unless otherwise indicated. In addition, the singular forms "a", "an", and "the" include plural referents unless the context clearly dictates otherwise.

As used herein, "about" refers to an amount ±10% of the recited value.

The term "2X-121" as used herein refers to 8-(isoindolin-2-ylmethyl)-2,9-dihydro-3H-pyridazino[3,4,5-de]quinazolin-3-one. 2X-121 has the following structure:

2X-121

2X-121 is a small molecule targeted inhibitor of Poly (ADP-ribose) Polymerase (PARP), a key enzyme involved in DNA damage repair in cancer cells. 2X-121 is an orally bioavailable, brain penetrable small molecule PARP inhibitor having novel dual-inhibitory action against both PARP 1/2 and Tankyrase 1/2 (important regulators of canonical Wnt/β-catenin, a critical checkpoint in metastases, particularly in triple-negative breast cancer). 2X-121 is not a substrate for P-glycoprotein, and is active in P-glycoprotein expressing cells, suggesting that it may overcome PARP inhibitor resistance. 2X-121 was formerly known as E7449. 2X-121 is described in McGonigle et al. (*Oncotarget* 6:41307-41323, 2015), hereby incorporated by reference.

By "biomarker" is meant a nucleic acid molecule (e.g., an mRNA or its complement, for example, a cDNA) or a protein encoded by the nucleic acid molecule present in, or from, a cell or tissue. The expression of the biomarker correlates to the responsiveness (e.g., sensitivity or resistance) of the cell or tissue (and thus, the patient containing the cell or tissue or the patient from which the cell or tissue was obtained) to a cancer treatment (e.g., 2X-121 or a pharmaceutically acceptable salt thereof). In particular, a biomarker of sensitivity is a nucleic acid molecule (e.g., a mRNA or its complement) expressed from any one of the genes shown in Table 2, or the protein encoded by the nucleic acid molecule, and a biomarker of resistance is a nucleic acid molecule (e.g., a mRNA or its complement) expressed from any one of the genes shown in Table 3, or the protein encoded by the nucleic acid molecule.

The terms "cancer" and "cancerous" refer to or describe the physiological condition in mammals (e.g., humans) that is typically characterized by unregulated cell proliferation. Examples of cancer include, but are not limited to, myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. The term cancer includes hematological cancers (e.g., cancer of the blood, such as multiple myeloma) and solid tumors (e.g., breast cancer).

The terms "expression level" and "level of expression," as used herein interchangeably, refer to the amount of a gene product in a cell, tissue, biological sample, organism, or patient, e.g., amounts of DNA, RNA (e.g. messenger RNA (mRNA)), or proteins of a given gene.

"Gene" as used herein indicates a coding or noncoding gene whose activity can be determined by measuring the produced RNA. Examples include protein coding genes, microRNAs, small nuclear RNAs and other RNAs with catalytic, regulatory or coding properties.

To "inhibit growth" as used herein means causing a reduction in cell growth (e.g., cancer cell growth, e.g., as compared to the growth inhibition of the NCI60 cancer cell lines as a reference) in vivo or in vitro by, e.g., 10%, 20%, 30%, 40%, 50%, 60%, 70%, 80%, 90%, 95%, or 99% or more, as evident by a reduction in the proliferation of cells exposed to a treatment (e.g., 2X-121 or a pharmaceutically acceptable salt thereof), relative to the proliferation of cells in the absence of the treatment. Growth inhibition may be the result of a treatment (e.g., 2X-121 or a pharmaceutically acceptable salt thereof) that induces apoptosis in a cell, induces necrosis in a cell, slows cell cycle progression, disrupts cellular metabolism, induces cell lysis, or induces some other mechanism that reduces the proliferation of cells.

"Microarray" as used herein means a device employed by any method that quantifies one or more subject oligonucleotides, e.g., RNA, DNA, cDNA, or analogues thereof, at a time. For example, many DNA microarrays, including those made by Affymetrix (e.g., an Affymetrix HG-U133A array), use several probes for determining the expression of a single gene. The DNA microarray may contain oligonucleotide probes that may be, e.g., full-length cDNAs complementary to an RNA or cDNA fragments that hybridize to part of an RNA. The DNA microarray may also contain modified versions of DNA or RNA, such as locked nucleic acids or LNA. Exemplary RNAs include mRNA, miRNA, and miRNA precursors.

As used herein, the term "percent (%) sequence identity" refers to the percentage of nucleic acid residues of a candidate sequence, e.g., a probe or primer of the invention, that are identical to the nucleic acid residues of a reference sequence, e.g., a biomarker sequence of the invention, after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using computer software, such as BLAST, BLAST-2, BLAST-P, BLAST-N, BLAST-X, WU-BLAST-2, ALIGN, ALIGN-2, CLUSTAL, Megalign (DNASTAR). In addition, those skilled in the art can determine appropriate parameters for measuring alignment, including any algorithms needed to achieve optimal alignment over the length of the sequences being compared.

"NCI60" as used herein means a panel of 60 cancer cell lines from lung, colon, breast, ovarian, leukemia, renal, melanoma, prostate and brain cancers including the following cancer cell lines: NSCLC_NCIH23, NSCLC_NCIH522, NSCLC_A549ATCC, NSCLC_EKVX, NSCLC_NCIH226, NSCLC_NCIH332M, NSCLC_H460, NSCLC_HOP62, NSCLC_HOP92, COLON_HT29, COLON_HCC-2998, COLON_HCT116, COLON_SW620, COLON_COLO205, COLON_HCT15, COLON_KM12, BREAST_MCF7, BREAST_MCF7ADRr, BREAST_MDAMB231, BREAST_HS578T, BREAST_MDAMB435, BREAST_MDN, BREAST_BT549, BREAST_T47D, OVAR_OVCAR3, OVAR_OVCAR4, OVAR_OVCAR5, OVAR_OVCAR8, OVAR_IGROV1, OVAR_SKOV3, LEUK_CCRFCEM, LEUK_K562, LEUK_MOLT4, LEUK_HL60, LEUK_RPMI8266, LEUK_SR, RENAL_UO31, RENAL_SN12C, RENAL_A498, RENAL_CAKI1, RENAL_RXF393, RENAL_7860, RENAL_ACHN, RENAL_TK10, MELAN_LOXIMVI, MELAN_MALME3M, MELAN_SKMEL2, MELAN_SKMEL5, MELAN_SKMEL28, MELAN_M14, MELAN_UACC62, MELAN_UACC257, PROSTATE_PC3, PROSTATE_DU145, CNS_SNB19, CNS_SNB75, CNS_U251, CNS_SF268, CNS_SF295, and CNS_SF539.

The terms "patient" and "subject," as used interchangeably herein, refer to any animal (e.g., a mammal, such as a human). A patient to be treated or tested for responsiveness to a treatment (e.g., 2X-121 or a pharmaceutically acceptable salt thereof) according to the methods described herein may be one who has been diagnosed with a cancer, such as ovarian cancer or breast cancer. Diagnosis may be performed by any method or techniques known in the art, such as x-ray, MRI, or biopsy, and confirmed by a physician. To minimize exposure of a patient to drug treatments that may not be therapeutic, the patient may be determined to be either responsive or non-responsive to a cancer treatment, such as 2X-121 or a pharmaceutically acceptable salt thereof, according to the methods described herein.

"Resistance" as used herein means that a cell (e.g., a cancer cell) or a tissue (e.g., a tumor) in vitro or in vivo (e.g., in a subject with a cancer, such as a human) is tolerant to treatment with an anti-cancer agent (e.g., 2X-121 or a pharmaceutically acceptable salt thereof), e.g., the cell or tissue is able to survive and grow despite exposure to (e.g., treatment with) an anti-cancer agent (e.g., 2X-121 or a pharmaceutically acceptable salt thereof). Resistance may arise via exploitation by a cell or tissue of one or more of drug inactivation, drug target alteration, drug efflux, DNA damage repair, cell death inhibition, cell cycle regulation, epithelial-mesenchymal transition (EMT), epigenetics, and other mechanisms. A "resistant" cell or tissue refers to a cell (e.g., a cancer cell) or a tissue (e.g., a tumor), respectively, in vitro or in vivo (e.g., in a subject with a cancer, such as a human) that has acquired and/or exhibits resistance to a treatment (e.g., 2X-121 or a pharmaceutically acceptable salt thereof). For example, a resistant cell or tissue is one that, upon exposure of the cell (e.g., a cancer cell) or the tissue (e.g., a tumor), respectively, to a cancer therapeutic (e.g., 2X-121 or a pharmaceutically acceptable salt thereof) exhibits an inhibition in growth of the cell or tumor of less than 30%, 25%, 20%, 15%, 10%, 5%, or 1% relative to the growth of a cell or tissue not exposed to the treatment. Resistance to treatment may be determined by a cell proliferation assay, e.g., a cell-based assay, which measures the growth of treated cells as a function of the absorbance of the cells of an incident light beam, such as the NCI60 assays described herein. In this assay, greater absorbance indicates greater cell growth, and thus, resistance to the treatment.

The terms "sensitivity" and "responsiveness," as used herein, refer to the likelihood that a cancer treatment (e.g., 2X-121 or a pharmaceutically acceptable salt thereof) has (e.g., induces) a desired effect, or alternatively refers to the strength of a desired effect caused or induced by the treatment in a cell (e.g., a cancer cell) or a tissue (e.g., a tumor) in vitro or in vivo (e.g., in a subject with a cancer, such as a human). For example, the desired effect can include inhibition of the growth of a cell (e.g., a cancer cell) in vitro by more than 30%, 35%, 40%, 45%, 50%, 55%, 60%, 65%, 70%, 75%, 80%, 85%, 90%, 95%, or 100% relative to the growth of a cell (e.g., a cancer cell) not exposed to the treatment. The desired effect can also include reduction in tumor mass by, e.g., about 30%, 35%, 40%, 45%, 50%, 55%, 60%, 65%, 70%, 75%, 80%, 85%, 90%, 95%, or 100%. "Sensitive" or "responsive" as used herein refer to a cell (e.g., a cancer cell) or a tissue (e.g., a tumor) in vitro or in vivo (e.g., in a subject with a cancer, such as a human) that exhibits sensitivity or responsiveness to a therapeutic (e.g., 2X-121 or a pharmaceutically acceptable salt thereof). Responsiveness to treatment may be determined by a cell proliferation assay, e.g., a cell-based assay, which measures the growth of treated cells as a function of the absorbance of the cells of an incident light beam, such as the NCI60 assays described herein. In this assay, lesser absorbance indicates lesser cell growth, and thus, sensitivity or responsiveness to the treatment. A greater reduction in growth indicates more sensitivity or responsiveness to the treatment.

The term "sample," as used herein, refers to any specimen (such as cells, tissue (e.g., a tissue sample obtained by biopsy), blood, serum, plasma, urine, cerebrospinal fluid, or pancreatic fluid) taken from a subject. Preferably, the sample is taken from a portion of the body affected by a cancer (e.g., a biopsy of the cancer tissue). Biopsy may involve fine needle aspiration biopsy, core needle biopsy (e.g., stereotactic core needle biopsy, vacuum-assisted core biopsy, or magnetic resonance imaging (MRI) guided biopsy), or surgical biopsy (e.g., incisional biopsy or excisional biopsy). The sample may undergo additional purification and processing, for example, to remove cell debris and other unwanted molecules. Additional processing may further involve amplification, e.g., using PCR (e.g., RT-PCR). The standard methods of sample purification, such as removal of unwanted molecules, are known in the art.

"Substantially similar" or "corresponds," as used herein with respect to a numerical value of a parameter of one or more of the biomarker(s) of sensitivity and/or resistance (e.g., biomarker expression level, difference score, or mean score), e.g., as determined in a test sample (e.g., a tumor biopsy) from a cancer patient, means that the numerical value of the parameter in the test sample is +0-30% of the numerical value of the parameter in a reference sample (e.g., a cell (e.g., a cancer cell) or tissue (e.g., a tumor) known to be sensitive or resistant to 2X-121 or a pharmaceutically acceptable salt thereof). For example, a numerical value of a parameter in a test sample may be substantially similar to, or may correspond to, the numerical value of the parameter in a reference sample if the parameter values of the test and reference samples differ by, e.g., less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%.

"Substantially dissimilar," as used herein with respect to a numerical value of a parameter of one or more of the biomarker(s) of sensitivity and/or resistance (e.g., biomarker expression level, difference score, or mean score), e.g., as determined in a test sample (e.g., a tumor biopsy) from a cancer patient, means that the numerical value of the parameter in the test sample deviates by greater than 30% from the numerical value of the parameter in a reference sample (e.g., a cell (e.g., a cancer cell) or tissue (e.g., a tumor) known to be sensitive or resistant to 2X-121 or a pharmaceutically acceptable salt thereof). For example, a numerical value of a parameter in a test sample may be substantially dissimilar to the numerical value of the parameter in a reference sample if the parameter values of the test and reference samples differ by, e.g., greater than 35%, 40%, 45%, 50%, 55%, 60%, 65%, 70%, 75%, 80%, 85%, 90%, 95%, 100% or more.

"Treatment," "medical treatment," to "treat," and "therapy," as used interchangeably herein, refer to administering or exposing a patient with a cancer (e.g., a human), a cancer cell, or a tumor to an anti-cancer agent (e.g., a drug, a protein, an antibody, a nucleic acid, a chemotherapeutic agent, or a radioactive agent), or to some other form of medical intervention used to treat or prevent a disease, disorder, or condition (e.g., surgery, cryotherapy, radiation therapy, or combinations thereof). In particular, a medical treatment can include 2X-121 or a pharmaceutically acceptable salt thereof. For example, the cancer to be treated is a hematological cancer or a solid tumor. Examples of cancer include, e.g., myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma, and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, or neoplasms of the central nervous system. Radiation therapy includes the administration of a radioactive agent to a patient or exposure of a patient to radiation. The radiation may be generated from sources such as particle accelerators and related medical devices or agents that emit, e.g., X-radiation, gamma radiation, or electron (Beta radiation) beams. A treatment may be or further include surgery, e.g., to remove a tumor from a subject or living organism.

Other features and advantages of the invention will be apparent from the following Detailed Description, the drawings, and the claims.

DETAILED DESCRIPTION OF THE INVENTION

Figure 1:
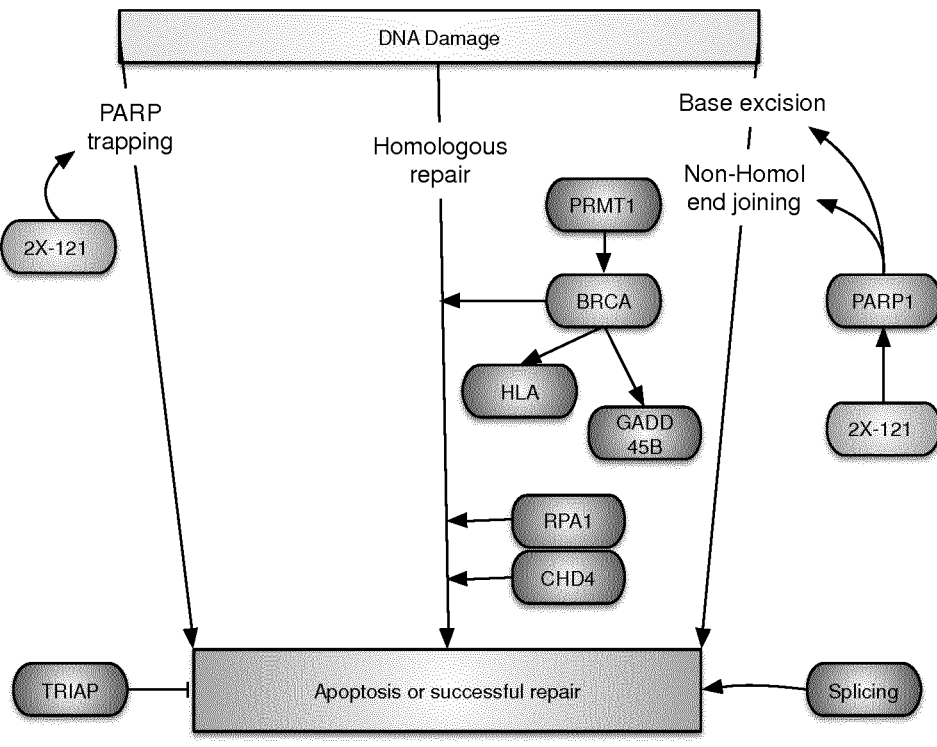
FIG. 1 is a schematic image depicting genes from Tables 2 and 3 associated with the known modes of action of 2X-121: PARP trapping, homologous repair and BRCA, base excision repair, and the Wnt/tankyrase pathway.
Figure 1:
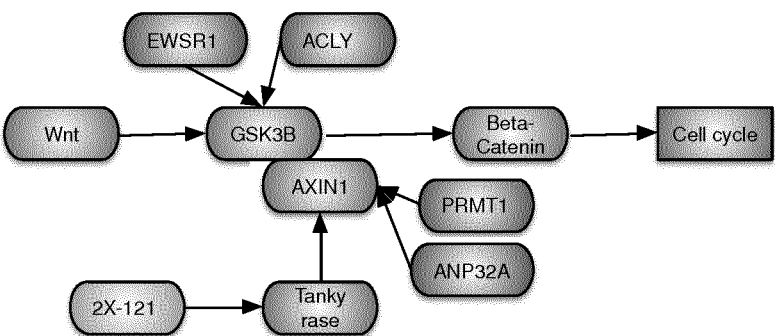

We have discovered that the expression levels of the biomarkers shown in Tables 2 and/or 3 can be used to determine whether a subject with a cancer will likely be responsive to 2X-121 or a pharmaceutically acceptable salt thereof. A device, such as a microarray, with one or more single-stranded oligonucleotide probes that have substantial identity (e.g., at least 85%, 90%, 95%, 99%, or 100% sequence identity) to a sequence that is complementary or identical to the nucleic acid sequence of one or more biomarkers shown in Tables 2 and/or 3 can be used according to the method described herein to assess the responsiveness of a cancer patient to treatment with 2X-121 or a pharmaceutically acceptable salt thereof. For example, the probes can be used to detect one or more (e.g., two, three, four, five, ten, fifteen, twenty, twenty five, or all) of the biomarkers of sensitivity listed in Table 2, such as SRSF7 (SEQ ID NO: 1), in a sample (e.g., a tumor sample) from a patient having cancer. Additionally, the probes can be used to detect one or more (e.g., two, three, four, five, ten, fifteen, twenty, twenty five, or all) of the biomarkers of resistance listed in Table 3, such as HLA-E (SEQ ID NO: 173 or 174 or 178), in a sample (e.g., a tumor sample) from a patient having cancer. Accordingly, the invention features individual biomarkers (e.g., SRSF7 (SEQ ID NO: 1) or HLA-E (SEQ ID NO: 173 or 174 or 178)) and sets of biomarkers shown in Tables 2 and/or 3 that can be used to determine the responsiveness of a cancer patient to 2X-121 or a pharmaceutically acceptable salt thereof at various stages of disease progression (e.g., patients diagnosed with cancer or patients after cancer recurrence) and at different times during the treatment process (e.g., prior to administration of any cancer treatment, after administration of one or more cancer treatments other than 2X-121 or a pharmaceutically acceptable salt thereof, prior to administration of 2X-121 or a pharmaceutically acceptable salt thereof, or during administration of 2X-121 or a pharmaceutically acceptable salt thereof).

In particular, featured are methods for determining whether a patient may be responsive to 2X-121 or a pharmaceutically acceptable salt thereof by, e.g., detecting the expression level (e.g., mRNA or protein expression level) of one or more of the biomarkers shown in Table(s) 2 and/or 3 (e.g., SRSF7 (SEQ ID NO: 1) and/or HLA-E (SEQ ID NO: 173 or 174 or 178)) in a biological sample (e.g., a tumor biopsy) obtained from the subject using a device (e.g., a microarray). The expression level of one or more of the biomarkers of sensitivity may then be compared to the expression level of the biomarker(s) in a cell or tissue known to be sensitive or resistant to 2X-121 or a pharmaceutically acceptable salt thereof to determine the patient's responsiveness to 2X-121 or a pharmaceutically acceptable salt thereof.

The patient may be responsive to 2X-121 or a pharmaceutically acceptable salt thereof if the expression level of the one or more of the biomarkers of sensitivity (e.g., one or more of SRSF7 (SEQ ID NO: 1), UCHL1 (SEQ ID NO: 2), MLLT11 (SEQ ID NO: 3), ADD2 (SEQ ID NO: 4 or 5), PRMT1 (SEQ ID NO: 6), SRSF3 (SEQ ID NO: 7), PRMT5 (SEQ ID NO: 8), COCH (SEQ ID NO: 9), RUVBL1 (SEQ ID NO: 10), MARCKSL1 (SEQ ID NO: 11), CHERP (SEQ ID NO: 12), MTSS1 (SEQ ID NO: 13), LSM4 (SEQ ID NO: 14), RAPGEF5 (SEQ ID NO: 15), PRPF4 (SEQ ID NO: 16), LSM4 (SEQ ID NO: 17), DESI2 (SEQ ID NO: 18), RNPS1 (SEQ ID NO: 19), SNX10 (SEQ ID NO: 20), CUL3 (SEQ ID NO: 21), CHD4 (SEQ ID NO: 22), MSH2 (SEQ ID NO: 23), HNRNPM (SEQ ID NO: 24), SRSF1 (SEQ ID NO: 25), NELL2 (SEQ ID NO: 26), PAICS (SEQ ID NO: 27), HOXA10 (SEQ ID NO: 28), BUB1B (SEQ ID NO: 29), E2F5 (SEQ ID NO: 30), MAGED4 MAGED4B SNORA11D SNORA11E (SEQ ID NO: 31), PRPF8 (SEQ ID NO: 32), SORD (SEQ ID NO: 33), HNRNPU (SEQ ID NO: 34), PEX5 (SEQ ID NO: 35), HYPK MIR1282 SERF2 SERF2-C15ORF63 (SEQ ID NO: 36), STRAP (SEQ ID NO: 37), NDUFAB1 (SEQ ID NO: 38), FARSA (SEQ ID NO: 39), STOML2 (SEQ ID NO: 40), ERH (SEQ ID NO: 41), HSBP1 (SEQ ID NO: 42), DDX39A (SEQ ID NO: 43), ODC1 (SEQ ID NO: 44), TAF5 (SEQ ID NO: 45), TBC1D31 (SEQ ID NO: 46), TRA2B (SEQ ID NO: 47), NUDC (SEQ ID NO: 48), DDX23 (SEQ ID NO: 49), PRPF31 (SEQ ID NO: 50), UBE2S (SEQ ID NO: 51), TCF4 (SEQ ID NO: 52), MLF2 (SEQ ID NO: 53), CCDC181

(SEQ ID NO: 54), TCF4 (SEQ ID NO: 55), DESI2 (SEQ ID NO: 56), RPF1 (SEQ ID NO: 57), PASK (SEQ ID NO: 58), NUP88 (SEQ ID NO: 59), RNASEH2A (SEQ ID NO: 60), FBL (SEQ ID NO: 61), LOC101928747 RBMX SNORD61 (SEQ ID NO: 62), NXF1 (SEQ ID NO: 63), PLEKHO1 (SEQ ID NO: 64), GAR1 (SEQ ID NO: 65), RPA1 (SEQ ID NO: 66), ZNF24 (SEQ ID NO: 67), BOP1 MIR7112 (SEQ ID NO: 68), RAB3B (SEQ ID NO: 69), SLC35G2 (SEQ ID NO: 70), TSPAN3 (SEQ ID NO: 71), DKC1 MIR664B SNORA56 (SEQ ID NO: 72), PSMC3IP (SEQ ID NO: 73), DNAJC7 (SEQ ID NO: 74), RRP1B (SEQ ID NO: 75), NME1 (SEQ ID NO: 76), SNRPA (SEQ ID NO: 77), DBN1 (SEQ ID NO: 78), KIAA0020 (SEQ ID NO: 79), SUPV3L1 (SEQ ID NO: 80), ZNF573 (SEQ ID NO: 81), FAM134B (SEQ ID NO: 82), TOX3 (SEQ ID NO: 83), HSPD1 (SEQ ID NO: 84), ACLY (SEQ ID NO: 85), TOX3 (SEQ ID NO: 86), MSANTD3-TMEFF1 TMEFF1 (SEQ ID NO: 87), AKIRIN1 (SEQ ID NO: 88), UBE2M (SEQ ID NO: 89), MTF2 (SEQ ID NO: 90), EWSR1 (SEQ ID NO: 91), FARSA (SEQ ID NO: 92), SKP2 (SEQ ID NO: 93), TMEM97 (SEQ ID NO: 94), HNRNPD (SEQ ID NO: 95), ILKAP (SEQ ID NO: 96), NASP (SEQ ID NO: 97), SNRPD1 (SEQ ID NO: 98), TIMM44 (SEQ ID NO: 99), PKN1 (SEQ ID NO: 100), STAU2 (SEQ ID NO: 101), DNAAF2 (SEQ ID NO: 102), SNRPD2 (SEQ ID NO: 103), FUS (SEQ ID NO: 104), PASK (SEQ ID NO: 105), ATP6V1G2-DDX39B DDX39B SNORD84 (SEQ ID NO: 106), PDSS1 (SEQ ID NO: 107), NUDC (SEQ ID NO: 108), TOX3 (SEQ ID NO: 109), TPGS2 (SEQ ID NO: 110), SLIRP (SEQ ID NO: 111), NCL (SEQ ID NO: 112), ANP32A (SEQ ID NO: 113), SAFB (SEQ ID NO: 114), STIP1 (SEQ ID NO: 115), CEP68 (SEQ ID NO: 116), STIP1 (SEQ ID NO: 117), C8orf33 (SEQ ID NO: 118), MRPL11 (SEQ ID NO: 119), POLR2I (SEQ ID NO: 120), FAM134B (SEQ ID NO: 121), MCAM MIR6756 (SEQ ID NO: 122), ECSIT (SEQ ID NO: 123), MDK (SEQ ID NO: 124), PUF60 (SEQ ID NO: 125), PFN2 (SEQ ID NO: 126), SYNCRIP (SEQ ID NO: 127), TSPAN3 (SEQ ID NO: 128), SLC16A1 (SEQ ID NO: 129), POLR2H (SEQ ID NO: 130), MAP3K7 (SEQ ID NO: 131), CSRP2 (SEQ ID NO: 132), BCL11A (SEQ ID NO: 133), PNKP (SEQ ID NO: 134), DNAJC6 (SEQ ID NO: 135), FDFT1 (SEQ ID NO: 136), FADS1 MIR1908 (SEQ ID NO: 137), RPARP-AS1 (SEQ ID NO: 138), DHRS7 (SEQ ID NO: 139), CCNB1IP1 (SEQ ID NO: 140), CCT3 LOC101927137 (SEQ ID NO: 141), DDX18 (SEQ ID NO: 142), AARSD1 PTGES3L PTGES3L-AARSD1 (SEQ ID NO: 143), HNRNPDL (SEQ ID NO: 144), ATXN7L3B (SEQ ID NO: 145), MRPS14 (SEQ ID NO: 146), SOX4 (SEQ ID NO: 147), ELOVL2 (SEQ ID NO: 148), KCNJ8 (SEQ ID NO: 149), TRIAP1 (SEQ ID NO: 150), EIF2B1 (SEQ ID NO: 151), FBXL14 (SEQ ID NO: 152), MAPRE2 (SEQ ID NO: 153), ORC4 (SEQ ID NO: 154), MDN1 (SEQ ID NO: 155), KNOP1 (SEQ ID NO: 156), KBTBD11 (SEQ ID NO: 157), FADS2 (SEQ ID NO: 158), RANBP1 (SEQ ID NO: 159), PLEKHB1 (SEQ ID NO: 160), HSPE1 (SEQ ID NO: 161), TMEM97 (SEQ ID NO: 162), ITFG2 LOC100507424 (SEQ ID NO: 163), SFPQ (SEQ ID NO: 164), RFC3 (SEQ ID NO: 165), SDR39U1 (SEQ ID NO: 166), PBK (SEQ ID NO: 167), PHB (SEQ ID NO: 168), KHDRBS1 (SEQ ID NO: 169), PDAP1 (SEQ ID NO: 170), SSRP1 (SEQ ID NO: 171), and B3GALT2 (SEQ ID NO: 172)) is substantially similar to the expression level of the biomarker(s) of sensitivity in a cell (e.g., a cancer cell) or tissue (e.g., a tumor) known to be sensitive to 2X-121 or a pharmaceutically acceptable salt thereof. The patient may also be responsive to 2X-121 or a pharmaceutically acceptable salt thereof if the level of expression of one or more of the biomarkers of resistance (e.g., one or more of HLA-E (SEQ ID NO: 173 or 174 or 178), GADD45B (SEQ ID NO: 175), CLIC1 (SEQ ID NO: 176), LASP1 (SEQ ID NO: 177), APOBEC3B (SEQ ID NO: 179), LGALS1 (SEQ ID NO: 180), TAPBP (SEQ ID NO: 181), AHNAK (SEQ ID NO: 182), BHLHE40 (SEQ ID NO: 183), S100A11 (SEQ ID NO: 184), LITAF (SEQ ID NO: 185), ZBTB38 (SEQ ID NO: 186), STAT1 (SEQ ID NO: 187), TCIRG1 (SEQ ID NO: 188), S100A11P1 (SEQ ID NO: 189), CTSA (SEQ ID NO: 190), VEGFA (SEQ ID NO: 191), STOM (SEQ ID NO: 192), P4HB (SEQ ID NO: 193), LITAF (SEQ ID NO: 194), FXYD5 (SEQ ID NO: 195), HLA-C(SEQ ID NO: 196), YPEL5 (SEQ ID NO: 197), HLA-C(SEQ ID NO: 198), HLA-C(SEQ ID NO: 199), STOM (SEQ ID NO: 200), PLIN3 (SEQ ID NO: 201), RRBP1 (SEQ ID NO: 202), IRF1 (SEQ ID NO: 203), LMNA (SEQ ID NO: 204), NPC2 (SEQ ID NO: 205), P4HB (SEQ ID NO: 206), KLF6 (SEQ ID NO: 207), HLA-B (SEQ ID NO: 208), RHOC (SEQ ID NO: 209), CD59 (SEQ ID NO: 210), SRGN (SEQ ID NO: 211), SRGN (SEQ ID NO: 212), STAT1 (SEQ ID NO: 213), TNFSF10 (SEQ ID NO: 214), HLA-B (SEQ ID NO: 215), PIEZO1 (SEQ ID NO: 216), LGALS3 (SEQ ID NO: 217), LDLRAP1 (SEQ ID NO: 218), CD97 (SEQ ID NO: 219), HLA-B (SEQ ID NO: 220), CFLAR (SEQ ID NO: 221), FNDC3B LOC101928615 (SEQ ID NO: 222), CKLF CKLF-CMTM1 (SEQ ID NO: 223), IFI35 (SEQ ID NO: 224), TIPARP (SEQ ID NO: 225), TAP1 (SEQ ID NO: 226), MICALL2 (SEQ ID NO: 227), RRBP1 (SEQ ID NO: 228), ZFP36 (SEQ ID NO: 229), HLA-G (SEQ ID NO: 230), TNIP1 (SEQ ID NO: 231), CD59 (SEQ ID NO: 232), VEGFA (SEQ ID NO: 233), LDLRAP1 (SEQ ID NO: 234), FLNB (SEQ ID NO: 235), PSG6 (SEQ ID NO: 236), CBX7 (SEQ ID NO: 237), RARRES3 (SEQ ID NO: 238), CFLAR (SEQ ID NO: 239), SUN2 (SEQ ID NO: 240), EHD2 (SEQ ID NO: 241), MAP3K5 (SEQ ID NO: 242), BTN3A2 (SEQ ID NO: 243), NOL12 TRIOBP (SEQ ID NO: 244), CKLF (SEQ ID NO: 245), ARPC1B (SEQ ID NO: 246), TNFSF10 (SEQ ID NO: 247), HLA-G (SEQ ID NO: 248), RP11-395B7.7 (SEQ ID NO: 249), EHD2 (SEQ ID NO: 250), LEPROT (SEQ ID NO: 251), BTN3A2 BTN3A3 (SEQ ID NO: 252), INPP4B (SEQ ID NO: 253), DUSP1 (SEQ ID NO: 254), EVI2A (SEQ ID NO: 255), TFPI (SEQ ID NO: 256), EHD1 (SEQ ID NO: 257), VEGFA (SEQ ID NO: 258), EPAS1 (SEQ ID NO: 259), IQGAP1 (SEQ ID NO: 260), IL6ST (SEQ ID NO: 261), CLIC3 (SEQ ID NO: 262), TFPI (SEQ ID NO: 263), NACC2 (SEQ ID NO: 264), TGFBI (SEQ ID NO: 265), IER3 (SEQ ID NO: 266), MICA (SEQ ID NO: 267), BTN3A2 (SEQ ID NO: 268), IQGAP1 (SEQ ID NO: 269), CNN2 (SEQ ID NO: 270), TNFAIP8 (SEQ ID NO: 271), VEGFA (SEQ ID NO: 272), MBNL1 (SEQ ID NO: 273), ISG15 (SEQ ID NO: 274), TNFAIP8 (SEQ ID NO: 275), COPG1 (SEQ ID NO: 276), CD99 (SEQ ID NO: 277), PSMB9 (SEQ ID NO: 278), ZFP36L1 (SEQ ID NO: 279), IL6ST (SEQ ID NO: 280), SHC1 (SEQ ID NO: 281), GSTK1 (SEQ ID NO: 282), CAV1 (SEQ ID NO: 283), HLA-F (SEQ ID NO: 284), KRT7 (SEQ ID NO: 285), TFPI (SEQ ID NO: 286), SPTBN1 (SEQ ID NO: 287), RHOG (SEQ ID NO: 288), CDH11 (SEQ ID NO: 289), ABCC3 (SEQ ID NO: 290), CAV1 (SEQ ID NO: 291), HLA-J (SEQ ID NO: 292), MYL12A (SEQ ID NO: 293), MRPS10 (SEQ ID NO: 294), RRAS (SEQ ID NO: 295), TMEM2 (SEQ ID NO: 296), SIDT2 (SEQ ID NO: 297), RAB11FIP1 (SEQ ID NO: 298), RTP4 (SEQ ID NO: 299), LOC101928916 NNMT (SEQ ID NO: 300), SPTBN1 (SEQ ID NO: 301), TMEM189 TMEM189-UBE2V1 UBE2V1 UBE2V2 (SEQ ID NO: 302), RPN2 (SEQ ID NO: 303), ITGA5 (SEQ ID NO: 304), CDC42EP1 (SEQ ID NO: 305), BTN3A3 (SEQ ID NO: 306), OSER1 (SEQ ID NO: 307), CHST15 (SEQ ID NO: 308), MDFIC (SEQ ID NO: 309), CAV2 (SEQ ID NO: 310), CARD10 (SEQ ID NO: 311), RAC2 (SEQ ID NO: 312), MLPH (SEQ ID NO: 313), F2R (SEQ ID NO: 314), ICAM3 (SEQ ID NO: 315), CRIM1 LOC101929500 (SEQ ID NO: 316), IFI16 (SEQ ID NO: 317), EVI2B (SEQ ID NO: 318), PFKFB3 (SEQ ID NO: 319), MIR6513 TMBIM1 (SEQ ID NO: 320), APOL3 (SEQ ID NO: 321), CD55 (SEQ ID NO: 322), TRAM2 (SEQ ID NO: 323), S100A4 (SEQ ID NO: 324), SERPINB1 (SEQ ID NO: 325), PIP4K2A (SEQ ID NO: 326), RPN2 (SEQ ID NO: 327), ALDOA (SEQ ID NO: 328), IFIT3 (SEQ ID NO: 329), PLAC8 (SEQ ID NO: 330), SDF4 (SEQ ID NO: 331), CAV2 (SEQ ID NO: 332), HLA-C(SEQ ID NO: 333), MVP (SEQ ID NO: 334), RNH1 (SEQ ID NO: 335), EIF1 (SEQ ID NO: 336), SERPINB1 (SEQ ID NO: 337), ASL (SEQ ID NO: 338), CD99 (SEQ ID NO: 339), USP4 (SEQ ID NO: 340), TACC1 (SEQ ID NO: 341), CD55 (SEQ ID NO: 342), PDXK (SEQ ID NO: 343), BST2 (SEQ ID NO: 344), LOC101928916 NNMT (SEQ ID NO: 345), DUSP5 (SEQ ID NO: 346), TNFSF13 (SEQ ID NO: 347), COMT (SEQ ID NO: 348), CYR61 (SEQ ID NO: 349), LY6E (SEQ ID NO: 350), ACSL5 (SEQ ID NO: 351), GBP2 (SEQ ID NO: 352), TNFRSF1B (SEQ ID NO: 353), PTRF (SEQ ID NO: 354), CYR61 (SEQ ID NO: 355), BTN3A1 (SEQ ID NO: 356), PLEC (SEQ ID NO: 357), CTNND1 TMX2-CTNND1 (SEQ ID NO: 358), TNFRSF14 (SEQ ID NO: 359), ABCC10 (SEQ ID NO: 360), SELPLG (SEQ ID NO: 361), GPX4 (SEQ ID NO: 362), EDEM1 (SEQ ID NO: 363), MIR6787 SLC16A3 (SEQ ID NO: 364), DMBT1 (SEQ ID NO: 365), PSMB8 (SEQ ID NO: 366), FN1 (SEQ ID NO: 367), COL1A1 (SEQ ID NO: 368), FOS (SEQ ID NO: 369), CYLD (SEQ ID NO: 370), ADAMTS1 (SEQ ID NO: 371), ALDOA (SEQ ID NO: 372), GATA6 (SEQ ID NO: 373), YWHAB (SEQ ID NO: 374), CIB1 (SEQ ID NO: 375), OPTN (SEQ ID NO: 376), IFI16 (SEQ ID NO: 377), CFLAR (SEQ ID NO: 378), PTGER4 (SEQ ID NO: 379), CCND1 (SEQ ID NO: 380), PDLIM5 (SEQ ID NO: 381), HLA-F (SEQ ID NO: 382), CYP1B1 (SEQ ID NO: 383), SVIL (SEQ ID NO: 384), RNASET2 (SEQ ID NO: 385), TAGLN2 (SEQ ID NO: 386), IFI27 (SEQ ID NO: 387), FLII (SEQ ID NO: 388), STAT6 (SEQ ID NO: 389), WWP2 (SEQ ID NO: 390), FLNC (SEQ ID NO: 391), PARP12 (SEQ ID NO: 392), VPS13D (SEQ ID NO: 393), IFITM2 (SEQ ID NO: 394), CTSZ (SEQ ID NO: 395), C19orf10 (SEQ ID NO: 396), DAPK1 (SEQ ID NO: 397), LOC101928189 RSRP1 (SEQ ID NO: 398), MYOF (SEQ ID NO: 399), ATP2B4 (SEQ ID NO: 400), AXL (SEQ ID NO: 401), MIR6787 SLC16A3 (SEQ ID NO: 402), LY96 (SEQ ID NO: 403), FN1 (SEQ ID NO: 404), CREB3L1 (SEQ ID NO: 405), TNFSF12-TNFSF13 TNFSF13 (SEQ ID NO: 406), POFUT2 (SEQ ID NO: 407), WDR1 (SEQ ID NO: 408), SLC7A7 (SEQ ID NO: 409), MICB (SEQ ID NO: 410), GATA3 (SEQ ID NO: 411), LRRFIP1 (SEQ ID NO: 412), RNASET2 (SEQ ID NO: 413), and ITM2A (SEQ ID NO: 414)) is substantially similar to the expression level of the biomarker(s) of resistance in a cell or tissue known to be sensitive to 2X-121 or a pharmaceutically acceptable salt thereof. The patient may also be responsive to 2X-121 or a pharmaceutically acceptable salt thereof if the level of expression of one or more of the biomarkers of sensitivity is substantially dissimilar to the expression level of the bio-marker(s) of sensitivity in a cell (e.g., a cancer cell) or tissue (e.g., a tumor) known to be resistant to 2X-121 or a pharmaceutically acceptable salt thereof. Also, the patient may be responsive to 2X-121 or a pharmaceutically accept-able salt thereof if the level of expression of one or more of the biomarkers of resistance is substantially dissimilar to the expression level of the biomarker(s) of resistance in a cell or tissue known to be resistant to 2X-121 or a pharmaceutically acceptable salt thereof.

Also featured are methods of treating a patient with a cancer, such as a patient having recurrence of cancer, by detecting the expression levels of one or more of the biomarkers shown in Tables 2 and/or 3 (e.g., SRSF7 (SEQ ID NO: 1) and/or HLA-E (SEQ ID NO: 173 or 174 or 178)) in a sample (e.g., a tumor sample) from the patient, and then administering 2X-121 or a pharmaceutically acceptable salt thereof based on the expression levels of the biomarker(s). In particular, a patient with a cancer may be administered 2X-121 or a pharmaceutically acceptable salt thereof if the expression level of one or more biomarkers of sensitivity is substantially similar to the expression level of the biomarker(s) of sensitivity in a cell or tissue known to be sensitive to 2X-121 or a pharmaceutically acceptable salt thereof. Moreover, a patient with a cancer may be administered 2X-121 or a pharmaceutically acceptable salt thereof if the expression level of one or more biomarkers of resistance is substantially similar to the expression level of the biomarker(s) of resistance in a cell or tissue known to be sensitive to 2X-121 or a pharmaceutically acceptable salt thereof. Additionally, a patient with a cancer may be administered 2X-121 or a pharmaceutically acceptable salt thereof if the expression level of one or more biomarkers of sensitivity is substantially dissimilar to the expression level of the biomarker(s) of sensitivity in a cell or tissue known to be resistant to 2X-121 or a pharmaceutically acceptable salt thereof. Also, a patient with a cancer may be administered 2X-121 or a pharmaceutically acceptable salt thereof if the expression level of one or more biomarkers of resistance is substantially dissimilar to the expression level of the biomarker(s) of resistance in a cell or tissue known to be resistant to 2X-121 or a pharmaceutically acceptable salt thereof. Thus, the methods can be used to treat a cancer patient predicted to be responsive to 2X-121 or a pharmaceutically acceptable salt thereof, such as a patient with, e.g., multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, estrogen receptor-positive (ERpos) breast cancer, lung cancer, non-small cell lung carcinoma (NSCLC), mesothelioma, intestinal cancer, colon cancer, bladder cancer, adrenal cancer, gallbladder cancer, and squamous cell carcinoma of the head and neck (SCCHN).

Methods are described herein for identifying biomarkers of drug responsiveness, detecting biomarker gene expression in a cancer patient, determining the responsiveness of a cancer patient to 2X-121 or a pharmaceutically acceptable salt thereof, and treating cancer in a patient with 2X-121 or a pharmaceutically acceptable salt thereof. Also described are devices and kits for use in these methods.

Methods for Identifying Biomarkers of Drug Responsiveness

Also featured are methods for identifying biomarkers (e.g., one or more of the biomarkers of Tables 2 and/or 3) that can be used to determine the responsiveness of a cancer patient to a cancer treatment, such as treatment with 2X-121 or a pharmaceutically acceptable salt thereof. Such methods can involve, for example, an algorithm based on growth inhibition values (GI50) of cell lines (e.g., NCI60 cell lines) subjected to treatment with 2X-121 or a pharmaceutically acceptable salt thereof, followed by measurement of gene expression (e.g., using a microarray (e.g., an Affymetrix HG-U133A Genechip array)).

Methodology of the In Vitro Cancer Growth Inhibition Screen

The human tumor cell lines of the cancer screening panel may be grown in RPMI 1640 medium containing 5% fetal bovine serum and 2 mM L-glutamine. Cells may be inoculated into 96 well microtiter plates in 100 μL at plating densities ranging from 5,000 to 40,000 cells/well depending on the doubling time of individual cell lines. After cell inoculation, the microtiter plates may be incubated at 37° C., 5% $CO_2$, 95% air and 100% relative humidity for 24 hours prior to addition of experimental compounds.

After 24 hours, two plates of each cell line may be fixed in situ with TCA, to represent a measurement of the cell population for each cell line at the time of compound addition (Tz). Experimental compounds may be solubilized in dimethyl sulfoxide at 400-fold the desired final maximum test concentration and stored frozen prior to use. At the time of compound (e.g., 2X-121 or a pharmaceutically acceptable salt thereof) addition, an aliquot of frozen concentrate may be thawed and diluted to twice the desired final maximum test concentration with complete medium containing 50 μg/ml Gentamicin. Additional four, 10-fold or 1/2 log serial dilutions are made to provide a total of five concentrations plus control. Aliquots of 100 μl of these different compound dilutions are added to the appropriate microtiter wells already containing 100 μl of medium, resulting in the required final compound concentrations.

Following compound (e.g., 2X-121 or a pharmaceutically acceptable salt thereof) addition, the plates may be incubated for an additional 48 h at 37° C., 5% $CO_2$, 95% air, and 100% relative humidity. For adherent cells, the assay may be terminated by the addition of cold TCA. Cells may be fixed in situ by the gentle addition of 50 μl of cold 50% (w/v) TCA (final concentration, 10% TCA) and incubated for 60 minutes at 4° C. The supernatant may be discarded, and the plates may be washed five times with tap water and air-dried. Sulforhodamine B (SRB) solution (100 μl) at 0.4% (w/v) in 1% acetic acid may be added to each well, and plates are incubated for 10 minutes at room temperature. After staining, unbound dye may be removed by washing five times with 1% acetic acid and the plates may be air-dried. Bound stain may be subsequently solubilized with 10 mM trizma base, and the absorbance may be read on an automated plate reader at a wavelength of 515 nm. For suspension cells, the methodology may be the same, except that the assay may be terminated by fixing settled cells at the bottom of the wells by gently adding 50 μl of 80% TCA (final concentration, 16% TCA). Using the seven absorbance measurements [time zero, (Tz), control growth, (C), and test growth in the presence of compound (e.g., 2X-121 or a pharmaceutically acceptable salt thereof) at the five concentration levels (Ti)], the percentage growth may be calculated at each of the compound concentrations levels. Percentage growth inhibition may be calculated as:

$$[(Ti-Tz)/(C-Tz)]\times 100 \text{for concentrations for which}$$
$$Ti>/=Tz$$

$$[(Ti-Tz)/Tz]\times 100 \text{for concentrations for which } Ti<Tz$$

Three dose response parameters may be calculated for each experimental agent (e.g., 2X-121 or a pharmaceutically acceptable salt thereof). Growth inhibition of 50% (GI50) is calculated from $[(Ti-Tz)/(C-Tz)] \times 100=50$, which is the agent (e.g., 2X-121 or a pharmaceutically acceptable salt thereof) concentration resulting in a 50% reduction in the net protein increase (as measured by SRB staining) in control cells during the compound incubation. The compound concentration resulting in total growth inhibition (TGI) is calculated from Ti=Tz. The LC50 (concentration of compound resulting in a 50% reduction in the measured protein at the end of the compound treatment as compared to that at the beginning) indicating a net loss of cells following treatment is calculated from $[(Ti-Tz)/Tz] \times 100=-50$. Values are calculated for each of these three parameters if the level of activity is reached; however, if the effect is not reached or is exceeded, the value for that parameter is expressed as greater or less than the maximum or minimum concentration tested.

Gene Expression and Growth Inhibition Analysis

The gene expression measurements of NCI60 cancer cell lines can be obtained from a publically available database (e.g., the National Cancer Institute and the Massachusetts Institute of Technology). Each dataset can be normalized so that sample expression measured by different chips can be compared. The preferred method of normalization is the logit transformation, which may be performed for each gene y on each chip, as follows:

$$logit(y)=log[(y-background)/(saturation-y)],$$

where background is calculated as the minimum intensity measured on the chip minus 0.1% of the signal intensity range: min-0.001*(max−min), and saturation is calculated as the maximum intensity measured on the chip plus 0.1% of the signal intensity range: max+0.001* (max−min). The resulting logit transformed data may then be z-transformed to mean zero and standard deviation 1.

Next, gene expression can be correlated to cancer cell growth inhibition. Growth inhibition data (GI50) of the NCI60 cell lines in the presence of a cancer treatment, such as 2X-121 or a pharmaceutically acceptable salt thereof, can be obtained from the NCI. The correlation between the logit-transformed expression level of each gene in each cell line and the logarithm of GI50 (the concentration of a given compound that results in a 50% inhibition of growth) can be calculated, e.g., using the Pearson correlation coefficient or the Spearman Rank-Order correlation coefficient. Instead of using GI50s, any other measure of patient sensitivity to a given treatment (e.g., 2X-121 or a pharmaceutically acceptable salt thereof) may be correlated to a gene expression levels of the patient. Since a plurality of measurements may be available for a single gene, the most accurate determination of correlation coefficient can be, e.g., the median of the correlation coefficients calculated for all probes measuring expression of the same gene.

For example, the median correlation coefficient of gene expression measured on a probe to growth inhibition or patient sensitivity to 2X-121 or a pharmaceutically acceptable salt thereof can be calculated for all genes of interest. Genes that have a median correlation above, e.g., 0.25, 0.30, 0.31, 0.32, 0.33, 0.34, 0.35, 0.36, 0.37, 0.38, 0.39, 0.40, or higher, can be used as biomarkers of sensitivity for assessing responsiveness of a cancer patient (e.g., a patient have recurrence of cancer) to 2X-121 or a pharmaceutically acceptable salt thereof. Likewise, genes that have a median correlation below, e.g., −0.25, −0.30, −0.31, −0.32, −0.33, −0.34, −0.35, −0.36, −0.37, −0.38, −0.39, −0.40, or lower, can be used as biomarkers of resistance for assessing responsiveness of a cancer patient (e.g., a patient have recurrence of cancer) to 2X-121 or a pharmaceutically acceptable salt thereof. Preferably, the correlation coefficient of a biomarker of sensitivity will exceed 0.25, while the correlation coefficient of a biomarker of resistance will be less than −0.25. The result is a list of biomarker genes that correlate to sensitivity or resistance to 2X-121 or a pharmaceutically acceptable salt thereof, as shown in Tables 2 and 3, respectively.

Cancer Types

The methods, devices, and kits of the invention can be used for diagnosing, prognosing, monitoring, treating, and/or reducing cancer in a subject suffering from, diagnosed with, or susceptible to cancer. Non-limiting examples of cancers that can be diagnosed, prognosed, monitored, treated, or reduced using the methods include hematological and solid tumors. In particular, cancers include, e.g., colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myeloma (e.g., multiple myeloma), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system.

In particular, the methods are useful for diagnosing, prognosing, monitoring, treating, or preventing, e.g., multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, estrogen receptor-positive (ERpos) breast cancer, lung cancer, non-small cell lung carcinoma (NSCLC), mesothelioma, intestinal cancer, colon cancer, bladder cancer, adrenal cancer, gallbladder cancer, and squamous cell carcinoma of the head and neck (SCCHN). For example, the cancer can be multiple myeloma, such as a Stage I, Stage II, or Stage III multiple myeloma. In particular, the cancer may be recurrent multiple myeloma. Alternatively, the cancer is a breast cancer, such as medullary carcinoma. The cancer can be estrogen receptor-positive (ER pos) breast cancer. The cancer can be a metastatic form of breast cancer. The breast cancer can be, for example, a Stage 0, Stage I, Stage II, Stage III, or Stage IV breast cancer.

Methods for Detecting Biomarker Gene Expression in a Cancer Patient

A cancer patient can be assessed for sensitivity or resistance to 2X-121 or a pharmaceutically acceptable salt thereof by detecting gene expression of a biomarker (e.g., one or more of the biomarkers of Tables 2 and/or 3) in a biological sample obtained from the cancer patient (e.g., a patient with the cancer or a recurrence thereof). The biological sample can include, for example, cells, tissue (e.g., a tissue sample obtained by biopsy), blood, serum, plasma, urine, sputum, cerebrospinal fluid, lymph tissue or fluid, or pancreatic fluid. For example, the biological sample can be fresh frozen or formalin-fixed paraffin embedded (FFPE) tissue obtained from the subject, such as a tumor sample (e.g., a biopsy) from the tissue of interest (e.g., lymph nodes, thymus, spleen, bone marrow, breast, colorectal, pancreatic, cervical, prostate, bladder, lung, gastrointestinal, head, neck, or ovarian tissue).

RNA Extraction and Biomarker Expression Measurement

Cell samples or tissue samples may be snap frozen in liquid nitrogen until processing. RNA may be extracted using, e.g., Trizol Reagent from Invitrogen following manufacturer's instructions, and detected directly or converted to cDNA for detection. RNA may be amplified using, e.g., MessageAmp kit from Ambion following manufacturer's instructions. Amplified RNA may be quantified using, e.g., HG-U133A or HG-U133_Plus2 GeneChip from Affymetrix Inc. and compatible apparatus e.g. GCS3000Dx from Affymetrix, using the manufacturer's instructions. The resulting biomarker expression measurements may be further analyzed as described herein. The procedures described can be implemented using, e.g., R software available from R-Project and supplemented with packages available from Bioconductor.

One or more of the biomarkers shown in Tables 2 and/or 3 (e.g., SRSF7 (SEQ ID NO: 1) and/or HLA-E (SEQ ID NO: 173 or 174 or 178)) may be measured in a biological sample (e.g., a tumor sample) obtained from the cancer patient (e.g., a patient with any of the cancer types described herein, such as a patient with recurrence of cancer) using, e.g., polymerase chain reaction (PCR), reverse transcriptase PCR (RT-PCR), quantitative real-time PCR (qPCR), an array (e.g., a microarray), a genechip, pyrosequencing, nanopore sequencing, sequencing by synthesis, sequencing by expansion, single molecule real time technology, sequencing by ligation, microfluidics, infrared fluorescence, next generation sequencing (e.g., RNA-Seq techniques), Northern blots, Western blots, Southern blots, NanoString nCounter technologies (e.g., those described in U.S. Patent Application Nos. US 2011/0201515, US 2011/0229888, and US 2013/0017971, each of which is incorporated by reference in its entirety), proteomic techniques (e.g., mass spectrometry or protein arrays), and combinations thereof.

Devices

Devices of the invention can be used for detecting the level of expression of one or more biomarkers shown in Table(s) 2 and/or 3. The device may include at least one single-stranded nucleic acid (e.g., a probe) having at least 85% sequence identity (e.g., 85%, 90%, 95%, 97%, 98%, 99%, or 100% sequence identity) to a nucleic acid sequence that is complementary or identical to at least 5 (e.g., at least 10, at least 15, at least 20, or more) consecutive nucleotides of one or more biomarkers shown in Table(s) 2 and/or 3 (e.g., SRSF7 (SEQ ID NO: 1) or HLA-E (SEQ ID NO: 173 or 174 or 178)), in which the at least one single-stranded nucleic acid is sufficient for the detection of the level of expression of the one or more biomarkers. The device may be used to detect the expression level of a given biomarker by specific hybridization between the single-stranded nucleic acid and the biomarker (e.g., an mRNA, genomic DNA, or non-coding RNA), a nucleic acid encoding the biomarker (e.g., an mRNA), or a complementary nucleic acid thereof. The device may be, or include a microarray. The device may also include or be used with reagents and materials for next generation sequencing (e.g., sequencing by synthesis). The device may also include or be used with NanoString reagents and at least one nCounter cartridge. The device may be, or include a protein array, which contains one or more protein binding moieties (e.g., proteins, antibodies, nucleic acids, aptamers, affibodies, lipids, phospholipids, small molecules, labeled variants of any of the above, and any other moieties useful for protein detection as well known in the art) capable of detectably binding to the polypeptide product(s) of one or more biomarkers shown in Table(s) 2 and/or 3.

Microarrays

The level of expression of the biomarkers (e.g., the biomarkers listed in Table(s) 2 and/or 3 (e.g., SRSF7 (SEQ ID NO: 1) or HLA-E (SEQ ID NO: 173 or 174 or 178)) may be determined using high-throughput expression profiling platforms, such as microarrays. In particular, a microarray for use in the methods for assessing the responsiveness of a subject with cancer (e.g., a patient with recurrence of cancer) to 2X-121 (e.g., 2X-121 or a pharmaceutically acceptable salt thereof) contains or is produced by generating oligonucleotide probes (e.g., DNA, cDNA, or RNA probes) capable of hybridizing to one or more biomarkers of interest (e.g., one or more of the biomarkers of Table(s) 2 and/or 3) or the complement sequences thereof. Each probe can have, e.g., at least 10, 15, 20, 25, 30, or more contiguous nucleic acid residues (e.g., at least 15) that are complementary or identical to a nucleic acid sequence of a selected biomarker. The probe nucleic sequence can also have at least 85% (e.g., 90%, 95%, 99%, or 100%) sequence identity to the nucleic acid sequence of the gene coding the biomarker (e.g., SRSF7 (SEQ ID NO: 1)) or the complement sequence thereof. In particular, the probe sequences can be complementary to all or a portion of the nucleic acid sequence of the biomarker(s).

For example, microarrays of the invention for determining 2X-121 (e.g., 2X-121 or a pharmaceutically acceptable salt thereof) responsiveness can include probes for one or more (e.g., at least 5, 10, 15, or 20 or more (e.g., all)) biomarkers of sensitivity shown in Table 2, such as SRSF7 (SEQ ID NO: 1), UCHL1 (SEQ ID NO: 2), MLLT11 (SEQ ID NO: 3), ADD2 (SEQ ID NO: 4), ADD2 (SEQ ID NO: 5), PRMT1 (SEQ ID NO: 6), SRSF3 (SEQ ID NO: 7), PRMT5 (SEQ ID NO: 8), COCH (SEQ ID NO: 9), RUVBL1 (SEQ ID NO: 10), MARCKSL1 (SEQ ID NO: 11), CHERP (SEQ ID NO: 12), MTSS1 (SEQ ID NO: 13), LSM4 (SEQ ID NO: 14), RAPGEF5 (SEQ ID NO: 15), PRPF4 (SEQ ID NO: 16), LSM4 (SEQ ID NO: 17), DESI2 (SEQ ID NO: 18), RNPS1 (SEQ ID NO: 19), SNX10 (SEQ ID NO: 20), CUL3 (SEQ ID NO: 21), CHD4 (SEQ ID NO: 22), MSH2 (SEQ ID NO: 23), HNRNPM (SEQ ID NO: 24), SRSF1 (SEQ ID NO: 25), NELL2 (SEQ ID NO: 26), PAICS (SEQ ID NO: 27), HOXA10 (SEQ ID NO: 28), BUB1B (SEQ ID NO: 29), E2F5 (SEQ ID NO: 30), MAGED4 MAGED4B SNORA11D SNORA11E (SEQ ID NO: 31), PRPF8 (SEQ ID NO: 32), SORD (SEQ ID NO: 33), HNRNPU (SEQ ID NO: 34), PEX5 (SEQ ID NO: 35), HYPK MIR1282 SERF2 SERF2-C15ORF63 (SEQ ID NO: 36), STRAP (SEQ ID NO: 37), NDUFAB1 (SEQ ID NO: 38), FARSA (SEQ ID NO: 39), STOML2 (SEQ ID NO: 40), ERH (SEQ ID NO: 41), HSBP1 (SEQ ID NO: 42), DDX39A (SEQ ID NO: 43), ODC1 (SEQ ID NO: 44), TAF5 (SEQ ID NO: 45), TBC1D31 (SEQ ID NO: 46), TRA2B (SEQ ID NO: 47), NUDC (SEQ ID NO: 48), DDX23 (SEQ ID NO: 49), PRPF31 (SEQ ID NO: 50), UBE2S (SEQ ID NO: 51), TCF4 (SEQ ID NO: 52), MLF2 (SEQ ID NO: 53), CCDC181 (SEQ ID NO: 54), TCF4 (SEQ ID NO: 55), DESI2 (SEQ ID NO: 56), RPF1 (SEQ ID NO: 57), PASK (SEQ ID NO: 58), NUP88 (SEQ ID NO: 59), RNASEH2A (SEQ ID NO: 60), FBL (SEQ ID NO: 61), LOC101928747 RBMX SNORD61 (SEQ ID NO: 62), NXF1 (SEQ ID NO: 63), PLEKHO1 (SEQ ID NO: 64), GAR1 (SEQ ID NO: 65), RPA1 (SEQ ID NO: 66), ZNF24 (SEQ ID NO: 67), BOP1 MIR7112 (SEQ ID NO: 68), RAB3B (SEQ ID NO: 69), SLC35G2 (SEQ ID NO: 70), TSPAN3 (SEQ ID NO: 71), DKC1 MIR664B SNORA56 (SEQ ID NO: 72), PSMC3IP (SEQ ID NO: 73), DNAJC7 (SEQ ID NO: 74), RRP1B (SEQ ID NO: 75), NME1 (SEQ ID NO: 76), SNRPA (SEQ ID NO: 77), DBN1 (SEQ ID NO: 78), KIAA0020 (SEQ ID NO: 79), SUPV3L1 (SEQ ID NO: 80), ZNF573 (SEQ ID NO: 81), FAM134B (SEQ ID NO: 82), TOX3 (SEQ ID NO: 83), HSPD1 (SEQ ID NO: 84), ACLY (SEQ ID NO: 85), TOX3 (SEQ ID NO: 86), MSANTD3-TMEFF1 TMEFF1 (SEQ ID NO: 87), AKIRIN1 (SEQ ID NO: 88), UBE2M (SEQ ID NO: 89), MTF2 (SEQ ID NO: 90), EWSR1 (SEQ ID NO: 91), FARSA (SEQ ID NO: 92), SKP2 (SEQ ID NO: 93), TMEM97 (SEQ ID NO: 94), HNRNPD (SEQ ID NO: 95), ILKAP (SEQ ID NO: 96), NASP (SEQ ID NO: 97), SNRPD1 (SEQ ID NO: 98), TIMM44 (SEQ ID NO: 99), PKN1 (SEQ ID NO: 100), STAU2 (SEQ ID NO: 101), DNAAF2 (SEQ ID NO: 102), SNRPD2 (SEQ ID NO: 103), FUS (SEQ ID NO: 104), PASK (SEQ ID NO: 105), ATP6V1G2-DDX39B DDX39B SNORD84 (SEQ ID NO: 106), PDSS1 (SEQ ID NO: 107), NUDC (SEQ ID NO: 108), TOX3 (SEQ ID NO: 109), TPGS2 (SEQ ID NO: 110), SLIRP (SEQ ID NO: 111), NCL (SEQ ID NO: 112), ANP32A (SEQ ID NO: 113), SAFB (SEQ ID NO: 114), STIP1 (SEQ ID NO: 115), CEP68 (SEQ ID NO: 116), STIP1 (SEQ ID NO: 117), C8orf33 (SEQ ID NO: 118), MRPL11 (SEQ ID NO: 119), POLR2I (SEQ ID NO: 120), FAM134B (SEQ ID NO: 121), MCAM MIR6756 (SEQ ID NO: 122), ECSIT (SEQ ID NO: 123), MDK (SEQ ID NO: 124), PUF60 (SEQ ID NO: 125), PFN2 (SEQ ID NO: 126), SYNCRIP (SEQ ID NO: 127), TSPAN3 (SEQ ID NO: 128), SLC16A1 (SEQ ID NO: 129), POLR2H (SEQ ID NO: 130), MAP3K7 (SEQ ID NO: 131), CSRP2 (SEQ ID NO: 132), BCL11A (SEQ ID NO: 133), PNKP (SEQ ID NO: 134), DNAJC6 (SEQ ID NO: 135), FDFT1 (SEQ ID NO: 136), FADS1 MIR1908 (SEQ ID NO: 137), RPARP-AS1 (SEQ ID NO: 138), DHRS7 (SEQ ID NO: 139), CCNB1IP1 (SEQ ID NO: 140), CCT3 LOC101927137 (SEQ ID NO: 141), DDX18 (SEQ ID NO: 142), AARSD1 PTGES3L PTGES3L-AARSD1 (SEQ ID NO: 143), HNRNPDL (SEQ ID NO: 144), ATXN7L3B (SEQ ID NO: 145), MRPS14 (SEQ ID NO: 146), SOX4 (SEQ ID NO: 147), ELOVL2 (SEQ ID NO: 148), KCNJ8 (SEQ ID NO: 149), TRIAP1 (SEQ ID NO: 150), EIF2B1 (SEQ ID NO: 151), FBXL14 (SEQ ID NO: 152), MAPRE2 (SEQ ID NO: 153), ORC4 (SEQ ID NO: 154), MDN1 (SEQ ID NO: 155), KNOP1 (SEQ ID NO: 156), KBTBD11 (SEQ ID NO: 157), FADS2 (SEQ ID NO: 158), RANBP1 (SEQ ID NO: 159), PLEKHB1 (SEQ ID NO: 160), HSPE1 (SEQ ID NO: 161), TMEM97 (SEQ ID NO: 162), ITFG2 LOC100507424 (SEQ ID NO: 163), SFPQ (SEQ ID NO: 164), RFC3 (SEQ ID NO: 165), SDR39U1 (SEQ ID NO: 166), PBK (SEQ ID NO: 167), PHB (SEQ ID NO: 168), KHDRBS1 (SEQ ID NO: 169), PDAP1 (SEQ ID NO: 170), SSRP1 (SEQ ID NO: 171), and B3GALT2 (SEQ ID NO: 172).

Microarrays of the invention for determining 2X-121 (e.g., 2X-121 or a pharmaceutically acceptable salt thereof) responsiveness can also include probes for one or more (e.g., at least 5, 10, 15, or 20 or more (e.g., all)) biomarkers of resistance listed in Table 3, such as HLA-E (SEQ ID NO: 173 or 174 or 178), GADD45B (SEQ ID NO: 175), CLIC1 (SEQ ID NO: 176), LASP1 (SEQ ID NO: 177), APOBEC3B (SEQ ID NO: 179), LGALS1 (SEQ ID NO: 180), TAPBP (SEQ ID NO: 181), AHNAK (SEQ ID NO: 182), BHLHE40 (SEQ ID NO: 183), S100A11 (SEQ ID NO: 184), LITAF (SEQ ID NO: 185), ZBTB38 (SEQ ID NO: 186), STAT1 (SEQ ID NO: 187), TCIRG1 (SEQ ID NO: 188), S100A11P1 (SEQ ID NO: 189), CTSA (SEQ ID NO: 190), VEGFA (SEQ ID NO: 191), STOM (SEQ ID NO: 192), P4HB (SEQ ID NO: 193), LITAF (SEQ ID NO: 194), FXYD5 (SEQ ID NO: 195), HLA-C (SEQ ID NO: 196), YPEL5 (SEQ ID NO: 197), HLA-C (SEQ ID NO: 198), HLA-C (SEQ ID NO: 199), STOM (SEQ ID NO: 200), PLIN3 (SEQ ID NO: 201), RRBP1 (SEQ ID NO: 202), IRF1 (SEQ ID NO: 203), LMNA (SEQ ID NO: 204), NPC2 (SEQ ID NO: 205), P4HB (SEQ ID NO: 206), KLF6 (SEQ ID NO: 207), HLA-B (SEQ ID NO: 208), RHOC (SEQ ID NO: 209), CD59 (SEQ ID NO: 210), SRGN (SEQ ID NO: 211), SRGN (SEQ ID NO: 212), STAT1 (SEQ ID NO: 213), TNFSF10 (SEQ ID NO: 214), HLA-B (SEQ ID NO: 215), PIEZO1 (SEQ ID NO: 216), LGALS3 (SEQ ID NO: 217), LDLRAP1 (SEQ ID NO: 218), CD97 (SEQ ID NO: 219), HLA-B (SEQ ID NO: 220), CFLAR (SEQ ID NO: 221), FNDC3B LOC101928615 (SEQ ID NO: 222), CKLF CKLF-CMTM1 (SEQ ID NO: 223), IFI35 (SEQ ID NO: 224), TIPARP (SEQ ID NO: 225), TAP1 (SEQ ID NO: 226), MICALL2 (SEQ ID NO: 227), RRBP1 (SEQ ID NO: 228), ZFP36 (SEQ ID NO: 229), HLA-G (SEQ ID NO: 230), TNIP1 (SEQ ID NO: 231), CD59 (SEQ ID NO: 232), VEGFA (SEQ ID NO: 233), LDLRAP1 (SEQ ID NO: 234), FLNB (SEQ ID NO: 235), PSG6 (SEQ ID NO: 236), CBX7 (SEQ ID NO: 237), RARRES3 (SEQ ID NO: 238), CFLAR (SEQ ID NO: 239), SUN2 (SEQ ID NO: 240), EHD2 (SEQ ID NO: 241), MAP3K5 (SEQ ID NO: 242), BTN3A2 (SEQ ID NO: 243), NOL12 TRIOBP (SEQ ID NO: 244), CKLF (SEQ ID NO: 245), ARPC1B (SEQ ID NO: 246), TNFSF10

(SEQ ID NO: 247), HLA-G (SEQ ID NO: 248), RP11-395B7.7 (SEQ ID NO: 249), EHD2 (SEQ ID NO: 250), LEPROT (SEQ ID NO: 251), BTN3A2 BTN3A3 (SEQ ID NO: 252), INPP4B (SEQ ID NO: 253), DUSP1 (SEQ ID NO: 254), EVI2A (SEQ ID NO: 255), TFPI (SEQ ID NO: 256), EHD1 (SEQ ID NO: 257), VEGFA (SEQ ID NO: 258), EPAS1 (SEQ ID NO: 259), IQGAP1 (SEQ ID NO: 260), IL6ST (SEQ ID NO: 261), CLIC3 (SEQ ID NO: 262), TFPI (SEQ ID NO: 263), NACC2 (SEQ ID NO: 264), TGFBI (SEQ ID NO: 265), IER3 (SEQ ID NO: 266), MICA (SEQ ID NO: 267), BTN3A2 (SEQ ID NO: 268), IQGAP1 (SEQ ID NO: 269), CNN2 (SEQ ID NO: 270), TNFAIP8 (SEQ ID NO: 271), VEGFA (SEQ ID NO: 272), MBNL1 (SEQ ID NO: 273), ISG15 (SEQ ID NO: 274), TNFAIP8 (SEQ ID NO: 275), COPG1 (SEQ ID NO: 276), CD99 (SEQ ID NO: 277), PSMB9 (SEQ ID NO: 278), ZFP36L1 (SEQ ID NO: 279), IL6ST (SEQ ID NO: 280), SHC1 (SEQ ID NO: 281), GSTK1 (SEQ ID NO: 282), CAV1 (SEQ ID NO: 283), HLA-F (SEQ ID NO: 284), KRT7 (SEQ ID NO: 285), TFPI (SEQ ID NO: 286), SPTBN1 (SEQ ID NO: 287), RHOG (SEQ ID NO: 288), CDH11 (SEQ ID NO: 289), ABCC3 (SEQ ID NO: 290), CAV1 (SEQ ID NO: 291), HLA-J (SEQ ID NO: 292), MYL 12A (SEQ ID NO: 293), MRPS10 (SEQ ID NO: 294), RRAS (SEQ ID NO: 295), TMEM2 (SEQ ID NO: 296), SIDT2 (SEQ ID NO: 297), RAB11FIP1 (SEQ ID NO: 298), RTP4 (SEQ ID NO: 299), LOC101928916 NNMT (SEQ ID NO: 300), SPTBN1 (SEQ ID NO: 301), TMEM189 TMEM189-UBE2V1 UBE2V1 UBE2V2 (SEQ ID NO: 302), RPN2 (SEQ ID NO: 303), ITGA5 (SEQ ID NO: 304), CDC42EP1 (SEQ ID NO: 305), BTN3A3 (SEQ ID NO: 306), OSER1 (SEQ ID NO: 307), CHST15 (SEQ ID NO: 308), MDFIC (SEQ ID NO: 309), CAV2 (SEQ ID NO: 310), CARD10 (SEQ ID NO: 311), RAC2 (SEQ ID NO: 312), MLPH (SEQ ID NO: 313), F2R (SEQ ID NO: 314), ICAM3 (SEQ ID NO: 315), CRIM1 LOC101929500 (SEQ ID NO: 316), IFI16 (SEQ ID NO: 317), EVI2B (SEQ ID NO: 318), PFKFB3 (SEQ ID NO: 319), MIR6513 TMBIM1 (SEQ ID NO: 320), APOL3 (SEQ ID NO: 321), CD55 (SEQ ID NO: 322), TRAM2 (SEQ ID NO: 323), S100A4 (SEQ ID NO: 324), SERPINB1 (SEQ ID NO: 325), PIP4K2A (SEQ ID NO: 326), RPN2 (SEQ ID NO: 327), ALDOA (SEQ ID NO: 328), IFIT3 (SEQ ID NO: 329), PLAC8 (SEQ ID NO: 330), SDF4 (SEQ ID NO: 331), CAV2 (SEQ ID NO: 332), HLA-C (SEQ ID NO: 333), MVP (SEQ ID NO: 334), RNH1 (SEQ ID NO: 335), EIF1 (SEQ ID NO: 336), SERPINB1 (SEQ ID NO: 337), ASL (SEQ ID NO: 338), CD99 (SEQ ID NO: 339), USP4 (SEQ ID NO: 340), TACC1 (SEQ ID NO: 341), CD55 (SEQ ID NO: 342), PDXK (SEQ ID NO: 343), BST2 (SEQ ID NO: 344), LOC101928916 NNMT (SEQ ID NO: 345), DUSP5 (SEQ ID NO: 346), TNFSF13 (SEQ ID NO: 347), COMT (SEQ ID NO: 348), CYR61 (SEQ ID NO: 349), LY6E (SEQ ID NO: 350), ACSL5 (SEQ ID NO: 351), GBP2 (SEQ ID NO: 352), TNFRSF1B (SEQ ID NO: 353), PTRF (SEQ ID NO: 354), CYR61 (SEQ ID NO: 355), BTN3A1 (SEQ ID NO: 356), PLEC (SEQ ID NO: 357), CTNND1 TMX2-CTNND1 (SEQ ID NO: 358), TNFRSF14 (SEQ ID NO: 359), ABCC10 (SEQ ID NO: 360), SELPLG (SEQ ID NO: 361), GPX4 (SEQ ID NO: 362), EDEM1 (SEQ ID NO: 363), MIR6787 SLC16A3 (SEQ ID NO: 364), DMBT1 (SEQ ID NO: 365), PSMB8 (SEQ ID NO: 366), FN1 (SEQ ID NO: 367), COL1A1 (SEQ ID NO: 368), FOS (SEQ ID NO: 369), CYLD (SEQ ID NO: 370), ADAMTS1 (SEQ ID NO: 371), ALDOA (SEQ ID NO: 372), GATA6 (SEQ ID NO: 373), YWHAB (SEQ ID NO: 374), CIB1 (SEQ ID NO: 375), OPTN (SEQ ID NO: 376), IFI16 (SEQ ID NO: 377), CFLAR (SEQ ID NO: 378), PTGER4 (SEQ ID NO: 379), CCND1 (SEQ ID NO: 380), PDLIM5 (SEQ

ID NO: 381), HLA-F (SEQ ID NO: 382), CYP1B1 (SEQ ID NO: 383), SVIL (SEQ ID NO: 384), RNASET2 (SEQ ID NO: 385), TAGLN2 (SEQ ID NO: 386), IFI27 (SEQ ID NO: 387), FLII (SEQ ID NO: 388), STAT6 (SEQ ID NO: 389), WWP2 (SEQ ID NO: 390), FLNC (SEQ ID NO: 391), PARP12 (SEQ ID NO: 392), VPS13D (SEQ ID NO: 393), IFITM2 (SEQ ID NO: 394), CTSZ (SEQ ID NO: 395), C19orf10 (SEQ ID NO: 396), DAPK1 (SEQ ID NO: 397), LOC101928189 RSRP1 (SEQ ID NO: 398), MYOF (SEQ ID NO: 399), ATP2B4 (SEQ ID NO: 400), AXL (SEQ ID NO: 401), MIR6787 SLC16A3 (SEQ ID NO: 402), LY96 (SEQ ID NO: 403), FN1 (SEQ ID NO: 404), CREB3L1 (SEQ ID NO: 405), TNFSF12-TNFSF13 TNFSF13 (SEQ ID NO: 406), POFUT2 (SEQ ID NO: 407), WDR1 (SEQ ID NO: 408), SLC7A7 (SEQ ID NO: 409), MICB (SEQ ID NO: 410), GATA3 (SEQ ID NO: 411), LRRFIP1 (SEQ ID NO: 412), RNASET2 (SEQ ID NO: 413), and ITM2A (SEQ ID NO: 414).

A microarray probe may be single-stranded or double-stranded. The probe may be labeled (e.g., detectably labeled with a fluorescent molecule, dye molecule, small molecule, epitope tag, barcode sequence, polypeptide, or any other detectable molecule). Probes can be detectably labeled and immobilized on a solid support to form the microarray. For example, probes can be either prefabricated and spotted to the surface or directly synthesized on to the surface (in situ) of the microarray. The microarray can also be configured such that the sequence and position of each member (e.g., probe) of the array is known. For example, a selection of biomarkers whose expression correlates with an increased likelihood of responsiveness to 2X-121 (e.g., 2X-121 or a pharmaceutically acceptable salt thereof) can be arrayed on a solid support. Hybridization of a labeled probe with a particular target nucleic acid (e.g., an mRNA corresponding to one or more biomarkers of Table(s) 2 and/or 3) indicates that the sample from which the mRNA was derived expresses that biomarker (e.g., the biomarker of sensitivity or resistance to 2X-121 or a pharmaceutically acceptable salt thereof).

PCR-Based Techniques

As few as one and up to 25 or more of the biomarkers (e.g., 5 to 25 or 10 to 25, or at least the first 25 of the biomarkers listed in Table(s) 2 and/or 3) may be used to determine responsiveness of a cancer patient to 2X-121 or a pharmaceutically acceptable salt thereof using the methods described herein. Tissue or cell samples from a cancer patient (e.g., a patient having recurrence of cancer) can be conveniently assayed for gene expression levels using nucleic acid amplification methods, such as polymerase chain reaction (PCR). Such PCR-based techniques may include reverse transcription PCR (RT-PCR), quantitative real-time PCR (qPCR), reverse transcription qPCR (RT-qPCR), or quantitative loop-mediated isothermal amplification (q-LAMP). For example, an mRNA corresponding to a biomarker of Table 2 or 3 can be detected in a biological sample by (a) producing cDNA from the sample by reverse transcription using at least one primer; (b) amplifying the cDNA so produced using a target polynucleotide as sense and antisense primers to amplify target cDNAs therein; and (c) detecting the presence of the amplified target cDNA using polynucleotide probes. The primers and probes including the target sequences shown in Table(s) 2 and/or 3, such as SRSF7 (SEQ ID NO: 1) and/or HLA-E (SEQ ID NO: 173 or 174 or 178), may be used to detect the level of expression of one or more of the indicated biomarkers using PCR. The methods can include one or more steps that allow determination of the levels of target mRNA in a biological sample (e.g., by simultaneously examining the levels of a comparative control mRNA sequence or "housekeeping" gene, such as an actin family member or GAPDH). The primers for these PCR-based techniques may be labeled for detection according to methods known in the art.

Sequencing

The level of expression of the biomarkers shown in Table(s) 2 and/or 3, such as SRSF7 (e.g., SEQ ID NO: 1) and/or HLA-E (e.g., SEQ ID NO: 173 or 174 or 178), may be determined using sequencing technologies, such as next generation sequencing platforms (e.g., RNA-Seq), as described in Mortazavi et al., *Nat. Methods* 5:621-628, 2008, hereby incorporated by reference. RNA-Seq is a robust technology for monitoring expression by direct sequencing of the RNA molecules in a sample. This methodology may include fragmentation of RNA to an average length of, e.g., 200 nucleotides, conversion to cDNA by random priming, and synthesis of double-stranded cDNA (e.g., using the Just cDNA DoubleStranded cDNA Synthesis Kit from Agilent Technology). The cDNA may then be converted into a molecular library for sequencing by addition of sequence adapters for each library (e.g., from Illumina®/Solexa), and the resulting 50 to 100 nucleotide reads are mapped onto the genome. Exemplary sequencing platforms suitable for use according to the methods include, e.g., 454 pyrosequencing, Illumina sequencing by synthesis, SOLID sequencing, Ion Torrent sequencing, and PacBio RS sequencing.

Methods of Determining the Responsiveness of a Patient to 2X-121 or a Pharmaceutically Acceptable Salt Thereof The invention features diagnostic methods for the detection and screening of cancer patients (e.g., patients with cancer or a recurrence thereof) that may be responsive to 2X-121 or a pharmaceutically acceptable salt thereof using one or more of the biomarkers shown in Table(s) 2 and/or 3 (e.g., SRSF7 (e.g., SEQ ID NO: 1) and/or HLA-E (e.g., SEQ ID NO: 173 or 174 or 178)). The methods of the invention may be used for predicting a patient's responsiveness to 2X-121 or a pharmaceutically acceptable salt thereof, and optionally, treating the cancer patient throughout the progression of cancer and/or in cases of recurrence (e.g., after a first line treatment, a second line treatment, and/or a third line treatment).

The invention provides individual biomarkers (e.g., SRSF7 (SEQ ID NO: 1) or HLA-E (SEQ ID NO: 173 or 174 or 178)) and sets of biomarkers (e.g., two or more of the biomarkers listed in Table(s) 2 and/or 3), the expression levels of which, as detected in a biological sample (e.g., a tumor sample, such as a biopsy) obtained from a cancer patient (e.g., a human with cancer), are indicative of responsiveness to 2X-121 or a pharmaceutically acceptable salt thereof. The biomarkers were identified using methods similar to those previously described in, e.g., Chen et al. (*Mol. Cancer Ther.* 11:34-33, 2012), Wang et al. (*J. Nat. Cancer Inst.* 105:1284-1291, 2013), Knudsen et al. (*PLoS One,* 9: e87415, 2014), and Buhl et al (*PLoS One* 13 (3): e0194609, 2018), each of which is incorporated by reference herein in their entirety. In particular, an algorithm based on growth inhibition values (GI50) of a cell line (e.g., NCI60 cells) is used. The cell line is subjected to treatment with 2X-121 or a pharmaceutically acceptable salt thereof and baseline gene expression is determined (e.g., by microarray analysis, RT-PCR, qPCR, or next generation sequencing). After normalization, genes with, e.g., a Pearson correlation coefficient greater than 0.25 or below-0.25 can be classified as biomarkers of sensitivity or resistance, respectively. In particular, a correlation coefficient of 0.25 or greater is a statistically significant cut-off known in the art for establishing whether the expression levels of, e.g., the genes shown in Table(s) 2 and/or 3, correlate with the likelihood of cancer treatment sensitivity, such as sensitivity to 2X-121 or a pharmaceutically acceptable salt thereof, as described in van't Veer et al. Nature 415 (6871): 530-536, 2002, hereby incorporated by reference.

Alternatively, after normalization, genes that have an expression level above a cutoff value of the 50th percentile in a reference population with the same diagnosis as the patient, or greater (e.g., $60^{th}$ percentile, $70^{th}$ percentile, or $80^{th}$ percentile, or greater), can be classified as biomarkers of sensitivity or resistance, respectively.

Comparison of Biomarker Expression Levels

One or more biomarkers of sensitivity and/or resistance, identified as described herein, can be used to predict responsiveness to 2X-121 or a pharmaceutically acceptable salt thereof by measuring the level of expression of the biomarker(s) in a biological sample obtained from the cancer patient. A single biomarker (e.g., any of the biomarkers of Table 2 or 3, such as SRSF7 (SEQ ID NO: 1) or HLA-E (SEQ ID NO: 173 or 174 or 178)) or a set of biomarkers (e.g., one, two, three, four, five, ten, fifteen, twenty, twenty five, or all of the biomarkers of Tables 2 and/or 3) may be used to determine the responsiveness of a cancer patient (e.g., a patient with cancer recurrence) to 2X-121 or a pharmaceutically acceptable salt thereof. After determining the level of expression of the biomarker(s) in a sample (e.g., a tumor sample) from the cancer patient, the level of expression of the biomarker(s) in the sample may be compared to the level of expression of the biomarker(s) in a cell (e.g., a cancer cell) or tissue (e.g., a tumor tissue) known to be sensitive to treatment with 2X-121 or a pharmaceutically acceptable salt thereof. If the level of expression of the biomarker(s) in the sample from the cancer patient is substantially similar to the expression level of the biomarker(s) in the cell or tissue known to be sensitive to 2X-121 or a pharmaceutically acceptable salt thereof, then the cancer patient is predicted to be responsive to treatment with 2X-121 or a pharmaceutically acceptable salt thereof. Alternatively, if the expression level of the biomarker(s) in the sample from the cancer patient is substantially dissimilar to the expression level of the biomarker(s) in the cell or tissue known to be sensitive to 2X-121 or a pharmaceutically acceptable salt thereof, then the cancer patient is predicted to be non-responsive to treatment with 2X-121 or a pharmaceutically acceptable salt thereof.

The expression level of the biomarker(s) (e.g., SRSF7 (SEQ ID NO: 1) or HLA-E (SEQ ID NO: 173 or 174 or 178)) in a sample from the cancer patient may also be compared to the expression level of the biomarker(s) in a cell (e.g., a cancer cell) or tissue (e.g., a tumor tissue) known to be resistant to treatment with 2X-121 or a pharmaceutically acceptable salt thereof. If the expression level of the biomarker(s) in the sample from the cancer patient is substantially similar to the expression level of the biomarker(s) in the cell or tissue known to be resistant to 2X-121 or a pharmaceutically acceptable salt thereof, then the cancer patient is predicted to be non-responsive to treatment with 2X-121 or a pharmaceutically acceptable salt thereof. Alternatively, if the expression level of the biomarker(s) in the sample from the cancer patient is substantially dissimilar to the expression level of the biomarker(s) in the cell or tissue known to be resistant to 2X-121 or a pharmaceutically acceptable salt thereof, then the cancer patient is predicted to be responsive to treatment with 2X-121 or a pharmaceutically acceptable salt thereof.

The responsiveness of a cancer patient (e.g., a patient with cancer recurrence) to 2X-121 or a pharmaceutically acceptable salt thereof can also be predicted by comparing the expression level of a biomarker (e.g., SRSF7 (SEQ ID NO: 1) or HLA-E (SEQ ID NO: 173 or 174 or 178)) to the expression level of the biomarker in one or more cells or tissues (e.g., from a cancer patient population) known to be sensitive to treatment with 2X-121 or a pharmaceutically acceptable salt thereof and one or more cells or tissues (e.g., from a cancer patient population) known to be resistant to treatment with 2X-121 or a pharmaceutically acceptable salt thereof. In particular, the patient may be responsive to treatment with 2X-121 or a pharmaceutically acceptable salt thereof if the expression level of the biomarker(s) is substantially similar to the expression level of the biomarker(s) in a cell or tissue known to be sensitive to treatment with 2X-121 or a pharmaceutically acceptable salt thereof and if the expression level of the biomarker(s) is substantially dissimilar to the expression level of the biomarker(s) in a cell or tissue known to be resistant to treatment with 2X-121 or a pharmaceutically acceptable salt thereof. Alternatively, the patient may be non-responsive to treatment with 2X-121 or a pharmaceutically acceptable salt thereof if the expression level of the biomarker(s) is substantially similar to the expression level of the biomarker(s) in a cell or tissue known to be resistant to treatment with 2X-121 or a pharmaceutically acceptable salt thereof and if the expression level of the biomarker(s) is substantially dissimilar to the expression level of the biomarker(s) in a cell or tissue known to be sensitive to treatment with 2X-121 or a pharmaceutically acceptable salt thereof.

Additionally, one or more biomarkers of sensitivity (e.g., one or more of SRSF7 (SEQ ID NO: 1), UCHL1 (SEQ ID NO: 2), MLLT11 (SEQ ID NO: 3), ADD2 (SEQ ID NO: 4), ADD2 (SEQ ID NO: 5), PRMT1 (SEQ ID NO: 6), SRSF3 (SEQ ID NO: 7), PRMT5 (SEQ ID NO: 8), COCH (SEQ ID NO: 9), RUVBL1 (SEQ ID NO: 10), MARCKSL1 (SEQ ID NO: 11), CHERP (SEQ ID NO: 12), MTSS1 (SEQ ID NO: 13), LSM4 (SEQ ID NO: 14), RAPGEF5 (SEQ ID NO: 15), PRPF4 (SEQ ID NO: 16), LSM4 (SEQ ID NO: 17), DESI2 (SEQ ID NO: 18), RNPS1 (SEQ ID NO: 19), SNX10 (SEQ ID NO: 20), CUL3 (SEQ ID NO: 21), CHD4 (SEQ ID NO: 22), MSH2 (SEQ ID NO: 23), HNRNPM (SEQ ID NO: 24), SRSF1 (SEQ ID NO: 25), NELL2 (SEQ ID NO: 26), PAICS (SEQ ID NO: 27), HOXA10 (SEQ ID NO: 28), BUB1B (SEQ ID NO: 29), E2F5 (SEQ ID NO: 30), MAGED4 MAGED4B SNORA11D SNORA11E (SEQ ID NO: 31), PRPF8 (SEQ ID NO: 32), SORD (SEQ ID NO: 33), HNRNPU (SEQ ID NO: 34), PEX5 (SEQ ID NO: 35), HYPK MIR1282 SERF2 SERF2-C15ORF63 (SEQ ID NO: 36), STRAP (SEQ ID NO: 37), NDUFAB1 (SEQ ID NO: 38), FARSA (SEQ ID NO: 39), STOML2 (SEQ ID NO: 40), ERH (SEQ ID NO: 41), HSBP1 (SEQ ID NO: 42), DDX39A (SEQ ID NO: 43), ODC1 (SEQ ID NO: 44), TAF5 (SEQ ID NO: 45), TBC1D31 (SEQ ID NO: 46), TRA2B (SEQ ID NO: 47), NUDC (SEQ ID NO: 48), DDX23 (SEQ ID NO: 49), PRPF31 (SEQ ID NO: 50), UBE2S (SEQ ID NO: 51), TCF4 (SEQ ID NO: 52), MLF2 (SEQ ID NO: 53), CCDC181 (SEQ ID NO: 54), TCF4 (SEQ ID NO: 55), DESI2 (SEQ ID NO: 56), RPF1 (SEQ ID NO: 57), PASK (SEQ ID NO: 58), NUP88 (SEQ ID NO: 59), RNASEH2A (SEQ ID NO: 60), FBL (SEQ ID NO: 61), LOC101928747 RBMX SNORD61 (SEQ ID NO: 62), NXF1 (SEQ ID NO: 63), PLEKHO1 (SEQ ID NO: 64), GAR1 (SEQ ID NO: 65), RPA1 (SEQ ID NO: 66), ZNF24 (SEQ ID NO: 67), BOP1 MIR7112 (SEQ ID NO: 68), RAB3B (SEQ ID NO: 69), SLC35G2 (SEQ ID NO: 70), TSPAN3 (SEQ ID NO: 71), DKC1 MIR664B SNORA56 (SEQ ID NO: 72), PSMC3IP (SEQ ID NO: 73), DNAJC7 (SEQ ID NO: 74), RRP1B (SEQ ID NO: 75), NME1 (SEQ ID NO: 76), SNRPA (SEQ ID NO: 77), DBN1 (SEQ ID NO: 78), KIAA0020 (SEQ ID NO: 79), SUPV3L1 (SEQ ID NO: 80), ZNF573 (SEQ ID NO: 81), FAM134B (SEQ ID NO: 82), TOX3 (SEQ ID NO: 83), HSPD1 (SEQ ID NO: 84), ACLY (SEQ ID NO: 85), TOX3 (SEQ ID NO: 86), MSANTD3-TMEFF1 TMEFF1 (SEQ ID NO: 87), AKIRIN1 (SEQ ID NO: 88), UBE2M (SEQ ID NO: 89), MTF2 (SEQ ID NO: 90), EWSR1 (SEQ ID NO: 91), FARSA (SEQ ID NO: 92), SKP2 (SEQ ID NO: 93), TMEM97 (SEQ ID NO: 94), HNRNPD (SEQ ID NO: 95), ILKAP (SEQ ID NO: 96), NASP (SEQ ID NO: 97), SNRPD1 (SEQ ID NO: 98), TIMM44 (SEQ ID NO: 99), PKN1 (SEQ ID NO: 100), STAU2 (SEQ ID NO: 101), DNAAF2 (SEQ ID NO: 102), SNRPD2 (SEQ ID NO: 103), FUS (SEQ ID NO: 104), PASK (SEQ ID NO: 105), ATP6V1G2-DDX39B DDX39B SNORD84 (SEQ ID NO: 106), PDSS1 (SEQ ID NO: 107), NUDC (SEQ ID NO: 108), TOX3 (SEQ ID NO: 109), TPGS2 (SEQ ID NO: 110), SLIRP (SEQ ID NO: 111), NCL (SEQ ID NO: 112), ANP32A (SEQ ID NO: 113), SAFB (SEQ ID NO: 114), STIP1 (SEQ ID NO: 115), CEP68 (SEQ ID NO: 116), STIP1 (SEQ ID NO: 117), C8orf33 (SEQ ID NO: 118), MRPL11 (SEQ ID NO: 119), POLR2I (SEQ ID NO: 120), FAM134B (SEQ ID NO: 121), MCAM MIR6756 (SEQ ID NO: 122), ECSIT (SEQ ID NO: 123), MDK (SEQ ID NO: 124), PUF60 (SEQ ID NO: 125), PFN2 (SEQ ID NO: 126), SYNCRIP (SEQ ID NO: 127), TSPAN3 (SEQ ID NO: 128), SLC16A1 (SEQ ID NO: 129), POLR2H (SEQ ID NO: 130), MAP3K7 (SEQ ID NO: 131), CSRP2 (SEQ ID NO: 132), BCL11A (SEQ ID NO: 133), PNKP (SEQ ID NO: 134), DNAJC6 (SEQ ID NO: 135), FDFT1 (SEQ ID NO: 136), FADS1 MIR1908 (SEQ ID NO: 137), RPARP-AS1 (SEQ ID NO: 138), DHRS7 (SEQ ID NO: 139), CCNB1IP1 (SEQ ID NO: 140), CCT3 LOC101927137 (SEQ ID NO: 141), DDX18 (SEQ ID NO: 142), AARSD1 PTGES3L PTGES3L-AARSD1 (SEQ ID NO: 143), HNRNPDL (SEQ ID NO: 144), ATXN7L3B (SEQ ID NO: 145), MRPS14 (SEQ ID NO: 146), SOX4 (SEQ ID NO: 147), ELOVL2 (SEQ ID NO: 148), KCNJ8 (SEQ ID NO: 149), TRIAP1 (SEQ ID NO: 150), EIF2B1 (SEQ ID NO: 151), FBXL14 (SEQ ID NO: 152), MAPRE2 (SEQ ID NO: 153), ORC4 (SEQ ID NO: 154), MDN1 (SEQ ID NO: 155), KNOP1 (SEQ ID NO: 156), KBTBD11 (SEQ ID NO: 157), FADS2 (SEQ ID NO: 158), RANBP1 (SEQ ID NO: 159), PLEKHB1 (SEQ ID NO: 160), HSPE1 (SEQ ID NO: 161), TMEM97 (SEQ ID NO: 162), ITFG2 LOC100507424 (SEQ ID NO: 163), SFPQ (SEQ ID NO: 164), RFC3 (SEQ ID NO: 165), SDR39U1 (SEQ ID NO: 166), PBK (SEQ ID NO: 167), PHB (SEQ ID NO: 168), KHDRBS1 (SEQ ID NO: 169), PDAP1 (SEQ ID NO: 170), SSRP1 (SEQ ID NO: 171), and B3GALT2 (SEQ ID NO: 172)) and one or more biomarkers of resistance (e.g., one or more of HLA-E (SEQ ID NO: 173 or 174 or 178), GADD45B (SEQ ID NO: 175), CLIC1 (SEQ ID NO: 176), LASP1 (SEQ ID NO: 177), APOBEC3B (SEQ ID NO: 179), LGALS1 (SEQ ID NO: 180), TAPBP (SEQ ID NO: 181), AHNAK (SEQ ID NO: 182), BHLHE40 (SEQ ID NO: 183), S100A11 (SEQ ID NO: 184), LITAF (SEQ ID NO: 185), ZBTB38 (SEQ ID NO: 186), STAT1 (SEQ ID NO: 187), TCIRG1 (SEQ ID NO: 188), S100A11P1 (SEQ ID NO: 189), CTSA (SEQ ID NO: 190), VEGFA (SEQ ID NO: 191), STOM (SEQ ID NO: 192), P4HB (SEQ ID NO: 193), LITAF (SEQ ID NO: 194), FXYD5 (SEQ ID NO: 195), HLA-C (SEQ ID NO: 196), YPEL5 (SEQ ID NO: 197), HLA-C (SEQ ID NO: 198), HLA-C (SEQ ID NO: 199), STOM (SEQ ID NO: 200), PLIN3 (SEQ ID NO: 201), RRBP1 (SEQ ID NO: 202), IRF1 (SEQ ID NO: 203), LMNA (SEQ ID NO: 204), NPC2 (SEQ ID NO: 205), P4HB (SEQ ID NO: 206), KLF6 (SEQ ID NO: 207), HLA-B (SEQ ID NO: 208), RHOC (SEQ ID NO: 209), CD59 (SEQ ID NO: 210), SRGN (SEQ ID NO: 211), SRGN (SEQ ID NO: 212), STAT1 (SEQ ID NO: 213), TNFSF10 (SEQ ID NO: 214), HLA-B (SEQ ID NO: 215), PIEZO1 (SEQ ID NO: 216), LGALS3 (SEQ ID NO: 217), LDLRAP1 (SEQ ID NO: 218), CD97 (SEQ ID NO: 219), HLA-B (SEQ ID NO: 220), CFLAR (SEQ ID NO: 221), FNDC3B LOC101928615 (SEQ ID NO: 222), CKLF CKLF-CMTM1 (SEQ ID NO: 223), IFI35 (SEQ ID NO: 224), TIPARP (SEQ ID NO: 225), TAP1 (SEQ ID NO: 226), MICALL2 (SEQ ID NO: 227), RRBP1 (SEQ ID NO: 228), ZFP36 (SEQ ID NO: 229), HLA-G (SEQ ID NO: 230), TNIP1 (SEQ ID NO: 231), CD59 (SEQ ID NO: 232), VEGFA (SEQ ID NO: 233), LDLRAP1 (SEQ ID NO: 234), FLNB (SEQ ID NO: 235), PSG6 (SEQ ID NO: 236), CBX7 (SEQ ID NO: 237), RARRES3 (SEQ ID NO: 238), CFLAR (SEQ ID NO: 239), SUN2 (SEQ ID NO: 240), EHD2 (SEQ ID NO: 241), MAP3K5 (SEQ ID NO: 242), BTN3A2 (SEQ ID NO: 243), NOL12 TRIOBP (SEQ ID NO: 244), CKLF (SEQ ID NO: 245), ARPC1B (SEQ ID NO: 246), TNFSF 10 (SEQ ID NO: 247), HLA-G (SEQ ID NO: 248), RP11-395B7.7 (SEQ ID NO: 249), EHD2 (SEQ ID NO: 250), LEPROT (SEQ ID NO: 251), BTN3A2 BTN3A3 (SEQ ID NO: 252), INPP4B (SEQ ID NO: 253), DUSP1 (SEQ ID NO: 254), EVI2A (SEQ ID NO: 255), TFPI (SEQ ID NO: 256), EHD1 (SEQ ID NO: 257), VEGFA (SEQ ID NO: 258), EPAS1 (SEQ ID NO: 259), IQGAP1 (SEQ ID NO: 260), IL6ST (SEQ ID NO: 261), CLIC3 (SEQ ID NO: 262), TFPI (SEQ ID NO: 263), NACC2 (SEQ ID NO: 264), TGFBI (SEQ ID NO: 265), IER3 (SEQ ID NO: 266), MICA (SEQ ID NO: 267), BTN3A2 (SEQ ID NO: 268), IQGAP1 (SEQ ID NO: 269), CNN2 (SEQ ID NO: 270), TNFAIP8 (SEQ ID NO: 271), VEGFA (SEQ ID NO: 272), MBNL1 (SEQ ID NO: 273), ISG15 (SEQ ID NO: 274), TNFAIP8 (SEQ ID NO: 275), COPG1 (SEQ ID NO: 276), CD99 (SEQ ID NO: 277), PSMB9 (SEQ ID NO: 278), ZFP36L1 (SEQ ID NO: 279), IL6ST (SEQ ID NO: 280), SHC1 (SEQ ID NO: 281), GSTK1 (SEQ ID NO: 282), CAV1 (SEQ ID NO: 283), HLA-F (SEQ ID NO: 284), KRT7 (SEQ ID NO: 285), TFPI (SEQ ID NO: 286), SPTBN1 (SEQ ID NO: 287), RHOG (SEQ ID NO: 288), CDH11 (SEQ ID NO: 289), ABCC3 (SEQ ID NO: 290), CAV1 (SEQ ID NO: 291), HLA-J (SEQ ID NO: 292), MYL12A (SEQ ID NO: 293), MRPS10 (SEQ ID NO: 294), RRAS (SEQ ID NO: 295), TMEM2 (SEQ ID NO: 296), SIDT2 (SEQ ID NO: 297), RAB11FIP1 (SEQ ID NO: 298), RTP4 (SEQ ID NO: 299), LOC101928916 NNMT (SEQ ID NO: 300), SPTBN1 (SEQ ID NO: 301), TMEM189 TMEM189-UBE2V1 UBE2V1 UBE2V2 (SEQ ID NO: 302), RPN2 (SEQ ID NO: 303), ITGA5 (SEQ ID NO: 304), CDC42EP1 (SEQ ID NO: 305), BTN3A3 (SEQ ID NO: 306), OSER1 (SEQ ID NO: 307), CHST15 (SEQ ID NO: 308), MDFIC (SEQ ID NO: 309), CAV2 (SEQ ID NO: 310), CARD10 (SEQ ID NO: 311), RAC2 (SEQ ID NO: 312), MLPH (SEQ ID NO: 313), F2R (SEQ ID NO: 314), ICAM3 (SEQ ID NO: 315), CRIM1 LOC101929500 (SEQ ID NO: 316), IFI16 (SEQ ID NO: 317), EVI2B (SEQ ID NO: 318), PFKFB3 (SEQ ID NO: 319), MIR6513 TMBIM1 (SEQ ID NO: 320), APOL3 (SEQ ID NO: 321), CD55 (SEQ ID NO: 322), TRAM2 (SEQ ID NO: 323), S100A4 (SEQ ID NO: 324), SERPINB1 (SEQ ID NO: 325), PIP4K2A (SEQ ID NO: 326), RPN2 (SEQ ID NO: 327), ALDOA (SEQ ID NO: 328), IFIT3 (SEQ ID NO: 329), PLAC8 (SEQ ID NO: 330), SDF4 (SEQ ID NO: 331), CAV2 (SEQ ID NO: 332), HLA-C(SEQ ID NO: 333), MVP (SEQ ID NO: 334), RNH1

(SEQ ID NO: 335), EIF1 (SEQ ID NO: 336), SERPINB1 (SEQ ID NO: 337), ASL (SEQ ID NO: 338), CD99 (SEQ ID NO: 339), USP4 (SEQ ID NO: 340), TACC1 (SEQ ID NO: 341), CD55 (SEQ ID NO: 342), PDXK (SEQ ID NO: 343), BST2 (SEQ ID NO: 344), LOC101928916 NNMT (SEQ ID NO: 345), DUSP5 (SEQ ID NO: 346), TNFSF13 (SEQ ID NO: 347), COMT (SEQ ID NO: 348), CYR61 (SEQ ID NO: 349), LY6E (SEQ ID NO: 350), ACSL5 (SEQ ID NO: 351), GBP2 (SEQ ID NO: 352), TNFRSF1B (SEQ ID NO: 353), PTRF (SEQ ID NO: 354), CYR61 (SEQ ID NO: 355), BTN3A1 (SEQ ID NO: 356), PLEC (SEQ ID NO: 357), CTNND1 TMX2-CTNND1 (SEQ ID NO: 358), TNFRSF14 (SEQ ID NO: 359), ABCC10 (SEQ ID NO: 360), SELPLG (SEQ ID NO: 361), GPX4 (SEQ ID NO: 362), EDEM1 (SEQ ID NO: 363), MIR6787 SLC16A3 (SEQ ID NO: 364), DMBT1 (SEQ ID NO: 365), PSMB8 (SEQ ID NO: 366), FN1 (SEQ ID NO: 367), COL1A1 (SEQ ID NO: 368), FOS (SEQ ID NO: 369), CYLD (SEQ ID NO: 370), ADAMTS1 (SEQ ID NO: 371), ALDOA (SEQ ID NO: 372), GATA6 (SEQ ID NO: 373), YWHAB (SEQ ID NO: 374), CIB1 (SEQ ID NO: 375), OPTN (SEQ ID NO: 376), IFI16 (SEQ ID NO: 377), CFLAR (SEQ ID NO: 378), PTGER4 (SEQ ID NO: 379), CCND1 (SEQ ID NO: 380), PDLIM5 (SEQ ID NO: 381), HLA-F (SEQ ID NO: 382), CYP1B1 (SEQ ID NO: 383), SVIL (SEQ ID NO: 384), RNASET2 (SEQ ID NO: 385), TAGLN2 (SEQ ID NO: 386), IFI27 (SEQ ID NO: 387), FLII (SEQ ID NO: 388), STAT6 (SEQ ID NO: 389), WWP2 (SEQ ID NO: 390), FLNC (SEQ ID NO: 391), PARP12 (SEQ ID NO: 392), VPS13D (SEQ ID NO: 393), IFITM2 (SEQ ID NO: 394), CTSZ (SEQ ID NO: 395), C19orf10 (SEQ ID NO: 396), DAPK1 (SEQ ID NO: 397), LOC101928189 RSRP1 (SEQ ID NO: 398), MYOF (SEQ ID NO: 399), ATP2B4 (SEQ ID NO: 400), AXL (SEQ ID NO: 401), MIR6787 SLC16A3 (SEQ ID NO: 402), LY96 (SEQ ID NO: 403), FN1 (SEQ ID NO: 404), CREB3L1 (SEQ ID NO: 405), TNFSF12-TNFSF13 TNFSF13 (SEQ ID NO: 406), POFUT2 (SEQ ID NO: 407), WDR1 (SEQ ID NO: 408), SLC7A7 (SEQ ID NO: 409), MICB (SEQ ID NO: 410), GATA3 (SEQ ID NO: 411), LRRFIP1 (SEQ ID NO: 412), RNASET2 (SEQ ID NO: 413), and ITM2A (SEQ ID NO: 414)) may be used in combination to determine the responsiveness of a cancer patient (e.g., a patient with cancer recurrence) to treatment with 2X-121 or a pharmaceutically acceptable salt thereof. For example, the predicted responsiveness of a cancer patient may be determined from, e.g., the difference score, which may be defined as the difference between the mean score (i.e., mean of the expression level) of the one or more biomarkers of sensitivity of Table 2 (e.g., SRSF7 (SEQ ID NO: 1)) and the mean score (i.e., mean of the expression level) of the one or more biomarkers of resistance of Table 3 (e.g., HLA-E (SEQ ID NO: 173 or 174 or 178)).

The difference score of the cancer patient can then be compared to the difference score in a cell (e.g., a cancer cell) or tissue (e.g., a tumor tissue) known to be sensitive or resistant to treatment with 2X-121 or a pharmaceutically acceptable salt thereof. In particular, the patient may be responsive to treatment with 2X-121 or a pharmaceutically acceptable salt thereof if the difference score is substantially similar to the difference score in a cell or tissue known to be sensitive to treatment with 2X-121 or a pharmaceutically acceptable salt thereof. Additionally, the patient may be responsive to treatment with 2X-121 or a pharmaceutically acceptable salt thereof if the difference score is substantially dissimilar to the difference score in a cell or tissue known to be resistant to treatment with 2X-121 or a pharmaceutically acceptable salt thereof. Alternatively, the patient may be non-responsive to treatment with 2X-121 or a pharmaceutically acceptable salt thereof if the difference score is substantially similar to the difference score in a cell or tissue known to be resistant to treatment with 2X-121 or a pharmaceutically acceptable salt thereof. Moreover, the patient may be non-responsive to treatment with 2X-121 or a pharmaceutically acceptable salt thereof if the difference score is substantially dissimilar to the difference score in a cell or tissue known to be sensitive to treatment with 2X-121 or a pharmaceutically acceptable salt thereof.

Additionally, the patient may be responsive to treatment with 2X-121 or a pharmaceutically acceptable salt thereof if the difference score is substantially similar to the difference score in a cell or tissue known to be sensitive to treatment with 2X-121 or a pharmaceutically acceptable salt thereof, relative to the difference score in a cell or tissue known to be resistant to treatment with 2X-121 or a pharmaceutically acceptable salt thereof. Also, the patient may be responsive to treatment with 2X-121 or a pharmaceutically acceptable salt thereof if the difference score is substantially dissimilar to the difference score in a cell or tissue known to be resistant to treatment with 2X-121 or a pharmaceutically acceptable salt thereof, relative to the difference score in a cell or tissue known to be sensitive to treatment with 2X-121 or a pharmaceutically acceptable salt thereof. Alternatively, the patient may be non-responsive to treatment with 2X-121 or a pharmaceutically acceptable salt thereof if the difference score is substantially similar to the difference score in a cell or tissue known to be resistant to treatment with 2X-121 or a pharmaceutically acceptable salt thereof, relative to the difference score in a cell or tissue known to be sensitive to treatment with 2X-121 or a pharmaceutically acceptable salt thereof. Furthermore, the patient may be non-responsive to treatment with 2X-121 or a pharmaceutically acceptable salt thereof if the difference score is substantially dissimilar to the difference score in a cell or tissue known to be sensitive to treatment with 2X-121 or a pharmaceutically acceptable salt thereof, relative to the difference score in a cell or tissue known to be resistant to treatment with 2X-121 or a pharmaceutically acceptable salt thereof.

Additionally, the cancer patient (e.g., a patient with cancer recurrence) may be determined to be responsive to treatment with 2X-121 or a pharmaceutically acceptable salt thereof if the difference score is above a cutoff value of about 0.3 (e.g., about 0.3, about 0.35, about 0.4, about 0.45, about 0.5, about 0.55, about 0.6, about 0.65, about 0.7, or more). Alternatively, the cancer patient (e.g., a patient with cancer recurrence) may be determined to be non-responsive to treatment with 2X-121 or a pharmaceutically acceptable salt thereof if the difference score is below a cutoff value of about 0.3 (e.g., about 0.29, about 0.28, about 0.27, about 0.26, about 0.2, about 0.15, about 0.1, about 0.05, about 0.02, about 0.01, or less).

Additionally, the mean score (i.e., mean of the expression level) of the one or more biomarkers of sensitivity of Table 2 and/or the mean score (i.e., mean of the expression level) of the one or more biomarkers of resistance of Table 3 can be used to predict responsiveness of a cancer patient (e.g., a patient with cancer recurrence) to 2X-121 or a pharmaceutically acceptable salt thereof. After determining the mean score of the biomarker(s) in a sample (e.g., a tumor sample) from the cancer patient, the mean score of the biomarker(s) in the sample may be compared to the mean score of the biomarker(s) in a cell (e.g., a cancer cell) or tissue (e.g., a tumor tissue) known to be sensitive to treatment with 2X-121 or a pharmaceutically acceptable salt thereof. If the mean score of the biomarker(s) in the sample from the cancer patient is substantially similar to the mean score of the biomarker(s) in the cell or tissue known to be sensitive to 2X-121 or a pharmaceutically acceptable salt thereof, then the cancer patient is predicted to be responsive to treatment with 2X-121 or a pharmaceutically acceptable salt thereof. Alternatively, if the mean score of the biomarker(s) in the sample from the cancer patient is substantially dissimilar to the mean score of the biomarker(s) in the cell or tissue known to be sensitive to 2X-121 or a pharmaceutically acceptable salt thereof, then the cancer patient is predicted to be non-responsive to treatment with 2X-121 or a pharmaceutically acceptable salt thereof.

The mean score (i.e., mean of the expression level) of the one or more biomarkers of sensitivity of Table 2 and/or the mean score (i.e., mean of the expression level) of the one or more biomarkers of resistance of Table 3 in a sample from the cancer patient may also be compared to the mean score of the biomarker(s) in a cell (e.g., a cancer cell) or tissue (e.g., a tumor tissue) known to be resistant to treatment with 2X-121 or a pharmaceutically acceptable salt thereof. If the mean score of the biomarker(s) in the sample from the cancer patient is substantially similar to the mean score of the biomarker(s) in the cell or tissue known to be resistant to 2X-121 or a pharmaceutically acceptable salt thereof, then the cancer patient is predicted to be non-responsive to treatment with 2X-121 or a pharmaceutically acceptable salt thereof. Alternatively, if the mean score of the biomarker(s) in the sample from the cancer patient is substantially dissimilar to the mean score of the biomarker(s) in the cell or tissue known to be resistant to 2X-121 or a pharmaceutically acceptable salt thereof, then the cancer patient is predicted to be responsive to treatment with 2X-121 or a pharmaceutically acceptable salt thereof.

The responsiveness of a cancer patient (e.g., a patient with cancer recurrence) to 2X-121 or a pharmaceutically acceptable salt thereof can also be predicted by comparing the mean score (i.e., mean of the expression level) of the one or more biomarkers of sensitivity of Table 2 and/or the mean score (i.e., mean of the expression level) of the one or more biomarkers of resistance of Table 3 in a sample from the cancer patient to the mean score of the biomarker(s) in one or more cells or tissues (e.g., from a cancer patient population) known to be sensitive to treatment with 2X-121 or a pharmaceutically acceptable salt thereof and one or more cells or tissues (e.g., from a cancer patient population) known to be resistant to treatment with 2X-121 or a pharmaceutically acceptable salt thereof. In particular, the patient may be responsive to treatment with 2X-121 or a pharmaceutically acceptable salt thereof if the mean score of the biomarker(s) is substantially similar to the mean score of the biomarker(s) in a cell or tissue known to be sensitive to treatment with 2X-121 or a pharmaceutically acceptable salt thereof, relative to the mean score in a cell or tissue known to be resistant to treatment with 2X-121 or a pharmaceutically acceptable salt thereof. Additionally, the patient may be responsive to treatment with 2X-121 or a pharmaceutically acceptable salt thereof if the mean score of the biomarker(s) is substantially dissimilar to the mean score of the biomarker(s) in a cell or tissue known to be resistant to treatment with 2X-121 or a pharmaceutically acceptable salt thereof, relative to the mean score in a cell or tissue known to be sensitive to treatment with 2X-121 or a pharmaceutically acceptable salt thereof. Alternatively, the patient may be non-responsive to treatment with 2X-121 or a pharmaceutically acceptable salt thereof if the mean score of the biomarker(s) is substantially similar to the mean score of the biomarker(s) in a cell or tissue known to be resistant to treatment with 2X-121 or a pharmaceutically acceptable salt thereof, relative to the mean score in a cell or tissue known to be sensitive to treatment with 2X-121 or a pharmaceutically acceptable salt thereof. Furthermore, the patient may be non-responsive to treatment with 2X-121 or a pharmaceutically acceptable salt thereof if the mean score of the biomarker(s) is substantially dissimilar to the mean score of the biomarker(s) in a cell or tissue known to be sensitive to treatment with 2X-121 or a pharmaceutically acceptable salt thereof, relative to the mean score in a cell or tissue known to be resistant to treatment with 2X-121 or a pharmaceutically acceptable salt thereof.

In addition, the cancer patient (e.g., a patient with cancer recurrence) may be determined to be responsive to treatment with 2X-121 or a pharmaceutically acceptable salt thereof if the mean score (i.e., mean of the expression level) of the one or more biomarkers of sensitivity of Table 2 is above a cutoff value of about 0.3 (e.g., about 0.3, about 0.35, about 0.4, about 0.45, about 0.5, about 0.55, about 0.6, about 0.65, about 0.7, or more). Alternatively, the cancer patient (e.g., a patient with cancer recurrence) may be determined to be non-responsive to treatment with 2X-121 or a pharmaceutically acceptable salt thereof if the mean score of the one or more biomarkers of sensitivity of Table 2 is below a cutoff value of about 0.3 (e.g., about 0.29, about 0.28, about 0.27, about 0.26, about 0.2, about 0.15, about 0.1, about 0.05, about 0.02, about 0.01, or less). Additionally, the cancer patient (e.g., a patient with cancer recurrence) may be determined to be non-responsive to treatment with 2X-121 or a pharmaceutically acceptable salt thereof if the mean score (i.e., mean of the expression level) of the one or more biomarkers of resistance of Table 3 is above a cutoff value of about about 0.3 (e.g., about 0.3, about 0.35, about 0.4, about 0.45, about 0.5, about 0.55, about 0.6, about 0.65, about 0.7, or more). Alternatively, the cancer patient (e.g., a patient with cancer recurrence) may be determined to be responsive to treatment with 2X-121 or a pharmaceutically acceptable salt thereof if the mean score of the one or more biomarkers of resistance of Table 3 is below a cutoff value of about 0.3 (e.g., about 0.29, about 0.28, about 0.27, about 0.26, about 0.2, about 0.15, about 0.1, about 0.05, about 0.02, about 0.01, or less).

One or more biomarkers of sensitivity and/or resistance, identified as described herein, can be used to predict responsiveness to 2X-121 or a pharmaceutically acceptable salt thereof by measuring the expression level of the biomarker(s) in a biological sample obtained from the cancer patient. A single biomarker (e.g., any of the biomarkers of Tables 2 and/or 3, such as SRSF7 (SEQ ID NO: 1) or HLA-E (SEQ ID NO: 173 or 174 or 178)) or a set of biomarkers (e.g., one, two, three, four, five, ten, fifteen, twenty, twenty five, or all of the biomarkers of Tables 2 and/or 3 (e.g., the top one biomarker of Tables 2 and/or 3, the top two biomarkers of Tables 2 and/or 3, the top three biomarkers of Tables 2 and/or 3, the top four biomarkers of Tables 2 and/or 3, the top five biomarkers of Tables 2 and/or 3, the top ten biomarkers of Tables 2 and/or 3, the top fifteen biomarkers of Tables 2 and/or 3, the top twenty biomarkers of Tables 2 and/or 3, the top twenty five biomarkers of Tables 2 and/or 3, or all of the biomarkers of Tables 2 and/or 3)) may be used to determine the responsiveness of a cancer patient (e.g., a patient with cancer recurrence) to 2X-121 or a pharmaceutically acceptable salt thereof. After determining the expression level of the biomarker(s) in a sample (e.g., a tumor sample) from the cancer patient, the expression level of the biomarker(s) in the sample may be compared to the expression level of the biomarker(s) in a cell (e.g., a cancer cell) or tissue (e.g., a tumor tissue) known to be sensitive to treatment with 2X-121 or a pharmaceutically acceptable salt thereof. If the expression level of the biomarker(s) in the sample from the cancer patient corresponds to the expression level of the biomarker(s) in the cell or tissue known to be sensitive to 2X-121 or a pharmaceutically acceptable salt thereof, then the cancer patient is predicted to be responsive to treatment with 2X-121 or a pharmaceutically acceptable salt thereof. Alternatively, if the expression level of the biomarker(s) in the sample from the cancer patient is substantially dissimilar to the expression level of the biomarker(s) in the cell or tissue known to be sensitive to 2X-121 or a pharmaceutically acceptable salt thereof, then the cancer patient is predicted to be non-responsive to treatment with 2X-121 or a pharmaceutically acceptable salt thereof.

The expression level of the biomarker(s) (e.g., SRSF7 (SEQ ID NO: 1) and/or HLA-E (SEQ ID NO: 173 or 174 or 178)) in a sample from the cancer patient may also be compared to the expression level of the biomarker(s) in a cell (e.g., a cancer cell) or tissue (e.g., a tumor tissue) known to be resistant to treatment with 2X-121 or a pharmaceutically acceptable salt thereof. If the expression level of the biomarker(s) in the sample from the cancer patient corresponds to the expression level of the biomarker(s) in the cell or tissue known to be resistant to 2X-121 or a pharmaceutically acceptable salt thereof, then the cancer patient is predicted to be non-responsive to treatment with 2X-121 or a pharmaceutically acceptable salt thereof. Alternatively, if the expression level of the biomarker(s) in the sample from the cancer patient is substantially dissimilar to the expression level of the biomarker(s) in the cell or tissue known to be resistant to 2X-121 or a pharmaceutically acceptable salt thereof, then the cancer patient is predicted to be responsive to treatment with 2X-121 or a pharmaceutically acceptable salt thereof.

The responsiveness of a cancer patient (e.g., a patient with cancer recurrence) to 2X-121 or a pharmaceutically acceptable salt thereof can also be predicted by comparing the expression level of the biomarker(s) (e.g., SRSF7 (SEQ ID NO: 1) and/or HLA-E (SEQ ID NO: 173 or 174 or 178)) to the expression level of the biomarker(s) in one or more cells or tissues (e.g., from a cancer patient population) known to be sensitive to treatment with 2X-121 or a pharmaceutically acceptable salt thereof and one or more cells or tissues (e.g., from a cancer patient population) known to be resistant to treatment with 2X-121 or a pharmaceutically acceptable salt thereof. In particular, the patient may be responsive to treatment with 2X-121 or a pharmaceutically acceptable salt thereof if the expression level of the biomarker(s) corresponds to the expression level of the biomarker(s) in a cell or tissue known to be sensitive to treatment with 2X-121 or a pharmaceutically acceptable salt thereof, relative to the expression level of the biomarker(s) in a cell or tissue known to be resistant to treatment with 2X-121 or a pharmaceutically acceptable salt thereof. Moreover, the patient may be responsive to treatment with 2X-121 or a pharmaceutically acceptable salt thereof if the expression level of the biomarker(s) is substantially dissimilar to the expression level of the biomarker(s) in a cell or tissue known to be resistant to treatment with 2X-121 or a pharmaceutically acceptable salt thereof, relative to the expression level of the biomarker(s) in a cell or tissue known to be sensitive to treatment with 2X-121 or a pharmaceutically acceptable salt thereof. Alternatively, the patient may be non-responsive to treatment with 2X-121 or a pharmaceutically acceptable salt thereof if the expression level of the biomarker(s) corresponds to the expression level of the biomarker(s) in a cell or tissue known to be resistant to treatment with 2X-121 or a pharmaceutically acceptable salt thereof, relative to the expression level of the biomarker(s) in a cell or tissue known to be sensitive to treatment with 2X-121 or a pharmaceutically acceptable salt thereof. Also, the patient may be non-responsive to treatment with 2X-121 or a pharmaceutically acceptable salt thereof if the expression level of the biomarker(s) is substantially dissimilar to the expression level of the biomarker(s) in a cell or tissue known to be sensitive to treatment with 2X-121 or a pharmaceutically acceptable salt thereof, relative to the expression level of the biomarker(s) in a cell or tissue known to be resistant to treatment with 2X-121 or a pharmaceutically acceptable salt thereof.

Additionally, one or more biomarkers of sensitivity (e.g., one or more of SRSF7 (SEQ ID NO: 1), UCHL1 (SEQ ID NO: 2), MLLT11 (SEQ ID NO: 3), ADD2 (SEQ ID NO: 4), ADD2 (SEQ ID NO: 5), PRMT1 (SEQ ID NO: 6), SRSF3 (SEQ ID NO: 7), PRMT5 (SEQ ID NO: 8), COCH (SEQ ID NO: 9), RUVBL1 (SEQ ID NO: 10), MARCKSL1 (SEQ ID NO: 11), CHERP (SEQ ID NO: 12), MTSS1 (SEQ ID NO: 13), LSM4 (SEQ ID NO: 14), RAPGEF5 (SEQ ID NO: 15), PRPF4 (SEQ ID NO: 16), LSM4 (SEQ ID NO: 17), DESI2 (SEQ ID NO: 18), RNPS1 (SEQ ID NO: 19), SNX10 (SEQ ID NO: 20), CUL3 (SEQ ID NO: 21), CHD4 (SEQ ID NO: 22), MSH2 (SEQ ID NO: 23), HNRNPM (SEQ ID NO: 24), SRSF1 (SEQ ID NO: 25), NELL2 (SEQ ID NO: 26), PAICS (SEQ ID NO: 27), HOXA10 (SEQ ID NO: 28), BUB1B (SEQ ID NO: 29), E2F5 (SEQ ID NO: 30), MAGED4 MAGED4B SNORA11D SNORA11E (SEQ ID NO: 31), PRPF8 (SEQ ID NO: 32), SORD (SEQ ID NO: 33), HNRNPU (SEQ ID NO: 34), PEX5 (SEQ ID NO: 35), HYPK MIR1282 SERF2 SERF2-C15ORF63 (SEQ ID NO: 36), STRAP (SEQ ID NO: 37), NDUFAB1 (SEQ ID NO: 38), FARSA (SEQ ID NO: 39), STOML2 (SEQ ID NO: 40), ERH (SEQ ID NO: 41), HSBP1 (SEQ ID NO: 42), DDX39A (SEQ ID NO: 43), ODC1 (SEQ ID NO: 44), TAF5 (SEQ ID NO: 45), TBC1D31 (SEQ ID NO: 46), TRA2B (SEQ ID NO: 47), NUDC (SEQ ID NO: 48), DDX23 (SEQ ID NO: 49), PRPF31 (SEQ ID NO: 50), UBE2S (SEQ ID NO: 51), TCF4 (SEQ ID NO: 52), MLF2 (SEQ ID NO: 53), CCDC181 (SEQ ID NO: 54), TCF4 (SEQ ID NO: 55), DESI2 (SEQ ID NO: 56), RPF1 (SEQ ID NO: 57), PASK (SEQ ID NO: 58), NUP88 (SEQ ID NO: 59), RNASEH2A (SEQ ID NO: 60), FBL (SEQ ID NO: 61), LOC101928747 RBMX SNORD61 (SEQ ID NO: 62), NXF1 (SEQ ID NO: 63), PLEKHO1 (SEQ ID NO: 64), GAR1 (SEQ ID NO: 65), RPA1 (SEQ ID NO: 66), ZNF24 (SEQ ID NO: 67), BOP1 MIR7112 (SEQ ID NO: 68), RAB3B (SEQ ID NO: 69), SLC35G2 (SEQ ID NO: 70), TSPAN3 (SEQ ID NO: 71), DKC1 MIR664B SNORA56 (SEQ ID NO: 72), PSMC3IP (SEQ ID NO: 73), DNAJC7 (SEQ ID NO: 74), RRP1B (SEQ ID NO: 75), NME1 (SEQ ID NO: 76), SNRPA (SEQ ID NO: 77), DBN1 (SEQ ID NO: 78), KIAA0020 (SEQ ID NO: 79), SUPV3L1 (SEQ ID NO: 80), ZNF573 (SEQ ID NO: 81), FAM134B (SEQ ID NO: 82), TOX3 (SEQ ID NO: 83), HSPD1 (SEQ ID NO: 84), ACLY (SEQ ID NO: 85), TOX3 (SEQ ID NO: 86), MSANTD3-TMEFF1 TMEFF1 (SEQ ID NO: 87), AKIRIN1 (SEQ ID NO: 88), UBE2M (SEQ ID NO: 89), MTF2 (SEQ ID NO: 90), EWSR1 (SEQ ID NO: 91), FARSA (SEQ ID NO: 92), SKP2 (SEQ ID NO: 93), TMEM97 (SEQ ID NO: 94), HNRNPD (SEQ ID NO: 95), ILKAP (SEQ ID NO: 96), NASP (SEQ ID NO: 97), SNRPD1 (SEQ ID NO: 98), TIMM44 (SEQ ID NO: 99), PKN1 (SEQ ID NO: 100), STAU2 (SEQ ID NO: 101), DNAAF2 (SEQ ID NO: 102), SNRPD2 (SEQ ID NO: 103), FUS (SEQ ID NO: 104), PASK (SEQ ID NO: 105), ATP6V1G2-DDX39B DDX39B SNORD84 (SEQ ID NO: 106), PDSS1 (SEQ ID NO: 107), NUDC (SEQ ID NO: 108), TOX3 (SEQ ID NO: 109), TPGS2 (SEQ ID NO: 110), SLIRP (SEQ ID NO: 111), NCL (SEQ ID NO: 112), ANP32A (SEQ ID NO: 113), SAFB (SEQ ID NO: 114), STIP1 (SEQ ID NO: 115), CEP68 (SEQ ID NO: 116), STIP1 (SEQ ID NO: 117), C8orf33 (SEQ ID NO: 118), MRPL11 (SEQ ID NO: 119), POLR2I (SEQ ID NO: 120), FAM134B (SEQ ID NO: 121), MCAM MIR6756 (SEQ ID NO: 122), ECSIT (SEQ ID NO: 123), MDK (SEQ ID NO: 124), PUF60 (SEQ ID NO: 125), PFN2 (SEQ ID NO: 126), SYNCRIP (SEQ ID NO: 127), TSPAN3 (SEQ ID NO: 128), SLC16A1 (SEQ ID NO: 129), POLR2H (SEQ ID NO: 130), MAP3K7 (SEQ ID NO: 131), CSRP2 (SEQ ID NO: 132), BCL11A (SEQ ID NO: 133), PNKP (SEQ ID NO: 134), DNAJC6 (SEQ ID NO: 135), FDFT1 (SEQ ID NO: 136), FADS1 MIR1908 (SEQ ID NO: 137), RPARP-AS1 (SEQ ID NO: 138), DHRS7 (SEQ ID NO: 139), CCNB1IP1 (SEQ ID NO: 140), CCT3 LOC101927137 (SEQ ID NO: 141), DDX18 (SEQ ID NO: 142), AARSD1 PTGES3L PTGES3L-AARSD1 (SEQ ID NO: 143), HNRNPDL (SEQ ID NO: 144), ATXN7L3B (SEQ ID NO: 145), MRPS14 (SEQ ID NO: 146), SOX4 (SEQ ID NO: 147), ELOVL2 (SEQ ID NO: 148), KCNJ8 (SEQ ID NO: 149), TRIAP1 (SEQ ID NO: 150), EIF2B1 (SEQ ID NO: 151), FBXL14 (SEQ ID NO: 152), MAPRE2 (SEQ ID NO: 153), ORC4 (SEQ ID NO: 154), MDN1 (SEQ ID NO: 155), KNOP1 (SEQ ID NO: 156), KBTBD11 (SEQ ID NO: 157), FADS2 (SEQ ID NO: 158), RANBP1 (SEQ ID NO: 159), PLEKHB1 (SEQ ID NO: 160), HSPE1 (SEQ ID NO: 161), TMEM97 (SEQ ID NO: 162), ITFG2 LOC100507424 (SEQ ID NO: 163), SFPQ (SEQ ID NO: 164), RFC3 (SEQ ID NO: 165), SDR39U1 (SEQ ID NO: 166), PBK (SEQ ID NO: 167), PHB (SEQ ID NO: 168), KHDRBS1 (SEQ ID NO: 169), PDAP1 (SEQ ID NO: 170), SSRP1 (SEQ ID NO: 171), and B3GALT2 (SEQ ID NO: 172)) and one or more biomarkers of resistance (e.g., one or more of HLA-E (SEQ ID NO: 173 or 174 or 178), GADD45B (SEQ ID NO: 175), CLIC1 (SEQ ID NO: 176), LASP1 (SEQ ID NO: 177), APOBEC3B (SEQ ID NO: 179), LGALS1 (SEQ ID NO: 180), TAPBP (SEQ ID NO: 181), AHNAK (SEQ ID NO: 182), BHLHE40 (SEQ ID NO: 183), S100A11 (SEQ ID NO: 184), LITAF (SEQ ID NO: 185), ZBTB38 (SEQ ID NO: 186), STAT1 (SEQ ID NO: 187), TCIRG1 (SEQ ID NO: 188), S100A11P1 (SEQ ID NO: 189), CTSA (SEQ ID NO: 190), VEGFA (SEQ ID NO: 191), STOM (SEQ ID NO: 192), P4HB (SEQ ID NO: 193), LITAF (SEQ ID NO: 194), FXYD5 (SEQ ID NO: 195), HLA-C (SEQ ID NO: 196), YPEL5 (SEQ ID NO: 197), HLA-C (SEQ ID NO: 198), HLA-C (SEQ ID NO: 199), STOM (SEQ ID NO: 200), PLIN3 (SEQ ID NO: 201), RRBP1 (SEQ ID NO: 202), IRF1 (SEQ ID NO: 203), LMNA (SEQ ID NO: 204), NPC2 (SEQ ID NO: 205), P4HB (SEQ ID NO: 206), KLF6 (SEQ ID NO: 207), HLA-B (SEQ ID NO: 208), RHOC (SEQ ID NO: 209), CD59 (SEQ ID NO: 210), SRGN (SEQ ID NO: 211), SRGN (SEQ ID NO: 212), STAT1 (SEQ ID NO: 213), TNFSF10 (SEQ ID NO: 214), HLA-B (SEQ ID NO: 215), PIEZO1 (SEQ ID NO: 216), LGALS3 (SEQ ID NO: 217), LDLRAP1 (SEQ ID NO: 218), CD97 (SEQ ID NO: 219), HLA-B (SEQ ID NO: 220), CFLAR (SEQ ID NO: 221), FNDC3B LOC101928615 (SEQ ID NO: 222), CKLF CKLF-CMTM1 (SEQ ID NO: 223), IFI35 (SEQ ID NO: 224), TIPARP (SEQ ID NO: 225), TAP1 (SEQ ID NO: 226), MICALL2 (SEQ ID NO: 227), RRBP1 (SEQ ID NO: 228), ZFP36 (SEQ ID NO: 229), HLA-G (SEQ ID NO: 230), TNIP1 (SEQ ID NO: 231), CD59 (SEQ ID NO: 232), VEGFA (SEQ ID NO: 233), LDLRAP1 (SEQ ID NO: 234), FLNB (SEQ ID NO: 235), PSG6 (SEQ ID NO: 236), CBX7 (SEQ ID NO: 237), RARRES3 (SEQ ID NO: 238), CFLAR (SEQ ID NO: 239), SUN2 (SEQ ID NO: 240), EHD2 (SEQ ID NO: 241), MAP3K5 (SEQ ID NO: 242), BTN3A2 (SEQ ID NO: 243), NOL12 TRIOBP (SEQ ID NO: 244), CKLF (SEQ ID NO: 245), ARPC1B (SEQ ID NO: 246), TNFSF10 (SEQ ID NO: 247), HLA-G (SEQ ID NO: 248), RP11-395B7.7 (SEQ ID NO: 249), EHD2 (SEQ ID NO: 250), LEPROT (SEQ ID NO: 251), BTN3A2 BTN3A3 (SEQ ID NO: 252), INPP4B (SEQ ID NO: 253), DUSP1 (SEQ ID NO: 254), EVI2A (SEQ ID NO: 255), TFPI (SEQ ID NO: 256), EHD1 (SEQ ID NO: 257), VEGFA (SEQ ID NO: 258), EPAS1 (SEQ ID NO: 259), IQGAP1 (SEQ ID NO: 260), IL6ST (SEQ ID NO: 261), CLIC3 (SEQ ID NO: 262), TFPI (SEQ ID NO: 263), NACC2 (SEQ ID NO: 264), TGFBI (SEQ ID NO: 265), IER3 (SEQ ID NO: 266), MICA (SEQ ID NO: 267), BTN3A2 (SEQ ID NO: 268), IQGAP1 (SEQ ID NO: 269), CNN2 (SEQ ID NO: 270), TNFAIP8 (SEQ ID NO: 271), VEGFA (SEQ ID NO: 272), MBNL1 (SEQ ID NO: 273), ISG15 (SEQ ID NO: 274), TNFAIP8 (SEQ ID NO: 275), COPG1 (SEQ ID NO: 276), CD99 (SEQ ID NO: 277), PSMB9 (SEQ ID NO: 278), ZFP36L1 (SEQ ID NO: 279), IL6ST (SEQ ID NO: 280), SHC1 (SEQ ID NO: 281), GSTK1 (SEQ ID NO: 282), CAV1 (SEQ ID NO: 283), HLA-F (SEQ ID NO: 284), KRT7 (SEQ ID NO: 285), TFPI (SEQ ID NO: 286), SPTBN1 (SEQ ID NO: 287), RHOG (SEQ ID NO: 288), CDH11 (SEQ ID NO: 289), ABCC3 (SEQ ID NO: 290), CAV1 (SEQ ID NO: 291), HLA-J (SEQ ID NO: 292), MYL12A (SEQ ID NO: 293), MRPS10 (SEQ ID NO: 294), RRAS (SEQ ID NO: 295), TMEM2 (SEQ ID NO: 296), SIDT2 (SEQ ID NO: 297), RAB11FIP1 (SEQ ID NO: 298), RTP4 (SEQ ID NO: 299), LOC101928916 NNMT (SEQ ID NO: 300), SPTBN1 (SEQ ID NO: 301), TMEM189 TMEM189-UBE2V1 UBE2V1 UBE2V2 (SEQ ID NO: 302), RPN2 (SEQ ID NO: 303), ITGA5 (SEQ ID NO: 304), CDC42EP1 (SEQ ID NO: 305), BTN3A3 (SEQ ID NO: 306), OSER1 (SEQ ID NO: 307), CHST15 (SEQ ID NO: 308), MDFIC (SEQ ID NO: 309), CAV2 (SEQ ID NO: 310), CARD10 (SEQ ID NO: 311), RAC2 (SEQ ID NO: 312), MLPH (SEQ ID NO: 313), F2R (SEQ ID NO: 314), ICAM3 (SEQ ID NO: 315), CRIM1 LOC101929500 (SEQ ID NO: 316), IFI16 (SEQ ID NO: 317), EVI2B (SEQ ID NO: 318), PFKFB3 (SEQ ID NO: 319), MIR6513 TMBIM1 (SEQ ID NO: 320), APOL3 (SEQ ID NO: 321), CD55 (SEQ ID NO: 322), TRAM2 (SEQ ID NO: 323), S100A4 (SEQ ID NO: 324), SERPINB1 (SEQ ID NO: 325), PIP4K2A (SEQ ID NO: 326), RPN2 (SEQ ID NO: 327), ALDOA (SEQ ID NO: 328), IFIT3 (SEQ ID NO: 329), PLAC8 (SEQ ID NO: 330), SDF4 (SEQ ID NO: 331), CAV2 (SEQ ID NO: 332), HLA-C(SEQ ID NO: 333), MVP (SEQ ID NO: 334), RNH1 (SEQ ID NO: 335), EIF1 (SEQ ID NO: 336), SERPINB1 (SEQ ID NO: 337), ASL (SEQ ID NO: 338), CD99 (SEQ ID NO: 339), USP4 (SEQ ID NO: 340), TACC1 (SEQ ID NO: 341), CD55 (SEQ ID NO: 342), PDXK (SEQ ID NO: 343), BST2 (SEQ ID NO: 344), LOC101928916 NNMT (SEQ ID NO: 345), DUSP5 (SEQ ID NO: 346), TNFSF13 (SEQ ID NO: 347), COMT (SEQ ID NO: 348), CYR61 (SEQ ID NO: 349), LY6E (SEQ ID NO: 350), ACSL5 (SEQ ID NO: 351), GBP2 (SEQ ID NO: 352), TNFRSF1B (SEQ ID NO: 353), PTRF (SEQ ID NO: 354), CYR61 (SEQ ID NO: 355), BTN3A1 (SEQ ID NO: 356), PLEC (SEQ ID NO: 357), CTNND1 TMX2-CTNND1 (SEQ ID NO: 358), TNFRSF14 (SEQ ID NO: 359), ABCC10 (SEQ ID NO: 360), SELPLG (SEQ ID NO: 361), GPX4 (SEQ ID NO: 362), EDEM1

(SEQ ID NO: 363), MIR6787 SLC16A3 (SEQ ID NO: 364), DMBT1 (SEQ ID NO: 365), PSMB8 (SEQ ID NO: 366), FN1 (SEQ ID NO: 367), COL1A1 (SEQ ID NO: 368), FOS (SEQ ID NO: 369), CYLD (SEQ ID NO: 370), ADAMTS1 (SEQ ID NO: 371), ALDOA (SEQ ID NO: 372), GATA6 (SEQ ID NO: 373), YWHAB (SEQ ID NO: 374), CIB1 (SEQ ID NO: 375), OPTN (SEQ ID NO: 376), IFI16 (SEQ ID NO: 377), CFLAR (SEQ ID NO: 378), PTGER4 (SEQ ID NO: 379), CCND1 (SEQ ID NO: 380), PDLIM5 (SEQ ID NO: 381), HLA-F (SEQ ID NO: 382), CYP1B1 (SEQ ID NO: 383), SVIL (SEQ ID NO: 384), RNASET2 (SEQ ID NO: 385), TAGLN2 (SEQ ID NO: 386), IFI27 (SEQ ID NO: 387), FLII (SEQ ID NO: 388), STAT6 (SEQ ID NO: 389), WWP2 (SEQ ID NO: 390), FLNC (SEQ ID NO: 391), PARP12 (SEQ ID NO: 392), VPS13D (SEQ ID NO: 393), IFITM2 (SEQ ID NO: 394), CTSZ (SEQ ID NO: 395), C19orf10 (SEQ ID NO: 396), DAPK1 (SEQ ID NO: 397), LOC101928189 RSRP1 (SEQ ID NO: 398), MYOF (SEQ ID NO: 399), ATP2B4 (SEQ ID NO: 400), AXL (SEQ ID NO: 401), MIR6787 SLC16A3 (SEQ ID NO: 402), LY96 (SEQ ID NO: 403), FN1 (SEQ ID NO: 404), CREB3L1 (SEQ ID NO: 405), TNFSF12-TNFSF13 TNFSF13 (SEQ ID NO: 406), POFUT2 (SEQ ID NO: 407), WDR1 (SEQ ID NO: 408), SLC7A7 (SEQ ID NO: 409), MICB (SEQ ID NO: 410), GATA3 (SEQ ID NO: 411), LRRFIP1 (SEQ ID NO: 412), RNASET2 (SEQ ID NO: 413), and ITM2A (SEQ ID NO: 414)) may be used in combination to determine the responsiveness of a cancer patient (e.g., a patient with cancer recurrence) to treatment with 2X-121 or a pharmaceutically acceptable salt thereof. For example, the predicted responsiveness of a cancer patient may be determined from, e.g., the difference score, which may be defined as the difference between the mean score (i.e., mean of the expression level) of the one or more biomarkers of sensitivity of Table 2 (e.g., SRSF7 (SEQ ID NO: 1)) and the mean score (i.e., mean of the expression level) of the one or more biomarkers of resistance of Table 3 (e.g., HLA-E (SEQ ID NO: 173 or 174 or 178)).

The difference score of the cancer patient can then be compared to the difference score in a cell (e.g., a cancer cell) or tissue (e.g., a tumor tissue) known to be sensitive or resistant to treatment with 2X-121 or a pharmaceutically acceptable salt thereof. In particular, the patient may be responsive to treatment with 2X-121 or a pharmaceutically acceptable salt thereof if the difference score corresponds to the difference score in a cell or tissue known to be sensitive to treatment with 2X-121 or a pharmaceutically acceptable salt thereof. Additionally, the patient may be responsive to treatment with 2X-121 or a pharmaceutically acceptable salt thereof if the difference score is substantially dissimilar to the difference score in a cell or tissue known to be resistant to treatment with 2X-121 or a pharmaceutically acceptable salt thereof. Alternatively, the patient may be non-responsive to treatment with 2X-121 or a pharmaceutically acceptable salt thereof if the difference score corresponds to the difference score in a cell or tissue known to be resistant to treatment with 2X-121 or a pharmaceutically acceptable salt thereof. Also, the patient may be non-responsive to treatment with 2X-121 or a pharmaceutically acceptable salt thereof if the difference score is substantially dissimilar to the difference score in a cell or tissue known to be sensitive to treatment with 2X-121 or a pharmaceutically acceptable salt thereof.

Additionally, the patient may be responsive to treatment with 2X-121 or a pharmaceutically acceptable salt thereof if the difference score corresponds to the difference score in a cell or tissue known to be sensitive to treatment with 2X-121 or a pharmaceutically acceptable salt thereof, relative to the difference score in a cell or tissue known to be resistant to treatment with 2X-121 or a pharmaceutically acceptable salt thereof. Furthermore, the patient may be responsive to treatment with 2X-121 or a pharmaceutically acceptable salt thereof if the difference score is substantially dissimilar to the difference score in a cell or tissue known to be resistant to treatment with 2X-121 or a pharmaceutically acceptable salt thereof, relative to the difference score in a cell or tissue known to be sensitive to treatment with 2X-121 or a pharmaceutically acceptable salt thereof. Alternatively, the patient may be non-responsive to treatment with 2X-121 or a pharmaceutically acceptable salt thereof if the difference score corresponds to the difference score in a cell or tissue known to be resistant to treatment with 2X-121 or a pharmaceutically acceptable salt thereof, relative to the difference score in a cell or tissue known to be sensitive to treatment with 2X-121 or a pharmaceutically acceptable salt thereof. Additionally, the patient may be non-responsive to treatment with 2X-121 or a pharmaceutically acceptable salt thereof if the difference score is substantially dissimilar to the difference score in a cell or tissue known to be sensitive to treatment with 2X-121 or a pharmaceutically acceptable salt thereof, relative to the difference score in a cell or tissue known to be resistant to treatment with 2X-121 or a pharmaceutically acceptable salt thereof.

Alternatively, the patient may be determined to be responsive to treatment with 2X-121 or a pharmaceutically acceptable salt thereof if the difference score is above a cutoff value of the 50th percentile in a reference population with the same diagnosis as the patient, or greater (e.g., the difference score is above a cutoff value of the 60th percentile, 70th percentile, or 80th percentile, or greater).

Preferably, the cell or tissue known to be either sensitive or resistant to 2X-121 or a pharmaceutically acceptable salt thereof is of the same cancer type as the cancer patient with an unknown responsiveness to 2X-121 or a pharmaceutically acceptable salt thereof. For example, the cancer patient and the cell or tissue known to be either sensitive or resistant to 2X-121 or a pharmaceutically acceptable salt thereof may both have a cancer type selected from a hematological cancer or a solid tumor, such as, e.g., myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. In particular, the cancer of the patient and the cell or tissue with known resistance or sensitivity to 2X-121 or a pharmaceutically acceptable salt thereof is, e.g., multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, estrogen receptor-positive (ERpos) breast cancer, lung cancer, non-small cell lung carcinoma (NSCLC), mesothelioma, intestinal cancer, colon cancer, bladder cancer, adrenal cancer, gallbladder cancer, and squamous cell carcinoma of the head and neck (SCCHN). In particular, the cancer of the patient and the cell or tissue with known resistance or sensitivity to 2X-121 or a pharmaceutically acceptable salt thereof may be estrogen receptor-positive (ER pos) breast cancer. In particular instances, the cancer of the patient and the cell or tissue with known resistance or sensitivity to 2X-121 or a pharmaceutically acceptable salt thereof may be a metastatic form of breast cancer. Alternatively, the cancer of the patient and the cell or tissue with known resistance or sensitivity to 2X-121 or a pharmaceutically acceptable salt thereof may be ovarian cancer. In additional embodiments, the cancer of the patient and the cell or tissue with known resistance or sensitivity to 2X-121 or a pharmaceutically acceptable salt thereof may be pancreatic cancer.

Machine learning techniques such as Neural Networks, Support Vector Machines, K Nearest Neighbor, and Nearest Centroids may also be employed to develop models that discriminate patients sensitive to treatment with 2X-121 or a pharmaceutically acceptable salt thereof from those resistant to treatment with 2X-121 or a pharmaceutically acceptable salt thereof using biomarker expression as model variables, which assign each patient a classification as sensitive or resistant to treatment with 2X-121 or a pharmaceutically acceptable salt thereof. Machine learning techniques used to classify patients using various measurements are described in U.S. Pat. No. 5,822,715; U.S. Patent Application Publication Nos. 2003/0073083, 2005/0227266, 2005/0208512, 2005/0123945, 2003/0129629, and 2002/0006613; and in Vapnik V N. Statistical Learning Theory, John Wiley & Sons, New York, 1998; Hastie et al., 2001, The Elements of Statistical Learning: Data Mining, Inference, and Prediction, Springer, N.Y.; Agresti, 1996, An Introduction to Categorical Data Analysis, John Wiley & Sons, New York; V. Tresp et al., "Neural Network Modeling of Physiological Processes," in Hanson S. J. et al. (Eds.), Computational Learning Theory and Natural Learning Systems 2, MIT Press, 1994, each of which are hereby incorporated by reference in their entirety.

Biomarkers of Sensitivity and Resistance

The expression levels of one or more biomarkers of Table(s) 2 and/or 3 can be used to determine responsiveness of a cancer patient to treatment with 2X-121 or a pharmaceutically acceptable salt thereof. In certain embodiments, the biomarker(s) of sensitivity can be selected from (a) one or more of SEQ ID NOs: 1-25; (b) one or more of SEQ ID NOs: 26-50; (c) one or more of SEQ ID NOs: 51-75; (d) one or more of SEQ ID NOs: 76-100; (e) one or more of SEQ ID NOs: 101-125; (f) one or more of SEQ ID NOs: 126-150; (g) one or more of SEQ ID NOs: 151-172; and/or (h) one or more of SEQ ID NOs: 1-172 from Table 2. Moreover, in certain embodiments, the biomarker(s) of resistance can be selected from (a) one or more of SEQ ID NOs: 173-200; (b) one or more of SEQ ID NOs: 201-225; (c) one or more of SEQ ID NOs: 226-250; (d) one or more of SEQ ID NOs: 251-275; (e) one or more of SEQ ID NOs: 276-300; (f) one or more of SEQ ID NOs: 301-325; (g) one or more of SEQ ID NOs: 326-350; (h) one or more of SEQ ID NOs: 351-375; (i) one or more of SEQ ID NOs: 376-400; (j) one or more of SEQ ID NOs: 401-414; and/or (k) one or more of SEQ ID NOs: 173-414 of Table 3. In particular embodiments, at least one (e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, or at least 172 (e.g., at least the top 1, at least the top 5, at least the top 10, at least the top 15, at least the top 20, at least the top 25, at least the top 30, at least the top 35, at least the top 40, at least the top 45, at least the top 50, at least the top 55, at least the top 60, at least the top 65, at least the top 70, at least the top 75, at least the top 80, at least the top 85, at least the top 90, at least the top 95, at least the top 100, at least the top 105, at least the top 110, at least the top 115, at least the top 120, at least the top 125, at least the top 130, at least the top 135, at least the top 140, at least the top 145, at least the top 150, at least the top 155, at least the top 160, at least the top 165, at least the top 170, or at least the top 172)) of the biomarkers of sensitivity of Table 2 and/or at least one (e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, or at least 242 (e.g., at least the top 1, at least the top 5, at least the top 10, at least the top 15, at least the top 20, at least the top 25, at least the top 30, at least the top 35, at least the top 40, at least the top 45, at least the top 50, at least the top 55, at least the top 60, at least the top 65, at least the top 70, at least the top 75, at least the top 80, at least the top 85, at least the top 90, at least the top 95, at least the top 100, at least the top 105, at least the top 110, at least the top 115, at least the top 120, at least the top 125, at least the top 130, at least the top 135, at least the top 140, at least the top 145, at least the top 150, at least the top 155, at least the top 160, at least the top 165, at least the top 170, or at least the top 175, at least the top 180, at least the top 185, at least the top 190, at least the top 195, at least the top 200, at least the top 205, at least the top 210, at least the top the top 215, at least the top 220, at least the top 225, at least the top 230, at least the top 235, at least the top 240, or at least the top 242)) of the biomarkers of resistance of Table 3 can be used to determine responsiveness of a cancer patient to treatment with 2X-121 or a pharmaceutically acceptable salt thereof. In more specific embodiments, one biomarker of sensitivity from Table 2 (e.g., SRSF7 (SEQ ID NO: 1)), and/or one biomarker of resistance from Table 3 (e.g., HLA-E (SEQ ID NO: 173 or 174 or 178)) can be used to determine responsiveness of a cancer patient to treatment with 2X-121 or a pharmaceutically acceptable salt thereof. Once determined to be sensitive, the patient can be treated with 2X-121 or a pharmaceutically acceptable salt thereof.

In particular, the biomarker of SEQ ID NO: 1 may be used to assess the responsiveness of a cancer patient (e.g., a patient with a cancer or a recurrence thereof) to 2X-121 or a pharmaceutically acceptable salt thereof. The expression level of the biomarker of SEQ ID NO: 1 may be assessed using nucleic acid amplification methods (e.g., PCR) or a device (e.g., a microarray). As is described above, the expression level of the biomarker of SEQ ID NO: 1 in the patient sample may then be compared, e.g., to the expression level of the biomarker of SEQ ID NO: 1 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 1 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 2-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 2 may be used to assess the responsiveness of a cancer patient (e.g., a patient with cancer recurrence) to 2X-121 or a pharmaceutically acceptable salt thereof. The expression level of the biomarker of SEQ ID NO: 2 may be assessed using nucleic acid amplification methods (e.g., PCR) or a device (e.g., a microarray). As is described above, the expression level of the biomarker of SEQ ID NO: 2 in the patient sample may then be compared, e.g., to the expression level of the biomarker of SEQ ID NO: 2 in a cell (e.g., a cancer cell) or tissue (e.g., a tumor tissue) known to be sensitive or resistant to treatment with 2X-121 or a pharmaceutically acceptable salt thereof and used to determine the cancer patient's respon- siveness to 2X-121 or a pharmaceutically acceptable salt thereof. The biomarker of SEQ ID NO: 2 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio- markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1, 3-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 3 may be used to assess the responsiveness of a cancer patient (e.g., a patient with cancer recurrence) to 2X-121 or a pharmaceutically accept- able salt thereof. The expression level of the biomarker of SEQ ID NO: 3 may be assessed using nucleic acid ampli- fication methods (e.g., PCR) or a device (e.g., a microarray). As is described above, the expression level of the biomarker of SEQ ID NO: 3 in the patient sample may then be compared, e.g., to the expression level of the biomarker of SEQ ID NO: 3 in a cell (e.g., a cancer cell) or tissue (e.g., a tumor tissue) known to be sensitive or resistant to treat- ment with 2X-121 or a pharmaceutically acceptable salt thereof and used to determine the cancer patient's respon- siveness to 2X-121 or a pharmaceutically acceptable salt thereof. The biomarker of SEQ ID NO: 3 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio- markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1, 2, 4-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 4 may be used to assess the responsiveness of a cancer patient (e.g., a patient with cancer recurrence) to 2X-121 or a pharmaceutically accept- able salt thereof. The expression level of the biomarker of SEQ ID NO: 4 may be assessed using nucleic acid ampli- fication methods (e.g., PCR) or a device (e.g., a microarray). As is described above, the expression level of the biomarker of SEQ ID NO: 4 in the patient sample may then be compared, e.g., to the expression level of the biomarker of SEQ ID NO: 4 in a cell (e.g., a cancer cell) or tissue (e.g., a tumor tissue) known to be sensitive or resistant to treat- ment with 2X-121 or a pharmaceutically acceptable salt thereof and used to determine the cancer patient's respon- siveness to 2X-121 or a pharmaceutically acceptable salt thereof.

The biomarker of SEQ ID NO: 4 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio- markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-3, 5-414. The expression level of the biomarker(s) may be determined using, e.g., a microarray, PCR, or other techniques described herein, for example, using a nucleic acid probe sequence based on the target The biomarker of SEQ ID NO: 5 may be used to assess the responsiveness of a cancer patient (e.g., a patient with cancer recurrence) to 2X-121 or a pharmaceutically accept- able salt thereof. The expression level of the biomarker of SEQ ID NO: 5 may be assessed using nucleic acid ampli- fication methods (e.g., PCR) or a device (e.g., a microarray). As is described above, the expression level of the biomarker of SEQ ID NO: 5 in the patient sample may then be compared, e.g., to the expression level of the biomarker of SEQ ID NO: 5 in a cell (e.g., a cancer cell) or tissue (e.g., a tumor tissue) known to be sensitive or resistant to treat- ment with 2X-121 or a pharmaceutically acceptable salt thereof and used to determine the cancer patient's respon- siveness to 2X-121 or a pharmaceutically acceptable salt thereof. The biomarker of SEQ ID NO: 5 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio- markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-4, 6-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 6 may be used to assess the responsiveness of a cancer patient (e.g., a patient with cancer recurrence) to 2X-121 or a pharmaceutically accept- able salt thereof. The expression level of the biomarker of SEQ ID NO: 6 may be assessed using nucleic acid amplification methods (e.g., PCR) or a device (e.g., a microarray). As is described above, the expression level of the biomarker of SEQ ID NO: 6 in the patient sample may then be compared, e.g., to the expression level of the biomarker of SEQ ID NO: 6 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 6 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-5, 7-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 7 may be used to assess the responsiveness of a cancer patient (e.g., a patient with cancer recurrence) to 2X-121 or a pharmaceutically acceptable salt thereof. The expression level of the biomarker of SEQ ID NO: 7 may be assessed using nucleic acid amplification methods (e.g., PCR) or a device (e.g., a microarray). As is described above, the expression level of the biomarker of SEQ ID NO: 7 in the patient sample may then be compared, e.g., to the expression level of the biomarker of SEQ ID NO: 7 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 7 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-6, 8-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 8 may be used to assess the responsiveness of a cancer patient (e.g., a patient with cancer recurrence) to 2X-121 or a pharmaceutically acceptable salt thereof. The expression level of the biomarker of SEQ ID NO: 8 may be assessed using nucleic acid amplification methods (e.g., PCR) or a device (e.g., a microarray). As is described above, the expression level of the biomarker of SEQ ID NO: 8 in the patient sample may then be compared, e.g., to the expression level of the biomarker of SEQ ID NO: 8 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 8 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-7, 9-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 9 may be used to assess the responsiveness of a cancer patient (e.g., a patient with cancer recurrence) to 2X-121 or a pharmaceutically acceptable salt thereof. The expression level of the biomarker of SEQ ID NO: 9 may be assessed using nucleic acid amplification methods (e.g., PCR) or a device (e.g., a microarray). As is described above, the expression level of the biomarker of SEQ ID NO: 9 in the patient sample may then be compared, e.g., to the expression level of the biomarker of SEQ ID NO: 9 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 9 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-8, 10-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 10 may be used to assess the responsiveness of a cancer patient (e.g., a patient with cancer recurrence) to 2X-121 or a pharmaceutically acceptable salt thereof. The expression level of the biomarker of SEQ ID NO: 10 may be assessed using nucleic acid amplification methods (e.g., PCR) or a device (e.g., a microarray). As is described above, the expression level of the biomarker of SEQ ID NO: 10 in the patient sample may then be compared, e.g., to the expression level of the biomarker of SEQ ID NO: 10 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 10 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-9, 11-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 11 may be used to assess the responsiveness of a cancer patient (e.g., a patient with cancer recurrence) to 2X-121 or a pharmaceutically acceptable salt thereof. The expression level of the biomarker of SEQ ID NO: 11 may be assessed using nucleic acid amplification methods (e.g., PCR) or a device (e.g., a microarray). As is described above, the expression level of the biomarker of SEQ ID NO: 11 in the patient sample may then be compared, e.g., to the expression level of the biomarker of SEQ ID NO: 11 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 11 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-10, 12-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 12 may be used to assess the responsiveness of a cancer patient (e.g., a patient with cancer recurrence) to 2X-121 or a pharmaceutically acceptable salt thereof. The expression level of the biomarker of SEQ ID NO: 12 may be assessed using nucleic acid amplification methods (e.g., PCR) or a device (e.g., a microarray). As is described above, the expression level of the biomarker of SEQ ID NO: 12 in the patient sample may then be compared, e.g., to the expression level of the biomarker of SEQ ID NO: 12 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 12 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-11, 13-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 13 may be used to assess the responsiveness of a cancer patient (e.g., a patient with cancer recurrence) to 2X-121 or a pharmaceutically acceptable salt thereof. The expression level of the biomarker of SEQ ID NO: 13 may be assessed using nucleic acid amplification methods (e.g., PCR) or a device (e.g., a microarray). As is described above, the expression level of the biomarker of SEQ ID NO: 13 in the patient sample may then be compared, e.g., to the expression level of the biomarker of SEQ ID NO: 13 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 13 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-12, 14-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 14 may be used to assess the responsiveness of a cancer patient (e.g., a patient with cancer recurrence) to 2X-121 or a pharmaceutically acceptable salt thereof. The expression level of the biomarker of SEQ ID NO: 14 may be assessed using nucleic acid amplification methods (e.g., PCR) or a device (e.g., a microarray). As is described above, the expression level of the biomarker of SEQ ID NO: 14 in the patient sample may then be compared, e.g., to the expression level of the biomarker of SEQ ID NO: 14 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 14 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-13, 15-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 15 may be used to assess the responsiveness of a cancer patient (e.g., a patient with cancer recurrence) to 2X-121 or a pharmaceutically acceptable salt thereof. The expression level of the biomarker of SEQ ID NO: 15 may be assessed using nucleic acid amplification methods (e.g., PCR) or a device (e.g., a microarray). As is described above, the expression level of the biomarker of SEQ ID NO: 15 in the patient sample may then be compared, e.g., to the expression level of the biomarker of SEQ ID NO: 15 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 15 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-14, 16-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 16 may be used to assess the responsiveness of a cancer patient (e.g., a patient with cancer recurrence) to 2X-121 or a pharmaceutically acceptable salt thereof. The expression level of the biomarker of SEQ ID NO: 16 may be assessed using nucleic acid amplification methods (e.g., PCR) or a device (e.g., a microarray). As is described above, the expression level of the biomarker of SEQ ID NO: 16 in the patient sample may then be compared, e.g., to the expression level of the biomarker of SEQ ID NO: 16 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 16 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-15, 17-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 17 may be used to assess the responsiveness of a cancer patient (e.g., a patient with cancer recurrence) to 2X-121 or a pharmaceutically acceptable salt thereof. The expression level of the biomarker of SEQ ID NO: 17 may be assessed using nucleic acid amplification methods (e.g., PCR) or a device (e.g., a microarray). As is described above, the expression level of the biomarker of SEQ ID NO: 17 in the patient sample may then be compared, e.g., to the expression level of the biomarker of SEQ ID NO: 17 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 17 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-16, 18-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 18 may be used to assess the responsiveness of a cancer patient (e.g., a patient with cancer recurrence) to 2X-121 or a pharmaceutically acceptable salt thereof. The expression level of the biomarker of SEQ ID NO: 18 may be assessed using nucleic acid amplification methods (e.g., PCR) or a device (e.g., a microarray). As is described above, the expression level of the biomarker of SEQ ID NO: 18 in the patient sample may then be compared, e.g., to the expression level of the biomarker of SEQ ID NO: 18 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 18 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-17, 19-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 19 may be used to assess the responsiveness of a cancer patient (e.g., a patient with cancer recurrence) to 2X-121 or a pharmaceutically acceptable salt thereof. The expression level of the biomarker of SEQ ID NO: 19 may be assessed using nucleic acid amplification methods (e.g., PCR) or a device (e.g., a microarray). As is described above, the expression level of the biomarker of SEQ ID NO: 19 in the patient sample may then be compared, e.g., to the expression level of the biomarker of SEQ ID NO: 19 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 19 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-18, 20-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 20 may be used to assess the responsiveness of a cancer patient (e.g., a patient with cancer recurrence) to 2X-121 or a pharmaceutically acceptable salt thereof. The expression level of the biomarker of SEQ ID NO: 20 may be assessed using nucleic acid amplification methods (e.g., PCR) or a device (e.g., a microarray). As is described above, the expression level of the biomarker of SEQ ID NO: 20 in the patient sample may then be compared, e.g., to the expression level of the biomarker of SEQ ID NO: 20 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 20 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-19, 21-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 21 may be used to assess the responsiveness of a cancer patient (e.g., a patient with cancer recurrence) to 2X-121 or a pharmaceutically acceptable salt thereof. The expression level of the biomarker of SEQ ID NO: 21 may be assessed using nucleic acid amplification methods (e.g., PCR) or a device (e.g., a microarray). As is described above, the expression level of the biomarker of SEQ ID NO: 21 in the patient sample may then be compared, e.g., to the expression level of the biomarker of SEQ ID NO: 21 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 21 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-20, 22-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 22 may be used to assess the responsiveness of a cancer patient (e.g., a patient with cancer recurrence) to 2X-121 or a pharmaceutically acceptable salt thereof. The expression level of the biomarker of SEQ ID NO: 22 may be assessed using nucleic acid amplification methods (e.g., PCR) or a device (e.g., a microarray). As is described above, the expression level of the biomarker of SEQ ID NO: 22 in the patient sample may then be compared, e.g., to the expression level of the biomarker of SEQ ID NO: 22 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 22 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-21, 23-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 23 may be used to assess the responsiveness of a cancer patient (e.g., a patient with cancer recurrence) to 2X-121 or a pharmaceutically acceptable salt thereof. The expression level of the biomarker of SEQ ID NO: 23 may be assessed using nucleic acid amplification methods (e.g., PCR) or a device (e.g., a microarray). As is described above, the expression level of the biomarker of SEQ ID NO: 23 in the patient sample may then be compared, e.g., to the expression level of the biomarker of SEQ ID NO: 23 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 23 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-22, 24-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 24 may be used to assess the responsiveness of a cancer patient (e.g., a patient with cancer recurrence) to 2X-121 or a pharmaceutically acceptable salt thereof. The expression level of the biomarker of SEQ ID NO: 24 may be assessed using nucleic acid amplification methods (e.g., PCR) or a device (e.g., a microarray). As is described above, the expression level of the biomarker of SEQ ID NO: 24 in the patient sample may then be compared, e.g., to the expression level of the biomarker of SEQ ID NO: 24 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 24 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-23, 25-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 25 may be used to assess the responsiveness of a cancer patient (e.g., a patient with cancer recurrence) to 2X-121 or a pharmaceutically acceptable salt thereof. The expression level of the biomarker of SEQ ID NO: 25 may be assessed using nucleic acid amplification methods (e.g., PCR) or a device (e.g., a microarray). As is described above, the expression level of the biomarker of SEQ ID NO: 25 in the patient sample may then be compared, e.g., to the expression level of the biomarker of SEQ ID NO: 25 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 25 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-24, 26-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 26 may be used to assess the responsiveness of a cancer patient (e.g., a patient with cancer recurrence) to 2X-121 or a pharmaceutically acceptable salt thereof. The expression level of the biomarker of SEQ ID NO: 26 may be assessed using nucleic acid amplification methods (e.g., PCR) or a device (e.g., a microarray). As is described above, the expression level of the biomarker of SEQ ID NO: 26 in the patient sample may then be compared, e.g., to the expression level of the biomarker of SEQ ID NO: 26 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 26 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-25, 27-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 27 may be used to assess the responsiveness of a cancer patient (e.g., a patient with cancer recurrence) to 2X-121 or a pharmaceutically acceptable salt thereof. The expression level of the biomarker of SEQ ID NO: 27 may be assessed using nucleic acid amplification methods (e.g., PCR) or a device (e.g., a microarray). As is described above, the expression level of the biomarker of SEQ ID NO: 27 in the patient sample may then be compared, e.g., to the expression level of the biomarker of SEQ ID NO: 27 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 27 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-26, 28-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 28 may be used to assess the responsiveness of a cancer patient (e.g., a patient with cancer recurrence) to 2X-121 or a pharmaceutically acceptable salt thereof. The expression level of the biomarker of SEQ ID NO: 28 may be assessed using nucleic acid amplification methods (e.g., PCR) or a device (e.g., a microarray). As is described above, the expression level of the biomarker of SEQ ID NO: 28 in the patient sample may then be compared, e.g., to the expression level of the biomarker of SEQ ID NO: 28 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 28 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-27, 29-414. The expression level of the biomarker(s) may be determined using, e.g., a microarray, PCR, or other techniques described herein, for example, using a nucleic acid probe sequence based on the target The biomarker of SEQ ID NO: 29 may be used to assess the responsiveness of a cancer patient (e.g., a patient with cancer recurrence) to 2X-121 or a pharmaceutically acceptable salt thereof. The expression level of the biomarker of SEQ ID NO: 29 may be assessed using nucleic acid amplification methods (e.g., PCR) or a device (e.g., a microarray). As is described above, the expression level of the biomarker of SEQ ID NO: 29 in the patient sample may then be compared, e.g., to the expression level of the biomarker of SEQ ID NO: 29 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 29 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-28, 30-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 30 may be used to assess the responsiveness of a cancer patient (e.g., a patient with cancer recurrence) to 2X-121 or a pharmaceutically acceptable salt thereof. The expression level of the biomarker of SEQ ID NO: 30 may be assessed using nucleic acid amplification methods (e.g., PCR) or a device (e.g., a microarray). As is described above, the expression level of the biomarker of SEQ ID NO: 30 in the patient sample may then be compared, e.g., to the expression level of the biomarker of SEQ ID NO: 30 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 30 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-29, 31-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 31 may be used to assess the responsiveness of a cancer patient (e.g., a patient with cancer recurrence) to 2X-121 or a pharmaceutically acceptable salt thereof. The expression level of the biomarker of SEQ ID NO: 31 may be assessed using nucleic acid amplification methods (e.g., PCR) or a device (e.g., a microarray). As is described above, the expression level of the biomarker of SEQ ID NO: 31 in the patient sample may then be compared, e.g., to the expression level of the biomarker of SEQ ID NO: 31 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 31 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-30, 32-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 32 may be used to assess the responsiveness of a cancer patient (e.g., a patient with cancer recurrence) to 2X-121 or a pharmaceutically acceptable salt thereof. The expression level of the biomarker of SEQ ID NO: 32 may be assessed using nucleic acid amplification methods (e.g., PCR) or a device (e.g., a microarray). As is described above, the expression level of the biomarker of SEQ ID NO: 32 in the patient sample may then be compared, e.g., to the expression level of the biomarker of SEQ ID NO: 32 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 32 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-31, 33-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 33 may be used to assess the responsiveness of a cancer patient (e.g., a patient with cancer recurrence) to 2X-121 or a pharmaceutically acceptable salt thereof. The expression level of the biomarker of SEQ ID NO: 33 may be assessed using nucleic acid amplification methods (e.g., PCR) or a device (e.g., a microarray). As is described above, the expression level of the biomarker of SEQ ID NO: 33 in the patient sample may then be compared, e.g., to the expression level of the biomarker of SEQ ID NO: 33 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 33 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-32, 34-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 34 may be used to assess the responsiveness of a cancer patient (e.g., a patient with cancer recurrence) to 2X-121 or a pharmaceutically acceptable salt thereof. The expression level of the biomarker of SEQ ID NO: 34 may be assessed using nucleic acid amplification methods (e.g., PCR) or a device (e.g., a microarray). As is described above, the expression level of the biomarker of SEQ ID NO: 34 in the patient sample may then be compared, e.g., to the expression level of the biomarker of SEQ ID NO: 34 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 34 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-33, 35-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 35 may be used to assess the responsiveness of a cancer patient (e.g., a patient with cancer recurrence) to 2X-121 or a pharmaceutically acceptable salt thereof. The expression level of the biomarker of SEQ ID NO: 35 may be assessed using nucleic acid amplification methods (e.g., PCR) or a device (e.g., a microarray). As is described above, the expression level of the biomarker of SEQ ID NO: 35 in the patient sample may then be compared, e.g., to the expression level of the biomarker of SEQ ID NO: 35 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 35 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-34, 36-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 36 may be used to assess the responsiveness of a cancer patient (e.g., a patient with cancer recurrence) to 2X-121 or a pharmaceutically acceptable salt thereof. The expression level of the biomarker of SEQ ID NO: 36 may be assessed using nucleic acid amplification methods (e.g., PCR) or a device (e.g., a microarray). As is described above, the expression level of the biomarker of SEQ ID NO: 36 in the patient sample may then be compared, e.g., to the expression level of the biomarker of SEQ ID NO: 36 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 36 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-35, 37-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 37 may be used to assess the responsiveness of a cancer patient (e.g., a patient with cancer recurrence) to 2X-121 or a pharmaceutically acceptable salt thereof. The expression level of the biomarker of SEQ ID NO: 37 may be assessed using nucleic acid amplification methods (e.g., PCR) or a device (e.g., a microarray). As is described above, the expression level of the biomarker of SEQ ID NO: 37 in the patient sample may then be compared, e.g., to the expression level of the biomarker of SEQ ID NO: 37 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 37 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-36, 38-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 38 may be used to assess the responsiveness of a cancer patient (e.g., a patient with cancer recurrence) to 2X-121 or a pharmaceutically acceptable salt thereof. The expression level of the biomarker of SEQ ID NO: 38 may be assessed using nucleic acid amplification methods (e.g., PCR) or a device (e.g., a microarray). As is described above, the expression level of the biomarker of SEQ ID NO: 38 in the patient sample may then be compared, e.g., to the expression level of the biomarker of SEQ ID NO: 38 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 38 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-37, 39-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 39 may be used to assess the responsiveness of a cancer patient (e.g., a patient with cancer recurrence) to 2X-121 or a pharmaceutically acceptable salt thereof. The expression level of the biomarker of SEQ ID NO: 39 may be assessed using nucleic acid amplification methods (e.g., PCR) or a device (e.g., a microarray). As is described above, the expression level of the biomarker of SEQ ID NO: 39 in the patient sample may then be compared, e.g., to the expression level of the biomarker of SEQ ID NO: 39 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 39 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-38, 40-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 40 may be used to assess the responsiveness of a cancer patient (e.g., a patient with cancer recurrence) to 2X-121 or a pharmaceutically acceptable salt thereof. The expression level of the biomarker of SEQ ID NO: 40 may be assessed using nucleic acid amplification methods (e.g., PCR) or a device (e.g., a microarray). As is described above, the expression level of the biomarker of SEQ ID NO: 40 in the patient sample may then be compared, e.g., to the expression level of the biomarker of SEQ ID NO: 40 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 40 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-39, 41-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 41 may be used to assess the responsiveness of a cancer patient (e.g., a patient with cancer recurrence) to 2X-121 or a pharmaceutically acceptable salt thereof. The expression level of the biomarker of SEQ ID NO: 41 may be assessed using nucleic acid amplification methods (e.g., PCR) or a device (e.g., a microarray). As is described above, the expression level of the biomarker of SEQ ID NO: 41 in the patient sample may then be compared, e.g., to the expression level of the biomarker of SEQ ID NO: 41 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 41 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-40, 42-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 42 may be used to assess the responsiveness of a cancer patient (e.g., a patient with cancer recurrence) to 2X-121 or a pharmaceutically acceptable salt thereof. The expression level of the biomarker of SEQ ID NO: 42 may be assessed using nucleic acid amplification methods (e.g., PCR) or a device (e.g., a microarray). As is described above, the expression level of the biomarker of SEQ ID NO: 42 in the patient sample may then be compared, e.g., to the expression level of the biomarker of SEQ ID NO: 42 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 42 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-41, 43-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 43 may be used to assess the responsiveness of a cancer patient (e.g., a patient with cancer recurrence) to 2X-121 or a pharmaceutically acceptable salt thereof. The expression level of the biomarker of SEQ ID NO: 43 may be assessed using nucleic acid amplification methods (e.g., PCR) or a device (e.g., a microarray). As is described above, the expression level of the biomarker of SEQ ID NO: 43 in the patient sample may then be compared, e.g., to the expression level of the biomarker of SEQ ID NO: 43 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 43 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-42, 44-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 44 may be used to assess the responsiveness of a cancer patient (e.g., a patient with cancer recurrence) to 2X-121 or a pharmaceutically acceptable salt thereof. The expression level of the biomarker of SEQ ID NO: 44 may be assessed using nucleic acid amplification methods (e.g., PCR) or a device (e.g., a microarray). As is described above, the expression level of the biomarker of SEQ ID NO: 44 in the patient sample may then be compared, e.g., to the expression level of the biomarker of SEQ ID NO: 44 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 44 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-43, 45-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 45 may be used to assess the responsiveness of a cancer patient (e.g., a patient with cancer recurrence) to 2X-121 or a pharmaceutically acceptable salt thereof. The expression level of the biomarker of SEQ ID NO: 45 may be assessed using nucleic acid amplification methods (e.g., PCR) or a device (e.g., a microarray). As is described above, the expression level of the biomarker of SEQ ID NO: 45 in the patient sample may then be compared, e.g., to the expression level of the biomarker of SEQ ID NO: 45 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 45 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-44, 46-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 46 may be used to assess the responsiveness of a cancer patient (e.g., a patient with cancer recurrence) to 2X-121 or a pharmaceutically acceptable salt thereof. The expression level of the biomarker of SEQ ID NO: 46 may be assessed using nucleic acid amplification methods (e.g., PCR) or a device (e.g., a microarray). As is described above, the expression level of the biomarker of SEQ ID NO: 46 in the patient sample may then be compared, e.g., to the expression level of the biomarker of SEQ ID NO: 46 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 46 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-45, 47-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 47 may be used to assess the responsiveness of a cancer patient (e.g., a patient with cancer recurrence) to 2X-121 or a pharmaceutically acceptable salt thereof. The expression level of the biomarker of SEQ ID NO: 47 may be assessed using nucleic acid amplification methods (e.g., PCR) or a device (e.g., a microarray). As is described above, the expression level of the biomarker of SEQ ID NO: 47 in the patient sample may then be compared, e.g., to the expression level of the biomarker of SEQ ID NO: 47 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 47 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-46, 48-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 48 may be used to assess the responsiveness of a cancer patient (e.g., a patient with cancer recurrence) to 2X-121 or a pharmaceutically acceptable salt thereof. The expression level of the biomarker of SEQ ID NO: 48 may be assessed using nucleic acid amplification methods (e.g., PCR) or a device (e.g., a microarray). As is described above, the expression level of the biomarker of SEQ ID NO: 48 in the patient sample may then be compared, e.g., to the expression level of the biomarker of SEQ ID NO: 48 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 48 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-47, 49-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 49 may be used to assess the responsiveness of a cancer patient (e.g., a patient with cancer recurrence) to 2X-121 or a pharmaceutically acceptable salt thereof. The expression level of the biomarker of SEQ ID NO: 49 may be assessed using nucleic acid amplification methods (e.g., PCR) or a device (e.g., a microarray). As is described above, the expression level of the biomarker of SEQ ID NO: 49 in the patient sample may then be compared, e.g., to the expression level of the biomarker of SEQ ID NO: 49 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 49 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-48, 50-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 50 may be used to assess the responsiveness of a cancer patient (e.g., a patient with cancer recurrence) to 2X-121 or a pharmaceutically acceptable salt thereof. The expression level of the biomarker of SEQ ID NO: 50 may be assessed using nucleic acid amplification methods (e.g., PCR) or a device (e.g., a microarray). As is described above, the expression level of the biomarker of SEQ ID NO: 50 in the patient sample may then be compared, e.g., to the expression level of the biomarker of SEQ ID NO: 50 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 50 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-49, 51-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 51 may be used to assess the responsiveness of a cancer patient (e.g., a patient with cancer recurrence) to 2X-121 or a pharmaceutically acceptable salt thereof. The expression level of the biomarker of SEQ ID NO: 51 may be assessed using nucleic acid amplification methods (e.g., PCR) or a device (e.g., a microarray). As is described above, the expression level of the biomarker of SEQ ID NO: 51 in the patient sample may then be compared, e.g., to the expression level of the biomarker of SEQ ID NO: 51 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 51 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-50, 52-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 52 may be used to assess the responsiveness of a cancer patient (e.g., a patient with cancer recurrence) to 2X-121 or a pharmaceutically acceptable salt thereof. The expression level of the biomarker of SEQ ID NO: 52 may be assessed using nucleic acid amplification methods (e.g., PCR) or a device (e.g., a microarray). As is described above, the expression level of the biomarker of SEQ ID NO: 52 in the patient sample may then be compared, e.g., to the expression level of the biomarker of SEQ ID NO: 52 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 52 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-51, 53-414. The expression level of the biomarker(s) may be determined using, e.g., a microarray, PCR, or other techniques described herein, for example, using a nucleic acid probe sequence based on the target The biomarker of SEQ ID NO: 53 may be used to assess the responsiveness of a cancer patient (e.g., a patient with cancer recurrence) to 2X-121 or a pharmaceutically acceptable salt thereof. The expression level of the biomarker of SEQ ID NO: 53 may be assessed using nucleic acid amplification methods (e.g., PCR) or a device (e.g., a microarray). As is described above, the expression level of the biomarker of SEQ ID NO: 53 in the patient sample may then be compared, e.g., to the expression level of the biomarker of SEQ ID NO: 53 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 53 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-52, 54-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 54 may be used to assess the responsiveness of a cancer patient (e.g., a patient with cancer recurrence) to 2X-121 or a pharmaceutically acceptable salt thereof. The expression level of the biomarker of SEQ ID NO: 54 may be assessed using nucleic acid amplification methods (e.g., PCR) or a device (e.g., a microarray). As is described above, the expression level of the biomarker of SEQ ID NO: 54 in the patient sample may then be compared, e.g., to the expression level of the biomarker of SEQ ID NO: 54 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 54 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-53, 55-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 55 may be used to assess the responsiveness of a cancer patient (e.g., a patient with cancer recurrence) to 2X-121 or a pharmaceutically acceptable salt thereof. The expression level of the biomarker of SEQ ID NO: 55 may be assessed using nucleic acid amplification methods (e.g., PCR) or a device (e.g., a microarray). As is described above, the expression level of the biomarker of SEQ ID NO: 55 in the patient sample may then be compared, e.g., to the expression level of the biomarker of SEQ ID NO: 55 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 55 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-54, 56-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 56 may be used to assess the responsiveness of a cancer patient (e.g., a patient with cancer recurrence) to 2X-121 or a pharmaceutically acceptable salt thereof. The expression level of the biomarker of SEQ ID NO: 56 may be assessed using nucleic acid amplification methods (e.g., PCR) or a device (e.g., a microarray). As is described above, the expression level of the biomarker of SEQ ID NO: 56 in the patient sample may then be compared, e.g., to the expression level of the biomarker of SEQ ID NO: 56 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 56 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-55, 57-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 57 may be used to assess the responsiveness of a cancer patient (e.g., a patient with cancer recurrence) to 2X-121 or a pharmaceutically acceptable salt thereof. The expression level of the biomarker of SEQ ID NO: 57 may be assessed using nucleic acid amplification methods (e.g., PCR) or a device (e.g., a microarray). As is described above, the expression level of the biomarker of SEQ ID NO: 57 in the patient sample may then be compared, e.g., to the expression level of the biomarker of SEQ ID NO: 57 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 57 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-56, 58-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 58 may be used to assess the responsiveness of a cancer patient (e.g., a patient with cancer recurrence) to 2X-121 or a pharmaceutically acceptable salt thereof. The expression level of the biomarker of SEQ ID NO: 58 may be assessed using nucleic acid amplification methods (e.g., PCR) or a device (e.g., a microarray). As is described above, the expression level of the biomarker of SEQ ID NO: 58 in the patient sample may then be compared, e.g., to the expression level of the biomarker of SEQ ID NO: 58 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 58 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-57, 59-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 59 may be used to assess the responsiveness of a cancer patient (e.g., a patient with cancer recurrence) to 2X-121 or a pharmaceutically acceptable salt thereof. The expression level of the biomarker of SEQ ID NO: 59 may be assessed using nucleic acid amplification methods (e.g., PCR) or a device (e.g., a microarray). As is described above, the expression level of the biomarker of SEQ ID NO: 59 in the patient sample may then be compared, e.g., to the expression level of the biomarker of SEQ ID NO: 59 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 59 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-58, 60-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 60 may be used to assess the responsiveness of a cancer patient (e.g., a patient with cancer recurrence) to 2X-121 or a pharmaceutically acceptable salt thereof. The expression level of the biomarker of SEQ ID NO: 60 may be assessed using nucleic acid amplification methods (e.g., PCR) or a device (e.g., a microarray). As is described above, the expression level of the biomarker of SEQ ID NO: 60 in the patient sample may then be compared, e.g., to the expression level of the biomarker of SEQ ID NO: 60 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 60 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-59, 61-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 61 may be used to assess the responsiveness of a cancer patient (e.g., a patient with cancer recurrence) to 2X-121 or a pharmaceutically acceptable salt thereof. The expression level of the biomarker of SEQ ID NO: 61 may be assessed using nucleic acid amplification methods (e.g., PCR) or a device (e.g., a microarray). As is described above, the expression level of the biomarker of SEQ ID NO: 61 in the patient sample may then be compared, e.g., to the expression level of the biomarker of SEQ ID NO: 61 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 61 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-60, 62-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 62 may be used to assess the responsiveness of a cancer patient (e.g., a patient with cancer recurrence) to 2X-121 or a pharmaceutically acceptable salt thereof. The expression level of the biomarker of SEQ ID NO: 62 may be assessed using nucleic acid amplification methods (e.g., PCR) or a device (e.g., a microarray). As is described above, the expression level of the biomarker of SEQ ID NO: 62 in the patient sample may then be compared, e.g., to the expression level of the biomarker of SEQ ID NO: 62 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 62 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-61, 63-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 63 may be used to assess the responsiveness of a cancer patient (e.g., a patient with cancer recurrence) to 2X-121 or a pharmaceutically acceptable salt thereof. The expression level of the biomarker of SEQ ID NO: 63 may be assessed using nucleic acid amplification methods (e.g., PCR) or a device (e.g., a microarray). As is described above, the expression level of the biomarker of SEQ ID NO: 63 in the patient sample may then be compared, e.g., to the expression level of the biomarker of SEQ ID NO: 63 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 63 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-62, 64-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 64 may be used to assess the responsiveness of a cancer patient (e.g., a patient with cancer recurrence) to 2X-121 or a pharmaceutically acceptable salt thereof. The expression level of the biomarker of SEQ ID NO: 64 may be assessed using nucleic acid amplification methods (e.g., PCR) or a device (e.g., a microarray). As is described above, the expression level of the biomarker of SEQ ID NO: 64 in the patient sample may then be compared, e.g., to the expression level of the biomarker of SEQ ID NO: 64 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 64 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-63, 65-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 65 may be used to assess the responsiveness of a cancer patient (e.g., a patient with cancer recurrence) to 2X-121 or a pharmaceutically acceptable salt thereof. The expression level of the biomarker of SEQ ID NO: 65 may be assessed using nucleic acid amplification methods (e.g., PCR) or a device (e.g., a microarray). As is described above, the expression level of the biomarker of SEQ ID NO: 65 in the patient sample may then be compared, e.g., to the expression level of the biomarker of SEQ ID NO: 65 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 65 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-64, 66-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 66 may be used to assess the responsiveness of a cancer patient (e.g., a patient with cancer recurrence) to 2X-121 or a pharmaceutically acceptable salt thereof. The expression level of the biomarker of SEQ ID NO: 66 may be assessed using nucleic acid amplification methods (e.g., PCR) or a device (e.g., a microarray). As is described above, the expression level of the biomarker of SEQ ID NO: 66 in the patient sample may then be compared, e.g., to the expression level of the biomarker of SEQ ID NO: 66 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 66 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-65, 67-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 67 may be used to assess the responsiveness of a cancer patient (e.g., a patient with cancer recurrence) to 2X-121 or a pharmaceutically acceptable salt thereof. The expression level of the biomarker of SEQ ID NO: 67 may be assessed using nucleic acid amplification methods (e.g., PCR) or a device (e.g., a microarray). As is described above, the expression level of the biomarker of SEQ ID NO: 67 in the patient sample may then be compared, e.g., to the expression level of the biomarker of SEQ ID NO: 67 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 67 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-66, 68-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 68 may be used to assess the responsiveness of a cancer patient (e.g., a patient with cancer recurrence) to 2X-121 or a pharmaceutically acceptable salt thereof. The expression level of the biomarker of SEQ ID NO: 68 may be assessed using nucleic acid amplification methods (e.g., PCR) or a device (e.g., a microarray). As is described above, the expression level of the biomarker of SEQ ID NO: 68 in the patient sample may then be compared, e.g., to the expression level of the biomarker of SEQ ID NO: 68 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 68 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-67, 69-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 69 may be used to assess the responsiveness of a cancer patient (e.g., a patient with cancer recurrence) to 2X-121 or a pharmaceutically acceptable salt thereof. The expression level of the biomarker of SEQ ID NO: 69 may be assessed using nucleic acid amplification methods (e.g., PCR) or a device (e.g., a microarray). As is described above, the expression level of the biomarker of SEQ ID NO: 69 in the patient sample may then be compared, e.g., to the expression level of the biomarker of SEQ ID NO: 69 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 69 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-68, 70-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 70 may be used to assess the responsiveness of a cancer patient (e.g., a patient with cancer recurrence) to 2X-121 or a pharmaceutically acceptable salt thereof. The expression level of the biomarker of SEQ ID NO: 70 may be assessed using nucleic acid amplification methods (e.g., PCR) or a device (e.g., a microarray). As is described above, the expression level of the biomarker of SEQ ID NO: 70 in the patient sample may then be compared, e.g., to the expression level of the biomarker of SEQ ID NO: 70 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 70 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-69, 71-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 71 may be used to assess the responsiveness of a cancer patient (e.g., a patient with cancer recurrence) to 2X-121 or a pharmaceutically acceptable salt thereof. The expression level of the biomarker of SEQ ID NO: 71 may be assessed using nucleic acid amplification methods (e.g., PCR) or a device (e.g., a microarray). As is described above, the expression level of the biomarker of SEQ ID NO: 71 in the patient sample may then be compared, e.g., to the expression level of the biomarker of SEQ ID NO: 71 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 71 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-70, 72-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 72 may be used to assess the responsiveness of a cancer patient (e.g., a patient with cancer recurrence) to 2X-121 or a pharmaceutically acceptable salt thereof. The expression level of the biomarker of SEQ ID NO: 72 may be assessed using nucleic acid amplification methods (e.g., PCR) or a device (e.g., a microarray). As is described above, the expression level of the biomarker of SEQ ID NO: 72 in the patient sample may then be compared, e.g., to the expression level of the biomarker of SEQ ID NO: 72 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 72 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-71, 73-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 73 may be used to assess the responsiveness of a cancer patient (e.g., a patient with cancer recurrence) to 2X-121 or a pharmaceutically acceptable salt thereof. The expression level of the biomarker of SEQ ID NO: 73 may be assessed using nucleic acid amplification methods (e.g., PCR) or a device (e.g., a microarray). As is described above, the expression level of the biomarker of SEQ ID NO: 73 in the patient sample may then be compared, e.g., to the expression level of the biomarker of SEQ ID NO: 73 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 73 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-72, 74-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 74 may be used to assess the responsiveness of a cancer patient (e.g., a patient with cancer recurrence) to 2X-121 or a pharmaceutically acceptable salt thereof. The expression level of the biomarker of SEQ ID NO: 74 may be assessed using nucleic acid amplification methods (e.g., PCR) or a device (e.g., a microarray). As is described above, the expression level of the biomarker of SEQ ID NO: 74 in the patient sample may then be compared, e.g., to the expression level of the biomarker of SEQ ID NO: 74 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 74 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-73, 75-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 75 may be used to assess the responsiveness of a cancer patient (e.g., a patient with cancer recurrence) to 2X-121 or a pharmaceutically acceptable salt thereof. The expression level of the biomarker of SEQ ID NO: 75 may be assessed using nucleic acid amplification methods (e.g., PCR) or a device (e.g., a microarray). As is described above, the expression level of the biomarker of SEQ ID NO: 75 in the patient sample may then be compared, e.g., to the expression level of the biomarker of SEQ ID NO: 75 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 75 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-74, 76-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 76 may be used to assess the responsiveness of a cancer patient (e.g., a patient with cancer recurrence) to 2X-121 or a pharmaceutically acceptable salt thereof. The expression level of the biomarker of SEQ ID NO: 76 may be assessed using nucleic acid amplification methods (e.g., PCR) or a device (e.g., a microarray). As is described above, the expression level of the biomarker of SEQ ID NO: 76 in the patient sample may then be compared, e.g., to the expression level of the biomarker of SEQ ID NO: 76 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 76 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-75, 77-414. The expression level of the biomarker(s) may be determined using, e.g., a microarray, PCR, or other techniques described herein, for example, using a nucleic acid probe sequence based on the target The biomarker of SEQ ID NO: 77 may be used to assess the responsiveness of a cancer patient (e.g., a patient with cancer recurrence) to 2X-121 or a pharmaceutically acceptable salt thereof. The expression level of the biomarker of SEQ ID NO: 77 may be assessed using nucleic acid amplification methods (e.g., PCR) or a device (e.g., a microarray). As is described above, the expression level of the biomarker of SEQ ID NO: 77 in the patient sample may then be compared, e.g., to the expression level of the biomarker of SEQ ID NO: 77 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 77 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-76, 78-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 78 may be used to assess the responsiveness of a cancer patient (e.g., a patient with cancer recurrence) to 2X-121 or a pharmaceutically acceptable salt thereof. The expression level of the biomarker of SEQ ID NO: 78 may be assessed using nucleic acid amplification methods (e.g., PCR) or a device (e.g., a microarray). As is described above, the expression level of the biomarker of SEQ ID NO: 78 in the patient sample may then be compared, e.g., to the expression level of the biomarker of SEQ ID NO: 78 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 78 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-77, 79-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 79 may be used to assess the responsiveness of a cancer patient (e.g., a patient with cancer recurrence) to 2X-121 or a pharmaceutically acceptable salt thereof. The expression level of the biomarker of SEQ ID NO: 79 may be assessed using nucleic acid amplification methods (e.g., PCR) or a device (e.g., a microarray). As is described above, the expression level of the biomarker of SEQ ID NO: 79 in the patient sample may then be compared, e.g., to the expression level of the biomarker of SEQ ID NO: 79 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 79 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-78, 80-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 80 may be used to assess the responsiveness of a cancer patient (e.g., a patient with cancer recurrence) to 2X-121 or a pharmaceutically acceptable salt thereof. The expression level of the biomarker of SEQ ID NO: 80 may be assessed using nucleic acid amplification methods (e.g., PCR) or a device (e.g., a microarray). As is described above, the expression level of the biomarker of SEQ ID NO: 80 in the patient sample may then be compared, e.g., to the expression level of the biomarker of SEQ ID NO: 80 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 80 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-79, 81-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 81 may be used to assess the responsiveness of a cancer patient (e.g., a patient with cancer recurrence) to 2X-121 or a pharmaceutically acceptable salt thereof. The expression level of the biomarker of SEQ ID NO: 81 may be assessed using nucleic acid amplification methods (e.g., PCR) or a device (e.g., a microarray). As is described above, the expression level of the biomarker of SEQ ID NO: 81 in the patient sample may then be compared, e.g., to the expression level of the biomarker of SEQ ID NO: 81 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 81 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-80, 82-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 82 may be used to assess the responsiveness of a cancer patient (e.g., a patient with cancer recurrence) to 2X-121 or a pharmaceutically acceptable salt thereof. The expression level of the biomarker of SEQ ID NO: 82 may be assessed using nucleic acid amplification methods (e.g., PCR) or a device (e.g., a microarray). As is described above, the expression level of the biomarker of SEQ ID NO: 82 in the patient sample may then be compared, e.g., to the expression level of the biomarker of SEQ ID NO: 82 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 82 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-81, 83-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 83 may be used to assess the responsiveness of a cancer patient (e.g., a patient with cancer recurrence) to 2X-121 or a pharmaceutically acceptable salt thereof. The expression level of the biomarker of SEQ ID NO: 83 may be assessed using nucleic acid amplification methods (e.g., PCR) or a device (e.g., a microarray). As is described above, the expression level of the biomarker of SEQ ID NO: 83 in the patient sample may then be compared, e.g., to the expression level of the biomarker of SEQ ID NO: 83 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 83 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-82, 84-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 84 may be used to assess the responsiveness of a cancer patient (e.g., a patient with cancer recurrence) to 2X-121 or a pharmaceutically acceptable salt thereof. The expression level of the biomarker of SEQ ID NO: 84 may be assessed using nucleic acid amplification methods (e.g., PCR) or a device (e.g., a microarray). As is described above, the expression level of the biomarker of SEQ ID NO: 84 in the patient sample may then be compared, e.g., to the expression level of the biomarker of SEQ ID NO: 84 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 84 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-83, 85-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 85 may be used to assess the responsiveness of a cancer patient (e.g., a patient with cancer recurrence) to 2X-121 or a pharmaceutically acceptable salt thereof. The expression level of the biomarker of SEQ ID NO: 85 may be assessed using nucleic acid amplification methods (e.g., PCR) or a device (e.g., a microarray). As is described above, the expression level of the biomarker of SEQ ID NO: 85 in the patient sample may then be compared, e.g., to the expression level of the biomarker of SEQ ID NO: 85 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 85 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-84, 86-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 86 may be used to assess the responsiveness of a cancer patient (e.g., a patient with cancer recurrence) to 2X-121 or a pharmaceutically acceptable salt thereof. The expression level of the biomarker of SEQ ID NO: 86 may be assessed using nucleic acid amplification methods (e.g., PCR) or a device (e.g., a microarray). As is described above, the expression level of the biomarker of SEQ ID NO: 86 in the patient sample may then be compared, e.g., to the expression level of the biomarker of SEQ ID NO: 86 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 86 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-85, 87-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 87 may be used to assess the responsiveness of a cancer patient (e.g., a patient with cancer recurrence) to 2X-121 or a pharmaceutically accept-able salt thereof. The expression level of the biomarker of SEQ ID NO: 87 may be assessed using nucleic acid ampli-fication methods (e.g., PCR) or a device (e.g., a microarray). As is described above, the expression level of the biomarker of SEQ ID NO: 87 in the patient sample may then be compared, e.g., to the expression level of the biomarker of SEQ ID NO: 87 in a cell (e.g., a cancer cell) or tissue (e.g., a tumor tissue) known to be sensitive or resistant to treat-ment with 2X-121 or a pharmaceutically acceptable salt thereof and used to determine the cancer patient's respon-siveness to 2X-121 or a pharmaceutically acceptable salt thereof. The biomarker of SEQ ID NO: 87 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomark-ers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-86, 88-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 88 may be used to assess the responsiveness of a cancer patient (e.g., a patient with cancer recurrence) to 2X-121 or a pharmaceutically accept-able salt thereof. The expression level of the biomarker of SEQ ID NO: 88 may be assessed using nucleic acid ampli-fication methods (e.g., PCR) or a device (e.g., a microarray). As is described above, the expression level of the biomarker of SEQ ID NO: 88 in the patient sample may then be compared, e.g., to the expression level of the biomarker of SEQ ID NO: 88 in a cell (e.g., a cancer cell) or tissue (e.g., a tumor tissue) known to be sensitive or resistant to treat-ment with 2X-121 or a pharmaceutically acceptable salt thereof and used to determine the cancer patient's respon-siveness to 2X-121 or a pharmaceutically acceptable salt thereof. The biomarker of SEQ ID NO: 88 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomark-ers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-87, 89-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 89 may be used to assess the responsiveness of a cancer patient (e.g., a patient with cancer recurrence) to 2X-121 or a pharmaceutically accept-able salt thereof. The expression level of the biomarker of SEQ ID NO: 89 may be assessed using nucleic acid ampli-fication methods (e.g., PCR) or a device (e.g., a microarray). As is described above, the expression level of the biomarker of SEQ ID NO: 89 in the patient sample may then be compared, e.g., to the expression level of the biomarker of SEQ ID NO: 89 in a cell (e.g., a cancer cell) or tissue (e.g., a tumor tissue) known to be sensitive or resistant to treat-ment with 2X-121 or a pharmaceutically acceptable salt thereof and used to determine the cancer patient's respon-siveness to 2X-121 or a pharmaceutically acceptable salt thereof. The biomarker of SEQ ID NO: 89 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomark-ers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-88, 90-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 90 may be used to assess the responsiveness of a cancer patient (e.g., a patient with cancer recurrence) to 2X-121 or a pharmaceutically accept-able salt thereof. The expression level of the biomarker of SEQ ID NO: 90 may be assessed using nucleic acid ampli-fication methods (e.g., PCR) or a device (e.g., a microarray). As is described above, the expression level of the biomarker of SEQ ID NO: 90 in the patient sample may then be compared, e.g., to the expression level of the biomarker of SEQ ID NO: 90 in a cell (e.g., a cancer cell) or tissue (e.g., a tumor tissue) known to be sensitive or resistant to treat-ment with 2X-121 or a pharmaceutically acceptable salt thereof and used to determine the cancer patient's respon-siveness to 2X-121 or a pharmaceutically acceptable salt thereof. The biomarker of SEQ ID NO: 90 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomark-ers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-89, 91-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 91 may be used to assess the responsiveness of a cancer patient (e.g., a patient with cancer recurrence) to 2X-121 or a pharmaceutically acceptable salt thereof. The expression level of the biomarker of SEQ ID NO: 91 may be assessed using nucleic acid amplification methods (e.g., PCR) or a device (e.g., a microarray). As is described above, the expression level of the biomarker of SEQ ID NO: 91 in the patient sample may then be compared, e.g., to the expression level of the biomarker of SEQ ID NO: 91 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 91 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-90, 92-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 92 may be used to assess the responsiveness of a cancer patient (e.g., a patient with cancer recurrence) to 2X-121 or a pharmaceutically acceptable salt thereof. The expression level of the biomarker of SEQ ID NO: 92 may be assessed using nucleic acid amplification methods (e.g., PCR) or a device (e.g., a microarray). As is described above, the expression level of the biomarker of SEQ ID NO: 92 in the patient sample may then be compared, e.g., to the expression level of the biomarker of SEQ ID NO: 92 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 92 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-91, 93-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 93 may be used to assess the responsiveness of a cancer patient (e.g., a patient with cancer recurrence) to 2X-121 or a pharmaceutically acceptable salt thereof. The expression level of the biomarker of SEQ ID NO: 93 may be assessed using nucleic acid amplification methods (e.g., PCR) or a device (e.g., a microarray). As is described above, the expression level of the biomarker of SEQ ID NO: 93 in the patient sample may then be compared, e.g., to the expression level of the biomarker of SEQ ID NO: 93 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 93 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-92, 94-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 94 may be used to assess the responsiveness of a cancer patient (e.g., a patient with cancer recurrence) to 2X-121 or a pharmaceutically acceptable salt thereof. The expression level of the biomarker of SEQ ID NO: 94 may be assessed using nucleic acid amplification methods (e.g., PCR) or a device (e.g., a microarray). As is described above, the expression level of the biomarker of SEQ ID NO: 94 in the patient sample may then be compared, e.g., to the expression level of the biomarker of SEQ ID NO: 94 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 94 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-93, 95-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 95 may be used to assess the responsiveness of a cancer patient (e.g., a patient with cancer recurrence) to 2X-121 or a pharmaceutically acceptable salt thereof. The expression level of the biomarker of SEQ ID NO: 95 may be assessed using nucleic acid amplification methods (e.g., PCR) or a device (e.g., a microarray). As is described above, the expression level of the biomarker of SEQ ID NO: 95 in the patient sample may then be compared, e.g., to the expression level of the biomarker of SEQ ID NO: 95 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 95 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-94, 96-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 96 may be used to assess the responsiveness of a cancer patient (e.g., a patient with cancer recurrence) to 2X-121 or a pharmaceutically acceptable salt thereof. The expression level of the biomarker of SEQ ID NO: 96 may be assessed using nucleic acid amplification methods (e.g., PCR) or a device (e.g., a microarray). As is described above, the expression level of the biomarker of SEQ ID NO: 96 in the patient sample may then be compared, e.g., to the expression level of the biomarker of SEQ ID NO: 96 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 96 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-95, 97-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 97 may be used to assess the responsiveness of a cancer patient (e.g., a patient with cancer recurrence) to 2X-121 or a pharmaceutically acceptable salt thereof. The expression level of the biomarker of SEQ ID NO: 97 may be assessed using nucleic acid amplification methods (e.g., PCR) or a device (e.g., a microarray). As is described above, the expression level of the biomarker of SEQ ID NO: 97 in the patient sample may then be compared, e.g., to the expression level of the biomarker of SEQ ID NO: 97 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 97 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-96, 98-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 98 may be used to assess the responsiveness of a cancer patient (e.g., a patient with cancer recurrence) to 2X-121 or a pharmaceutically acceptable salt thereof. The expression level of the biomarker of SEQ ID NO: 98 may be assessed using nucleic acid amplification methods (e.g., PCR) or a device (e.g., a microarray). As is described above, the expression level of the biomarker of SEQ ID NO: 98 in the patient sample may then be compared, e.g., to the expression level of the biomarker of SEQ ID NO: 98 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 98 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-97, 99-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 99 may be used to assess the responsiveness of a cancer patient (e.g., a patient with cancer recurrence) to 2X-121 or a pharmaceutically acceptable salt thereof. The expression level of the biomarker of SEQ ID NO: 99 may be assessed using nucleic acid amplification methods (e.g., PCR) or a device (e.g., a microarray). As is described above, the expression level of the biomarker of SEQ ID NO: 99 in the patient sample may then be compared, e.g., to the expression level of the biomarker of SEQ ID NO: 99 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 99 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-98, 100-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 100 may be used to assess the responsiveness of a cancer patient (e.g., a patient with cancer recurrence) to 2X-121 or a pharmaceutically acceptable salt thereof. The expression level of the biomarker of SEQ ID NO: 100 may be assessed using nucleic acid amplification methods (e.g., PCR) or a device (e.g., a microarray). As is described above, the expression level of the biomarker of SEQ ID NO: 100 in the patient sample may then be compared, e.g., to the expression level of the biomarker of SEQ ID NO: 100 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 100 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-99, 101-414. The expression level of the biomarker(s) may be determined using, e.g., a microarray, PCR, or other techniques described herein, for example, using a nucleic acid probe sequence based on the target The biomarker of SEQ ID NO: 101 may be used to assess the responsiveness of a cancer patient (e.g., a patient with cancer recurrence) to 2X-121 or a pharmaceutically acceptable salt thereof. The expression level of the biomarker of SEQ ID NO: 101 may be assessed using nucleic acid amplification methods (e.g., PCR) or a device (e.g., a microarray). As is described above, the expression level of the biomarker of SEQ ID NO: 101 in the patient sample may then be compared, e.g., to the expression level of the biomarker of SEQ ID NO: 101 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 101 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-100, 102-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 102 may be used to assess the responsiveness of a cancer patient (e.g., a patient with cancer recurrence) to 2X-121 or a pharmaceutically acceptable salt thereof. The expression level of the biomarker of SEQ ID NO: 102 may be assessed using nucleic acid amplification methods (e.g., PCR) or a device (e.g., a microarray). As is described above, the expression level of the biomarker of SEQ ID NO: 102 in the patient sample may then be compared, e.g., to the expression level of the biomarker of SEQ ID NO: 102 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 102 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-101, 103-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 103 may be used to assess the responsiveness of a cancer patient (e.g., a patient with cancer recurrence) to 2X-121 or a pharmaceutically acceptable salt thereof. The expression level of the biomarker of SEQ ID NO: 103 may be assessed using nucleic acid amplification methods (e.g., PCR) or a device (e.g., a microarray). As is described above, the expression level of the biomarker of SEQ ID NO: 103 in the patient sample may then be compared, e.g., to the expression level of the biomarker of SEQ ID NO: 103 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 103 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-102, 104-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 104 may be used to assess the responsiveness of a cancer patient (e.g., a patient with cancer recurrence) to 2X-121 or a pharmaceutically acceptable salt thereof. The expression level of the biomarker of SEQ ID NO: 104 may be assessed using nucleic acid amplification methods (e.g., PCR) or a device (e.g., a microarray). As is described above, the expression level of the biomarker of SEQ ID NO: 104 in the patient sample may then be compared, e.g., to the expression level of the biomarker of SEQ ID NO: 104 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 104 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-103, 105-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 105 may be used to assess the responsiveness of a cancer patient (e.g., a patient with cancer recurrence) to 2X-121 or a pharmaceutically acceptable salt thereof. The expression level of the biomarker of SEQ ID NO: 105 may be assessed using nucleic acid amplification methods (e.g., PCR) or a device (e.g., a microarray). As is described above, the expression level of the biomarker of SEQ ID NO: 105 in the patient sample may then be compared, e.g., to the expression level of the biomarker of SEQ ID NO: 105 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 105 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-104, 106-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 106 may be used to assess the responsiveness of a cancer patient (e.g., a patient with cancer recurrence) to 2X-121 or a pharmaceutically acceptable salt thereof. The expression level of the biomarker of SEQ ID NO: 106 may be assessed using nucleic acid amplification methods (e.g., PCR) or a device (e.g., a microarray). As is described above, the expression level of the biomarker of SEQ ID NO: 106 in the patient sample may then be compared, e.g., to the expression level of the biomarker of SEQ ID NO: 106 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 106 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-105, 107-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 107 may be used to assess the responsiveness of a cancer patient (e.g., a patient with cancer recurrence) to 2X-121 or a pharmaceutically acceptable salt thereof. The expression level of the biomarker of SEQ ID NO: 107 may be assessed using nucleic acid amplification methods (e.g., PCR) or a device (e.g., a microarray). As is described above, the expression level of the biomarker of SEQ ID NO: 107 in the patient sample may then be compared, e.g., to the expression level of the biomarker of SEQ ID NO: 107 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 107 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-106, 108-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 108 may be used to assess the responsiveness of a cancer patient (e.g., a patient with cancer recurrence) to 2X-121 or a pharmaceutically acceptable salt thereof. The expression level of the biomarker of SEQ ID NO: 108 may be assessed using nucleic acid amplification methods (e.g., PCR) or a device (e.g., a microarray). As is described above, the expression level of the biomarker of SEQ ID NO: 108 in the patient sample may then be compared, e.g., to the expression level of the biomarker of SEQ ID NO: 108 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 108 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-107, 109-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 109 may be used to assess the responsiveness of a cancer patient (e.g., a patient with cancer recurrence) to 2X-121 or a pharmaceutically acceptable salt thereof. The expression level of the biomarker of SEQ ID NO: 109 may be assessed using nucleic acid amplification methods (e.g., PCR) or a device (e.g., a microarray). As is described above, the expression level of the biomarker of SEQ ID NO: 109 in the patient sample may then be compared, e.g., to the expression level of the biomarker of SEQ ID NO: 109 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 109 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-108, 110-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 110 may be used to assess the responsiveness of a cancer patient (e.g., a patient with cancer recurrence) to 2X-121 or a pharmaceutically acceptable salt thereof. The expression level of the biomarker of SEQ ID NO: 110 may be assessed using nucleic acid amplification methods (e.g., PCR) or a device (e.g., a microarray). As is described above, the expression level of the biomarker of SEQ ID NO: 110 in the patient sample may then be compared, e.g., to the expression level of the biomarker of SEQ ID NO: 110 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 110 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-109, 111-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 111 may be used to assess the responsiveness of a cancer patient (e.g., a patient with cancer recurrence) to 2X-121 or a pharmaceutically acceptable salt thereof. The expression level of the biomarker of SEQ ID NO: 111 may be assessed using nucleic acid amplification methods (e.g., PCR) or a device (e.g., a microarray). As is described above, the expression level of the biomarker of SEQ ID NO: 111 in the patient sample may then be compared, e.g., to the expression level of the biomarker of SEQ ID NO: 111 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 111 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-110, 112-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 112 may be used to assess the responsiveness of a cancer patient (e.g., a patient with cancer recurrence) to 2X-121 or a pharmaceutically acceptable salt thereof. The expression level of the biomarker of SEQ ID NO: 112 may be assessed using nucleic acid amplification methods (e.g., PCR) or a device (e.g., a microarray). As is described above, the expression level of the biomarker of SEQ ID NO: 112 in the patient sample may then be compared, e.g., to the expression level of the biomarker of SEQ ID NO: 112 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 112 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-111, 113-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 113 may be used to assess the responsiveness of a cancer patient (e.g., a patient with cancer recurrence) to 2X-121 or a pharmaceutically accept-able salt thereof. The expression level of the biomarker of SEQ ID NO: 113 may be assessed using nucleic acid amplification methods (e.g., PCR) or a device (e.g., a microarray). As is described above, the expression level of the biomarker of SEQ ID NO: 113 in the patient sample may then be compared, e.g., to the expression level of the biomarker of SEQ ID NO: 113 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 113 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-112, 114-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 114 may be used to assess the responsiveness of a cancer patient (e.g., a patient with cancer recurrence) to 2X-121 or a pharmaceutically accept-able salt thereof. The expression level of the biomarker of SEQ ID NO: 114 may be assessed using nucleic acid amplification methods (e.g., PCR) or a device (e.g., a microarray). As is described above, the expression level of the biomarker of SEQ ID NO: 114 in the patient sample may then be compared, e.g., to the expression level of the biomarker of SEQ ID NO: 114 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 114 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-113, 115-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 115 may be used to assess the responsiveness of a cancer patient (e.g., a patient with cancer recurrence) to 2X-121 or a pharmaceutically acceptable salt thereof. The expression level of the biomarker of SEQ ID NO: 115 may be assessed using nucleic acid amplification methods (e.g., PCR) or a device (e.g., a microarray). As is described above, the expression level of the biomarker of SEQ ID NO: 115 in the patient sample may then be compared, e.g., to the expression level of the biomarker of SEQ ID NO: 115 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 115 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-114, 116-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 116 may be used to assess the responsiveness of a cancer patient (e.g., a patient with cancer recurrence) to 2X-121 or a pharmaceutically acceptable salt thereof. The expression level of the biomarker of SEQ ID NO: 116 may be assessed using nucleic acid amplification methods (e.g., PCR) or a device (e.g., a microarray). As is described above, the expression level of the biomarker of SEQ ID NO: 116 in the patient sample may then be compared, e.g., to the expression level of the biomarker of SEQ ID NO: 116 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 116 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-115, 117-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 117 may be used to assess the responsiveness of a cancer patient (e.g., a patient with cancer recurrence) to 2X-121 or a pharmaceutically acceptable salt thereof. The expression level of the biomarker of SEQ ID NO: 117 may be assessed using nucleic acid amplification methods (e.g., PCR) or a device (e.g., a microarray). As is described above, the expression level of the biomarker of SEQ ID NO: 117 in the patient sample may then be compared, e.g., to the expression level of the biomarker of SEQ ID NO: 117 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 117 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-116, 118-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 118 may be used to assess the responsiveness of a cancer patient (e.g., a patient with cancer recurrence) to 2X-121 or a pharmaceutically acceptable salt thereof. The expression level of the biomarker of SEQ ID NO: 118 may be assessed using nucleic acid amplification methods (e.g., PCR) or a device (e.g., a microarray). As is described above, the expression level of the biomarker of SEQ ID NO: 118 in the patient sample may then be compared, e.g., to the expression level of the biomarker of SEQ ID NO: 118 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 118 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-117, 119-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 119 may be used to assess the responsiveness of a cancer patient (e.g., a patient with cancer recurrence) to 2X-121 or a pharmaceutically acceptable salt thereof. The expression level of the biomarker of SEQ ID NO: 119 may be assessed using nucleic acid amplification methods (e.g., PCR) or a device (e.g., a microarray). As is described above, the expression level of the biomarker of SEQ ID NO: 119 in the patient sample may then be compared, e.g., to the expression level of the biomarker of SEQ ID NO: 119 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 119 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-118, 120-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 120 may be used to assess the responsiveness of a cancer patient (e.g., a patient with cancer recurrence) to 2X-121 or a pharmaceutically acceptable salt thereof. The expression level of the biomarker of SEQ ID NO: 120 may be assessed using nucleic acid amplification methods (e.g., PCR) or a device (e.g., a microarray). As is described above, the expression level of the biomarker of SEQ ID NO: 120 in the patient sample may then be compared, e.g., to the expression level of the biomarker of SEQ ID NO: 120 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 120 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-119, 121-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 121 may be used to assess the responsiveness of a cancer patient (e.g., a patient with cancer recurrence) to 2X-121 or a pharmaceutically acceptable salt thereof. The expression level of the biomarker of SEQ ID NO: 121 may be assessed using nucleic acid amplification methods (e.g., PCR) or a device (e.g., a microarray). As is described above, the expression level of the biomarker of SEQ ID NO: 121 in the patient sample may then be compared, e.g., to the expression level of the biomarker of SEQ ID NO: 121 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 121 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-120, 122-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 122 may be used to assess the responsiveness of a cancer patient (e.g., a patient with cancer recurrence) to 2X-121 or a pharmaceutically acceptable salt thereof. The expression level of the biomarker of SEQ ID NO: 122 may be assessed using nucleic acid amplification methods (e.g., PCR) or a device (e.g., a microarray). As is described above, the expression level of the biomarker of SEQ ID NO: 122 in the patient sample may then be compared, e.g., to the expression level of the biomarker of SEQ ID NO: 122 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 122 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-121, 123-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 123 may be used to assess the responsiveness of a cancer patient (e.g., a patient with cancer recurrence) to 2X-121 or a pharmaceutically acceptable salt thereof. The expression level of the biomarker of SEQ ID NO: 123 may be assessed using nucleic acid amplification methods (e.g., PCR) or a device (e.g., a microarray). As is described above, the expression level of the biomarker of SEQ ID NO: 123 in the patient sample may then be compared, e.g., to the expression level of the biomarker of SEQ ID NO: 123 in a cell (e.g., a cancer cell)

or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 123 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-122, 124-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 124 may be used to assess the responsiveness of a cancer patient (e.g., a patient with cancer recurrence) to 2X-121 or a pharmaceutically acceptable salt thereof. The expression level of the biomarker of SEQ ID NO: 124 may be assessed using nucleic acid amplification methods (e.g., PCR) or a device (e.g., a microarray). As is described above, the expression level of the biomarker of SEQ ID NO: 124 in the patient sample may then be compared, e.g., to the expression level of the biomarker of SEQ ID NO: 124 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 124 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-123, 125-414. The expression level of the biomarker(s) may be determined using, e.g., a microarray, PCR, or other techniques described herein, for example, using a nucleic acid probe sequence based on the target The biomarker of SEQ ID NO: 125 may be used to assess the responsiveness of a cancer patient (e.g., a patient with cancer recurrence) to 2X-121 or a pharmaceutically acceptable salt thereof. The expression level of the biomarker of SEQ ID NO: 125 may be assessed using nucleic acid amplification methods (e.g., PCR) or a device (e.g., a microarray). As is described above, the expression level of the biomarker of SEQ ID NO: 125 in the patient sample may then be compared, e.g., to the expression level of the biomarker of SEQ ID NO: 125 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 125 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-124, 126-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 126 may be used to assess the responsiveness of a cancer patient (e.g., a patient with cancer recurrence) to 2X-121 or a pharmaceutically acceptable salt thereof. The expression level of the biomarker of SEQ ID NO: 126 may be assessed using nucleic acid amplification methods (e.g., PCR) or a device (e.g., a microarray). As is described above, the expression level of the biomarker of SEQ ID NO: 126 in the patient sample may then be compared, e.g., to the expression level of the biomarker of SEQ ID NO: 126 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 126 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-125, 127-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 127 may be used to assess the responsiveness of a cancer patient (e.g., a patient with cancer recurrence) to 2X-121 or a pharmaceutically acceptable salt thereof. The expression level of the biomarker of SEQ ID NO: 127 may be assessed using nucleic acid amplification methods (e.g., PCR) or a device (e.g., a microarray). As is described above, the expression level of the biomarker of SEQ ID NO: 127 in the patient sample may then be compared, e.g., to the expression level of the biomarker of SEQ ID NO: 127 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 127 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-126, 128-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 128 may be used to assess the responsiveness of a cancer patient (e.g., a patient with cancer recurrence) to 2X-121 or a pharmaceutically acceptable salt thereof. The expression level of the biomarker of SEQ ID NO: 128 may be assessed using nucleic acid amplification methods (e.g., PCR) or a device (e.g., a microarray). As is described above, the expression level of the biomarker of SEQ ID NO: 128 in the patient sample may then be compared, e.g., to the expression level of the biomarker of SEQ ID NO: 128 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 128 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-127, 129-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 129 may be used to assess the responsiveness of a cancer patient (e.g., a patient with cancer recurrence) to 2X-121 or a pharmaceutically acceptable salt thereof. The expression level of the biomarker of SEQ ID NO: 129 may be assessed using nucleic acid amplification methods (e.g., PCR) or a device (e.g., a microarray). As is described above, the expression level of the biomarker of SEQ ID NO: 129 in the patient sample may then be compared, e.g., to the expression level of the biomarker of SEQ ID NO: 129 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 129 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-128, 130-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 130 may be used to assess the responsiveness of a cancer patient (e.g., a patient with cancer recurrence) to 2X-121 or a pharmaceutically acceptable salt thereof. The expression level of the biomarker of SEQ ID NO: 130 may be assessed using nucleic acid amplification methods (e.g., PCR) or a device (e.g., a microarray). As is described above, the expression level of the biomarker of SEQ ID NO: 130 in the patient sample may then be compared, e.g., to the expression level of the biomarker of SEQ ID NO: 130 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 130 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-129, 131-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 131 may be used to assess the responsiveness of a cancer patient (e.g., a patient with cancer recurrence) to 2X-121 or a pharmaceutically acceptable salt thereof. The expression level of the biomarker of SEQ ID NO: 131 may be assessed using nucleic acid amplification methods (e.g., PCR) or a device (e.g., a microarray). As is described above, the expression level of the biomarker of SEQ ID NO: 131 in the patient sample may then be compared, e.g., to the expression level of the biomarker of SEQ ID NO: 131 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 131 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-130, 132-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 132 may be used to assess the responsiveness of a cancer patient (e.g., a patient with cancer recurrence) to 2X-121 or a pharmaceutically acceptable salt thereof. The expression level of the biomarker of SEQ ID NO: 132 may be assessed using nucleic acid amplification methods (e.g., PCR) or a device (e.g., a microarray). As is described above, the expression level of the biomarker of SEQ ID NO: 132 in the patient sample may then be compared, e.g., to the expression level of the biomarker of SEQ ID NO: 132 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 132 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-131, 133-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 133 may be used to assess the responsiveness of a cancer patient (e.g., a patient with cancer recurrence) to 2X-121 or a pharmaceutically acceptable salt thereof. The expression level of the biomarker of SEQ ID NO: 133 may be assessed using nucleic acid amplification methods (e.g., PCR) or a device (e.g., a microarray). As is described above, the expression level of the biomarker of SEQ ID NO: 133 in the patient sample may then be compared, e.g., to the expression level of the biomarker of SEQ ID NO: 133 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 133 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-132, 134-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 134 may be used to assess the responsiveness of a cancer patient (e.g., a patient with cancer recurrence) to 2X-121 or a pharmaceutically acceptable salt thereof. The expression level of the biomarker of SEQ ID NO: 134 may be assessed using nucleic acid amplification methods (e.g., PCR) or a device (e.g., a microarray). As is described above, the expression level of the biomarker of SEQ ID NO: 134 in the patient sample may then be compared, e.g., to the expression level of the biomarker of SEQ ID NO: 134 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 134 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-133, 135-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 135 may be used to assess the responsiveness of a cancer patient (e.g., a patient with cancer recurrence) to 2X-121 or a pharmaceutically acceptable salt thereof. The expression level of the biomarker of SEQ ID NO: 135 may be assessed using nucleic acid amplification methods (e.g., PCR) or a device (e.g., a microarray). As is described above, the expression level of the biomarker of SEQ ID NO: 135 in the patient sample may then be compared, e.g., to the expression level of the biomarker of SEQ ID NO: 135 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 135 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-134, 136-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 136 may be used to assess the responsiveness of a cancer patient (e.g., a patient with cancer recurrence) to 2X-121 or a pharmaceutically acceptable salt thereof. The expression level of the biomarker of SEQ ID NO: 136 may be assessed using nucleic acid amplification methods (e.g., PCR) or a device (e.g., a microarray). As is described above, the expression level of the biomarker of SEQ ID NO: 136 in the patient sample may then be compared, e.g., to the expression level of the biomarker of SEQ ID NO: 136 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 136 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-135, 137-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 137 may be used to assess the responsiveness of a cancer patient (e.g., a patient with cancer recurrence) to 2X-121 or a pharmaceutically acceptable salt thereof. The expression level of the biomarker of SEQ ID NO: 137 may be assessed using nucleic acid amplification methods (e.g., PCR) or a device (e.g., a microarray). As is described above, the expression level of the biomarker of SEQ ID NO: 137 in the patient sample may then be compared, e.g., to the expression level of the biomarker of SEQ ID NO: 137 in a cell (e.g., a cancer cell)

or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 137 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-136, 138-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 138 may be used to assess the responsiveness of a cancer patient (e.g., a patient with cancer recurrence) to 2X-121 or a pharmaceutically acceptable salt thereof. The expression level of the biomarker of SEQ ID NO: 138 may be assessed using nucleic acid amplification methods (e.g., PCR) or a device (e.g., a microarray). As is described above, the expression level of the biomarker of SEQ ID NO: 138 in the patient sample may then be compared, e.g., to the expression level of the biomarker of SEQ ID NO: 138 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 138 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-137, 139-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 139 may be used to assess the responsiveness of a cancer patient (e.g., a patient with cancer recurrence) to 2X-121 or a pharmaceutically acceptable salt thereof. The expression level of the biomarker of SEQ ID NO: 139 may be assessed using nucleic acid amplification methods (e.g., PCR) or a device (e.g., a microarray). As is described above, the expression level of the biomarker of SEQ ID NO: 139 in the patient sample may then be compared, e.g., to the expression level of the biomarker of SEQ ID NO: 139 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 139 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-138, 140-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 140 may be used to assess the responsiveness of a cancer patient (e.g., a patient with cancer recurrence) to 2X-121 or a pharmaceutically accept- able salt thereof. The expression level of the biomarker of SEQ ID NO: 140 may be assessed using nucleic acid amplification methods (e.g., PCR) or a device (e.g., a microarray). As is described above, the expression level of the biomarker of SEQ ID NO: 140 in the patient sample may then be compared, e.g., to the expression level of the biomarker of SEQ ID NO: 140 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 140 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-139, 141-414. The expres- sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 141 may be used to assess the responsiveness of a cancer patient (e.g., a patient with cancer recurrence) to 2X-121 or a pharmaceutically accept- able salt thereof. The expression level of the biomarker of SEQ ID NO: 141 may be assessed using nucleic acid amplification methods (e.g., PCR) or a device (e.g., a microarray). As is described above, the expression level of the biomarker of SEQ ID NO: 141 in the patient sample may then be compared, e.g., to the expression level of the biomarker of SEQ ID NO: 141 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 141 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-140, 142-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 142 may be used to assess the responsiveness of a cancer patient (e.g., a patient with cancer recurrence) to 2X-121 or a pharmaceutically accept- able salt thereof. The expression level of the biomarker of SEQ ID NO: 142 may be assessed using nucleic acid amplification methods (e.g., PCR) or a device (e.g., a microarray). As is described above, the expression level of the biomarker of SEQ ID NO: 142 in the patient sample may then be compared, e.g., to the expression level of the biomarker of SEQ ID NO: 142 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 142 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-141, 143-414. The expres- sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 143 may be used to assess the responsiveness of a cancer patient (e.g., a patient with cancer recurrence) to 2X-121 or a pharmaceutically accept- able salt thereof. The expression level of the biomarker of SEQ ID NO: 143 may be assessed using nucleic acid amplification methods (e.g., PCR) or a device (e.g., a microarray). As is described above, the expression level of the biomarker of SEQ ID NO: 143 in the patient sample may then be compared, e.g., to the expression level of the biomarker of SEQ ID NO: 143 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 143 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-142, 144-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 144 may be used to assess the responsiveness of a cancer patient (e.g., a patient with cancer recurrence) to 2X-121 or a pharmaceutically acceptable salt thereof. The expression level of the biomarker of SEQ ID NO: 144 may be assessed using nucleic acid amplification methods (e.g., PCR) or a device (e.g., a microarray). As is described above, the expression level of the biomarker of SEQ ID NO: 144 in the patient sample may then be compared, e.g., to the expression level of the biomarker of SEQ ID NO: 144 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 144 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-143, 145-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 145 may be used to assess the responsiveness of a cancer patient (e.g., a patient with cancer recurrence) to 2X-121 or a pharmaceutically acceptable salt thereof. The expression level of the biomarker of SEQ ID NO: 145 may be assessed using nucleic acid amplification methods (e.g., PCR) or a device (e.g., a microarray). As is described above, the expression level of the biomarker of SEQ ID NO: 145 in the patient sample may then be compared, e.g., to the expression level of the biomarker of SEQ ID NO: 145 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 145 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-144, 146-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 146 may be used to assess the responsiveness of a cancer patient (e.g., a patient with cancer recurrence) to 2X-121 or a pharmaceutically acceptable salt thereof. The expression level of the biomarker of SEQ ID NO: 146 may be assessed using nucleic acid amplification methods (e.g., PCR) or a device (e.g., a microarray). As is described above, the expression level of the biomarker of SEQ ID NO: 146 in the patient sample may then be compared, e.g., to the expression level of the biomarker of SEQ ID NO: 146 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 146 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-145, 147-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 147 may be used to assess the responsiveness of a cancer patient (e.g., a patient with cancer recurrence) to 2X-121 or a pharmaceutically acceptable salt thereof. The expression level of the biomarker of SEQ ID NO: 147 may be assessed using nucleic acid amplification methods (e.g., PCR) or a device (e.g., a microarray). As is described above, the expression level of the biomarker of SEQ ID NO: 147 in the patient sample may then be compared, e.g., to the expression level of the biomarker of SEQ ID NO: 147 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 147 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-146, 148-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 149 may be used to assess the responsiveness of a cancer patient (e.g., a patient with cancer recurrence) to 2X-121 or a pharmaceutically acceptable salt thereof. The expression level of the biomarker of SEQ ID NO: 149 may be assessed using nucleic acid amplification methods (e.g., PCR) or a device (e.g., a microarray). As is described above, the expression level of the biomarker of SEQ ID NO: 149 in the patient sample may then be compared, e.g., to the expression level of the biomarker of SEQ ID NO: 149 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 149 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-148, 150-414. The expression level of the biomarker(s) may be determined using, e.g., a microarray, PCR, or other techniques described herein, for example, using a nucleic acid probe sequence based on the target The biomarker of SEQ ID NO: 150 may be used to assess the responsiveness of a cancer patient (e.g., a patient with cancer recurrence) to 2X-121 or a pharmaceutically acceptable salt thereof. The expression level of the biomarker of SEQ ID NO: 150 may be assessed using nucleic acid amplification methods (e.g., PCR) or a device (e.g., a microarray). As is described above, the expression level of the biomarker of SEQ ID NO: 150 in the patient sample may then be compared, e.g., to the expression level of the biomarker of SEQ ID NO: 150 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 150 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-149, 151-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 151 may be used to assess the responsiveness of a cancer patient (e.g., a patient with cancer recurrence) to 2X-121 or a pharmaceutically acceptable salt thereof. The expression level of the biomarker of SEQ ID NO: 151 may be assessed using nucleic acid amplification methods (e.g., PCR) or a device (e.g., a microarray). As is described above, the expression level of the biomarker of SEQ ID NO: 151 in the patient sample may then be compared, e.g., to the expression level of the biomarker of SEQ ID NO: 151 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 151 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-150, 152-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 152 may be used to assess the responsiveness of a cancer patient (e.g., a patient with cancer recurrence) to 2X-121 or a pharmaceutically acceptable salt thereof. The expression level of the biomarker of SEQ ID NO: 152 may be assessed using nucleic acid amplification methods (e.g., PCR) or a device (e.g., a microarray). As is described above, the expression level of the biomarker of SEQ ID NO: 152 in the patient sample may then be compared, e.g., to the expression level of the biomarker of SEQ ID NO: 152 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 152 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker (s) of SEQ ID NOs: 1-151, 153-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 153 may be used to assess the responsiveness of a cancer patient (e.g., a patient with cancer recurrence) to 2X-121 or a pharmaceutically acceptable salt thereof. The expression level of the biomarker of SEQ ID NO: 153 may be assessed using nucleic acid amplification methods (e.g., PCR) or a device (e.g., a microarray). As is described above, the expression level of the biomarker of SEQ ID NO: 153 in the patient sample may then be compared, e.g., to the expression level of the biomarker of SEQ ID NO: 153 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 153 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-152, 154-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 155 may be used to assess the responsiveness of a cancer patient (e.g., a patient with cancer recurrence) to 2X-121 or a pharmaceutically acceptable salt thereof. The expression level of the biomarker of SEQ ID NO: 155 may be assessed using nucleic acid amplification methods (e.g., PCR) or a device (e.g., a microarray). As is described above, the expression level of the biomarker of SEQ ID NO: 155 in the patient sample may then be compared, e.g., to the expression level of the biomarker of SEQ ID NO: 155 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 155 may be used alone to predict responsiveness of the cancer patient to treatment with 2X-121 or a pharmaceutically acceptable salt thereof or in combination with one or more additional biomarker(s)

(e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-154, 156-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 156 may be used to assess the responsiveness of a cancer patient (e.g., a patient with cancer recurrence) to 2X-121 or a pharmaceutically acceptable salt thereof. The expression level of the biomarker of SEQ ID NO: 156 may be assessed using nucleic acid amplification methods (e.g., PCR) or a device (e.g., a microarray). As is described above, the expression level of the biomarker of SEQ ID NO: 156 in the patient sample may then be compared, e.g., to the expression level of the biomarker of SEQ ID NO: 156 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 156 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-155, 157-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 157 may be used to assess the responsiveness of a cancer patient (e.g., a patient with cancer recurrence) to 2X-121 or a pharmaceutically acceptable salt thereof. The expression level of the biomarker of SEQ ID NO: 157 may be assessed using nucleic acid amplification methods (e.g., PCR) or a device (e.g., a microarray). As is described above, the expression level of the biomarker of SEQ ID NO: 157 in the patient sample may then be compared, e.g., to the expression level of the biomarker of SEQ ID NO: 157 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 157 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker (s) of SEQ ID NOs: 1-156, 158-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 158 may be used to assess the responsiveness of a cancer patient (e.g., a patient with cancer recurrence) to 2X-121 or a pharmaceutically acceptable salt thereof. The expression level of the biomarker of SEQ ID NO: 158 may be assessed using nucleic acid amplification methods (e.g., PCR) or a device (e.g., a microarray). As is described above, the expression level of the biomarker of SEQ ID NO: 158 in the patient sample may then be compared, e.g., to the expression level of the biomarker of SEQ ID NO: 158 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 158 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-157, 159-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 159 may be used to assess the responsiveness of a cancer patient (e.g., a patient with cancer recurrence) to 2X-121 or a pharmaceutically acceptable salt thereof. The expression level of the biomarker of SEQ ID NO: 159 may be assessed using nucleic acid amplification methods (e.g., PCR) or a device (e.g., a microarray). As is described above, the expression level of the biomarker of SEQ ID NO: 159 in the patient sample may then be compared, e.g., to the expression level of the biomarker of SEQ ID NO: 159 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 159 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-158, 160-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 160 may be used to assess the responsiveness of a cancer patient (e.g., a patient with cancer recurrence) to 2X-121 or a pharmaceutically acceptable salt thereof. The expression level of the biomarker of SEQ ID NO: 160 may be assessed using nucleic acid amplification methods (e.g., PCR) or a device (e.g., a microarray). As is described above, the expression level of the biomarker of SEQ ID NO: 160 in the patient sample may then be compared, e.g., to the expression level of the biomarker of SEQ ID NO: 160 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 160 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-159, 161-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 161 may be used to assess the responsiveness of a cancer patient (e.g., a patient with cancer recurrence) to 2X-121 or a pharmaceutically acceptable salt thereof. The expression level of the biomarker of SEQ ID NO: 161 may be assessed using nucleic acid amplification methods (e.g., PCR) or a device (e.g., a microarray). As is described above, the expression level of the biomarker of SEQ ID NO: 161 in the patient sample may then be compared, e.g., to the expression level of the biomarker of SEQ ID NO: 161 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 161 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-160, 162-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 162 may be used to assess the responsiveness of a cancer patient (e.g., a patient with cancer recurrence) to 2X-121 or a pharmaceutically acceptable salt thereof. The expression level of the biomarker of SEQ ID NO: 162 may be assessed using nucleic acid amplification methods (e.g., PCR) or a device (e.g., a microarray). As is described above, the expression level of the biomarker of SEQ ID NO: 162 in the patient sample may then be compared, e.g., to the expression level of the biomarker of SEQ ID NO: 162 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 162 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-161, 163-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 163 may be used to assess the responsiveness of a cancer patient (e.g., a patient with cancer recurrence) to 2X-121 or a pharmaceutically acceptable salt thereof. The expression level of the biomarker of SEQ ID NO: 163 may be assessed using nucleic acid amplification methods (e.g., PCR) or a device (e.g., a microarray). As is described above, the expression level of the biomarker of SEQ ID NO: 163 in the patient sample may then be compared, e.g., to the expression level of the biomarker of SEQ ID NO: 163 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 163 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-162, 164-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 164 may be used to assess the responsiveness of a cancer patient (e.g., a patient with cancer recurrence) to 2X-121 or a pharmaceutically acceptable salt thereof. The expression level of the biomarker of SEQ ID NO: 164 may be assessed using nucleic acid amplification methods (e.g., PCR) or a device (e.g., a microarray). As is described above, the expression level of the biomarker of SEQ ID NO: 164 in the patient sample may then be compared, e.g., to the expression level of the biomarker of SEQ ID NO: 164 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 164 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-163, 165-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 165 may be used to assess the responsiveness of a cancer patient (e.g., a patient with cancer recurrence) to 2X-121 or a pharmaceutically acceptable salt thereof. The expression level of the biomarker of SEQ ID NO: 165 may be assessed using nucleic acid amplification methods (e.g., PCR) or a device (e.g., a microarray). As is described above, the expression level of the biomarker of SEQ ID NO: 165 in the patient sample may then be compared, e.g., to the expression level of the biomarker of SEQ ID NO: 165 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 165 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-164, 166-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 166 may be used to assess the responsiveness of a cancer patient (e.g., a patient with cancer recurrence) to 2X-121 or a pharmaceutically acceptable salt thereof. The expression level of the biomarker of SEQ ID NO: 166 may be assessed using nucleic acid amplification methods (e.g., PCR) or a device (e.g., a microarray). As is described above, the expression level of the biomarker of SEQ ID NO: 166 in the patient sample may then be compared, e.g., to the expression level of the biomarker of SEQ ID NO: 166 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 166 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-165, 167-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 167 may be used to assess the responsiveness of a cancer patient (e.g., a patient with cancer recurrence) to 2X-121 or a pharmaceutically acceptable salt thereof. The expression level of the biomarker of SEQ ID NO: 167 may be assessed using nucleic acid amplification methods (e.g., PCR) or a device (e.g., a microarray). As is described above, the expression level of the biomarker of SEQ ID NO: 167 in the patient sample may then be compared, e.g., to the expression level of the biomarker of SEQ ID NO: 167 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 167 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-166, 168-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 168 may be used to assess the responsiveness of a cancer patient (e.g., a patient with cancer recurrence) to 2X-121 or a pharmaceutically acceptable salt thereof. The expression level of the biomarker of SEQ ID NO: 168 may be assessed using nucleic acid amplification methods (e.g., PCR) or a device (e.g., a microarray). As is described above, the expression level of the biomarker of SEQ ID NO: 168 in the patient sample may then be compared, e.g., to the expression level of the biomarker of SEQ ID NO: 168 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 168 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-167, 169-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 169 may be used to assess the responsiveness of a cancer patient (e.g., a patient with cancer recurrence) to 2X-121 or a pharmaceutically acceptable salt thereof. The expression level of the biomarker of SEQ ID NO: 169 may be assessed using nucleic acid amplification methods (e.g., PCR) or a device (e.g., a microarray). As is described above, the expression level of the biomarker of SEQ ID NO: 169 in the patient sample may then be compared, e.g., to the expression level of the biomarker of SEQ ID NO: 169 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 169 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-168, 170-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 170 may be used to assess the responsiveness of a cancer patient (e.g., a patient with cancer recurrence) to 2X-121 or a pharmaceutically acceptable salt thereof. The expression level of the biomarker of SEQ ID NO: 170 may be assessed using nucleic acid amplification methods (e.g., PCR) or a device (e.g., a microarray). As is described above, the expression level of the biomarker of SEQ ID NO: 170 in the patient sample may then be compared, e.g., to the expression level of the biomarker of SEQ ID NO: 170 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 170 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-169, 171-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 171 may be used to assess the responsiveness of a cancer patient (e.g., a patient with cancer recurrence) to 2X-121 or a pharmaceutically acceptable salt thereof. The expression level of the biomarker of SEQ ID NO: 171 may be assessed using nucleic acid amplification methods (e.g., PCR) or a device (e.g., a microarray). As is described above, the expression level of the biomarker of SEQ ID NO: 171 in the patient sample may then be compared, e.g., to the expression level of the biomarker of SEQ ID NO: 171 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 171 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-170, 172-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 172 may be used to assess the responsiveness of a cancer patient (e.g., a patient with cancer recurrence) to 2X-121 or a pharmaceutically acceptable salt thereof. The expression level of the biomarker of SEQ ID NO: 172 may be assessed using nucleic acid amplification methods (e.g., PCR) or a device (e.g., a microarray). As is described above, the expression level of the biomarker of SEQ ID NO: 172 in the patient sample may then be compared, e.g., to the expression level of the biomarker of SEQ ID NO: 172 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 172 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-171, 173-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 173 may be used to assess the responsiveness of a cancer patient (e.g., a patient with cancer recurrence) to 2X-121 or a pharmaceutically acceptable salt thereof. The expression level of the biomarker of SEQ ID NO: 173 may be assessed using nucleic acid amplification methods (e.g., PCR) or a device (e.g., a microarray). As is described above, the expression level of the biomarker of SEQ ID NO: 173 in the patient sample may then be compared, e.g., to the expression level of the biomarker of SEQ ID NO: 173 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 173 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-172, 174-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 174 may be used to assess the responsiveness of a cancer patient (e.g., a patient with cancer recurrence) to 2X-121 or a pharmaceutically acceptable salt thereof. The expression level of the biomarker of SEQ ID NO: 174 may be assessed using nucleic acid amplification methods (e.g., PCR) or a device (e.g., a microarray). As is described above, the expression level of the biomarker of SEQ ID NO: 174 in the patient sample may then be compared, e.g., to the expression level of the biomarker of SEQ ID NO: 174 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 174 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-173, 175-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 175 may be used to assess the responsiveness of a cancer patient (e.g., a patient with cancer recurrence) to 2X-121 or a pharmaceutically acceptable salt thereof. The expression level of the biomarker of SEQ ID NO: 175 may be assessed using nucleic acid amplification methods (e.g., PCR) or a device (e.g., a microarray). As is described above, the expression level of the biomarker of SEQ ID NO: 175 in the patient sample may then be compared, e.g., to the expression level of the biomarker of SEQ ID NO: 175 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 175 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-174, 176-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 176 may be used to assess the responsiveness of a cancer patient (e.g., a patient with cancer recurrence) to 2X-121 or a pharmaceutically acceptable salt thereof. The expression level of the biomarker of SEQ ID NO: 176 may be assessed using nucleic acid amplification methods (e.g., PCR) or a device (e.g., a microarray). As is described above, the expression level of the biomarker of SEQ ID NO: 176 in the patient sample may then be compared, e.g., to the expression level of the biomarker of SEQ ID NO: 176 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 176 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-175, 177-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 177 may be used to assess the responsiveness of a cancer patient (e.g., a patient with cancer recurrence) to 2X-121 or a pharmaceutically acceptable salt thereof. The expression level of the biomarker of SEQ ID NO: 177 may be assessed using nucleic acid amplification methods (e.g., PCR) or a device (e.g., a microarray). As is described above, the expression level of the biomarker of SEQ ID NO: 177 in the patient sample may then be compared, e.g., to the expression level of the biomarker of SEQ ID NO: 177 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 177 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-176, 178-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 178 may be used to assess the responsiveness of a cancer patient (e.g., a patient with cancer recurrence) to 2X-121 or a pharmaceutically acceptable salt thereof. The expression level of the biomarker of SEQ ID NO: 178 may be assessed using nucleic acid amplification methods (e.g., PCR) or a device (e.g., a microarray). As is described above, the expression level of the biomarker of SEQ ID NO: 178 in the patient sample may then be compared, e.g., to the expression level of the biomarker of SEQ ID NO: 178 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 178 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-177, 179-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 179 may be used to assess the responsiveness of a cancer patient (e.g., a patient with cancer recurrence) to 2X-121 or a pharmaceutically acceptable salt thereof. The expression level of the biomarker of SEQ ID NO: 179 may be assessed using nucleic acid amplification methods (e.g., PCR) or a device (e.g., a microarray). As is described above, the expression level of the biomarker of SEQ ID NO: 179 in the patient sample may then be compared, e.g., to the expression level of the biomarker of SEQ ID NO: 179 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 179 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-178, 180-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 180 may be used to assess the responsiveness of a cancer patient (e.g., a patient with cancer recurrence) to 2X-121 or a pharmaceutically acceptable salt thereof. The expression level of the biomarker of SEQ ID NO: 180 may be assessed using nucleic acid amplification methods (e.g., PCR) or a device (e.g., a microarray). As is described above, the expression level of the biomarker of SEQ ID NO: 180 in the patient sample may then be compared, e.g., to the expression level of the biomarker of SEQ ID NO: 180 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 180 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-179, 181-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 181 may be used to assess the responsiveness of a cancer patient (e.g., a patient with cancer recurrence) to 2X-121 or a pharmaceutically acceptable salt thereof. The expression level of the biomarker of SEQ ID NO: 181 may be assessed using nucleic acid amplification methods (e.g., PCR) or a device (e.g., a microarray). As is described above, the expression level of the biomarker of SEQ ID NO: 181 in the patient sample may then be compared, e.g., to the expression level of the biomarker of SEQ ID NO: 181 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 181 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-180, 182-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 182 may be used to assess the responsiveness of a cancer patient (e.g., a patient with cancer recurrence) to 2X-121 or a pharmaceutically accept-able salt thereof. The expression level of the biomarker of SEQ ID NO: 182 may be assessed using nucleic acid amplification methods (e.g., PCR) or a device (e.g., a microarray). As is described above, the expression level of the biomarker of SEQ ID NO: 182 in the patient sample may then be compared, e.g., to the expression level of the biomarker of SEQ ID NO: 182 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 182 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-181, 183-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 183 may be used to assess the responsiveness of a cancer patient (e.g., a patient with cancer recurrence) to 2X-121 or a pharmaceutically accept-able salt thereof. The expression level of the biomarker of SEQ ID NO: 183 may be assessed using nucleic acid amplification methods (e.g., PCR) or a device (e.g., a microarray). As is described above, the expression level of the biomarker of SEQ ID NO: 183 in the patient sample may then be compared, e.g., to the expression level of the biomarker of SEQ ID NO: 183 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 183 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-182, 184-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 184 may be used to assess the responsiveness of a cancer patient (e.g., a patient with cancer recurrence) to 2X-121 or a pharmaceutically accept-able salt thereof. The expression level of the biomarker of SEQ ID NO: 184 may be assessed using nucleic acid amplification methods (e.g., PCR) or a device (e.g., a microarray). As is described above, the expression level of the biomarker of SEQ ID NO: 184 in the patient sample may then be compared, e.g., to the expression level of the biomarker of SEQ ID NO: 184 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 184 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-183, 185-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 185 may be used to assess the responsiveness of a cancer patient (e.g., a patient with cancer recurrence) to 2X-121 or a pharmaceutically accept-able salt thereof. The expression level of the biomarker of SEQ ID NO: 185 may be assessed using nucleic acid amplification methods (e.g., PCR) or a device (e.g., a microarray). As is described above, the expression level of the biomarker of SEQ ID NO: 185 in the patient sample may then be compared, e.g., to the expression level of the biomarker of SEQ ID NO: 185 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 185 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-184, 186-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 186 may be used to assess the responsiveness of a cancer patient (e.g., a patient with cancer recurrence) to 2X-121 or a pharmaceutically acceptable salt thereof. The expression level of the biomarker of SEQ ID NO: 186 may be assessed using nucleic acid amplification methods (e.g., PCR) or a device (e.g., a microarray). As is described above, the expression level of the biomarker of SEQ ID NO: 186 in the patient sample may then be compared, e.g., to the expression level of the biomarker of SEQ ID NO: 186 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 186 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-185, 187-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 187 may be used to assess the responsiveness of a cancer patient (e.g., a patient with cancer recurrence) to 2X-121 or a pharmaceutically acceptable salt thereof. The expression level of the biomarker of SEQ ID NO: 187 may be assessed using nucleic acid amplification methods (e.g., PCR) or a device (e.g., a microarray). As is described above, the expression level of the biomarker of SEQ ID NO: 187 in the patient sample may then be compared, e.g., to the expression level of the biomarker of SEQ ID NO: 187 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 187 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-186, 188-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 188 may be used to assess the responsiveness of a cancer patient (e.g., a patient with cancer recurrence) to 2X-121 or a pharmaceutically acceptable salt thereof. The expression level of the biomarker of SEQ ID NO: 188 may be assessed using nucleic acid amplification methods (e.g., PCR) or a device (e.g., a microarray). As is described above, the expression level of the biomarker of SEQ ID NO: 188 in the patient sample may then be compared, e.g., to the expression level of the biomarker of SEQ ID NO: 188 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 188 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-187, 189-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 189 may be used to assess the responsiveness of a cancer patient (e.g., a patient with cancer recurrence) to 2X-121 or a pharmaceutically acceptable salt thereof. The expression level of the biomarker of SEQ ID NO: 189 may be assessed using nucleic acid amplification methods (e.g., PCR) or a device (e.g., a microarray). As is described above, the expression level of the biomarker of SEQ ID NO: 189 in the patient sample may then be compared, e.g., to the expression level of the biomarker of SEQ ID NO: 189 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 189 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-188, 190-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 190 may be used to assess the responsiveness of a cancer patient (e.g., a patient with cancer recurrence) to 2X-121 or a pharmaceutically acceptable salt thereof. The expression level of the biomarker of SEQ ID NO: 190 may be assessed using nucleic acid amplification methods (e.g., PCR) or a device (e.g., a microarray). As is described above, the expression level of the biomarker of SEQ ID NO: 190 in the patient sample may then be compared, e.g., to the expression level of the biomarker of SEQ ID NO: 190 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 190 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-189, 191-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 191 may be used to assess the responsiveness of a cancer patient (e.g., a patient with cancer recurrence) to 2X-121 or a pharmaceutically acceptable salt thereof. The expression level of the biomarker of SEQ ID NO: 191 may be assessed using nucleic acid amplification methods (e.g., PCR) or a device (e.g., a microarray). As is described above, the expression level of the biomarker of SEQ ID NO: 191 in the patient sample may then be compared, e.g., to the expression level of the biomarker of SEQ ID NO: 191 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 191 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-190, 192-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 192 may be used to assess the responsiveness of a cancer patient (e.g., a patient with cancer recurrence) to 2X-121 or a pharmaceutically acceptable salt thereof. The expression level of the biomarker of SEQ ID NO: 192 may be assessed using nucleic acid amplification methods (e.g., PCR) or a device (e.g., a microarray). As is described above, the expression level of the biomarker of SEQ ID NO: 192 in the patient sample may then be compared, e.g., to the expression level of the biomarker of SEQ ID NO: 192 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 192 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-191, 193-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 193 may be used to assess the responsiveness of a cancer patient (e.g., a patient with cancer recurrence) to 2X-121 or a pharmaceutically acceptable salt thereof. The expression level of the biomarker of SEQ ID NO: 193 may be assessed using nucleic acid amplification methods (e.g., PCR) or a device (e.g., a microarray). As is described above, the expression level of the biomarker of SEQ ID NO: 193 in the patient sample may then be compared, e.g., to the expression level of the biomarker of SEQ ID NO: 193 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 193 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-192, 194-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 194 may be used to assess the responsiveness of a cancer patient (e.g., a patient with cancer recurrence) to 2X-121 or a pharmaceutically acceptable salt thereof. The expression level of the biomarker of SEQ ID NO: 194 may be assessed using nucleic acid amplification methods (e.g., PCR) or a device (e.g., a microarray). As is described above, the expression level of the biomarker of SEQ ID NO: 194 in the patient sample may then be compared, e.g., to the expression level of the biomarker of SEQ ID NO: 194 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 194 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-193, 195-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 195 may be used to assess the responsiveness of a cancer patient (e.g., a patient with cancer recurrence) to 2X-121 or a pharmaceutically acceptable salt thereof. The expression level of the biomarker of SEQ ID NO: 195 may be assessed using nucleic acid amplification methods (e.g., PCR) or a device (e.g., a microarray). As is described above, the expression level of the biomarker of SEQ ID NO: 195 in the patient sample may then be compared, e.g., to the expression level of the biomarker of SEQ ID NO: 195 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 195 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-194, 196-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 196 may be used to assess the responsiveness of a cancer patient (e.g., a patient with cancer recurrence) to 2X-121 or a pharmaceutically acceptable salt thereof. The expression level of the biomarker of SEQ ID NO: 196 may be assessed using nucleic acid amplification methods (e.g., PCR) or a device (e.g., a microarray). As is described above, the expression level of the biomarker of SEQ ID NO: 196 in the patient sample may then be compared, e.g., to the expression level of the biomarker of SEQ ID NO: 196 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 196 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-195, 197-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 197 may be used to assess the responsiveness of a cancer patient (e.g., a patient with cancer recurrence) to 2X-121 or a pharmaceutically acceptable salt thereof. The expression level of the biomarker of SEQ ID NO: 197 may be assessed using nucleic acid amplification methods (e.g., PCR) or a device (e.g., a microarray). As is described above, the expression level of the biomarker of SEQ ID NO: 197 in the patient sample may then be compared, e.g., to the expression level of the biomarker of SEQ ID NO: 197 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 197 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-196, 198-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 198 may be used to assess the responsiveness of a cancer patient (e.g., a patient with cancer recurrence) to 2X-121 or a pharmaceutically acceptable salt thereof. The expression level of the biomarker of SEQ ID NO: 198 may be assessed using nucleic acid amplification methods (e.g., PCR) or a device (e.g., a microarray). As is described above, the expression level of the biomarker of SEQ ID NO: 198 in the patient sample may then be compared, e.g., to the expression level of the biomarker of SEQ ID NO: 198 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 198 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-197, 199-414. The expression level of the biomarker(s) may be determined using, e.g., a microarray, PCR, or other techniques described herein, for example, using a nucleic acid probe sequence based on the target The biomarker of SEQ ID NO: 199 may be used to assess the responsiveness of a cancer patient (e.g., a patient with cancer recurrence) to 2X-121 or a pharmaceutically acceptable salt thereof. The expression level of the biomarker of SEQ ID NO: 199 may be assessed using nucleic acid amplification methods (e.g., PCR) or a device (e.g., a microarray). As is described above, the expression level of the biomarker of SEQ ID NO: 199 in the patient sample may then be compared, e.g., to the expression level of the biomarker of SEQ ID NO: 199 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 199 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-198, 200-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 200 may be used to assess the responsiveness of a cancer patient (e.g., a patient with cancer recurrence) to 2X-121 or a pharmaceutically acceptable salt thereof. The expression level of the biomarker of SEQ ID NO: 200 may be assessed using nucleic acid amplification methods (e.g., PCR) or a device (e.g., a microarray). As is described above, the expression level of the biomarker of SEQ ID NO: 200 in the patient sample may then be compared, e.g., to the expression level of the biomarker of SEQ ID NO: 200 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 200 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-199, 201-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 201 may be used to assess the responsiveness of a cancer patient (e.g., a patient with cancer recurrence) to 2X-121 or a pharmaceutically acceptable salt thereof. The expression level of the biomarker of SEQ ID NO: 201 may be assessed using nucleic acid amplification methods (e.g., PCR) or a device (e.g., a microarray). As is described above, the expression level of the biomarker of SEQ ID NO: 201 in the patient sample may then be compared, e.g., to the expression level of the biomarker of SEQ ID NO: 201 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 201 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-200, 202-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 202 may be used to assess the responsiveness of a cancer patient (e.g., a patient with cancer recurrence) to 2X-121 or a pharmaceutically acceptable salt thereof. The expression level of the biomarker of SEQ ID NO: 202 may be assessed using nucleic acid amplification methods (e.g., PCR) or a device (e.g., a microarray). As is described above, the expression level of the biomarker of SEQ ID NO: 202 in the patient sample may then be compared, e.g., to the expression level of the biomarker of SEQ ID NO: 202 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 202 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-201, 203-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 203 may be used to assess the responsiveness of a cancer patient (e.g., a patient with cancer recurrence) to 2X-121 or a pharmaceutically acceptable salt thereof. The expression level of the biomarker of SEQ ID NO: 203 may be assessed using nucleic acid amplification methods (e.g., PCR) or a device (e.g., a microarray). As is described above, the expression level of the biomarker of SEQ ID NO: 203 in the patient sample may then be compared, e.g., to the expression level of the biomarker of SEQ ID NO: 203 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 203 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio-markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-202, 204-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 204 may be used to assess the responsiveness of a cancer patient (e.g., a patient with cancer recurrence) to 2X-121 or a pharmaceutically acceptable salt thereof. The expression level of the biomarker of SEQ ID NO: 204 may be assessed using nucleic acid amplification methods (e.g., PCR) or a device (e.g., a microarray). As is described above, the expression level of the biomarker of SEQ ID NO: 204 in the patient sample may then be compared, e.g., to the expression level of the biomarker of SEQ ID NO: 204 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 204 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-203, 205-414. The expression level of the bio-marker(s) may be determined using, e.g., a microarray, PCR, or other techniques described herein, for example, using a nucleic acid probe sequence based on the target sequences shown in Tables 2 and 3.

The biomarker of SEQ ID NO: 205 may be used to assess the responsiveness of a cancer patient (e.g., a patient with cancer recurrence) to 2X-121 or a pharmaceutically acceptable salt thereof. The expression level of the biomarker of SEQ ID NO: 205 may be assessed using nucleic acid amplification methods (e.g., PCR) or a device (e.g., a microarray). As is described above, the expression level of the biomarker of SEQ ID NO: 205 in the patient sample may then be compared, e.g., to the expression level of the biomarker of SEQ ID NO: 205 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 205 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-204, 206-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 206 may be used to assess the responsiveness of a cancer patient (e.g., a patient with cancer recurrence) to 2X-121 or a pharmaceutically acceptable salt thereof. The expression level of the biomarker of SEQ ID NO: 206 may be assessed using nucleic acid amplification methods (e.g., PCR) or a device (e.g., a microarray). As is described above, the expression level of the biomarker of SEQ ID NO: 206 in the patient sample may then be compared, e.g., to the expression level of the biomarker of SEQ ID NO: 206 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 206 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-205, 207-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 207 may be used to assess the responsiveness of a cancer patient (e.g., a patient with cancer recurrence) to 2X-121 or a pharmaceutically acceptable salt thereof. The expression level of the biomarker of SEQ ID NO: 207 may be assessed using nucleic acid amplification methods (e.g., PCR) or a device (e.g., a microarray). As is described above, the expression level of the biomarker of SEQ ID NO: 207 in the patient sample may then be compared, e.g., to the expression level of the biomarker of SEQ ID NO: 207 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 207 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-206, 208-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 208 may be used to assess the responsiveness of a cancer patient (e.g., a patient with cancer recurrence) to 2X-121 or a pharmaceutically acceptable salt thereof. The expression level of the biomarker of SEQ ID NO: 208 may be assessed using nucleic acid amplification methods (e.g., PCR) or a device (e.g., a microarray). As is described above, the expression level of the biomarker of SEQ ID NO: 208 in the patient sample may then be compared, e.g., to the expression level of the biomarker of SEQ ID NO: 208 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 208 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-207, 209-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 209 may be used to assess the responsiveness of a cancer patient (e.g., a patient with cancer recurrence) to 2X-121 or a pharmaceutically acceptable salt thereof. The expression level of the biomarker of SEQ ID NO: 209 may be assessed using nucleic acid amplification methods (e.g., PCR) or a device (e.g., a microarray). As is described above, the expression level of the biomarker of SEQ ID NO: 209 in the patient sample may then be compared, e.g., to the expression level of the biomarker of SEQ ID NO: 209 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 209 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-208, 210-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 210 may be used to assess the responsiveness of a cancer patient (e.g., a patient with cancer recurrence) to 2X-121 or a pharmaceutically accept-able salt thereof. The expression level of the biomarker of SEQ ID NO: 210 may be assessed using nucleic acid amplification methods (e.g., PCR) or a device (e.g., a microarray). As is described above, the expression level of the biomarker of SEQ ID NO: 210 in the patient sample may then be compared, e.g., to the expression level of the biomarker of SEQ ID NO: 210 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 210 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-209, 211-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 211 may be used to assess the responsiveness of a cancer patient (e.g., a patient with cancer recurrence) to 2X-121 or a pharmaceutically accept-able salt thereof. The expression level of the biomarker of SEQ ID NO: 211 may be assessed using nucleic acid amplification methods (e.g., PCR) or a device (e.g., a microarray). As is described above, the expression level of the biomarker of SEQ ID NO: 211 in the patient sample may then be compared, e.g., to the expression level of the biomarker of SEQ ID NO: 211 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 211 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-210, 212-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 212 may be used to assess the responsiveness of a cancer patient (e.g., a patient with cancer recurrence) to 2X-121 or a pharmaceutically accept-able salt thereof. The expression level of the biomarker of SEQ ID NO: 212 may be assessed using nucleic acid amplification methods (e.g., PCR) or a device (e.g., a microarray). As is described above, the expression level of the biomarker of SEQ ID NO: 212 in the patient sample may then be compared, e.g., to the expression level of the biomarker of SEQ ID NO: 212 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 212 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-211, 213-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 213 may be used to assess the responsiveness of a cancer patient (e.g., a patient with cancer recurrence) to 2X-121 or a pharmaceutically accept-able salt thereof. The expression level of the biomarker of SEQ ID NO: 213 may be assessed using nucleic acid amplification methods (e.g., PCR) or a device (e.g., a microarray). As is described above, the expression level of the biomarker of SEQ ID NO: 213 in the patient sample may then be compared, e.g., to the expression level of the biomarker of SEQ ID NO: 213 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 213 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-212, 214-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 214 may be used to assess the responsiveness of a cancer patient (e.g., a patient with cancer recurrence) to 2X-121 or a pharmaceutically acceptable salt thereof. The expression level of the biomarker of SEQ ID NO: 214 may be assessed using nucleic acid amplification methods (e.g., PCR) or a device (e.g., a microarray). As is described above, the expression level of the biomarker of SEQ ID NO: 214 in the patient sample may then be compared, e.g., to the expression level of the biomarker of SEQ ID NO: 214 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 214 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-213, 215-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 215 may be used to assess the responsiveness of a cancer patient (e.g., a patient with cancer recurrence) to 2X-121 or a pharmaceutically acceptable salt thereof. The expression level of the biomarker of SEQ ID NO: 215 may be assessed using nucleic acid amplification methods (e.g., PCR) or a device (e.g., a microarray). As is described above, the expression level of the biomarker of SEQ ID NO: 215 in the patient sample may then be compared, e.g., to the expression level of the biomarker of SEQ ID NO: 215 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 215 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-214, 216-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 216 may be used to assess the responsiveness of a cancer patient (e.g., a patient with cancer recurrence) to 2X-121 or a pharmaceutically acceptable salt thereof. The expression level of the biomarker of SEQ ID NO: 216 may be assessed using nucleic acid amplification methods (e.g., PCR) or a device (e.g., a microarray). As is described above, the expression level of the biomarker of SEQ ID NO: 216 in the patient sample may then be compared, e.g., to the expression level of the biomarker of SEQ ID NO: 216 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 216 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-215, 217-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 217 may be used to assess the responsiveness of a cancer patient (e.g., a patient with cancer recurrence) to 2X-121 or a pharmaceutically acceptable salt thereof. The expression level of the biomarker of SEQ ID NO: 217 may be assessed using nucleic acid amplification methods (e.g., PCR) or a device (e.g., a microarray). As is described above, the expression level of the biomarker of SEQ ID NO: 217 in the patient sample may then be compared, e.g., to the expression level of the biomarker of SEQ ID NO: 217 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 217 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-216, 218-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 218 may be used to assess the responsiveness of a cancer patient (e.g., a patient with cancer recurrence) to 2X-121 or a pharmaceutically acceptable salt thereof. The expression level of the biomarker of SEQ ID NO: 218 may be assessed using nucleic acid amplification methods (e.g., PCR) or a device (e.g., a microarray). As is described above, the expression level of the biomarker of SEQ ID NO: 218 in the patient sample may then be compared, e.g., to the expression level of the biomarker of SEQ ID NO: 218 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 218 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio-markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-217, 219-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 219 may be used to assess the responsiveness of a cancer patient (e.g., a patient with cancer recurrence) to 2X-121 or a pharmaceutically accept-able salt thereof. The expression level of the biomarker of SEQ ID NO: 219 may be assessed using nucleic acid amplification methods (e.g., PCR) or a device (e.g., a microarray). As is described above, the expression level of the biomarker of SEQ ID NO: 219 in the patient sample may then be compared, e.g., to the expression level of the biomarker of SEQ ID NO: 219 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 219 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-218, 220-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 220 may be used to assess the responsiveness of a cancer patient (e.g., a patient with cancer recurrence) to 2X-121 or a pharmaceutically accept-able salt thereof. The expression level of the biomarker of SEQ ID NO: 220 may be assessed using nucleic acid amplification methods (e.g., PCR) or a device (e.g., a microarray). As is described above, the expression level of the biomarker of SEQ ID NO: 220 in the patient sample may then be compared, e.g., to the expression level of the biomarker of SEQ ID NO: 220 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 220 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-219, 221-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 221 may be used to assess the responsiveness of a cancer patient (e.g., a patient with cancer recurrence) to 2X-121 or a pharmaceutically accept-able salt thereof. The expression level of the biomarker of SEQ ID NO: 221 may be assessed using nucleic acid amplification methods (e.g., PCR) or a device (e.g., a microarray). As is described above, the expression level of the biomarker of SEQ ID NO: 221 in the patient sample may then be compared, e.g., to the expression level of the biomarker of SEQ ID NO: 221 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 221 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-220, 222-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 222 may be used to assess the responsiveness of a cancer patient (e.g., a patient with cancer recurrence) to 2X-121 or a pharmaceutically accept-able salt thereof. The expression level of the biomarker of SEQ ID NO: 222 may be assessed using nucleic acid amplification methods (e.g., PCR) or a device (e.g., a microarray). As is described above, the expression level of the biomarker of SEQ ID NO: 222 in the patient sample may then be compared, e.g., to the expression level of the biomarker of SEQ ID NO: 222 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 222 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-221, 223-414. The expres-sion level of the biomarker(s) may be determined using, e.g., a microarray, PCR, or other techniques described herein, for example, using a nucleic acid probe sequence based on the target The biomarker of SEQ ID NO: 223 may be used to assess the responsiveness of a cancer patient (e.g., a patient with cancer recurrence) to 2X-121 or a pharmaceutically accept-able salt thereof. The expression level of the biomarker of SEQ ID NO: 223 may be assessed using nucleic acid amplification methods (e.g., PCR) or a device (e.g., a microarray). As is described above, the expression level of the biomarker of SEQ ID NO: 223 in the patient sample may then be compared, e.g., to the expression level of the biomarker of SEQ ID NO: 223 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 223 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-222, 224-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 224 may be used to assess the responsiveness of a cancer patient (e.g., a patient with cancer recurrence) to 2X-121 or a pharmaceutically accept-able salt thereof. The expression level of the biomarker of SEQ ID NO: 224 may be assessed using nucleic acid amplification methods (e.g., PCR) or a device (e.g., a microarray). As is described above, the expression level of the biomarker of SEQ ID NO: 224 in the patient sample may then be compared, e.g., to the expression level of the biomarker of SEQ ID NO: 224 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 224 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-223, 225-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 225 may be used to assess the responsiveness of a cancer patient (e.g., a patient with cancer recurrence) to 2X-121 or a pharmaceutically accept-able salt thereof. The expression level of the biomarker of SEQ ID NO: 225 may be assessed using nucleic acid amplification methods (e.g., PCR) or a device (e.g., a microarray). As is described above, the expression level of the biomarker of SEQ ID NO: 225 in the patient sample may then be compared, e.g., to the expression level of the biomarker of SEQ ID NO: 225 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 225 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-224, 226-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 226 may be used to assess the responsiveness of a cancer patient (e.g., a patient with cancer recurrence) to 2X-121 or a pharmaceutically acceptable salt thereof. The expression level of the biomarker of SEQ ID NO: 226 may be assessed using nucleic acid amplification methods (e.g., PCR) or a device (e.g., a microarray). As is described above, the expression level of the biomarker of SEQ ID NO: 226 in the patient sample may then be compared, e.g., to the expression level of the biomarker of SEQ ID NO: 226 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 226 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-225, 227-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 227 may be used to assess the responsiveness of a cancer patient (e.g., a patient with cancer recurrence) to 2X-121 or a pharmaceutically acceptable salt thereof. The expression level of the biomarker of SEQ ID NO: 227 may be assessed using nucleic acid amplification methods (e.g., PCR) or a device (e.g., a microarray). As is described above, the expression level of the biomarker of SEQ ID NO: 227 in the patient sample may then be compared, e.g., to the expression level of the biomarker of SEQ ID NO: 227 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 227 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-226, 228-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 228 may be used to assess the responsiveness of a cancer patient (e.g., a patient with cancer recurrence) to 2X-121 or a pharmaceutically acceptable salt thereof. The expression level of the biomarker of SEQ ID NO: 228 may be assessed using nucleic acid amplification methods (e.g., PCR) or a device (e.g., a microarray). As is described above, the expression level of the biomarker of SEQ ID NO: 228 in the patient sample may then be compared, e.g., to the expression level of the biomarker of SEQ ID NO: 228 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 228 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-227, 229-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 229 may be used to assess the responsiveness of a cancer patient (e.g., a patient with cancer recurrence) to 2X-121 or a pharmaceutically acceptable salt thereof. The expression level of the biomarker of SEQ ID NO: 229 may be assessed using nucleic acid amplification methods (e.g., PCR) or a device (e.g., a microarray). As is described above, the expression level of the biomarker of SEQ ID NO: 229 in the patient sample may then be compared, e.g., to the expression level of the biomarker of SEQ ID NO: 229 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 229 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-228, 230-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 230 may be used to assess the responsiveness of a cancer patient (e.g., a patient with cancer recurrence) to 2X-121 or a pharmaceutically acceptable salt thereof. The expression level of the biomarker of SEQ ID NO: 230 may be assessed using nucleic acid amplification methods (e.g., PCR) or a device (e.g., a microarray). As is described above, the expression level of the biomarker of SEQ ID NO: 230 in the patient sample may then be compared, e.g., to the expression level of the biomarker of SEQ ID NO: 230 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 230 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-229, 231-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 231 may be used to assess the responsiveness of a cancer patient (e.g., a patient with cancer recurrence) to 2X-121 or a pharmaceutically acceptable salt thereof. The expression level of the biomarker of SEQ ID NO: 231 may be assessed using nucleic acid amplification methods (e.g., PCR) or a device (e.g., a microarray). As is described above, the expression level of the biomarker of SEQ ID NO: 231 in the patient sample may then be compared, e.g., to the expression level of the biomarker of SEQ ID NO: 231 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 231 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-230, 232-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 232 may be used to assess the responsiveness of a cancer patient (e.g., a patient with cancer recurrence) to 2X-121 or a pharmaceutically acceptable salt thereof. The expression level of the biomarker of SEQ ID NO: 232 may be assessed using nucleic acid amplification methods (e.g., PCR) or a device (e.g., a microarray). As is described above, the expression level of the biomarker of SEQ ID NO: 232 in the patient sample may then be compared, e.g., to the expression level of the biomarker of SEQ ID NO: 232 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 232 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-231, 233-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 233 may be used to assess the responsiveness of a cancer patient (e.g., a patient with cancer recurrence) to 2X-121 or a pharmaceutically acceptable salt thereof. The expression level of the biomarker of SEQ ID NO: 233 may be assessed using nucleic acid amplification methods (e.g., PCR) or a device (e.g., a microarray). As is described above, the expression level of the biomarker of SEQ ID NO: 233 in the patient sample may then be compared, e.g., to the expression level of the biomarker of SEQ ID NO: 233 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 233 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-232, 234-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 234 may be used to assess the responsiveness of a cancer patient (e.g., a patient with cancer recurrence) to 2X-121 or a pharmaceutically acceptable salt thereof. The expression level of the biomarker of SEQ ID NO: 234 may be assessed using nucleic acid amplification methods (e.g., PCR) or a device (e.g., a microarray). As is described above, the expression level of the biomarker of SEQ ID NO: 234 in the patient sample may then be compared, e.g., to the expression level of the biomarker of SEQ ID NO: 234 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 234 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-233, 235-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 235 may be used to assess the responsiveness of a cancer patient (e.g., a patient with cancer recurrence) to 2X-121 or a pharmaceutically acceptable salt thereof. The expression level of the biomarker of SEQ ID NO: 235 may be assessed using nucleic acid amplification methods (e.g., PCR) or a device (e.g., a microarray). As is described above, the expression level of the biomarker of SEQ ID NO: 235 in the patient sample may then be compared, e.g., to the expression level of the biomarker of SEQ ID NO: 235 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 235 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-234, 236-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 236 may be used to assess the responsiveness of a cancer patient (e.g., a patient with cancer recurrence) to 2X-121 or a pharmaceutically acceptable salt thereof. The expression level of the biomarker of SEQ ID NO: 236 may be assessed using nucleic acid amplification methods (e.g., PCR) or a device (e.g., a microarray). As is described above, the expression level of the biomarker of SEQ ID NO: 236 in the patient sample may then be compared, e.g., to the expression level of the biomarker of SEQ ID NO: 236 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 236 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-235, 237-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 237 may be used to assess the responsiveness of a cancer patient (e.g., a patient with cancer recurrence) to 2X-121 or a pharmaceutically acceptable salt thereof. The expression level of the biomarker of SEQ ID NO: 237 may be assessed using nucleic acid amplification methods (e.g., PCR) or a device (e.g., a microarray). As is described above, the expression level of the biomarker of SEQ ID NO: 237 in the patient sample may then be compared, e.g., to the expression level of the biomarker of SEQ ID NO: 237 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 237 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-236, 238-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 238 may be used to assess the responsiveness of a cancer patient (e.g., a patient with cancer recurrence) to 2X-121 or a pharmaceutically acceptable salt thereof. The expression level of the biomarker of SEQ ID NO: 238 may be assessed using nucleic acid amplification methods (e.g., PCR) or a device (e.g., a microarray). As is described above, the expression level of the biomarker of SEQ ID NO: 238 in the patient sample may then be compared, e.g., to the expression level of the biomarker of SEQ ID NO: 238 in a cell (e.g., a cancer cell)

or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 238 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-237, 239-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 239 may be used to assess the responsiveness of a cancer patient (e.g., a patient with cancer recurrence) to 2X-121 or a pharmaceutically acceptable salt thereof. The expression level of the biomarker of SEQ ID NO: 239 may be assessed using nucleic acid amplification methods (e.g., PCR) or a device (e.g., a microarray). As is described above, the expression level of the biomarker of SEQ ID NO: 239 in the patient sample may then be compared, e.g., to the expression level of the biomarker of SEQ ID NO: 239 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 239 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-238, 240-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 240 may be used to assess the responsiveness of a cancer patient (e.g., a patient with cancer recurrence) to 2X-121 or a pharmaceutically acceptable salt thereof. The expression level of the biomarker of SEQ ID NO: 240 may be assessed using nucleic acid amplification methods (e.g., PCR) or a device (e.g., a microarray). As is described above, the expression level of the biomarker of SEQ ID NO: 240 in the patient sample may then be compared, e.g., to the expression level of the biomarker of SEQ ID NO: 240 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 240 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-239, 241-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 241 may be used to assess the responsiveness of a cancer patient (e.g., a patient with cancer recurrence) to 2X-121 or a pharmaceutically acceptable salt thereof. The expression level of the biomarker of SEQ ID NO: 241 may be assessed using nucleic acid amplification methods (e.g., PCR) or a device (e.g., a microarray). As is described above, the expression level of the biomarker of SEQ ID NO: 241 in the patient sample may then be compared, e.g., to the expression level of the biomarker of SEQ ID NO: 241 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 241 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-240, 242-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 242 may be used to assess the responsiveness of a cancer patient (e.g., a patient with cancer recurrence) to 2X-121 or a pharmaceutically acceptable salt thereof. The expression level of the biomarker of SEQ ID NO: 242 may be assessed using nucleic acid amplification methods (e.g., PCR) or a device (e.g., a microarray). As is described above, the expression level of the biomarker of SEQ ID NO: 242 in the patient sample may then be compared, e.g., to the expression level of the biomarker of SEQ ID NO: 242 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 242 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio-markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-241, 243-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 243 may be used to assess the responsiveness of a cancer patient (e.g., a patient with cancer recurrence) to 2X-121 or a pharmaceutically accept-able salt thereof. The expression level of the biomarker of SEQ ID NO: 243 may be assessed using nucleic acid amplification methods (e.g., PCR) or a device (e.g., a microarray). As is described above, the expression level of the biomarker of SEQ ID NO: 243 in the patient sample may then be compared, e.g., to the expression level of the biomarker of SEQ ID NO: 243 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 243 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-242, 244-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 244 may be used to assess the responsiveness of a cancer patient (e.g., a patient with cancer recurrence) to 2X-121 or a pharmaceutically accept-able salt thereof. The expression level of the biomarker of SEQ ID NO: 244 may be assessed using nucleic acid amplification methods (e.g., PCR) or a device (e.g., a microarray). As is described above, the expression level of the biomarker of SEQ ID NO: 244 in the patient sample may then be compared, e.g., to the expression level of the biomarker of SEQ ID NO: 244 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 244 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-243, 245-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 245 may be used to assess the responsiveness of a cancer patient (e.g., a patient with cancer recurrence) to 2X-121 or a pharmaceutically accept-able salt thereof. The expression level of the biomarker of SEQ ID NO: 245 may be assessed using nucleic acid amplification methods (e.g., PCR) or a device (e.g., a microarray). As is described above, the expression level of the biomarker of SEQ ID NO: 245 in the patient sample may then be compared, e.g., to the expression level of the biomarker of SEQ ID NO: 245 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 245 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-244, 246-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 246 may be used to assess the responsiveness of a cancer patient (e.g., a patient with cancer recurrence) to 2X-121 or a pharmaceutically accept-able salt thereof. The expression level of the biomarker of SEQ ID NO: 246 may be assessed using nucleic acid amplification methods (e.g., PCR) or a device (e.g., a microarray). As is described above, the expression level of the biomarker of SEQ ID NO: 246 in the patient sample may then be compared, e.g., to the expression level of the biomarker of SEQ ID NO: 246 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 246 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-245, 247-414. The expression level of the biomarker(s) may be determined using, e.g., a microarray, PCR, or other techniques described herein, for example, using a nucleic acid probe sequence based on the target The biomarker of SEQ ID NO: 247 may be used to assess the responsiveness of a cancer patient (e.g., a patient with cancer recurrence) to 2X-121 or a pharmaceutically acceptable salt thereof. The expression level of the biomarker of SEQ ID NO: 247 may be assessed using nucleic acid amplification methods (e.g., PCR) or a device (e.g., a microarray). As is described above, the expression level of the biomarker of SEQ ID NO: 247 in the patient sample may then be compared, e.g., to the expression level of the biomarker of SEQ ID NO: 247 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 247 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-246, 248-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 248 may be used to assess the responsiveness of a cancer patient (e.g., a patient with cancer recurrence) to 2X-121 or a pharmaceutically acceptable salt thereof. The expression level of the biomarker of SEQ ID NO: 248 may be assessed using nucleic acid amplification methods (e.g., PCR) or a device (e.g., a microarray). As is described above, the expression level of the biomarker of SEQ ID NO: 248 in the patient sample may then be compared, e.g., to the expression level of the biomarker of SEQ ID NO: 248 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 248 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-247, 249-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 249 may be used to assess the responsiveness of a cancer patient (e.g., a patient with cancer recurrence) to 2X-121 or a pharmaceutically acceptable salt thereof. The expression level of the biomarker of SEQ ID NO: 249 may be assessed using nucleic acid amplification methods (e.g., PCR) or a device (e.g., a microarray). As is described above, the expression level of the biomarker of SEQ ID NO: 249 in the patient sample may then be compared, e.g., to the expression level of the biomarker of SEQ ID NO: 249 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 249 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-248, 250-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 250 may be used to assess the responsiveness of a cancer patient (e.g., a patient with cancer recurrence) to 2X-121 or a pharmaceutically acceptable salt thereof. The expression level of the biomarker of SEQ ID NO: 250 may be assessed using nucleic acid amplification methods (e.g., PCR) or a device (e.g., a microarray). As is described above, the expression level of the biomarker of SEQ ID NO: 250 in the patient sample may then be compared, e.g., to the expression level of the biomarker of SEQ ID NO: 250 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 250 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-249, 251-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 251 may be used to assess the responsiveness of a cancer patient (e.g., a patient with cancer recurrence) to 2X-121 or a pharmaceutically acceptable salt thereof. The expression level of the biomarker of SEQ ID NO: 251 may be assessed using nucleic acid amplification methods (e.g., PCR) or a device (e.g., a microarray). As is described above, the expression level of the biomarker of SEQ ID NO: 251 in the patient sample may then be compared, e.g., to the expression level of the biomarker of SEQ ID NO: 251 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 251 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-250, 252-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 252 may be used to assess the responsiveness of a cancer patient (e.g., a patient with cancer recurrence) to 2X-121 or a pharmaceutically acceptable salt thereof. The expression level of the biomarker of SEQ ID NO: 252 may be assessed using nucleic acid amplification methods (e.g., PCR) or a device (e.g., a microarray). As is described above, the expression level of the biomarker of SEQ ID NO: 252 in the patient sample may then be compared, e.g., to the expression level of the biomarker of SEQ ID NO: 252 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 252 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-251, 253-414. The expression level of the bio-marker(s) may be determined using, e.g., a microarray, PCR, or other techniques described herein, for example, using a nucleic acid probe sequence based on the target sequences shown in Tables 2 and 3.

The biomarker of SEQ ID NO: 253 may be used to assess the responsiveness of a cancer patient (e.g., a patient with cancer recurrence) to 2X-121 or a pharmaceutically acceptable salt thereof. The expression level of the biomarker of SEQ ID NO: 253 may be assessed using nucleic acid amplification methods (e.g., PCR) or a device (e.g., a microarray). As is described above, the expression level of the biomarker of SEQ ID NO: 253 in the patient sample may then be compared, e.g., to the expression level of the biomarker of SEQ ID NO: 253 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 253 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-252, 254-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 254 may be used to assess the responsiveness of a cancer patient (e.g., a patient with cancer recurrence) to 2X-121 or a pharmaceutically acceptable salt thereof. The expression level of the biomarker of SEQ ID NO: 254 may be assessed using nucleic acid amplification methods (e.g., PCR) or a device (e.g., a microarray). As is described above, the expression level of the biomarker of SEQ ID NO: 254 in the patient sample may then be compared, e.g., to the expression level of the biomarker of SEQ ID NO: 254 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 254 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-253, 255-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 255 may be used to assess the responsiveness of a cancer patient (e.g., a patient with cancer recurrence) to 2X-121 or a pharmaceutically acceptable salt thereof. The expression level of the biomarker of SEQ ID NO: 255 may be assessed using nucleic acid amplification methods (e.g., PCR) or a device (e.g., a microarray). As is described above, the expression level of the biomarker of SEQ ID NO: 255 in the patient sample may then be compared, e.g., to the expression level of the biomarker of SEQ ID NO: 255 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 255 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-254, 256-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 256 may be used to assess the responsiveness of a cancer patient (e.g., a patient with cancer recurrence) to 2X-121 or a pharmaceutically acceptable salt thereof. The expression level of the biomarker of SEQ ID NO: 256 may be assessed using nucleic acid amplification methods (e.g., PCR) or a device (e.g., a microarray). As is described above, the expression level of the biomarker of SEQ ID NO: 256 in the patient sample may then be compared, e.g., to the expression level of the biomarker of SEQ ID NO: 256 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 256 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-255, 257-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 257 may be used to assess the responsiveness of a cancer patient (e.g., a patient with cancer recurrence) to 2X-121 or a pharmaceutically acceptable salt thereof. The expression level of the biomarker of SEQ ID NO: 257 may be assessed using nucleic acid amplification methods (e.g., PCR) or a device (e.g., a microarray). As is described above, the expression level of the biomarker of SEQ ID NO: 257 in the patient sample may then be compared, e.g., to the expression level of the biomarker of SEQ ID NO: 257 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 257 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-256, 258-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 258 may be used to assess the responsiveness of a cancer patient (e.g., a patient with cancer recurrence) to 2X-121 or a pharmaceutically acceptable salt thereof. The expression level of the biomarker of SEQ ID NO: 258 may be assessed using nucleic acid amplification methods (e.g., PCR) or a device (e.g., a microarray). As is described above, the expression level of the biomarker of SEQ ID NO: 258 in the patient sample may then be compared, e.g., to the expression level of the biomarker of SEQ ID NO: 258 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 258 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-257, 259-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 259 may be used to assess the responsiveness of a cancer patient (e.g., a patient with cancer recurrence) to 2X-121 or a pharmaceutically acceptable salt thereof. The expression level of the biomarker of SEQ ID NO: 259 may be assessed using nucleic acid amplification methods (e.g., PCR) or a device (e.g., a microarray). As is described above, the expression level of the biomarker of SEQ ID NO: 259 in the patient sample may then be compared, e.g., to the expression level of the biomarker of SEQ ID NO: 259 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 259 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-258, 260-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 260 may be used to assess the responsiveness of a cancer patient (e.g., a patient with cancer recurrence) to 2X-121 or a pharmaceutically acceptable salt thereof. The expression level of the biomarker of SEQ ID NO: 260 may be assessed using nucleic acid amplification methods (e.g., PCR) or a device (e.g., a microarray). As is described above, the expression level of the biomarker of SEQ ID NO: 260 in the patient sample may then be compared, e.g., to the expression level of the biomarker of SEQ ID NO: 260 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 260 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-259, 261-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 261 may be used to assess the responsiveness of a cancer patient (e.g., a patient with cancer recurrence) to 2X-121 or a pharmaceutically acceptable salt thereof. The expression level of the biomarker of SEQ ID NO: 261 may be assessed using nucleic acid amplification methods (e.g., PCR) or a device (e.g., a microarray). As is described above, the expression level of the biomarker of SEQ ID NO: 261 in the patient sample may then be compared, e.g., to the expression level of the biomarker of SEQ ID NO: 261 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 261 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-260, 262-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 262 may be used to assess the responsiveness of a cancer patient (e.g., a patient with cancer recurrence) to 2X-121 or a pharmaceutically acceptable salt thereof. The expression level of the biomarker of SEQ ID NO: 262 may be assessed using nucleic acid amplification methods (e.g., PCR) or a device (e.g., a microarray). As is described above, the expression level of the biomarker of SEQ ID NO: 262 in the patient sample may then be compared, e.g., to the expression level of the biomarker of SEQ ID NO: 262 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 262 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-261, 263-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 263 may be used to assess the responsiveness of a cancer patient (e.g., a patient with cancer recurrence) to 2X-121 or a pharmaceutically acceptable salt thereof. The expression level of the biomarker of SEQ ID NO: 263 may be assessed using nucleic acid amplification methods (e.g., PCR) or a device (e.g., a microarray). As is described above, the expression level of the biomarker of SEQ ID NO: 263 in the patient sample may then be compared, e.g., to the expression level of the biomarker of SEQ ID NO: 263 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 263 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-262, 264-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 264 may be used to assess the responsiveness of a cancer patient (e.g., a patient with cancer recurrence) to 2X-121 or a pharmaceutically acceptable salt thereof. The expression level of the biomarker of SEQ ID NO: 264 may be assessed using nucleic acid amplification methods (e.g., PCR) or a device (e.g., a microarray). As is described above, the expression level of the biomarker of SEQ ID NO: 264 in the patient sample may then be compared, e.g., to the expression level of the biomarker of SEQ ID NO: 264 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 264 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-263, 265-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 265 may be used to assess the responsiveness of a cancer patient (e.g., a patient with cancer recurrence) to 2X-121 or a pharmaceutically acceptable salt thereof. The expression level of the biomarker of SEQ ID NO: 265 may be assessed using nucleic acid amplification methods (e.g., PCR) or a device (e.g., a microarray). As is described above, the expression level of the biomarker of SEQ ID NO: 265 in the patient sample may then be compared, e.g., to the expression level of the biomarker of SEQ ID NO: 265 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 265 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-264, 266-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 266 may be used to assess the responsiveness of a cancer patient (e.g., a patient with cancer recurrence) to 2X-121 or a pharmaceutically acceptable salt thereof. The expression level of the biomarker of SEQ ID NO: 266 may be assessed using nucleic acid amplification methods (e.g., PCR) or a device (e.g., a microarray). As is described above, the expression level of the biomarker of SEQ ID NO: 266 in the patient sample may then be compared, e.g., to the expression level of the biomarker of SEQ ID NO: 266 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 266 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-265, 267-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 267 may be used to assess the responsiveness of a cancer patient (e.g., a patient with cancer recurrence) to 2X-121 or a pharmaceutically acceptable salt thereof. The expression level of the biomarker of SEQ ID NO: 267 may be assessed using nucleic acid amplification methods (e.g., PCR) or a device (e.g., a microarray). As is described above, the expression level of the biomarker of SEQ ID NO: 267 in the patient sample may then be compared, e.g., to the expression level of the biomarker of SEQ ID NO: 267 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 267 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-266, 268-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 268 may be used to assess the responsiveness of a cancer patient (e.g., a patient with cancer recurrence) to 2X-121 or a pharmaceutically acceptable salt thereof. The expression level of the biomarker of SEQ ID NO: 268 may be assessed using nucleic acid amplification methods (e.g., PCR) or a device (e.g., a microarray). As is described above, the expression level of the biomarker of SEQ ID NO: 268 in the patient sample may then be compared, e.g., to the expression level of the biomarker of SEQ ID NO: 268 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 268 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-267, 269-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 269 may be used to assess the responsiveness of a cancer patient (e.g., a patient with cancer recurrence) to 2X-121 or a pharmaceutically acceptable salt thereof. The expression level of the biomarker of SEQ ID NO: 269 may be assessed using nucleic acid amplification methods (e.g., PCR) or a device (e.g., a microarray). As is described above, the expression level of the biomarker of SEQ ID NO: 269 in the patient sample may then be compared, e.g., to the expression level of the biomarker of SEQ ID NO: 269 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 269 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-268, 270-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 270 may be used to assess the responsiveness of a cancer patient (e.g., a patient with cancer recurrence) to 2X-121 or a pharmaceutically acceptable salt thereof. The expression level of the biomarker of SEQ ID NO: 270 may be assessed using nucleic acid amplification methods (e.g., PCR) or a device (e.g., a microarray). As is described above, the expression level of the biomarker of SEQ ID NO: 270 in the patient sample may then be compared, e.g., to the expression level of the biomarker of SEQ ID NO: 270 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 270 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-269, 271-414. The expression level of the biomarker(s) may be determined using, e.g., a microarray, PCR, or other techniques described herein, for example, using a nucleic acid probe sequence based on the target The biomarker of SEQ ID NO: 271 may be used to assess the responsiveness of a cancer patient (e.g., a patient with cancer recurrence) to 2X-121 or a pharmaceutically acceptable salt thereof. The expression level of the biomarker of SEQ ID NO: 271 may be assessed using nucleic acid amplification methods (e.g., PCR) or a device (e.g., a microarray). As is described above, the expression level of the biomarker of SEQ ID NO: 271 in the patient sample may then be compared, e.g., to the expression level of the biomarker of SEQ ID NO: 271 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 271 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-270, 272-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 272 may be used to assess the responsiveness of a cancer patient (e.g., a patient with cancer recurrence) to 2X-121 or a pharmaceutically acceptable salt thereof. The expression level of the biomarker of SEQ ID NO: 272 may be assessed using nucleic acid amplification methods (e.g., PCR) or a device (e.g., a microarray). As is described above, the expression level of the biomarker of SEQ ID NO: 272 in the patient sample may then be compared, e.g., to the expression level of the biomarker of SEQ ID NO: 272 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 272 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-271, 273-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 273 may be used to assess the responsiveness of a cancer patient (e.g., a patient with cancer recurrence) to 2X-121 or a pharmaceutically acceptable salt thereof. The expression level of the biomarker of SEQ ID NO: 273 may be assessed using nucleic acid amplification methods (e.g., PCR) or a device (e.g., a microarray). As is described above, the expression level of the biomarker of SEQ ID NO: 273 in the patient sample may then be compared, e.g., to the expression level of the biomarker of SEQ ID NO: 273 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 273 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-272, 274-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 274 may be used to assess the responsiveness of a cancer patient (e.g., a patient with cancer recurrence) to 2X-121 or a pharmaceutically acceptable salt thereof. The expression level of the biomarker of SEQ ID NO: 274 may be assessed using nucleic acid amplification methods (e.g., PCR) or a device (e.g., a microarray). As is described above, the expression level of the biomarker of SEQ ID NO: 274 in the patient sample may then be compared, e.g., to the expression level of the biomarker of SEQ ID NO: 274 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 274 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-273, 275-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 275 may be used to assess the responsiveness of a cancer patient (e.g., a patient with cancer recurrence) to 2X-121 or a pharmaceutically acceptable salt thereof. The expression level of the biomarker of SEQ ID NO: 275 may be assessed using nucleic acid amplification methods (e.g., PCR) or a device (e.g., a microarray). As is described above, the expression level of the biomarker of SEQ ID NO: 275 in the patient sample may then be compared, e.g., to the expression level of the biomarker of SEQ ID NO: 275 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 275 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-274, 276-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 276 may be used to assess the responsiveness of a cancer patient (e.g., a patient with cancer recurrence) to 2X-121 or a pharmaceutically acceptable salt thereof. The expression level of the biomarker of SEQ ID NO: 276 may be assessed using nucleic acid amplification methods (e.g., PCR) or a device (e.g., a microarray). As is described above, the expression level of the biomarker of SEQ ID NO: 276 in the patient sample may then be compared, e.g., to the expression level of the biomarker of SEQ ID NO: 276 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 276 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-275, 277-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 277 may be used to assess the responsiveness of a cancer patient (e.g., a patient with cancer recurrence) to 2X-121 or a pharmaceutically acceptable salt thereof. The expression level of the biomarker of SEQ ID NO: 277 may be assessed using nucleic acid amplification methods (e.g., PCR) or a device (e.g., a microarray). As is described above, the expression level of the biomarker of SEQ ID NO: 277 in the patient sample may then be compared, e.g., to the expression level of the biomarker of SEQ ID NO: 277 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 277 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-276, 278-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 278 may be used to assess the responsiveness of a cancer patient (e.g., a patient with cancer recurrence) to 2X-121 or a pharmaceutically acceptable salt thereof. The expression level of the biomarker of SEQ ID NO: 278 may be assessed using nucleic acid amplification methods (e.g., PCR) or a device (e.g., a microarray). As is described above, the expression level of the biomarker of SEQ ID NO: 278 in the patient sample may then be compared, e.g., to the expression level of the biomarker of SEQ ID NO: 278 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 278 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-277, 279-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 279 may be used to assess the responsiveness of a cancer patient (e.g., a patient with cancer recurrence) to 2X-121 or a pharmaceutically acceptable salt thereof. The expression level of the biomarker of SEQ ID NO: 279 may be assessed using nucleic acid amplification methods (e.g., PCR) or a device (e.g., a microarray). As is described above, the expression level of the biomarker of SEQ ID NO: 279 in the patient sample may then be compared, e.g., to the expression level of the biomarker of SEQ ID NO: 279 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 279 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker (s) of SEQ ID NOs: 1-278, 280-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 280 may be used to assess the responsiveness of a cancer patient (e.g., a patient with cancer recurrence) to 2X-121 or a pharmaceutically acceptable salt thereof. The expression level of the biomarker of SEQ ID NO: 280 may be assessed using nucleic acid amplification methods (e.g., PCR) or a device (e.g., a microarray). As is described above, the expression level of the biomarker of SEQ ID NO: 280 in the patient sample may then be compared, e.g., to the expression level of the biomarker of SEQ ID NO: 280 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 280 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-279, 281-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 281 may be used to assess the responsiveness of a cancer patient (e.g., a patient with cancer recurrence) to 2X-121 or a pharmaceutically acceptable salt thereof. The expression level of the biomarker of SEQ ID NO: 281 may be assessed using nucleic acid amplification methods (e.g., PCR) or a device (e.g., a microarray). As is described above, the expression level of the biomarker of SEQ ID NO: 281 in the patient sample may then be compared, e.g., to the expression level of the biomarker of SEQ ID NO: 281 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 281 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-280, 282-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 282 may be used to assess the responsiveness of a cancer patient (e.g., a patient with cancer recurrence) to 2X-121 or a pharmaceutically acceptable salt thereof. The expression level of the biomarker of SEQ ID NO: 282 may be assessed using nucleic acid amplification methods (e.g., PCR) or a device (e.g., a microarray). As is described above, the expression level of the biomarker of SEQ ID NO: 282 in the patient sample may then be compared, e.g., to the expression level of the biomarker of SEQ ID NO: 282 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 282 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-281, 283-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 283 may be used to assess the responsiveness of a cancer patient (e.g., a patient with cancer recurrence) to 2X-121 or a pharmaceutically acceptable salt thereof. The expression level of the biomarker of SEQ ID NO: 283 may be assessed using nucleic acid amplification methods (e.g., PCR) or a device (e.g., a microarray). As is described above, the expression level of the biomarker of SEQ ID NO: 283 in the patient sample may then be compared, e.g., to the expression level of the biomarker of SEQ ID NO: 283 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 283 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-282, 284-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 284 may be used to assess the responsiveness of a cancer patient (e.g., a patient with cancer recurrence) to 2X-121 or a pharmaceutically acceptable salt thereof. The expression level of the biomarker of SEQ ID NO: 284 may be assessed using nucleic acid amplification methods (e.g., PCR) or a device (e.g., a microarray). As is described above, the expression level of the biomarker of SEQ ID NO: 284 in the patient sample may then be compared, e.g., to the expression level of the biomarker of SEQ ID NO: 284 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 284 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-283, 285-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 285 may be used to assess the responsiveness of a cancer patient (e.g., a patient with cancer recurrence) to 2X-121 or a pharmaceutically acceptable salt thereof. The expression level of the biomarker of SEQ ID NO: 285 may be assessed using nucleic acid amplification methods (e.g., PCR) or a device (e.g., a microarray). As is described above, the expression level of the biomarker of SEQ ID NO: 285 in the patient sample may then be compared, e.g., to the expression level of the biomarker of SEQ ID NO: 285 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 285 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-284, 286-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 286 may be used to assess the responsiveness of a cancer patient (e.g., a patient with cancer recurrence) to 2X-121 or a pharmaceutically acceptable salt thereof. The expression level of the biomarker of SEQ ID NO: 286 may be assessed using nucleic acid amplification methods (e.g., PCR) or a device (e.g., a microarray). As is described above, the expression level of the biomarker of SEQ ID NO: 286 in the patient sample may then be compared, e.g., to the expression level of the biomarker of SEQ ID NO: 286 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 286 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-285, 287-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 287 may be used to assess the responsiveness of a cancer patient (e.g., a patient with cancer recurrence) to 2X-121 or a pharmaceutically acceptable salt thereof. The expression level of the biomarker of SEQ ID NO: 287 may be assessed using nucleic acid amplification methods (e.g., PCR) or a device (e.g., a microarray). As is described above, the expression level of the biomarker of SEQ ID NO: 287 in the patient sample may then be compared, e.g., to the expression level of the biomarker of SEQ ID NO: 287 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 287 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-286, 288-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 288 may be used to assess the responsiveness of a cancer patient (e.g., a patient with cancer recurrence) to 2X-121 or a pharmaceutically acceptable salt thereof. The expression level of the biomarker of SEQ ID NO: 288 may be assessed using nucleic acid amplification methods (e.g., PCR) or a device (e.g., a microarray). As is described above, the expression level of the biomarker of SEQ ID NO: 288 in the patient sample may then be compared, e.g., to the expression level of the biomarker of SEQ ID NO: 288 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 288 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-287, 289-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 289 may be used to assess the responsiveness of a cancer patient (e.g., a patient with cancer recurrence) to 2X-121 or a pharmaceutically acceptable salt thereof. The expression level of the biomarker of SEQ ID NO: 289 may be assessed using nucleic acid amplification methods (e.g., PCR) or a device (e.g., a microarray). As is described above, the expression level of the biomarker of SEQ ID NO: 289 in the patient sample may then be compared, e.g., to the expression level of the biomarker of SEQ ID NO: 289 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 289 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-288, 290-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 290 may be used to assess the responsiveness of a cancer patient (e.g., a patient with cancer recurrence) to 2X-121 or a pharmaceutically acceptable salt thereof. The expression level of the biomarker of SEQ ID NO: 290 may be assessed using nucleic acid amplification methods (e.g., PCR) or a device (e.g., a microarray). As is described above, the expression level of the biomarker of SEQ ID NO: 290 in the patient sample may then be compared, e.g., to the expression level of the biomarker of SEQ ID NO: 290 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 290 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-289, 291-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 291 may be used to assess the responsiveness of a cancer patient (e.g., a patient with cancer recurrence) to 2X-121 or a pharmaceutically acceptable salt thereof. The expression level of the biomarker of SEQ ID NO: 291 may be assessed using nucleic acid amplification methods (e.g., PCR) or a device (e.g., a microarray). As is described above, the expression level of the biomarker of SEQ ID NO: 291 in the patient sample may then be compared, e.g., to the expression level of the biomarker of SEQ ID NO: 291 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 291 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-290, 292-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 292 may be used to assess the responsiveness of a cancer patient (e.g., a patient with cancer recurrence) to 2X-121 or a pharmaceutically acceptable salt thereof. The expression level of the biomarker of SEQ ID NO: 292 may be assessed using nucleic acid amplification methods (e.g., PCR) or a device (e.g., a microarray). As is described above, the expression level of the biomarker of SEQ ID NO: 292 in the patient sample may then be compared, e.g., to the expression level of the biomarker of SEQ ID NO: 292 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 292 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-291, 293-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 293 may be used to assess the responsiveness of a cancer patient (e.g., a patient with cancer recurrence) to 2X-121 or a pharmaceutically acceptable salt thereof. The expression level of the biomarker of SEQ ID NO: 293 may be assessed using nucleic acid amplification methods (e.g., PCR) or a device (e.g., a microarray). As is described above, the expression level of the biomarker of SEQ ID NO: 293 in the patient sample may then be compared, e.g., to the expression level of the biomarker of SEQ ID NO: 293 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 293 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-292, 294-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 294 may be used to assess the responsiveness of a cancer patient (e.g., a patient with cancer recurrence) to 2X-121 or a pharmaceutically acceptable salt thereof. The expression level of the biomarker of SEQ ID NO: 294 may be assessed using nucleic acid amplification methods (e.g., PCR) or a device (e.g., a microarray). As is described above, the expression level of the biomarker of SEQ ID NO: 294 in the patient sample may then be compared, e.g., to the expression level of the biomarker of SEQ ID NO: 294 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 294 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-293, 295-414. The expression level of the biomarker(s) may be determined using, e.g., a microarray, PCR, or other techniques described herein, for example, using a nucleic acid probe sequence based on the target The biomarker of SEQ ID NO: 295 may be used to assess the responsiveness of a cancer patient (e.g., a patient with cancer recurrence) to 2X-121 or a pharmaceutically acceptable salt thereof. The expression level of the biomarker of SEQ ID NO: 295 may be assessed using nucleic acid amplification methods (e.g., PCR) or a device (e.g., a microarray). As is described above, the expression level of the biomarker of SEQ ID NO: 295 in the patient sample may then be compared, e.g., to the expression level of the biomarker of SEQ ID NO: 295 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 295 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-294, 296-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 296 may be used to assess the responsiveness of a cancer patient (e.g., a patient with cancer recurrence) to 2X-121 or a pharmaceutically acceptable salt thereof. The expression level of the biomarker of SEQ ID NO: 296 may be assessed using nucleic acid amplification methods (e.g., PCR) or a device (e.g., a microarray). As is described above, the expression level of the biomarker of SEQ ID NO: 296 in the patient sample may then be compared, e.g., to the expression level of the biomarker of SEQ ID NO: 296 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 296 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-295, 297-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 297 may be used to assess the responsiveness of a cancer patient (e.g., a patient with cancer recurrence) to 2X-121 or a pharmaceutically acceptable salt thereof. The expression level of the biomarker of SEQ ID NO: 297 may be assessed using nucleic acid amplification methods (e.g., PCR) or a device (e.g., a microarray). As is described above, the expression level of the biomarker of SEQ ID NO: 297 in the patient sample may then be compared, e.g., to the expression level of the biomarker of SEQ ID NO: 297 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 297 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-296, 298-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 298 may be used to assess the responsiveness of a cancer patient (e.g., a patient with cancer recurrence) to 2X-121 or a pharmaceutically acceptable salt thereof. The expression level of the biomarker of SEQ ID NO: 298 may be assessed using nucleic acid amplification methods (e.g., PCR) or a device (e.g., a microarray). As is described above, the expression level of the biomarker of SEQ ID NO: 298 in the patient sample may then be compared, e.g., to the expression level of the biomarker of SEQ ID NO: 298 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 298 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-297, 299-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 299 may be used to assess the responsiveness of a cancer patient (e.g., a patient with cancer recurrence) to 2X-121 or a pharmaceutically acceptable salt thereof. The expression level of the biomarker of SEQ ID NO: 299 may be assessed using nucleic acid amplification methods (e.g., PCR) or a device (e.g., a microarray). As is described above, the expression level of the biomarker of SEQ ID NO: 299 in the patient sample may then be compared, e.g., to the expression level of the biomarker of SEQ ID NO: 299 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 299 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-298, 300-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 300 may be used to assess the responsiveness of a cancer patient (e.g., a patient with cancer recurrence) to 2X-121 or a pharmaceutically acceptable salt thereof. The expression level of the biomarker of SEQ ID NO: 300 may be assessed using nucleic acid amplification methods (e.g., PCR) or a device (e.g., a microarray). As is described above, the expression level of the biomarker of SEQ ID NO: 300 in the patient sample may then be compared, e.g., to the expression level of the biomarker of SEQ ID NO: 300 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 300 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-299, 301-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 301 may be used to assess the responsiveness of a cancer patient (e.g., a patient with cancer recurrence) to 2X-121 or a pharmaceutically acceptable salt thereof. The expression level of the biomarker of SEQ ID NO: 301 may be assessed using nucleic acid amplification methods (e.g., PCR) or a device (e.g., a microarray). As is described above, the expression level of the biomarker of SEQ ID NO: 301 in the patient sample may then be compared, e.g., to the expression level of the biomarker of SEQ ID NO: 301 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 301 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-300, 302-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 302 may be used to assess the responsiveness of a cancer patient (e.g., a patient with cancer recurrence) to 2X-121 or a pharmaceutically acceptable salt thereof. The expression level of the biomarker of SEQ ID NO: 302 may be assessed using nucleic acid amplification methods (e.g., PCR) or a device (e.g., a microarray). As is described above, the expression level of the biomarker of SEQ ID NO: 302 in the patient sample may then be compared, e.g., to the expression level of the biomarker of SEQ ID NO: 302 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 302 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker (s) of SEQ ID NOs: 1-301, 303-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 303 may be used to assess the responsiveness of a cancer patient (e.g., a patient with cancer recurrence) to 2X-121 or a pharmaceutically acceptable salt thereof. The expression level of the biomarker of SEQ ID NO: 303 may be assessed using nucleic acid amplification methods (e.g., PCR) or a device (e.g., a microarray). As is described above, the expression level of the biomarker of SEQ ID NO: 303 in the patient sample may then be compared, e.g., to the expression level of the biomarker of SEQ ID NO: 303 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 303 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-302, 304-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 304 may be used to assess the responsiveness of a cancer patient (e.g., a patient with cancer recurrence) to 2X-121 or a pharmaceutically acceptable salt thereof. The expression level of the biomarker of SEQ ID NO: 304 may be assessed using nucleic acid amplification methods (e.g., PCR) or a device (e.g., a microarray). As is described above, the expression level of the biomarker of SEQ ID NO: 304 in the patient sample may then be compared, e.g., to the expression level of the biomarker of SEQ ID NO: 304 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 304 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-303, 305-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 305 may be used to assess the responsiveness of a cancer patient (e.g., a patient with cancer recurrence) to 2X-121 or a pharmaceutically acceptable salt thereof. The expression level of the biomarker of SEQ ID NO: 305 may be assessed using nucleic acid amplification methods (e.g., PCR) or a device (e.g., a microarray). As is described above, the expression level of the biomarker of SEQ ID NO: 305 in the patient sample may then be compared, e.g., to the expression level of the biomarker of SEQ ID NO: 305 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 305 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-304, 306-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 306 may be used to assess the responsiveness of a cancer patient (e.g., a patient with cancer recurrence) to 2X-121 or a pharmaceutically acceptable salt thereof. The expression level of the biomarker of SEQ ID NO: 306 may be assessed using nucleic acid amplification methods (e.g., PCR) or a device (e.g., a microarray). As is described above, the expression level of the biomarker of SEQ ID NO: 306 in the patient sample may then be compared, e.g., to the expression level of the biomarker of SEQ ID NO: 306 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 306 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-305, 307-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 307 may be used to assess the responsiveness of a cancer patient (e.g., a patient with cancer recurrence) to 2X-121 or a pharmaceutically acceptable salt thereof. The expression level of the biomarker of SEQ ID NO: 307 may be assessed using nucleic acid amplification methods (e.g., PCR) or a device (e.g., a microarray). As is described above, the expression level of the biomarker of SEQ ID NO: 307 in the patient sample may then be compared, e.g., to the expression level of the biomarker of SEQ ID NO: 307 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 307 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-306, 308-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 308 may be used to assess the responsiveness of a cancer patient (e.g., a patient with cancer recurrence) to 2X-121 or a pharmaceutically acceptable salt thereof. The expression level of the biomarker of SEQ ID NO: 308 may be assessed using nucleic acid amplification methods (e.g., PCR) or a device (e.g., a microarray). As is described above, the expression level of the biomarker of SEQ ID NO: 308 in the patient sample may then be compared, e.g., to the expression level of the biomarker of SEQ ID NO: 308 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 308 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-307, 309-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 309 may be used to assess the responsiveness of a cancer patient (e.g., a patient with cancer recurrence) to 2X-121 or a pharmaceutically acceptable salt thereof. The expression level of the biomarker of SEQ ID NO: 309 may be assessed using nucleic acid amplification methods (e.g., PCR) or a device (e.g., a microarray). As is described above, the expression level of the biomarker of SEQ ID NO: 309 in the patient sample may then be compared, e.g., to the expression level of the biomarker of SEQ ID NO: 309 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 309 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-308, 310-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 310 may be used to assess the responsiveness of a cancer patient (e.g., a patient with cancer recurrence) to 2X-121 or a pharmaceutically acceptable salt thereof. The expression level of the biomarker of SEQ ID NO: 310 may be assessed using nucleic acid amplification methods (e.g., PCR) or a device (e.g., a microarray). As is described above, the expression level of the biomarker of SEQ ID NO: 310 in the patient sample may then be compared, e.g., to the expression level of the biomarker of SEQ ID NO: 310 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 310 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-309, 311-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 311 may be used to assess the responsiveness of a cancer patient (e.g., a patient with cancer recurrence) to 2X-121 or a pharmaceutically acceptable salt thereof. The expression level of the biomarker of SEQ ID NO: 311 may be assessed using nucleic acid amplification methods (e.g., PCR) or a device (e.g., a microarray). As is described above, the expression level of the biomarker of SEQ ID NO: 311 in the patient sample may then be compared, e.g., to the expression level of the biomarker of SEQ ID NO: 311 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 311 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-310, 312-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 312 may be used to assess the responsiveness of a cancer patient (e.g., a patient with cancer recurrence) to 2X-121 or a pharmaceutically acceptable salt thereof. The expression level of the biomarker of SEQ ID NO: 312 may be assessed using nucleic acid amplification methods (e.g., PCR) or a device (e.g., a microarray). As is described above, the expression level of the biomarker of SEQ ID NO: 312 in the patient sample may then be compared, e.g., to the expression level of the biomarker of SEQ ID NO: 312 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 312 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-311, 313-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 313 may be used to assess the responsiveness of a cancer patient (e.g., a patient with cancer recurrence) to 2X-121 or a pharmaceutically acceptable salt thereof. The expression level of the biomarker of SEQ ID NO: 313 may be assessed using nucleic acid amplification methods (e.g., PCR) or a device (e.g., a microarray). As is described above, the expression level of the biomarker of SEQ ID NO: 313 in the patient sample may then be compared, e.g., to the expression level of the biomarker of SEQ ID NO: 313 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 313 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-312, 314-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 314 may be used to assess the responsiveness of a cancer patient (e.g., a patient with cancer recurrence) to 2X-121 or a pharmaceutically acceptable salt thereof. The expression level of the biomarker of SEQ ID NO: 314 may be assessed using nucleic acid amplification methods (e.g., PCR) or a device (e.g., a microarray). As is described above, the expression level of the biomarker of SEQ ID NO: 314 in the patient sample may then be compared, e.g., to the expression level of the biomarker of SEQ ID NO: 314 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 314 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3)), such as biomarker(s) of SEQ ID NOs: 1-313, 315-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 315 may be used to assess the responsiveness of a cancer patient (e.g., a patient with cancer recurrence) to 2X-121 or a pharmaceutically acceptable salt thereof. The expression level of the biomarker of SEQ ID NO: 315 may be assessed using nucleic acid amplification methods (e.g., PCR) or a device (e.g., a microarray). As is described above, the expression level of the biomarker of SEQ ID NO: 315 in the patient sample may then be compared, e.g., to the expression level of the biomarker of SEQ ID NO: 315 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 315 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-314, 316-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 316 may be used to assess the responsiveness of a cancer patient (e.g., a patient with cancer recurrence) to 2X-121 or a pharmaceutically acceptable salt thereof. The expression level of the biomarker of SEQ ID NO: 316 may be assessed using nucleic acid amplification methods (e.g., PCR) or a device (e.g., a microarray). As is described above, the expression level of the biomarker of SEQ ID NO: 316 in the patient sample may then be compared, e.g., to the expression level of the biomarker of SEQ ID NO: 316 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 316 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-315, 317-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 317 may be used to assess the responsiveness of a cancer patient (e.g., a patient with cancer recurrence) to 2X-121 or a pharmaceutically acceptable salt thereof. The expression level of the biomarker of SEQ ID NO: 317 may be assessed using nucleic acid amplification methods (e.g., PCR) or a device (e.g., a microarray). As is described above, the expression level of the biomarker of SEQ ID NO: 317 in the patient sample may then be compared, e.g., to the expression level of the biomarker of SEQ ID NO: 317 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 317 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-316, 318-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 318 may be used to assess the responsiveness of a cancer patient (e.g., a patient with cancer recurrence) to 2X-121 or a pharmaceutically acceptable salt thereof. The expression level of the biomarker of SEQ ID NO: 318 may be assessed using nucleic acid amplification methods (e.g., PCR) or a device (e.g., a microarray). As is described above, the expression level of the biomarker of SEQ ID NO: 318 in the patient sample may then be compared, e.g., to the expression level of the biomarker of SEQ ID NO: 318 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 318 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-317, 319-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 319 may be used to assess the responsiveness of a cancer patient (e.g., a patient with cancer recurrence) to 2X-121 or a pharmaceutically acceptable salt thereof. The expression level of the biomarker of SEQ ID NO: 319 may be assessed using nucleic acid amplification methods (e.g., PCR) or a device (e.g., a microarray). As is described above, the expression level of the biomarker of SEQ ID NO: 319 in the patient sample may then be compared, e.g., to the expression level of the biomarker of SEQ ID NO: 319 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 319 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-318, 320-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 320 may be used to assess the responsiveness of a cancer patient (e.g., a patient with cancer recurrence) to 2X-121 or a pharmaceutically acceptable salt thereof. The expression level of the biomarker of SEQ ID NO: 320 may be assessed using nucleic acid amplification methods (e.g., PCR) or a device (e.g., a microarray). As is described above, the expression level of the biomarker of SEQ ID NO: 320 in the patient sample may then be compared, e.g., to the expression level of the biomarker of SEQ ID NO: 320 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 320 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-319, 321-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 321 may be used to assess the responsiveness of a cancer patient (e.g., a patient with cancer recurrence) to 2X-121 or a pharmaceutically acceptable salt thereof. The expression level of the biomarker of SEQ ID NO: 321 may be assessed using nucleic acid amplification methods (e.g., PCR) or a device (e.g., a microarray). As is described above, the expression level of the biomarker of SEQ ID NO: 321 in the patient sample may then be compared, e.g., to the expression level of the biomarker of SEQ ID NO: 321 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 321 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-320, 322-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 322 may be used to assess the responsiveness of a cancer patient (e.g., a patient with cancer recurrence) to 2X-121 or a pharmaceutically acceptable salt thereof. The expression level of the biomarker of SEQ ID NO: 322 may be assessed using nucleic acid amplification methods (e.g., PCR) or a device (e.g., a microarray). As is described above, the expression level of the biomarker of SEQ ID NO: 322 in the patient sample may then be compared, e.g., to the expression level of the biomarker of SEQ ID NO: 322 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 322 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-321, 323-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 323 may be used to assess the responsiveness of a cancer patient (e.g., a patient with cancer recurrence) to 2X-121 or a pharmaceutically acceptable salt thereof. The expression level of the biomarker of SEQ ID NO: 323 may be assessed using nucleic acid amplification methods (e.g., PCR) or a device (e.g., a microarray). As is described above, the expression level of the biomarker of SEQ ID NO: 323 in the patient sample may then be compared, e.g., to the expression level of the biomarker of SEQ ID NO: 323 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 323 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio-markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-322, 324-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 324 may be used to assess the responsiveness of a cancer patient (e.g., a patient with cancer recurrence) to 2X-121 or a pharmaceutically acceptable salt thereof. The expression level of the biomarker of SEQ ID NO: 324 may be assessed using nucleic acid amplification methods (e.g., PCR) or a device (e.g., a microarray). As is described above, the expression level of the biomarker of SEQ ID NO: 324 in the patient sample may then be compared, e.g., to the expression level of the biomarker of SEQ ID NO: 324 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 324 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-323, 325-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 325 may be used to assess the responsiveness of a cancer patient (e.g., a patient with cancer recurrence) to 2X-121 or a pharmaceutically acceptable salt thereof. The expression level of the biomarker of SEQ ID NO: 325 may be assessed using nucleic acid amplification methods (e.g., PCR) or a device (e.g., a microarray). As is described above, the expression level of the biomarker of SEQ ID NO: 325 in the patient sample may then be compared, e.g., to the expression level of the biomarker of SEQ ID NO: 325 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 325 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-324, 326-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 326 may be used to assess the responsiveness of a cancer patient (e.g., a patient with cancer recurrence) to 2X-121 or a pharmaceutically acceptable salt thereof. The expression level of the biomarker of SEQ ID NO: 326 may be assessed using nucleic acid amplification methods (e.g., PCR) or a device (e.g., a microarray). As is described above, the expression level of the biomarker of SEQ ID NO: 326 in the patient sample may then be compared, e.g., to the expression level of the biomarker of SEQ ID NO: 326 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 326 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-325, 327-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 327 may be used to assess the responsiveness of a cancer patient (e.g., a patient with cancer recurrence) to 2X-121 or a pharmaceutically acceptable salt thereof. The expression level of the biomarker of SEQ ID NO: 327 may be assessed using nucleic acid amplification methods (e.g., PCR) or a device (e.g., a microarray). As is described above, the expression level of the biomarker of SEQ ID NO: 327 in the patient sample may then be compared, e.g., to the expression level of the biomarker of SEQ ID NO: 327 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 327 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-326, 328-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 328 may be used to assess the responsiveness of a cancer patient (e.g., a patient with cancer recurrence) to 2X-121 or a pharmaceutically acceptable salt thereof. The expression level of the biomarker of SEQ ID NO: 328 may be assessed using nucleic acid amplification methods (e.g., PCR) or a device (e.g., a microarray). As is described above, the expression level of the biomarker of SEQ ID NO: 328 in the patient sample may then be compared, e.g., to the expression level of the biomarker of SEQ ID NO: 328 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 328 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-327, 329-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 329 may be used to assess the responsiveness of a cancer patient (e.g., a patient with cancer recurrence) to 2X-121 or a pharmaceutically acceptable salt thereof. The expression level of the biomarker of SEQ ID NO: 329 may be assessed using nucleic acid amplification methods (e.g., PCR) or a device (e.g., a microarray). As is described above, the expression level of the biomarker of SEQ ID NO: 329 in the patient sample may then be compared, e.g., to the expression level of the biomarker of SEQ ID NO: 329 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 329 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-328, 330-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 330 may be used to assess the responsiveness of a cancer patient (e.g., a patient with cancer recurrence) to 2X-121 or a pharmaceutically acceptable salt thereof. The expression level of the biomarker of SEQ ID NO: 330 may be assessed using nucleic acid amplification methods (e.g., PCR) or a device (e.g., a microarray). As is described above, the expression level of the biomarker of SEQ ID NO: 330 in the patient sample may then be compared, e.g., to the expression level of the biomarker of SEQ ID NO: 330 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 330 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-329, 331-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 331 may be used to assess the responsiveness of a cancer patient (e.g., a patient with cancer recurrence) to 2X-121 or a pharmaceutically accept-able salt thereof. The expression level of the biomarker of SEQ ID NO: 331 may be assessed using nucleic acid amplification methods (e.g., PCR) or a device (e.g., a microarray). As is described above, the expression level of the biomarker of SEQ ID NO: 331 in the patient sample may then be compared, e.g., to the expression level of the biomarker of SEQ ID NO: 331 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 331 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-330, 332-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 332 may be used to assess the responsiveness of a cancer patient (e.g., a patient with cancer recurrence) to 2X-121 or a pharmaceutically accept-able salt thereof. The expression level of the biomarker of SEQ ID NO: 332 may be assessed using nucleic acid amplification methods (e.g., PCR) or a device (e.g., a microarray). As is described above, the expression level of the biomarker of SEQ ID NO: 332 in the patient sample may then be compared, e.g., to the expression level of the biomarker of SEQ ID NO: 332 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 332 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-331, 333-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 333 may be used to assess the responsiveness of a cancer patient (e.g., a patient with cancer recurrence) to 2X-121 or a pharmaceutically accept-able salt thereof. The expression level of the biomarker of SEQ ID NO: 333 may be assessed using nucleic acid amplification methods (e.g., PCR) or a device (e.g., a microarray). As is described above, the expression level of the biomarker of SEQ ID NO: 333 in the patient sample may then be compared, e.g., to the expression level of the biomarker of SEQ ID NO: 333 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 333 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-332, 334-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 334 may be used to assess the responsiveness of a cancer patient (e.g., a patient with cancer recurrence) to 2X-121 or a pharmaceutically accept-able salt thereof. The expression level of the biomarker of SEQ ID NO: 334 may be assessed using nucleic acid amplification methods (e.g., PCR) or a device (e.g., a microarray). As is described above, the expression level of the biomarker of SEQ ID NO: 334 in the patient sample may then be compared, e.g., to the expression level of the biomarker of SEQ ID NO: 334 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 334 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-333, 335-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 335 may be used to assess the responsiveness of a cancer patient (e.g., a patient with cancer recurrence) to 2X-121 or a pharmaceutically acceptable salt thereof. The expression level of the biomarker of SEQ ID NO: 335 may be assessed using nucleic acid amplification methods (e.g., PCR) or a device (e.g., a microarray). As is described above, the expression level of the biomarker of SEQ ID NO: 335 in the patient sample may then be compared, e.g., to the expression level of the biomarker of SEQ ID NO: 335 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 335 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-334, 336-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 336 may be used to assess the responsiveness of a cancer patient (e.g., a patient with cancer recurrence) to 2X-121 or a pharmaceutically acceptable salt thereof. The expression level of the biomarker of SEQ ID NO: 336 may be assessed using nucleic acid amplification methods (e.g., PCR) or a device (e.g., a microarray). As is described above, the expression level of the biomarker of SEQ ID NO: 336 in the patient sample may then be compared, e.g., to the expression level of the biomarker of SEQ ID NO: 336 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 336 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-335, 337-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 337 may be used to assess the responsiveness of a cancer patient (e.g., a patient with cancer recurrence) to 2X-121 or a pharmaceutically acceptable salt thereof. The expression level of the biomarker of SEQ ID NO: 337 may be assessed using nucleic acid amplification methods (e.g., PCR) or a device (e.g., a microarray). As is described above, the expression level of the biomarker of SEQ ID NO: 337 in the patient sample may then be compared, e.g., to the expression level of the biomarker of SEQ ID NO: 337 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 337 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-336, 338-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 338 may be used to assess the responsiveness of a cancer patient (e.g., a patient with cancer recurrence) to 2X-121 or a pharmaceutically acceptable salt thereof. The expression level of the biomarker of SEQ ID NO: 338 may be assessed using nucleic acid amplification methods (e.g., PCR) or a device (e.g., a microarray). As is described above, the expression level of the biomarker of SEQ ID NO: 338 in the patient sample may then be compared, e.g., to the expression level of the biomarker of SEQ ID NO: 338 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 338 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-337, 339-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 339 may be used to assess the responsiveness of a cancer patient (e.g., a patient with cancer recurrence) to 2X-121 or a pharmaceutically acceptable salt thereof. The expression level of the biomarker of SEQ ID NO: 339 may be assessed using nucleic acid amplification methods (e.g., PCR) or a device (e.g., a microarray). As is described above, the expression level of the biomarker of SEQ ID NO: 339 in the patient sample may then be compared, e.g., to the expression level of the biomarker of SEQ ID NO: 339 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 339 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-338, 340-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 340 may be used to assess the responsiveness of a cancer patient (e.g., a patient with cancer recurrence) to 2X-121 or a pharmaceutically acceptable salt thereof. The expression level of the biomarker of SEQ ID NO: 340 may be assessed using nucleic acid amplification methods (e.g., PCR) or a device (e.g., a microarray). As is described above, the expression level of the biomarker of SEQ ID NO: 340 in the patient sample may then be compared, e.g., to the expression level of the biomarker of SEQ ID NO: 340 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 340 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-339, 341-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 341 may be used to assess the responsiveness of a cancer patient (e.g., a patient with cancer recurrence) to 2X-121 or a pharmaceutically acceptable salt thereof. The expression level of the biomarker of SEQ ID NO: 341 may be assessed using nucleic acid amplification methods (e.g., PCR) or a device (e.g., a microarray). As is described above, the expression level of the biomarker of SEQ ID NO: 341 in the patient sample may then be compared, e.g., to the expression level of the biomarker of SEQ ID NO: 341 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 341 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-340, 342-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 342 may be used to assess the responsiveness of a cancer patient (e.g., a patient with cancer recurrence) to 2X-121 or a pharmaceutically acceptable salt thereof. The expression level of the biomarker of SEQ ID NO: 342 may be assessed using nucleic acid amplification methods (e.g., PCR) or a device (e.g., a microarray). As is described above, the expression level of the biomarker of SEQ ID NO: 342 in the patient sample may then be compared, e.g., to the expression level of the biomarker of SEQ ID NO: 342 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 342 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-341, 343-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 343 may be used to assess the responsiveness of a cancer patient (e.g., a patient with cancer recurrence) to 2X-121 or a pharmaceutically accept-able salt thereof. The expression level of the biomarker of SEQ ID NO: 343 may be assessed using nucleic acid amplification methods (e.g., PCR) or a device (e.g., a microarray). As is described above, the expression level of the biomarker of SEQ ID NO: 343 in the patient sample may then be compared, e.g., to the expression level of the biomarker of SEQ ID NO: 343 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 343 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-342, 344-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 344 may be used to assess the responsiveness of a cancer patient (e.g., a patient with cancer recurrence) to 2X-121 or a pharmaceutically accept-able salt thereof. The expression level of the biomarker of SEQ ID NO: 344 may be assessed using nucleic acid amplification methods (e.g., PCR) or a device (e.g., a microarray). As is described above, the expression level of the biomarker of SEQ ID NO: 344 in the patient sample may then be compared, e.g., to the expression level of the biomarker of SEQ ID NO: 344 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 344 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-343, 345-414. The expres-sion level of the biomarker(s) may be determined using, e.g., a microarray, PCR, or other techniques described herein, for example, using a nucleic acid probe sequence based on the target sequences shown in Tables 2 and 3.

example, using a nucleic acid probe sequence based on the target sequences shown in Tables 2 and 3.

The biomarker of SEQ ID NO: 345 may be used to assess the responsiveness of a cancer patient (e.g., a patient with cancer recurrence) to 2X-121 or a pharmaceutically accept-able salt thereof. The expression level of the biomarker of SEQ ID NO: 345 may be assessed using nucleic acid amplification methods (e.g., PCR) or a device (e.g., a microarray). As is described above, the expression level of the biomarker of SEQ ID NO: 345 in the patient sample may then be compared, e.g., to the expression level of the biomarker of SEQ ID NO: 345 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 345 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-344, 346-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 346 may be used to assess the responsiveness of a cancer patient (e.g., a patient with cancer recurrence) to 2X-121 or a pharmaceutically accept-able salt thereof. The expression level of the biomarker of SEQ ID NO: 346 may be assessed using nucleic acid amplification methods (e.g., PCR) or a device (e.g., a microarray). As is described above, the expression level of the biomarker of SEQ ID NO: 346 in the patient sample may then be compared, e.g., to the expression level of the biomarker of SEQ ID NO: 346 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 346 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-345, 347-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 347 may be used to assess the responsiveness of a cancer patient (e.g., a patient with cancer recurrence) to 2X-121 or a pharmaceutically accept-able salt thereof. The expression level of the biomarker of SEQ ID NO: 347 may be assessed using nucleic acid amplification methods (e.g., PCR) or a device (e.g., a microarray). As is described above, the expression level of the biomarker of SEQ ID NO: 347 in the patient sample may then be compared, e.g., to the expression level of the biomarker of SEQ ID NO: 347 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 347 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio-markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-346, 348-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 348 may be used to assess the responsiveness of a cancer patient (e.g., a patient with cancer recurrence) to 2X-121 or a pharmaceutically accept-able salt thereof. The expression level of the biomarker of SEQ ID NO: 348 may be assessed using nucleic acid amplification methods (e.g., PCR) or a device (e.g., a microarray). As is described above, the expression level of the biomarker of SEQ ID NO: 348 in the patient sample may then be compared, e.g., to the expression level of the biomarker of SEQ ID NO: 348 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 348 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-347, 349-414. The expression level of the bio-marker(s) may be determined using, e.g., a microarray, PCR, or other techniques described herein, for example, using a nucleic acid probe sequence based on the target sequences shown in Tables 2 and 3.

The biomarker of SEQ ID NO: 349 may be used to assess the responsiveness of a cancer patient (e.g., a patient with cancer recurrence) to 2X-121 or a pharmaceutically accept-able salt thereof. The expression level of the biomarker of SEQ ID NO: 349 may be assessed using nucleic acid amplification methods (e.g., PCR) or a device (e.g., a microarray). As is described above, the expression level of the biomarker of SEQ ID NO: 349 in the patient sample may then be compared, e.g., to the expression level of the biomarker of SEQ ID NO: 349 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 349 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-348, 350-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 350 may be used to assess the responsiveness of a cancer patient (e.g., a patient with cancer recurrence) to 2X-121 or a pharmaceutically accept-able salt thereof. The expression level of the biomarker of SEQ ID NO: 350 may be assessed using nucleic acid amplification methods (e.g., PCR) or a device (e.g., a microarray). As is described above, the expression level of the biomarker of SEQ ID NO: 350 in the patient sample may then be compared, e.g., to the expression level of the biomarker of SEQ ID NO: 350 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 350 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-349, 351-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 351 may be used to assess the responsiveness of a cancer patient (e.g., a patient with cancer recurrence) to 2X-121 or a pharmaceutically accept-able salt thereof. The expression level of the biomarker of SEQ ID NO: 351 may be assessed using nucleic acid amplification methods (e.g., PCR) or a device (e.g., a microarray). As is described above, the expression level of the biomarker of SEQ ID NO: 351 in the patient sample may then be compared, e.g., to the expression level of the biomarker of SEQ ID NO: 351 in a cell (e.g., a cancer cell)

or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 351 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-350, 352-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 352 may be used to assess the responsiveness of a cancer patient (e.g., a patient with cancer recurrence) to 2X-121 or a pharmaceutically acceptable salt thereof. The expression level of the biomarker of SEQ ID NO: 352 may be assessed using nucleic acid amplification methods (e.g., PCR) or a device (e.g., a microarray). As is described above, the expression level of the biomarker of SEQ ID NO: 352 in the patient sample may then be compared, e.g., to the expression level of the biomarker of SEQ ID NO: 352 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 352 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-351, 353-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 353 may be used to assess the responsiveness of a cancer patient (e.g., a patient with cancer recurrence) to 2X-121 or a pharmaceutically acceptable salt thereof. The expression level of the biomarker of SEQ ID NO: 353 may be assessed using nucleic acid amplification methods (e.g., PCR) or a device (e.g., a microarray). As is described above, the expression level of the biomarker of SEQ ID NO: 353 in the patient sample may then be compared, e.g., to the expression level of the biomarker of SEQ ID NO: 353 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 353 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-352, 354-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 354 may be used to assess the responsiveness of a cancer patient (e.g., a patient with cancer recurrence) to 2X-121 or a pharmaceutically acceptable salt thereof. The expression level of the biomarker of SEQ ID NO: 354 may be assessed using nucleic acid amplification methods (e.g., PCR) or a device (e.g., a microarray). As is described above, the expression level of the biomarker of SEQ ID NO: 354 in the patient sample may then be compared, e.g., to the expression level of the biomarker of SEQ ID NO: 354 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 354 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-353, 355-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 355 may be used to assess the responsiveness of a cancer patient (e.g., a patient with cancer recurrence) to 2X-121 or a pharmaceutically acceptable salt thereof. The expression level of the biomarker of SEQ ID NO: 355 may be assessed using nucleic acid amplification methods (e.g., PCR) or a device (e.g., a microarray). As is described above, the expression level of the biomarker of SEQ ID NO: 355 in the patient sample may then be compared, e.g., to the expression level of the biomarker of SEQ ID NO: 355 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 355 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-354, 356-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 356 may be used to assess the responsiveness of a cancer patient (e.g., a patient with cancer recurrence) to 2X-121 or a pharmaceutically acceptable salt thereof. The expression level of the biomarker of SEQ ID NO: 356 may be assessed using nucleic acid amplification methods (e.g., PCR) or a device (e.g., a microarray). As is described above, the expression level of the biomarker of SEQ ID NO: 356 in the patient sample may then be compared, e.g., to the expression level of the biomarker of SEQ ID NO: 356 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 356 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-355, 357-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 357 may be used to assess the responsiveness of a cancer patient (e.g., a patient with cancer recurrence) to 2X-121 or a pharmaceutically acceptable salt thereof. The expression level of the biomarker of SEQ ID NO: 357 may be assessed using nucleic acid amplification methods (e.g., PCR) or a device (e.g., a microarray). As is described above, the expression level of the biomarker of SEQ ID NO: 357 in the patient sample may then be compared, e.g., to the expression level of the biomarker of SEQ ID NO: 357 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 357 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-356, 358-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 358 may be used to assess the responsiveness of a cancer patient (e.g., a patient with cancer recurrence) to 2X-121 or a pharmaceutically acceptable salt thereof. The expression level of the biomarker of SEQ ID NO: 358 may be assessed using nucleic acid amplification methods (e.g., PCR) or a device (e.g., a microarray). As is described above, the expression level of the biomarker of SEQ ID NO: 358 in the patient sample may then be compared, e.g., to the expression level of the biomarker of SEQ ID NO: 358 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 358 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-357, 359-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 359 may be used to assess the responsiveness of a cancer patient (e.g., a patient with cancer recurrence) to 2X-121 or a pharmaceutically acceptable salt thereof. The expression level of the biomarker of SEQ ID NO: 359 may be assessed using nucleic acid amplification methods (e.g., PCR) or a device (e.g., a microarray). As is described above, the expression level of the biomarker of SEQ ID NO: 359 in the patient sample may then be compared, e.g., to the expression level of the biomarker of SEQ ID NO: 359 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 359 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-358, 360-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 360 may be used to assess the responsiveness of a cancer patient (e.g., a patient with cancer recurrence) to 2X-121 or a pharmaceutically acceptable salt thereof. The expression level of the biomarker of SEQ ID NO: 360 may be assessed using nucleic acid amplification methods (e.g., PCR) or a device (e.g., a microarray). As is described above, the expression level of the biomarker of SEQ ID NO: 360 in the patient sample may then be compared, e.g., to the expression level of the biomarker of SEQ ID NO: 360 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 360 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-359, 361-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 361 may be used to assess the responsiveness of a cancer patient (e.g., a patient with cancer recurrence) to 2X-121 or a pharmaceutically acceptable salt thereof. The expression level of the biomarker of SEQ ID NO: 361 may be assessed using nucleic acid amplification methods (e.g., PCR) or a device (e.g., a microarray). As is described above, the expression level of the biomarker of SEQ ID NO: 361 in the patient sample may then be compared, e.g., to the expression level of the biomarker of SEQ ID NO: 361 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 361 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-360, 362-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 362 may be used to assess the responsiveness of a cancer patient (e.g., a patient with cancer recurrence) to 2X-121 or a pharmaceutically acceptable salt thereof. The expression level of the biomarker of SEQ ID NO: 362 may be assessed using nucleic acid amplification methods (e.g., PCR) or a device (e.g., a microarray). As is described above, the expression level of the biomarker of SEQ ID NO: 362 in the patient sample may then be compared, e.g., to the expression level of the biomarker of SEQ ID NO: 362 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 362 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-361, 363-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 363 may be used to assess the responsiveness of a cancer patient (e.g., a patient with cancer recurrence) to 2X-121 or a pharmaceutically acceptable salt thereof. The expression level of the biomarker of SEQ ID NO: 363 may be assessed using nucleic acid amplification methods (e.g., PCR) or a device (e.g., a microarray). As is described above, the expression level of the biomarker of SEQ ID NO: 363 in the patient sample may then be compared, e.g., to the expression level of the biomarker of SEQ ID NO: 363 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 363 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-362, 364-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 364 may be used to assess the responsiveness of a cancer patient (e.g., a patient with cancer recurrence) to 2X-121 or a pharmaceutically acceptable salt thereof. The expression level of the biomarker of SEQ ID NO: 364 may be assessed using nucleic acid amplification methods (e.g., PCR) or a device (e.g., a microarray). As is described above, the expression level of the biomarker of SEQ ID NO: 364 in the patient sample may then be compared, e.g., to the expression level of the biomarker of SEQ ID NO: 364 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 364 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-363, 365-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 365 may be used to assess the responsiveness of a cancer patient (e.g., a patient with cancer recurrence) to 2X-121 or a pharmaceutically acceptable salt thereof. The expression level of the biomarker of SEQ ID NO: 365 may be assessed using nucleic acid amplification methods (e.g., PCR) or a device (e.g., a microarray). As is described above, the expression level of the biomarker of SEQ ID NO: 365 in the patient sample may then be compared, e.g., to the expression level of the biomarker of SEQ ID NO: 365 in a cell (e.g., a cancer cell)

or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 365 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-364, 366-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 366 may be used to assess the responsiveness of a cancer patient (e.g., a patient with cancer recurrence) to 2X-121 or a pharmaceutically acceptable salt thereof. The expression level of the biomarker of SEQ ID NO: 366 may be assessed using nucleic acid amplification methods (e.g., PCR) or a device (e.g., a microarray). As is described above, the expression level of the biomarker of SEQ ID NO: 366 in the patient sample may then be compared, e.g., to the expression level of the biomarker of SEQ ID NO: 366 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 366 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-365, 367-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 367 may be used to assess the responsiveness of a cancer patient (e.g., a patient with cancer recurrence) to 2X-121 or a pharmaceutically acceptable salt thereof. The expression level of the biomarker of SEQ ID NO: 367 may be assessed using nucleic acid amplification methods (e.g., PCR) or a device (e.g., a microarray). As is described above, the expression level of the biomarker of SEQ ID NO: 367 in the patient sample may then be compared, e.g., to the expression level of the biomarker of SEQ ID NO: 367 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 367 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-366, 368-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 368 may be used to assess the responsiveness of a cancer patient (e.g., a patient with cancer recurrence) to 2X-121 or a pharmaceutically acceptable salt thereof. The expression level of the biomarker of SEQ ID NO: 368 may be assessed using nucleic acid amplification methods (e.g., PCR) or a device (e.g., a microarray). As is described above, the expression level of the biomarker of SEQ ID NO: 368 in the patient sample may then be compared, e.g., to the expression level of the biomarker of SEQ ID NO: 368 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 368 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-367, 369-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 369 may be used to assess the responsiveness of a cancer patient (e.g., a patient with cancer recurrence) to 2X-121 or a pharmaceutically acceptable salt thereof. The expression level of the biomarker of SEQ ID NO: 369 may be assessed using nucleic acid amplification methods (e.g., PCR) or a device (e.g., a microarray). As is described above, the expression level of the biomarker of SEQ ID NO: 369 in the patient sample may then be compared, e.g., to the expression level of the biomarker of SEQ ID NO: 369 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 369 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-368, 370-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 370 may be used to assess the responsiveness of a cancer patient (e.g., a patient with cancer recurrence) to 2X-121 or a pharmaceutically acceptable salt thereof. The expression level of the biomarker of SEQ ID NO: 370 may be assessed using nucleic acid amplification methods (e.g., PCR) or a device (e.g., a microarray). As is described above, the expression level of the biomarker of SEQ ID NO: 370 in the patient sample may then be compared, e.g., to the expression level of the biomarker of SEQ ID NO: 370 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 370 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-369, 371-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 371 may be used to assess the responsiveness of a cancer patient (e.g., a patient with cancer recurrence) to 2X-121 or a pharmaceutically acceptable salt thereof. The expression level of the biomarker of SEQ ID NO: 371 may be assessed using nucleic acid amplification methods (e.g., PCR) or a device (e.g., a microarray). As is described above, the expression level of the biomarker of SEQ ID NO: 371 in the patient sample may then be compared, e.g., to the expression level of the biomarker of SEQ ID NO: 371 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 371 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio-markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-370, 372-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 372 may be used to assess the responsiveness of a cancer patient (e.g., a patient with cancer recurrence) to 2X-121 or a pharmaceutically accept-able salt thereof. The expression level of the biomarker of SEQ ID NO: 372 may be assessed using nucleic acid amplification methods (e.g., PCR) or a device (e.g., a microarray). As is described above, the expression level of the biomarker of SEQ ID NO: 372 in the patient sample may then be compared, e.g., to the expression level of the biomarker of SEQ ID NO: 372 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 372 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-371, 373-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 373 may be used to assess the responsiveness of a cancer patient (e.g., a patient with cancer recurrence) to 2X-121 or a pharmaceutically accept-able salt thereof. The expression level of the biomarker of SEQ ID NO: 373 may be assessed using nucleic acid amplification methods (e.g., PCR) or a device (e.g., a microarray). As is described above, the expression level of the biomarker of SEQ ID NO: 373 in the patient sample may then be compared, e.g., to the expression level of the biomarker of SEQ ID NO: 373 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 373 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-372, 374-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 374 may be used to assess the responsiveness of a cancer patient (e.g., a patient with cancer recurrence) to 2X-121 or a pharmaceutically accept-able salt thereof. The expression level of the biomarker of SEQ ID NO: 374 may be assessed using nucleic acid amplification methods (e.g., PCR) or a device (e.g., a microarray). As is described above, the expression level of the biomarker of SEQ ID NO: 374 in the patient sample may then be compared, e.g., to the expression level of the biomarker of SEQ ID NO: 374 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 374 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-373, 375-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 375 may be used to assess the responsiveness of a cancer patient (e.g., a patient with cancer recurrence) to 2X-121 or a pharmaceutically accept-able salt thereof. The expression level of the biomarker of SEQ ID NO: 375 may be assessed using nucleic acid amplification methods (e.g., PCR) or a device (e.g., a microarray). As is described above, the expression level of the biomarker of SEQ ID NO: 375 in the patient sample may then be compared, e.g., to the expression level of the biomarker of SEQ ID NO: 375 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 375 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-374, 376-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 376 may be used to assess the responsiveness of a cancer patient (e.g., a patient with cancer recurrence) to 2X-121 or a pharmaceutically acceptable salt thereof. The expression level of the biomarker of SEQ ID NO: 376 may be assessed using nucleic acid amplification methods (e.g., PCR) or a device (e.g., a microarray). As is described above, the expression level of the biomarker of SEQ ID NO: 376 in the patient sample may then be compared, e.g., to the expression level of the biomarker of SEQ ID NO: 376 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 376 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-375, 377-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 377 may be used to assess the responsiveness of a cancer patient (e.g., a patient with cancer recurrence) to 2X-121 or a pharmaceutically acceptable salt thereof. The expression level of the biomarker of SEQ ID NO: 377 may be assessed using nucleic acid amplification methods (e.g., PCR) or a device (e.g., a microarray). As is described above, the expression level of the biomarker of SEQ ID NO: 377 in the patient sample may then be compared, e.g., to the expression level of the biomarker of SEQ ID NO: 377 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 377 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-376, 378-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 378 may be used to assess the responsiveness of a cancer patient (e.g., a patient with cancer recurrence) to 2X-121 or a pharmaceutically acceptable salt thereof. The expression level of the biomarker of SEQ ID NO: 378 may be assessed using nucleic acid amplification methods (e.g., PCR) or a device (e.g., a microarray). As is described above, the expression level of the biomarker of SEQ ID NO: 378 in the patient sample may then be compared, e.g., to the expression level of the biomarker of SEQ ID NO: 378 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 378 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-377, 379-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 379 may be used to assess the responsiveness of a cancer patient (e.g., a patient with cancer recurrence) to 2X-121 or a pharmaceutically acceptable salt thereof. The expression level of the biomarker of SEQ ID NO: 379 may be assessed using nucleic acid amplification methods (e.g., PCR) or a device (e.g., a microarray). As is described above, the expression level of the biomarker of SEQ ID NO: 379 in the patient sample may then be compared, e.g., to the expression level of the biomarker of SEQ ID NO: 379 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 379 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-378, 380-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 380 may be used to assess the responsiveness of a cancer patient (e.g., a patient with cancer recurrence) to 2X-121 or a pharmaceutically acceptable salt thereof. The expression level of the biomarker of SEQ ID NO: 380 may be assessed using nucleic acid amplification methods (e.g., PCR) or a device (e.g., a microarray). As is described above, the expression level of the biomarker of SEQ ID NO: 380 in the patient sample may then be compared, e.g., to the expression level of the biomarker of SEQ ID NO: 380 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 380 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-379, 381-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 381 may be used to assess the responsiveness of a cancer patient (e.g., a patient with cancer recurrence) to 2X-121 or a pharmaceutically acceptable salt thereof. The expression level of the biomarker of SEQ ID NO: 381 may be assessed using nucleic acid amplification methods (e.g., PCR) or a device (e.g., a microarray). As is described above, the expression level of the biomarker of SEQ ID NO: 381 in the patient sample may then be compared, e.g., to the expression level of the biomarker of SEQ ID NO: 381 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 381 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-380, 382-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 382 may be used to assess the responsiveness of a cancer patient (e.g., a patient with cancer recurrence) to 2X-121 or a pharmaceutically acceptable salt thereof. The expression level of the biomarker of SEQ ID NO: 382 may be assessed using nucleic acid amplification methods (e.g., PCR) or a device (e.g., a microarray). As is described above, the expression level of the biomarker of SEQ ID NO: 382 in the patient sample may then be compared, e.g., to the expression level of the biomarker of SEQ ID NO: 382 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 382 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-381, 383-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 383 may be used to assess the responsiveness of a cancer patient (e.g., a patient with cancer recurrence) to 2X-121 or a pharmaceutically acceptable salt thereof. The expression level of the biomarker of SEQ ID NO: 383 may be assessed using nucleic acid amplification methods (e.g., PCR) or a device (e.g., a microarray). As is described above, the expression level of the biomarker of SEQ ID NO: 383 in the patient sample may then be compared, e.g., to the expression level of the biomarker of SEQ ID NO: 383 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 383 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-382, 384-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 384 may be used to assess the responsiveness of a cancer patient (e.g., a patient with cancer recurrence) to 2X-121 or a pharmaceutically acceptable salt thereof. The expression level of the biomarker of SEQ ID NO: 384 may be assessed using nucleic acid amplification methods (e.g., PCR) or a device (e.g., a microarray). As is described above, the expression level of the biomarker of SEQ ID NO: 384 in the patient sample may then be compared, e.g., to the expression level of the biomarker of SEQ ID NO: 384 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 384 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-383, 385-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 385 may be used to assess the responsiveness of a cancer patient (e.g., a patient with cancer recurrence) to 2X-121 or a pharmaceutically acceptable salt thereof. The expression level of the biomarker of SEQ ID NO: 385 may be assessed using nucleic acid amplification methods (e.g., PCR) or a device (e.g., a microarray). As is described above, the expression level of the biomarker of SEQ ID NO: 385 in the patient sample may then be compared, e.g., to the expression level of the biomarker of SEQ ID NO: 385 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 385 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-384, 386-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 386 may be used to assess the responsiveness of a cancer patient (e.g., a patient with cancer recurrence) to 2X-121 or a pharmaceutically acceptable salt thereof. The expression level of the biomarker of SEQ ID NO: 386 may be assessed using nucleic acid amplification methods (e.g., PCR) or a device (e.g., a microarray). As is described above, the expression level of the biomarker of SEQ ID NO: 386 in the patient sample may then be compared, e.g., to the expression level of the biomarker of SEQ ID NO: 386 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 386 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-385, 387-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 387 may be used to assess the responsiveness of a cancer patient (e.g., a patient with cancer recurrence) to 2X-121 or a pharmaceutically acceptable salt thereof. The expression level of the biomarker of SEQ ID NO: 387 may be assessed using nucleic acid amplification methods (e.g., PCR) or a device (e.g., a microarray). As is described above, the expression level of the biomarker of SEQ ID NO: 387 in the patient sample may then be compared, e.g., to the expression level of the biomarker of SEQ ID NO: 387 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 387 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-386, 388-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 388 may be used to assess the responsiveness of a cancer patient (e.g., a patient with cancer recurrence) to 2X-121 or a pharmaceutically acceptable salt thereof. The expression level of the biomarker of SEQ ID NO: 388 may be assessed using nucleic acid amplification methods (e.g., PCR) or a device (e.g., a microarray). As is described above, the expression level of the biomarker of SEQ ID NO: 388 in the patient sample may then be compared, e.g., to the expression level of the biomarker of SEQ ID NO: 388 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 388 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-387, 389-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 389 may be used to assess the responsiveness of a cancer patient (e.g., a patient with cancer recurrence) to 2X-121 or a pharmaceutically acceptable salt thereof. The expression level of the biomarker of SEQ ID NO: 389 may be assessed using nucleic acid amplification methods (e.g., PCR) or a device (e.g., a microarray). As is described above, the expression level of the biomarker of SEQ ID NO: 389 in the patient sample may then be compared, e.g., to the expression level of the biomarker of SEQ ID NO: 389 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 389 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-388, 390-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 390 may be used to assess the responsiveness of a cancer patient (e.g., a patient with cancer recurrence) to 2X-121 or a pharmaceutically acceptable salt thereof. The expression level of the biomarker of SEQ ID NO: 390 may be assessed using nucleic acid amplification methods (e.g., PCR) or a device (e.g., a microarray). As is described above, the expression level of the biomarker of SEQ ID NO: 390 in the patient sample may then be compared, e.g., to the expression level of the biomarker of SEQ ID NO: 390 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 390 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-389, 391-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 391 may be used to assess the responsiveness of a cancer patient (e.g., a patient with cancer recurrence) to 2X-121 or a pharmaceutically acceptable salt thereof. The expression level of the biomarker of SEQ ID NO: 391 may be assessed using nucleic acid amplification methods (e.g., PCR) or a device (e.g., a microarray). As is described above, the expression level of the biomarker of SEQ ID NO: 391 in the patient sample may then be compared, e.g., to the expression level of the biomarker of SEQ ID NO: 391 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 391 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-390, 392-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 392 may be used to assess the responsiveness of a cancer patient (e.g., a patient with cancer recurrence) to 2X-121 or a pharmaceutically acceptable salt thereof. The expression level of the biomarker of SEQ ID NO: 392 may be assessed using nucleic acid amplification methods (e.g., PCR) or a device (e.g., a microarray). As is described above, the expression level of the biomarker of SEQ ID NO: 392 in the patient sample may then be compared, e.g., to the expression level of the biomarker of SEQ ID NO: 392 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 392 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-391, 393-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 393 may be used to assess the responsiveness of a cancer patient (e.g., a patient with cancer recurrence) to 2X-121 or a pharmaceutically acceptable salt thereof. The expression level of the biomarker of SEQ ID NO: 393 may be assessed using nucleic acid amplification methods (e.g., PCR) or a device (e.g., a microarray). As is described above, the expression level of the biomarker of SEQ ID NO: 393 in the patient sample may then be compared, e.g., to the expression level of the biomarker of SEQ ID NO: 393 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 393 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-392, 394-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 394 may be used to assess the responsiveness of a cancer patient (e.g., a patient with cancer recurrence) to 2X-121 or a pharmaceutically acceptable salt thereof. The expression level of the biomarker of SEQ ID NO: 394 may be assessed using nucleic acid amplification methods (e.g., PCR) or a device (e.g., a microarray). As is described above, the expression level of the biomarker of SEQ ID NO: 394 in the patient sample may then be compared, e.g., to the expression level of the biomarker of SEQ ID NO: 394 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 394 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-393, 395-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 395 may be used to assess the responsiveness of a cancer patient (e.g., a patient with cancer recurrence) to 2X-121 or a pharmaceutically acceptable salt thereof. The expression level of the biomarker of SEQ ID NO: 395 may be assessed using nucleic acid amplification methods (e.g., PCR) or a device (e.g., a microarray). As is described above, the expression level of the biomarker of SEQ ID NO: 395 in the patient sample may then be compared, e.g., to the expression level of the biomarker of SEQ ID NO: 395 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 395 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio-markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-394, 396-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 396 may be used to assess the responsiveness of a cancer patient (e.g., a patient with cancer recurrence) to 2X-121 or a pharmaceutically accept-able salt thereof. The expression level of the biomarker of SEQ ID NO: 396 may be assessed using nucleic acid amplification methods (e.g., PCR) or a device (e.g., a microarray). As is described above, the expression level of the biomarker of SEQ ID NO: 396 in the patient sample may then be compared, e.g., to the expression level of the biomarker of SEQ ID NO: 396 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 396 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-395, 397-414. The expression level of the bio-marker(s) may be determined using, e.g., a microarray, PCR, or other techniques described herein, for example, using a nucleic acid probe sequence based on the target sequences shown in Tables 2 and 3.

The biomarker of SEQ ID NO: 397 may be used to assess the responsiveness of a cancer patient (e.g., a patient with cancer recurrence) to 2X-121 or a pharmaceutically accept-able salt thereof. The expression level of the biomarker of SEQ ID NO: 397 may be assessed using nucleic acid amplification methods (e.g., PCR) or a device (e.g., a microarray). As is described above, the expression level of the biomarker of SEQ ID NO: 397 in the patient sample may then be compared, e.g., to the expression level of the biomarker of SEQ ID NO: 397 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 397 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-396, 398-414. The expres-sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 398 may be used to assess the responsiveness of a cancer patient (e.g., a patient with cancer recurrence) to 2X-121 or a pharmaceutically accept-able salt thereof. The expression level of the biomarker of SEQ ID NO: 398 may be assessed using nucleic acid amplification methods (e.g., PCR) or a device (e.g., a microarray). As is described above, the expression level of the biomarker of SEQ ID NO: 398 in the patient sample may then be compared, e.g., to the expression level of the biomarker of SEQ ID NO: 398 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 398 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio-markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-397, 399-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 399 may be used to assess the responsiveness of a cancer patient (e.g., a patient with cancer recurrence) to 2X-121 or a pharmaceutically accept-able salt thereof. The expression level of the biomarker of SEQ ID NO: 399 may be assessed using nucleic acid amplification methods (e.g., PCR) or a device (e.g., a microarray). As is described above, the expression level of the biomarker of SEQ ID NO: 399 in the patient sample may then be compared, e.g., to the expression level of the biomarker of SEQ ID NO: 399 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 399 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-398, 400-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 400 may be used to assess the responsiveness of a cancer patient (e.g., a patient with cancer recurrence) to 2X-121 or a pharmaceutically acceptable salt thereof. The expression level of the biomarker of SEQ ID NO: 400 may be assessed using nucleic acid amplification methods (e.g., PCR) or a device (e.g., a microarray). As is described above, the expression level of the biomarker of SEQ ID NO: 400 in the patient sample may then be compared, e.g., to the expression level of the biomarker of SEQ ID NO: 400 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 400 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-399, 401-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 401 may be used to assess the responsiveness of a cancer patient (e.g., a patient with cancer recurrence) to 2X-121 or a pharmaceutically acceptable salt thereof. The expression level of the biomarker of SEQ ID NO: 401 may be assessed using nucleic acid amplification methods (e.g., PCR) or a device (e.g., a microarray). As is described above, the expression level of the biomarker of SEQ ID NO: 401 in the patient sample may then be compared, e.g., to the expression level of the biomarker of SEQ ID NO: 401 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 401 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-400, 402-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 402 may be used to assess the responsiveness of a cancer patient (e.g., a patient with cancer recurrence) to 2X-121 or a pharmaceutically acceptable salt thereof. The expression level of the biomarker of SEQ ID NO: 402 may be assessed using nucleic acid amplification methods (e.g., PCR) or a device (e.g., a microarray). As is described above, the expression level of the biomarker of SEQ ID NO: 402 in the patient sample may then be compared, e.g., to the expression level of the biomarker of SEQ ID NO: 402 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 402 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-401, 403-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 403 may be used to assess the responsiveness of a cancer patient (e.g., a patient with cancer recurrence) to 2X-121 or a pharmaceutically acceptable salt thereof. The expression level of the biomarker of SEQ ID NO: 403 may be assessed using nucleic acid amplification methods (e.g., PCR) or a device (e.g., a microarray). As is described above, the expression level of the biomarker of SEQ ID NO: 403 in the patient sample may then be compared, e.g., to the expression level of the biomarker of SEQ ID NO: 403 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 403 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-402, 404-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 404 may be used to assess the responsiveness of a cancer patient (e.g., a patient with cancer recurrence) to 2X-121 or a pharmaceutically acceptable salt thereof. The expression level of the biomarker of SEQ ID NO: 404 may be assessed using nucleic acid amplification methods (e.g., PCR) or a device (e.g., a microarray). As is described above, the expression level of the biomarker of SEQ ID NO: 404 in the patient sample may then be compared, e.g., to the expression level of the biomarker of SEQ ID NO: 404 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 404 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-403, 405-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 405 may be used to assess the responsiveness of a cancer patient (e.g., a patient with cancer recurrence) to 2X-121 or a pharmaceutically acceptable salt thereof. The expression level of the biomarker of SEQ ID NO: 405 may be assessed using nucleic acid amplification methods (e.g., PCR) or a device (e.g., a microarray). As is described above, the expression level of the biomarker of SEQ ID NO: 405 in the patient sample may then be compared, e.g., to the expression level of the biomarker of SEQ ID NO: 405 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 405 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-404, 406-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 406 may be used to assess the responsiveness of a cancer patient (e.g., a patient with cancer recurrence) to 2X-121 or a pharmaceutically acceptable salt thereof. The expression level of the biomarker of SEQ ID NO: 406 may be assessed using nucleic acid amplification methods (e.g., PCR) or a device (e.g., a microarray). As is described above, the expression level of the biomarker of SEQ ID NO: 406 in the patient sample may then be compared, e.g., to the expression level of the biomarker of SEQ ID NO: 406 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 406 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-405, 407-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 407 may be used to assess the responsiveness of a cancer patient (e.g., a patient with cancer recurrence) to 2X-121 or a pharmaceutically acceptable salt thereof. The expression level of the biomarker of SEQ ID NO: 407 may be assessed using nucleic acid amplification methods (e.g., PCR) or a device (e.g., a microarray). As is described above, the expression level of the biomarker of SEQ ID NO: 407 in the patient sample may then be compared, e.g., to the expression level of the biomarker of SEQ ID NO: 407 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 407 may be used alone to predict responsiveness of the cancer patient to treatment with 2X-121 or a pharmaceutically acceptable salt thereof or in combination with one or more 3, or all of the biomarkers shown in Tables 2 and/or 3)), such as biomarker(s) of SEQ ID NOs: 1-406, 408-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 408 may be used to assess the responsiveness of a cancer patient (e.g., a patient with cancer recurrence) to 2X-121 or a pharmaceutically accept- able salt thereof. The expression level of the biomarker of SEQ ID NO: 408 may be assessed using nucleic acid amplification methods (e.g., PCR) or a device (e.g., a microarray). As is described above, the expression level of the biomarker of SEQ ID NO: 408 in the patient sample may then be compared, e.g., to the expression level of the biomarker of SEQ ID NO: 408 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 408 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-407, 409-414. The expres- sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 409 may be used to assess the responsiveness of a cancer patient (e.g., a patient with cancer recurrence) to 2X-121 or a pharmaceutically accept- able salt thereof. The expression level of the biomarker of SEQ ID NO: 409 may be assessed using nucleic acid amplification methods (e.g., PCR) or a device (e.g., a microarray). As is described above, the expression level of the biomarker of SEQ ID NO: 409 in the patient sample may then be compared, e.g., to the expression level of the biomarker of SEQ ID NO: 409 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 409 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-408, 410-414. The expres- sion level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 410 may be used to assess the responsiveness of a cancer patient (e.g., a patient with cancer recurrence) to 2X-121 or a pharmaceutically accept- able salt thereof. The expression level of the biomarker of SEQ ID NO: 410 may be assessed using nucleic acid amplification methods (e.g., PCR) or a device (e.g., a microarray). As is described above, the expression level of the biomarker of SEQ ID NO: 410 in the patient sample may then be compared, e.g., to the expression level of the biomarker of SEQ ID NO: 410 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof.

The biomarker of SEQ ID NO: 410 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four bio- markers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-409, 411-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 411 may be used to assess the responsiveness of a cancer patient (e.g., a patient with cancer recurrence) to 2X-121 or a pharmaceutically accept- able salt thereof. The expression level of the biomarker of SEQ ID NO: 411 may be assessed using nucleic acid amplification methods (e.g., PCR) or a device (e.g., a microarray). As is described above, the expression level of the biomarker of SEQ ID NO: 411 in the patient sample may then be compared, e.g., to the expression level of the biomarker of SEQ ID NO: 411 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 411 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-410, 412-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 412 may be used to assess the responsiveness of a cancer patient (e.g., a patient with cancer recurrence) to 2X-121 or a pharmaceutically acceptable salt thereof. The expression level of the biomarker of SEQ ID NO: 412 may be assessed using nucleic acid amplification methods (e.g., PCR) or a device (e.g., a microarray). As is described above, the expression level of the biomarker of SEQ ID NO: 412 in the patient sample may then be compared, e.g., to the expression level of the biomarker of SEQ ID NO: 412 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 412 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-411, 413-414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 413 may be used to assess the responsiveness of a cancer patient (e.g., a patient with cancer recurrence) to 2X-121 or a pharmaceutically acceptable salt thereof. The expression level of the biomarker of SEQ ID NO: 413 may be assessed using nucleic acid amplification methods (e.g., PCR) or a device (e.g., a microarray). As is described above, the expression level of the biomarker of SEQ ID NO: 413 in the patient sample may then be compared, e.g., to the expression level of the biomarker of SEQ ID NO: 413 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 413 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-412, 414. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 414 may be used to assess the responsiveness of a cancer patient (e.g., a patient with cancer recurrence) to 2X-121 or a pharmaceutically acceptable salt thereof. The expression level of the biomarker of SEQ ID NO: 414 may be assessed using nucleic acid amplification methods (e.g., PCR) or a device (e.g., a microarray). As is described above, the expression level of the biomarker of SEQ ID NO: 414 in the patient sample may then be compared, e.g., to the expression level of the biomarker of SEQ ID NO: 414 in a cell (e.g., a cancer cell) or tissue (e.g., a tumor tissue) known to be sensitive or resistant to treatment with 2X-121 or a pharmaceutically acceptable salt thereof and used to determine the cancer patient's responsiveness to 2X-121 or a pharmaceutically acceptable salt thereof. The biomarker of SEQ ID NO: 414 may be used alone to predict responsiveness of the cancer patient to treatment with 2X-121 or a pharmaceutically acceptable salt thereof or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarkers shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-413.

The expression level of the biomarker(s) may be determined using, e.g., a microarray, PCR, or other techniques described herein, for example, using a nucleic acid probe sequence based on the target sequences shown in Tables 2 and 3.

Methods of Treatment

The diagnostic methods of the invention permit the assessment of whether a patient is likely to be responsive to treatment with 2X-121 or a pharmaceutically acceptable salt thereof, and can thus be used to direct the patient's treatment (e.g., as a first line therapy and/or as a second or third line therapy). A patient to be treated or tested for responsiveness to 2X-121 or a pharmaceutically acceptable salt thereof according to the methods may include, e.g., a patient that has been diagnosed with cancer, a patient that has not received a cancer treatment (e.g., an anti-cancer agent other than 2X-121 or a pharmaceutically acceptable salt thereof or radiation), a patient that has received a cancer treatment (e.g., an anti-cancer agent other than 2X-121 or a pharmaceutically acceptable salt thereof or radiation), or a patient during treatment with 2X-121 or a pharmaceutically acceptable salt thereof. For example, the patient may have a hematological cancer or a solid tumor, such as a cancer type selected from myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. In particular, the cancer of the patient is, e.g., multiple myeloma, breast cancer, acute myelogenous leukemia (AML), acute lymphoblastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, estrogen receptor-positive (ERpos) breast cancer, lung cancer, non-small cell lung carcinoma (NSCLC), mesothelioma, intestinal cancer, colon cancer, bladder cancer, adrenal cancer, gallbladder cancer, and squamous cell carcinoma of the head and neck (SCCHN). The patient may have estrogen receptor-positive (ER pos) breast cancer. The patient may also have a metastatic form of breast cancer. The patient may also have recurrence of cancer, such as a recurrent form of any of the above cancer types, e.g., recurrent breast cancer, recurrent ovarian cancer or recurrent pancreatic cancer.

A patient found to be responsive to 2X-121 or a pharmaceutically acceptable salt thereof according to the methods of the invention may be preferentially selected for treatment with 2X-121 or a pharmaceutically acceptable salt thereof. For example, a patient can be identified as responsive to 2X-121 or a pharmaceutically acceptable salt thereof by determining the expression level of one or more biomarkers (e.g., one or more of the biomarkers shown in Table(s) 2 and/or 3, such as SRSF7 (SEQ ID NO: 1) and/or HLA-E (SEQ ID NO: 173 or 174 or 178)) in a biological sample (e.g., a tumor sample) obtained from the patient, and subsequently administered 2X-121 or a pharmaceutically acceptable salt thereof. One or more additional therapies (e.g., surgery, radiation, or a therapeutic agent) may also be administered to the patient prior to, concurrently, or after administration of 2X-121 or a pharmaceutically acceptable salt thereof. In particular, the therapeutic agent may be one or more of a histone deacetylase (HDAC) inhibitor, a PD1/PD-L1 inhibitor, ipilimumab, bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, fulvestrant, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, tamoxifen, floxuridine, thioguanine, PSC 833, herceptin, bevacizumab, celecoxib, iressa, anastrozole, letrozole, and rituximab. The therapeutic agent can be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally, or topically.

Alternatively, a patient can be, e.g., identified as less likely to be responsive to 2X-121 or a pharmaceutically acceptable salt thereof by determining the expression level of one or more biomarkers (e.g., one or more of the biomarkers shown in Table(s) 2 and/or 3, such as SRSF7 (SEQ ID NO: 1) and/or HLA-E (SEQ ID NO: 173 or 174 or 178)) in a biological sample obtained from the patient. If the patient exhibits expression levels of one or more biomarkers indicative of non-responsiveness to 2X-121 or a pharmaceutically acceptable salt thereof, the patient can be administered a treatment other than 2X-121 or a pharmaceutically acceptable salt thereof (e.g., surgery, radiation, or a therapeutic agent). In particular, the therapeutic agent may be one or more of a histone deacetylase (HDAC) inhibitor, a PD1/PD-L1 inhibitor, ipilimumab, bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, fulvestrant, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, tamoxifen, floxuridine, thioguanine, PSC 833, herceptin, bevacizumab, celecoxib, iressa, anastrozole, letrozole, and rituximab. The therapeutic agent can be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally, or topically. In particular, the patient may be treated with, e.g., surgery, radiation, and/or administration of a therapeutic agent, such as a histone deacetylase (HDAC) inhibitor and/or docetaxel.

Administration of 2X-121 or a Pharmaceutically Acceptable Salt Thereof

Once a patient has been determined to be responsive to 2X-121 or a pharmaceutically acceptable salt thereof, according to the methods described herein, 2X-121 or a pharmaceutically acceptable salt thereof may be administered to the patient, for example, parenterally, enterally, or topically. Enteral routes of 2X-121 or a pharmaceutically acceptable salt thereof administration may include oral, buccal, sublabial, sublingual, or by inhalation. Parenteral routes of 2X-121 or a pharmaceutically acceptable salt thereof administration include intravenous, transdermal, intradermal, intramuscular, intra-arterial, intracranial, subcutaneous, intraorbital, intraventricular, intraspinal, intraperitoneal, or intranasal. The preferred route for administration of 2X-121 or a pharmaceutically acceptable salt thereof may be oral.

2X-121 or a pharmaceutically acceptable salt thereof can be administered at, e.g., a dose of about 5-5000 mg, 10-4500 mg, 15-4000 mg, 20-3500 mg, 25-3000 mg, 30-2500 mg, 35-2000 mg, 40-1500 mg, 45-1000 mg, 50-1000 mg, 50-950 mg, 50-900 mg, 50-850 mg, 50-800 mg, 55-800 mg, 60-800 mg, 65-800 mg, 70-800 mg, 75-800 mg, 80-800 mg, 85-800 mg, 90-800 mg, 95-800 mg, 100-800 mg, 125-800 mg, 150-800 mg, 175-800 mg, 200-800 mg, 225-800 mg, 250-800 mg, 275-800 mg, 300-800 mg, 325-800 mg, 350-800 g, 375-800 mg, 400-800 mg, 425-800 mg, 450-800 mg, 475-800 mg, 500-800 mg, 525-800 mg, 550-800 mg, 575-800 mg, 600-800 mg, 625-800 mg, 650-800 mg, 675-800 mg, 700-800 mg, 725-800 mg, 750-800 mg, or 775-800 mg. In particular, 2X-121 or a pharmaceutically acceptable salt thereof may be administered at doses of about 10 mg, 50 mg, 200 mg, or 600 mg. Preferably, 2X-121 or a pharmaceutically acceptable salt thereof can be administered at a dose of about 600 mg, 2X-121 or a pharmaceutically acceptable salt thereof may be administered to the patient two or more times, such as one or more times hourly, daily (e.g., once daily for up to six days), weekly, every two weeks, every three weeks, every four weeks, monthly, every two months, every three months, every six months, or every year. Preferably, 2X-121 or a pharmaceutically acceptable salt thereof may be administered once daily. The method may further include administering a second dose of 2X-121 or a pharmaceutically acceptable salt thereof to the patient one week, two weeks, three weeks, four weeks, or five weeks after administration of a first dose of 2X-121 or a pharmaceutically acceptable salt thereof. The administration of 2X-121 or a pharmaceutically acceptable salt thereof can be repeated at such a frequency for a certain period of time, followed by a period without treatment. Such repeated administrations can occur over a course of therapy lasting a specified length of time (e.g., at least 1 week, 2 weeks, 3 weeks, 1 month, 2 months, 3 months, 6 months, 8 months, 10 months, 12 months, 18 months, 24 months, 36 months, 48 months, or 60 months).

The patient may be administered a pharmaceutically acceptable salt of 2X-121 or a pharmaceutically acceptable salt thereof. Pharmaceutically acceptable salts of 2X-121 or a pharmaceutically acceptable salt thereof described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of 2X-121 or a pharmaceutically acceptable salt thereof described herein or separately by reacting a free base group with a suitable organic acid.

2X-121 or a pharmaceutically acceptable salt thereof may have ionizable groups so as to be capable of preparation as pharmaceutically acceptable salts. These salts may be acid addition salts involving inorganic or organic acids or the salts may, in the case of acidic forms of 2X-121 or a pharmaceutically acceptable salt thereof be prepared from inorganic or organic bases. Frequently, 2X-121 or a pharmaceutically acceptable salt thereof may be prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

2X-121 or a pharmaceutically acceptable salt thereof can be administered in a pharmaceutical composition that includes one or more pharmaceutically acceptable carriers, excipients, or diluents. Examples of suitable carriers, excipients, or diluents of 2X-121 or a pharmaceutically acceptable salt thereof include, e.g., saline, sterile water, polyalkylene glycols, oils of vegetable origin, hydrogenated napthalenes, suitable buffer, 1,3-butanediol, Ringer's solution and/or sodium chloride solution. Exemplary formulations for parenteral administration can include solutions prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Other exemplary carriers, excipients, or diluents are described in the Handbook of Pharmaceutical Excipients, 6th Edition, Rowe et al., Eds., Pharmaceutical Press (2009), hereby incorporated by reference in its entirety.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating 2X-121 or a pharmaceutically acceptable salt thereof in the required amount in an appropriate solvent with one or a combination of ingredients enumerated above, as required, followed by filtered sterilization. Dispersions can be prepared by incorporating 2X-121 or a pharmaceutically acceptable salt thereof into a sterile vehicle which contains a basic dispersion medium and the required other ingredients from those enumerated above. In the case of sterile powders for the preparation of sterile injectable solutions, the preferred methods of preparation can be vacuum drying and freeze-drying which yields a powder of 2X-121 or a pharmaceutically acceptable salt thereof plus any additional desired ingredient from a previously sterile-filtered solution thereof.

Oral compositions can include an inert diluent or an edible carrier. The composition can be enclosed in a gelatin capsule or compressed into a tablet. For the purpose of oral therapeutic administration, 2X-121 or a pharmaceutically acceptable salt thereof can be incorporated with excipients and used in the form of tablets, troches, or gelatin capsules. In particular, 2X-121 or a pharmaceutically acceptable salt thereof can be formulated as hard gelatin capsules (e.g., hard gelatin capsules of 10 mg, 50 mg, or 200 mg) or film coated tablets (e.g., film coated tablets of 10 mg, 50 mg, or 200 mg). Preferably, 2X-121 or a pharmaceutically acceptable salt thereof can be formulated as hard gelatin capsules (e.g., hard gelatin capsules of 200 mg). Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated can be used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, 2X-121 or a pharmaceutically acceptable salt thereof may be formulated into ointments, salves, gels, or creams as generally known in the art.

2X-121 or a pharmaceutically acceptable salt thereof can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art.

The pharmaceutical compositions can be included in a container, pack, or dispenser together with instructions for administration.

Methods of formulating pharmaceutical agents are known in the art, e.g., Niazi, Handbook of Pharmaceutical Manufacturing Formulations (Second Edition), CRC Press 2009, describes formulation development for liquid, sterile, compressed, semi-compressed and OTC forms. Transdermal and mucosal delivery, lymphatic system delivery, nanoparticles, controlled drug release systems, theranostics, protein and peptide drugs, and biologics delivery are described in Wang et al., Drug Delivery: Principles and Applications (Second Edition), Wiley 2016; formulation and delivery of peptide and protein agent is described, e.g., in Banga, Therapeutic Peptides and Proteins: Formulation, Processing, and Delivery Systems (Third Edition), CRC Press 2015.

Kits

Kits of the invention can be used for determining the responsiveness of a cancer patient (e.g., a hematological cancer, such as multiple myeloma, or a solid tumor, such as breast cancer or ovarian cancer) to 2X-121 or a pharmaceutically acceptable salt thereof. Kits of the invention can include reagents and/or materials for, e.g., collecting and/or purifying nucleic acids from biological samples (such as those obtained from a patient to be treated with 2X-121 or a pharmaceutically acceptable salt thereof), reagents for amplifying such nucleic acids to produce an amplified sample, and/or at least one device of the invention. Reagents for amplifying nucleic acids may include, e.g., PCR reagents, including but not limited to DNA polymerase, RNA polymerase, PCR buffer, magnesium chloride solutions, nucleic acid primers (e.g., primers designed to target particular biomarkers of responsiveness to 2X-121 or a pharmaceutically acceptable salt thereof), and/or any other PCR reagents as are well known in the art. In particular, kits useful in the method may include includes one or more of the following: a kit for RNA extraction from tumors (e.g., Trizol for mRNA, mirVana miRNA isolation kit from Ambion Inc), a kit for RNA labeling (e.g., MessageAmp from Ambion Inc., FlashTag from Genisphere Inc), a microarray for measuring biomarker expression (e.g., HG-U133A, HG-U133_Plus2 or miRNA-1.0 from Affymetrix Inc), a microarray hybridization station and scanner (e.g., GeneChip System 3000Dx from Affymetrix Inc), and/or software for analyzing the expression of biomarker genes or RNAs (e.g., miRNAs) as described in herein (e.g., implemented in R from R-Project or S-Plus from Insightful Corp.).

For example, a kit of the invention can include one or more probes capable of detecting one or more biomarkers of Table(s) 2 and/or 3 (e.g., the kit may include probes for the biomarkers of Tables 2 and 3). Such probes can, for example, include nucleic acids capable of hybridizing to the biomarker based on nucleic acid sequence complementarity. In particular, a probe has at least 85% sequence identity (e.g., 85%, 90%, 95%, 97%, 98%, 99%, or 100% sequence identity) to a nucleic acid sequence that is complementary or identical to at least 5 (e.g., at least 15) consecutive nucleotides of one or more biomarkers. The probes can be attached a solid surface, such as a microarray. The kit may include NanoString capture probes, NanoString reporter probes, and/or one or more nCounter cartridges. The kit may include reagents for next generation sequencing, including but not limited to poly(T) oligonucleotides, dye terminators, sequencing adapters, adapter ligation reagents, reverse transcriptase, primers (e.g., random primers), DNA-cleaving enzymes, polymerases, and/or any combination thereof. The kit may also be one that includes a protein array and/or reagents for detection of the polypeptide product(s) of one or more biomarkers of Table(s) 2 and/or 3.

The following examples are intended to illustrate, rather than limit, the invention.

EXAMPLES

Example 1. Identification of Biomarkers of Sensitivity and Resistance to 2X-121

The NCI60 panel of cell lines can be used to determine sensitivity to 2X-121, but it is also possible to use other cell line panels. Here we used a panel of 74 cell lines shown in Table 1.

262

TABLE 1

Measured growth inhibition (IC50 in μM) of cell lines treated with 2X-121.

| Cell line origin | Name | IC50 (μM) |
|---|---|---|
| Breast | T47D | 7.8 |
| Breast | MDA-MB-231 | 25 |
| Breast | Hs578T | 9.6 |
| Breast | HCC1143 | 3.7 |
| Breast | HCC70 | 9.3 |
| Breast | HCC1806 | 1.8 |
| Breast | MDA-MB-436 | 0.19 |
| Breast | MDA-MB-157 | 6.8 |
| Breast | MDA-MB-468 | 2.5 |
| Breast | MDA-MB-453 | 6.2 |
| Breast | MCF-7 | 1.9 |
| Breast | BT-20 | 7.9 |
| Fibrosarcoma | HT-1080 | 0.83 |
| Melanoma | M14 | 6.7 |
| Prostate | DU145 | 1.8 |
| NSCLC | A549 | 2.2 |
| GBM | SF-295 | 2.6 |
| Colon | HCT-116 | 1.7 |
| Colon | HCT-15 | 2.2 |
| HCC | HepG2 | 3.8 |
| HCC | C3A | 2.54 |
| HCC | SNU-423 | 19 |
| HCC | SNU-182 | 5.4 |
| Endometrial | HEC-1 | 1.28 |
| Endometrial | HEC-251 | 1.26 |
| Endometrial | HEC-108 | 5.97 |
| Endometrial | HEC-59 | 2.44 |
| Endometrial | HEC-6 | 1.88 |
| Endometrial | ECC-1 | 0.68 |
| Endometrial | SNG-M | 1.36 |
| Endometrial | HEC-50B | 3.45 |
| Endometrial | SNG-II | 5.26 |
| Endometrial | KLE | 2.59 |
| Endometrial | HEC-1B | 7.27 |
| Endometrial | HEC-1A | 2.96 |
| Endometrial | HEC-88nu | 1.14 |
| Endometrial | MFE-296 | 0.67 |
| Endometrial | MFE-280 | 0.77 |
| Endometrial | RL95-2 | 2.13 |
| Endometrial | HEC-151 | 1.44 |
| Endometrial | AN3 CA | 1.49 |
| Endometrial | HEC-265 | 2.40 |
| SCLC | NCI-H1694 | 2.47 |
| SCLC | NCI-H209 | 0.62 |
| SCLC | NCI-H146 | 0.93 |
| SCLC | NCI-H211 | 0.48 |
| SCLC | NCI-H524 | 0.69 |
| SCLC | NCI-H82 | 0.47 |
| SCLC | NCI-H446 | 0.61 |
| SCLC | NCI-H69 | 1.33 |
| Promyelocytic leukemia | HL-60 | 10.3 |
| Erythroleukemia from CML Pt | K562 | 4.3 |
| B cell lymphoma | SR | 0.26 |
| B lymphoblast | IM-9 | 2.1 |
| NHL B cell lymphoma | RL | 2.5 |
| Histiocytic lymphoma-monocytic | U937 | 2.7 |
| Burkitts lymphoma | Namalwa | 2.5 |
| Myeloma | MC/CAR | 2.3 |
| Myeloma | NCI-H929 | 5.2 |
| Myeloma | U266 | 6.7 |
| DLBCL (GC) | DB | 1.6 |
| DLBCL (GC) | HT | 0.66 |
| DLBCL (GC) | Pfeiffer | 0.71 |
| DLBCL (GC) | Toledo | 1.6 |
| MCL | Jeko-1 | 1.9 |
| MCL | JVM-13 | 7.3 |
| MCL | JVM-2 | 14 |
| MCL | Mino | 3.4 |
| MCL | NCEB-1 | 5.3 |
| AML | KG-1 | 2.0 |
| AML | THP-1 | 5.4 |

TABLE 1-continued

| Measured growth inhibition (IC50 in μM) of cell lines treated with 2X-121. | | |
|---|---|---|
| Cell line origin | Name | IC50 (μM) |
| AML | MV-4-11 | 0.95 |
| Myeloma | RPMI-8226 | 9.3 |
| Myeloma | ARH-77 | 3.2 |

Baseline DNA chip measurements of 61 of the cancer cell lines in Table 1 (excluding M14 HEC-1 ECC-1 SNG-II HEC-88nu SR IM-9 Namalwa MC/CAR U266 JVM-13 NCEB-1 ARH-77) were performed using Affymetrix HG-U133Plus2 arrays and logit normalized. For each array, the logit transformation was performed followed by a Z-transformation to mean zero and SD 1, and correlated to growth inhibition (–log(GI50)). The expression level of each of the genes of Tables 2 and 3 in each cell line was correlated to the growth of those cell lines (log(GI50)) in the presence of 2X-121. The Pearson correlation coefficient was then determined to identify genes positively and negatively correlated to sensitivity to 2X-121. Tables 2 and 3 show the top positively correlated genes (the biomarkers of sensitivity) and negatively correlated genes (the biomarkers of resistance). In particular, genes with a Pearson correlation greater than 0.25 or below –0.25 can be classified as biomarkers of sensitivity or resistance, respectively.

TABLE 2

Biomarkers of sensitivity to 2X-121. Dashes mean that the Affymetrix probeset has not been mapped to a specific gene. Affymetrix IDs refer to the array type HG-U133_Plus 2.

| Gene | Affymetrix ID | Correlation | Affymetrix Probe Sequence | SEQ ID NO: |
|---|---|---|---|---|
| SRSF7 | 214141_x_at | 0.516 | GATCAAGATCTATCTCTCTTCGTAG | 1 |
| UCHL1 | 201387_s_at | 0.494 | GAGGGACTTTGCTGATTTCCCCTCT | 2 |
| MLLT11 | 211071_s_at | 0.491 | TCAGTGGGCACAGTTCTTCAGCTAC | 3 |
| ADD2 | 205268_s_at | 0.487 | CCTGGAGCAATGCACTGTACCTGCC | 4 |
| ADD2 | 213484_at | 0.451 | GTCTGTGTCTGACAATCGTCACGCA | 5 |
| PRMT1 | 206445_s_at | 0.441 | TCCCCGTACACGCACTGGAAGCAGA | 6 |
| SRSF3 | 202899_s_at | 0.439 | TTGAAGATCCCCGAGATGCAGCTGA | 7 |
| PRMT5 | 217786_at | 0.412 | GCGTTTCTGGCGATGCAGCAATTCC | 8 |
| COCH | 205229_s_at | 0.402 | AACCATGCCTACTAAATGTACAGAT | 9 |
| RUVBL1 | 201614_s_at | 0.391 | AGATCATTAAAATCCGTGCCCAGAC | 10 |
| MARCKSL1 | 200644_at | 0.39 | TTACTCAAGTTCAAACCTCCAGCCT | 11 |
| CHERP | 202230_s_at | 0.39 | TGTTCTAGATTTCCTGTAGCTGTGA | 12 |
| MTSS1 | 203037_s_at | 0.39 | GTGCTTTAGTTGCTAGTTTGTACTG | 13 |
| LSM4 | 202736_s_at | 0.385 | CCTGCGAGAAGTCATCTGCACGTCC | 14 |
| RAPGEF5 | 204681_s_at | 0.379 | GCCATTAACAGTGTTTTCTTTCCCA | 15 |
| PRPF4 | 209161_at | 0.367 | CGCAGCCACGCCGATGGTTATACAG | 16 |
| LSM4 | 202737_s_at | 0.366 | TCTTGCTAAAACCGGCAATTCTCCG | 17 |
| DESI2 | 212371_at | 0.365 | TGACTCCATTTCTGTAAGCTACTCT | 18 |
| RNPS1 | 200060_s_at | 0.363 | GGTGGTCTTTCAGGTTATCTTGGCA | 19 |
| SNX10 | 218404_at | 0.362 | TGTGTCTTAGATCCTCATTATTTTA | 20 |
| CUL3 | 201371_s_at | 0.361 | CTGTACTCTTCGCATGGACTGGGAA | 21 |
| CHD4 | 201184_s_at | 0.36 | CGGCTCTAGCCACTGAGCGGCTAAA | 22 |
| MSH2 | 209421_at | 0.359 | AAGATTGGTGCTTTTTGCATGTTTG | 23 |
| HNRNPM | 200072_s_at | 0.358 | GCCGAGAGAGCCTGCCGGATGATGA | 24 |
| SRSF1 | 211784_s_at | 0.358 | GGAGCAATCTCCTTGGAAGGATTCA | 25 |
| NELL2 | 203413_at | 0.357 | GAAAAGTCATCCCTATTTCCTTGTT | 26 |
| PAICS | 201014_s_at | 0.356 | AGTGTTGATGGGCTCTACTTCTGAT | 27 |
| HOXA10 | 213150_at | 0.356 | ATTTACCTCTAAATTTCCATATCCT | 28 |

TABLE 2-continued

Biomarkers of sensitivity to 2X-121. Dashes mean that the Affymetrix probeset has not been mapped to a specific gene. Affymetrix IDs refer to the array type HG-U133_Plus_2.

| Gene | Affymetrix ID | Correlation | Affymetrix Probe Sequence | SEQ ID NO: |
|------|---------------|-------------|---------------------------|------------|
| BUB1B | 203755_at | 0.354 | GGCCTTGTCTAACTTTTGTGAAGAA | 29 |
| E2F5 | 221586_s_at | 0.352 | CCACAGAAATCCAGCATGGCAACTC | 30 |
| MAGED4 MAGED4B SNORA11D SNORA11E | 221261_x_at | 0.351 | AAGATGAAGCTCTCTTTGCTCTTCC | 31 |
| PRPF8 | 200000_s_at | 0.349 | GAGGGGGAGGTTTACTCTGCGGATC | 32 |
| SORD | 201563_at | 0.348 | ATCGCATCATGCCAACTTGTGACTT | 33 |
| HNRNPU | 200593_s_at | 0.346 | TTTTCCTGGCCGTGGTAGTTACTCA | 34 |
| PEX5 | 203244_at | 0.344 | TCATCCTCTTAGAAGCACCTGTGAA | 35 |
| HYPK MIR 1282 SERF2 SERF2-C15ORF63 | 218680_x_at | 0.344 | GGTAGAGGCGCTTATTGCCCTAACC | 36 |
| STRAP | 200870_at | 0.343 | TCTTTCCTTCAGCTCCTGATGTTAA | 37 |
| NDUFAB1 | 202077_at | 0.341 | CATCCAGGACCGTGTTCTTTACGTA | 38 |
| FARSA | 216602_s_at | 0.341 | TATTCCGGAATGAGACCCTGGACGC | 39 |
| STOML2 | 215416_s_at | 0.339 | GCTGCAGCTCTGACACAACATAATG | 40 |
| ERH | 200043_at | 0.337 | GAGGATCTTGTTCAATCGGAAACCC | 41 |
| HSBP1 | 200941_at | 0.337 | TGATGTTCTCAAGCCTCGGAAGTGG | 42 |
| DDX39A | 201584_s_at | 0.337 | TTAACTACGACATGCCTGAGGACTC | 43 |
| ODC1 | 200790_at | 0.335 | CCAGAGGCCGACGATCTACTATGTG | 44 |
| TAF5 | 210053_at | 0.334 | GCTACATACAACCTAGTACACTTGA | 45 |
| TBC1D31 | 214061_at | 0.334 | AATGCGGCTGTAGAACATGCTGAAA | 46 |
| TRA2B | 200892_s_at | 0.333 | CCTTCTCCTTACTATAGTCGTGGAG | 47 |
| NUDC | 201173_x_at | 0.333 | CACAGGTCCCGGGGCATCAGGAGAA | 48 |
| DDX23 | 201440_at | 0.333 | CCAAGGGGTGCTGTATGCTCTAGGC | 49 |
| PRPF31 | 202407_s_at | 0.333 | CAGTTTCCACGAGAGCACAGAAGGG | 50 |
| UBE2S | 202779_s_at | 0.333 | GGCGCCAATGGCGAGATCTGCGTCA | 51 |
| TCF4 | 222146_s_at | 0.332 | GAGAAGGAGCGGAGGATGGCCAACA | 52 |
| MLF2 | 200948_at | 0.33 | GGGTCAATGCATTTTGGGGTGAGCT | 53 |
| CCDC181 | 206721_at | 0.329 | CAAACCTTTTCGTTTTACTGATCAT | 54 |
| TCF4 | 213891_s_at | 0.328 | TTGGTCAAGGCCATTACCTGTTTCC | 55 |
| DESI2 | 222158_s_at | 0.328 | TATACCCTTTCTACAGAGTTGCCTC | 56 |
| RPF1 | 218462_at | 0.327 | GCTGAACAGGCCTATCTTGAACTTT | 57 |
| PASK | 216945_x_at | 0.326 | TAATGGCCAAGGCTGTTTGCATCCC | 58 |
| NUP88 | 202900_s_at | 0.325 | AGCGAAAGTGCATTCAGTCCATCCT | 59 |
| RNASEH2A | 203022_at | 0.325 | ACTGATTATGGCTCAGGCTACCCCA | 60 |
| FBL | 211623_s_at | 0.325 | GTGATCGAGGATGCTCGACACCCAC | 61 |
| LOC101928747 RBMX SNORD61 | 213762_x_at | 0.325 | GGCAGGCAATTCTAAGATCTTCCAC | 62 |
| NXF1 | 208922_s_at | 0.324 | GTGATCGTAGTCATGCCTCAGAAGC | 63 |

TABLE 2-continued

Biomarkers of sensitivity to 2X-121. Dashes mean that the Affymetrix probeset has not been
mapped to a specific gene. Affymetrix IDs refer to the array type HG-U133_Plus_2.

| Gene | Affymetrix ID | Correlation | Affymetrix Probe Sequence | SEQ ID NO: |
|------|---------------|-------------|---------------------------|------------|
| PLEKHO1 | 218223_s_at | 0.323 | GATGGGAAGCGAAAGGCCAAGGACC | 64 |
| GAR1 | 219110_at | 0.323 | ACAGACATCACCAGTTGACTTCTGC | 65 |
| RPA1 | 201529_s_at | 0.321 | GTAACTAGGTTTTTGCTTCTCCAGT | 66 |
| ZNF24 | 212534_at | 0.321 | CACAGCTTCCTAGCCACAGTGATAA | 67 |
| BOP1 MIR7112 | 216397_s_at | 0.321 | CGGCAGCGCAAGATGAGGGTGAATG | 68 |
| RAB3B | 205924_at | 0.32 | AGATACTCAGCACTAGACTAACATA | 69 |
| SLC35G2 | 219569_s_at | 0.319 | CATTGCTATATGTGTCTGTTCTACT | 70 |
| TSPAN3 | 200973_s_at | 0.318 | GAGACAGCTGCATTGTTGTGGAATT | 71 |
| DKC1 MIR664B SNORA56 | 201479_at | 0.318 | GCCTGATGGGCCTGGTAGTTTTCCA | 72 |
| PSMC3IP | 213951_s_at | 0.318 | GTAACCGTAGCAAAACTGCATTGGT | 73 |
| DNAJC7 | 202416_at | 0.316 | AGATCGGCATAGTGGAGCCAGTGCT | 74 |
| RRP1B | 212846_at | 0.316 | TTTGTAAAATGATGCTTCCCCCTTC | 75 |
| NME1 | 201577_at | 0.315 | AAGGAGATCGGCTTGTGGTTTCACC | 76 |
| SNRPA | 201770_at | 0.315 | ACAGCATTGTACCCAGAGTCTGTCC | 77 |
| DBN1 | 217025_s_at | 0.315 | TGCCCAATCGGAAGAGCTCTGTGCC | 78 |
| KIAA0020 | 203712_at | 0.314 | AGGTGCCATTATTCTTTCTAGCCTC | 79 |
| SUPV3L1 | 212894_at | 0.313 | GAAGCTGTCCACGATGTCTTGGATC | 80 |
| ZNF573 | 217627_at | 0.31 | GGAGCATAAAAGTGTAAGACCGTAA | 81 |
| FAM134B | 218510_x_at | 0.31 | GATCTTTCAGATTTTCCATCTCTAG | 82 |
| TOX3 | 214774_x_at | 0.309 | ATGACCACTGTTAGCCCATTATATT | 83 |
| HSPD1 | 200806_s_at | 0.306 | TAGTATCCAGTCCATTGTACCTGCT | 84 |
| ACLY | 210337_s_at | 0.306 | AGATGGTCTCATCGGAGTCGCATTT | 85 |
| TOX3 | 216623_x_at | 0.306 | ATATCTATGACCACTGTTAGCCCAT | 86 |
| MSANTD3-TMEFF1 TMEFF1 | 205122_at | 0.305 | TAAAGCCTATTCTACCAGTTAAACT | 87 |
| AKIRIN1 | 217893_s_at | 0.305 | GGAGCATCAGGGTTGGCTTGGGAGC | 88 |
| UBE2M | 203109_at | 0.304 | CATTGACCTCGAGGGCAACGTCTGC | 89 |
| MTF2 | 203345_s_at | 0.304 | TTATACGTTTATATGCTCTGTCTGC | 90 |
| EWSR1 | 209214_s_at | 0.304 | GTTGGCCACAACATTATGATTATTC | 91 |
| FARSA | 202159_at | 0.303 | TCCTGTGTGGTGTGTCTACTGTGAG | 92 |
| SKP2 | 203625_x_at | 0.303 | AGAGCTGGGGTTAGGATCCGGTTGG | 93 |
| TMEM97 | 212279_at | 0.303 | TCCTTTCTGTTTTGCGAGCTTGTGT | 94 |
| HNRNPD | 221481_x_at | 0.303 | AAAAGCCCAGTGTGACAGTGTCATG | 95 |
| ILKAP | 221548_s_at | 0.303 | CAGTACAAGCGCTGCGGTGTCACCT | 96 |
| NASP | 201970_s_at | 0.302 | GAAAGCCAACAGACGGTGCTTCCTC | 97 |
| SNRPD1 | 202690_s_at | 0.301 | GTTTACCTCTGGATACACTACTTGT | 98 |
| TIMM44 | 203093_s_at | 0.301 | CGCTCTGCCGAGACCAGGACGAGCT | 99 |
| PKN1 | 202161_at | 0.3 | CACCGACGTCAGCAACTTCGACGAG | 100 |

TABLE 2-continued

Biomarkers of sensitivity to 2X-121. Dashes mean that the Affymetrix probeset has not been
mapped to a specific gene. Affymetrix IDs refer to the array type HG-U133_Plus_2.

| Gene | Affymetrix ID | Correlation | Affymetrix Probe Sequence | SEQ ID NO: |
|------|---------------|-------------|---------------------------|------------|
| STAU2 | 204226_at | 0.299 | AAGCCTACTAGAGCCATTGTATGTG | 101 |
| DNAAF2 | 219166_at | 0.299 | CTTCATTACTGAACAAAACTACGGT | 102 |
| SNRPD2 | 200826_at | 0.297 | TGCTCATCAACTGCCGCAACAATAA | 103 |
| FUS | 200959_at | 0.297 | ATCCCACCTGTGAGAATATGAACTT | 104 |
| PASK | 213534_s_at | 0.297 | AGCTAAACACCAATTTCTTCCTGCT | 105 |
| ATP6V1G2-DDX39B DDX39B SNORD84 | 200041_s_at | 0.296 | TAGTGAGCTGCCTGATGAGATAGAC | 106 |
| PDSS1 | 220865_s_at | 0.296 | GCAGCTATCTTACCAGACTGTGCCT | 107 |
| NUDC | 210574_s_at | 0.295 | GAAGTTCATGGATCAACATCCGGAG | 108 |
| TOX3 | 215108_x_at | 0.295 | GGTGACATAAACCATTCATTGCTAC | 109 |
| TPGS2 | 212055_at | 0.294 | AAGTGCCCAAATAAGTCTGAGTGCT | 110 |
| SLIRP | 221434_s_at | 0.294 | TTTGACAAGGAGACTGGCTTTCACA | 111 |
| NCL | 200610_s_at | 0.293 | AAGTTTGAATAGCTTCTGTCCCTCT | 112 |
| ANP32A | 201051_at | 0.293 | TTTGGAGTTCTCTTACGTTTCCTGG | 113 |
| SAFB | 201748_s_at | 0.293 | TGGCGAGAGAAGCATGTCCGGTCAC | 114 |
| STIP1 | 212009_s_at | 0.293 | AATAAGTGCCGGGAGCTTTGTGAGA | 115 |
| CEP68 | 212677_s_at | 0.293 | GGCCAGAAACCTTGGGTCTTTTCAT | 116 |
| STIP1 | 213330_s_at | 0.291 | GGATGTGGGTCTGATTGCAATTCGG | 117 |
| C8orf33 | 218187_s_at | 0.291 | TGGACCATGGTCTAGCAGTAGCATC | 118 |
| MRPL11 | 219162_s_at | 0.29 | GGGCATTCGCGTGGTGAAGGACCTC | 119 |
| POLR21 | 212955_s_at | 0.288 | GCTGTACCCCAAGGAAGACAAGGAG | 120 |
| FAM134B | 218532_s_at | 0.288 | AAATCTCTGAACTGTGTGGGTTTTG | 121 |
| MCAM MIR6756 | 211042_x_at | 0.286 | TGCCCTCAAACATACAGAACTTCCA | 122 |
| ECSIT | 218225_at | 0.285 | TCATCTCTAGCAGTATGGCATCCCC | 123 |
| MDK | 209035_at | 0.284 | GCAAGGATTGCGGCGTGGGTTTCCG | 124 |
| PUF60 | 209899_s_at | 0.283 | TCAATGGCCGCTGGTTTGCTGGCCG | 125 |
| PFN2 | 204992_s_at | 0.282 | CACACCAGCTCTACTCTTTAGTAAA | 126 |
| SYNCRIP | 209025_s_at | 0.282 | AGAAACTCACCCTAAATCTGAACGG | 127 |
| TSPAN3 | 200972_at | 0.281 | AAGTGGTAACAGGACTGATGCCGAA | 128 |
| SLC16A1 | 202236_s_at | 0.281 | TGTTTATAGATCACTGCCCTTTTTG | 129 |
| POLR2H | 209302_at | 0.281 | AAGTCACTCAGGTCATGGGCATTGT | 130 |
| MAP3K7 | 211537_x_at | 0.281 | TGATTACTACCTCAGGACCAACCTC | 131 |
| CSRP2 | 207030_s_at | 0.28 | GTACTTGGATAGGCTGGCTAACTCG | 132 |
| BCL11A | 210347_s_at | 0.28 | GAAGCTCGAGAGCCCTTAAGTTCTG | 133 |
| PNKP | 218961_s_at | 0.279 | CCATCGACAACACAAACCCAGACGC | 134 |
| DNAJC6 | 204720_s_at | 0.278 | AGCTTGTTGTTGATCAGATTCACTG | 135 |
| FDFT1 | 208647_at | 0.278 | GCAGAGCATTCAGTGCCACGGTTTA | 136 |

TABLE 2-continued

Biomarkers of sensitivity to 2X-121. Dashes mean that the Affymetrix probeset has not been
mapped to a specific gene. Affymetrix IDs refer to the array type HG-U133_Plus_2.

| Gene | Affymetrix ID | Correlation | Affymetrix Probe Sequence | SEQ ID NO: |
|---|---|---|---|---|
| FADS1 MIR1908 | 208963_x_at | 0.278 | CTCTTCAGCAGCATCTACTCTAGGC | 137 |
| RPARP-AS1 | 214857_at | 0.277 | CTGCTGTAAGGACTGGTTCCAGAAT | 138 |
| DHRS7 | 210788_s_at | 0.276 | GAACTTGCCACATACCCAGGTATAA | 139 |
| CCNB1IP1 | 217988_at | 0.276 | CATGAAGGCACCCTTGAACCATCCA | 140 |
| CCT3 LOC101927137 | 200910_at | 0.275 | GGAGCCATTGGCTGTGAAGCTGCAG | 141 |
| DDX18 | 208895_s_at | 0.274 | AATCTGACCCTATCGGAAACTCAAA | 142 |
| AARSD1 PTGES3L PTGES3L-AARSD1 | 222064_s_at | 0.273 | ATAGCCTCAGGAACAGTCCAGACTG | 143 |
| HNRNPDL | 209067_s_at | 0.272 | GGTGGTGATCAAAACTATAGTGGCT | 144 |
| ATXN7L3B | 212114_at | 0.272 | TGATCACCCTGCAATCCTATTATGT | 145 |
| MRPS14 | 203801_at | 0.271 | ACTTAGAATCCATCTCACTACCAAT | 146 |
| SOX4 | 201416_at | 0.269 | TAGAGACTATGTCGCTTTCCTGAGC | 147 |
| ELOVL2 | 213712_at | 0.268 | TACTGTGATGGGCAGAACAGCCTTT | 148 |
| KCNJ8 | 205303_at | 0.267 | TCTCATTTAGGACTGGGTTCCCCAC | 149 |
| TRIAP1 | 218403_at | 0.267 | ACAGCTTTTAACACAGTTCCCTGCC | 150 |
| EIF2B1 | 201632_at | 0.266 | GATGAAAGATGAGCCCAAGTCCACC | 151 |
| FBXL14 | 213145_at | 0.266 | GATCCTCTTAAAACGTTTATATTCT | 152 |
| MAPRE2 | 213489_at | 0.266 | CCCTGGTCACATGTCATCGGGCTGG | 153 |
| ORC4 | 203352_at | 0.264 | ATCCACATCAGAATCCCTTGTAGGA | 154 |
| MDN1 | 212693_at | 0.264 | ACTGCTTTCAAGCTGGACTGAGCCA | 155 |
| KNOP1 | 213237_at | 0.264 | TAAACATTCCGTCCCTGTTTGAGAC | 156 |
| KBTBD11 | 204301_at | 0.263 | GTGAGATCAAAGCTCCTCCAAAGCC | 157 |
| FADS2 | 202218_s_at | 0.262 | CCTCGGTGGCCCTGACTGTCAGGGA | 158 |
| RANBP1 | 202483_s_at | 0.262 | TCACGCCGATGATGGAGCTGAAGCC | 159 |
| PLEKHB1 | 209504_s_at | 0.261 | GAGTTCTATTTGAGACTTCCAGCCC | 160 |
| HSPE1 | 205133_s_at | 0.26 | CCAAAGGAGGCATTATGCTTCCAGA | 161 |
| TMEM97 | 212282_at | 0.26 | GAAGTGTGCTAGTATGCTCCCTAGT | 162 |
| ITFG2 LOC100507424 | 220589_s_at | 0.26 | GTTGGGGTTGGAGACGTGTGTAATA | 163 |
| SFPQ | 201586_s_at | 0.259 | GGAGGCTAAGTATTGCTTTCTACAA | 164 |
| RFC3 | 204127_at | 0.259 | TCATTAGCTCTGCCCTTTTTAATTA | 165 |
| SDR39U1 | 213398_s_at | 0.259 | CACTTCTCCTTTACGCTGTGTAGAG | 166 |
| PBK | 219148_at | 0.259 | GTACTTTGATACTGCTCATGCTGAC | 167 |
| PHB | 200658_s_at | 0.258 | CAGGGGATGGCCTGATCGAGCTGCG | 168 |
| KHDRBS1 | 201488_x_at | 0.258 | CCTTATTCCATTCTTAACTCTGCAT | 169 |
| PDAP1 | 202290_at | 0.256 | GCAGTCACTCTCCCTGAATAAGTAA | 170 |
| SSRP1 | 200957_s_at | 0.255 | GAAGAAGAACTAGCCAGTACTCCCC | 171 |
| B3GALT2 | 210121_at | 0.251 | GGAGTGCCAAGTTTGCAAACCTGCA | 172 |

TABLE 3

Biomarkers of resistance to 2X-121. Dashes mean that the Affymetrix probeset has not been
mapped to a specific gene. Affymetrix IDs refer to the array type HG-U133_Plus_2.
All correlations are negative.

| Gene ID | Affymetrix ID | Correlation | Probe sequence | SEQ ID no |
|---|---|---|---|---|
| HLA-E | 200904_at | 0.488 | AATGGGTTATCACAGGAATGGGACT | 173 |
| HLA-E | 200905_x_at | 0.477 | TGGGCAGAGTGCGGCAGCTCATGCC | 174 |
| GADD45B | 209304_x_at | 0.47 | TGGAGTGAGACTGACTGCAAGCCCC | 175 |
| CLIC1 | 208659_at | 0.454 | TTTTTGGATGGCAACGAGCTCACCC | 176 |
| LASP1 | 200618_at | 0.451 | TTATTGCTTAATTTCTGCCTTTCCC | 177 |
| HLA-E | 217456_x_at | 0.445 | GCTGCCTTGTGTGCGACTGAGATGC | 178 |
| APOBEC3B | 206632_s_at | 0.441 | CTACGATGAGTTTGAGTACTGCTGG | 179 |
| LGALS1 | 201105_at | 0.435 | CTCCTGGACTCAATCATGGCTTGTG | 180 |
| TAPBP | 208829_at | 0.435 | TGGAGGGCGCTCATCAAGTAGCTGC | 181 |
| AHNAK | 211986_at | 0.432 | TGGTCCCAGCCAGTTTGGTGCTGAC | 182 |
| BHLHE40 | 201170_s_at | 0.427 | GATCCTTTCTGTAGGCTAATTCCTC | 183 |
| S100A11 | 200660_at | 0.423 | TTCCCAGAAGCGGACCTGAGGACCC | 184 |
| LITAF | 200704_at | 0.413 | GACCTTCAAGGGTCCTCGTTTTGAT | 185 |
| ZBTB38 | 219221_at | 0.409 | GACGGTGCTTTTCGGTGCAAGGAAA | 186 |
| STAT1 | 209969_s_at | 0.408 | TGAACTTGTTGAGATCCCCGTGTTA | 187 |
| TCIRG1 | 204158_s_at | 0.404 | TTCTACTCAGGCACGGGCTACAAGC | 188 |
| S100A11P1 | 208540_x_at | 0.397 | CCGGTGTCCTTGACCACATGAAGAA | 189 |
| CTSA | 200661_at | 0.39 | TGATGCACTGATTCCATCCCAGGAA | 190 |
| VEGFA | 210512_s_at | 0.39 | TGACAGTCACTAGCTTATCTTGAAC | 191 |
| STOM | 201061_s_at | 0.388 | TTGTGTGAAGTGGTTCACCCTTGAG | 192 |
| P4HB | 200654_at | 0.387 | GACTTCCGGATCCTGTCAGGGTGTC | 193 |
| LITAF | 200706_s_at | 0.387 | GACAAAGATCTTGCCTTACAGACTT | 194 |
| FXYD5 | 218084_x_at | 0.384 | TGGTCGCAGCTGTGCTGTTCATCAC | 195 |
| HLA-C | 208812_x_at | 0.382 | GTGACTTCAAGAGCCTCTGGCATCT | 196 |
| YPEL5 | 217783_s_at | 0.38 | GAGAACAACAGCATTCATTTCCATT | 197 |
| HLA-C | 214459_x_at | 0.379 | CCCTCACCCTGAGATGGGAGCCGTC | 198 |
| HLA-C | 211799_x_at | 0.374 | CACCATCCCCAACTTGGGCATCGTT | 199 |
| STOM | 201060_x_at | 0.373 | AGTAAATGATTCCTCCTTGTTCTGT | 200 |
| PLIN3 | 202122_s_at | 0.373 | CAAAACGGGCATCACCCAGTTGACC | 201 |
| RRBP1 | 201206_s_at | 0.37 | AAGGAGGGCACCTCTGTCTGAGTTT | 202 |
| IRF1 | 202531_at | 0.37 | TTATTTATACAGTGCCTTGCTCGGG | 203 |
| LMNA | 212086_x_at | 0.37 | TTCGGGGACAATCTGGTCACCCGCT | 204 |
| NPC2 | 200701_at | 0.369 | CCTCATTGAGTTCGGTGCATCTGGC | 205 |
| P4HB | 200656_s_at | 0.368 | TGCTTGCTACCGTGTTCGGAGTCTC | 206 |
| KLF6 | 208961_s_at | 0.367 | CCCTGCACATGAAGAGGCACCTCTG | 207 |
| HLA-B | 209140_x_at | 0.365 | GGCTGTCCTAGCAGTTGTGGTCATC | 208 |
| RHOC | 200885_at | 0.362 | GTCACACACCAGCACTTTATACACT | 209 |

TABLE 3-continued

Biomarkers of resistance to 2X-121. Dashes mean that the Affymetrix probeset has not been
mapped to a specific gene. Affymetrix IDs refer to the array type HG-U133_Plus_2.
All correlations are negative.

| Gene ID | Affymetrix ID | Correlation | Probe sequence | SEQ ID no |
|---|---|---|---|---|
| CD59 | 200985_s_at | 0.362 | GAACACTCTACTACATGTGACTGGC | 210 |
| SRGN | 201858_s_at | 0.362 | GAGGACTACTCTGGATCAGGCTTCG | 211 |
| SRGN | 201859_at | 0.359 | GAGCTAGTGGATGTGTTTGTCTACA | 212 |
| STAT1 | 200887_s_at | 0.358 | TTCCTTCCTTATCACTGACACAAAA | 213 |
| TNFSF10 | 202687_s_at | 0.358 | GGACTCTATTCCATCTATCAAGGGG | 214 |
| HLA-B | 211911_x_at | 0.358 | CCCCATCGTGGGCATTGTTGCTGGC | 215 |
| PIEZO1 | 202771_at | 0.357 | GCGGATTCTTCAGCGAGATCTCGCA | 216 |
| LGALS3 | 208949_s_at | 0.355 | CTCACCAGTGCTTCATATACCATGA | 217 |
| LDLRAP1 | 221790_s_at | 0.355 | GCAAGTTTCATCAGCCCTAGGGAAA | 218 |
| CD97 | 202910_s_at | 0.353 | CTCAGCTTCCCTCTTAAGCTAAGAC | 219 |
| HLA-B | 208729_x_at | 0.353 | CCCCATCGTGGGCATTGTTGCTGGC | 220 |
| CFLAR | 209939_x_at | 0.353 | GAATGTTCTCCAAGCAGCAATCCAA | 221 |
| FNDC3B LOC101928615 | 218618_s_at | 0.353 | ATGTGCGTGTCGTCGCTGTTTAGAC | 222 |
| CKLF CKLF-CMTM1 | 219161_s_at | 0.353 | CACAAGCCCCTGAACCATATATTGT | 223 |
| IFI35 | 209417_s_at | 0.351 | GATGTGGACGTTCGGGAGCTACTGC | 224 |
| TIPARP | 212665_at | 0.35 | TCCTGTTGTTTGCTGCCATTGGCAT | 225 |
| TAP1 | 202307_s_at | 0.348 | GTGGCCAGCACTCTGAAACTGAGAA | 226 |
| MICALL2 | 219332_at | 0.348 | AGTTCCGCTTGTCCAAGATCTGGTC | 227 |
| RRBP1 | 201204_s_at | 0.347 | AGAGCCCCAGTTTGTAAATGAACCT | 228 |
| ZFP36 | 201531_at | 0.347 | GTCCCCAAGTGTGCAAGCTCAGTAT | 229 |
| HLA-G | 211528_x_at | 0.347 | GACGTGGAGCTCGTGGAGACCAGGC | 230 |
| TNIP1 | 207196_s_at | 0.346 | TTTTTGCTTCAAGCTCTGTAGCAGG | 231 |
| CD59 | 200983_x_at | 0.345 | TCCATTTCTGGCAGCAGCCTGGAGC | 232 |
| VEGFA | 212171_x_at | 0.345 | TCTACCCCAGGTCAGACGGACAGAA | 233 |
| LDLRAP1 | 57082_at | 0.345 | ACGGGCTGTCCGTGTGCCTCCTGTG | 234 |
| FLNB | 208613_s_at | 0.343 | GGTGGAGTCAGTGACCAGGTCGTCT | 235 |
| PSG6 | 209738_x_at | 0.343 | CTAACCCACCGGCAGAGTATTTTTG | 236 |
| CBX7 | 212914_at | 0.342 | GCTTTCGAAGTGGCCAGCTGCGGCC | 237 |
| RARRES3 | 204070_at | 0.339 | GTGTTAGAAGCAGCTGTGGGGGTCC | 238 |
| CFLAR | 210563_x_at | 0.339 | GAGTGAGGCGATTTGACCTGCTCAA | 239 |
| SUN2 | 212144_at | 0.337 | TAAGGGCTTGATTCCTAGCCCCGTT | 240 |
| EHD2 | 45297_at | 0.337 | AGGGGCCTCTGAACGGAACAGTGTC | 241 |
| MAP3K5 | 203836_s_at | 0.336 | TGAGCACGCTCAGTTCTACTGTGTC | 242 |
| BTN3A2 | 209846_s_at | 0.336 | GTCTTCGTCCGATACCAATAAGTCA | 243 |
| NOL 12 TRIOBP | 210276_s_at | 0.336 | AGCTGAGCCACATCAAGACACGGTC | 244 |
| CKLF | 221058_s_at | 0.336 | CTTATTTACCGGAAGCTTCTGTTCA | 245 |

TABLE 3-continued

Biomarkers of resistance to 2X-121. Dashes mean that the Affymetrix probeset has not been
mapped to a specific gene. Affymetrix IDs refer to the array type HG-U133_Plus_2.
All correlations are negative.

| Gene ID | Affymetrix ID | Correlation | Probe sequence | SEQ ID no |
|---|---|---|---|---|
| ARPC1B | 201954_at | 0.335 | TGCCTTCATCCTAACTGCTGGGGAA | 246 |
| TNFSF10 | 202688_at | 0.335 | GAGGCACCACTAAAAGATCGCAGTT | 247 |
| HLA-G | 211529_x_at | 0.335 | TACCCTGCGGAGATCATACTGACCT | 248 |
| RP11-395B7.7 | 214808_at | 0.335 | GGATGGGAAGTGTTGCATTGAGCAT | 249 |
| EHD2 | 221870_at | 0.335 | CTTGGAGATATTTCCGTCCTCCACC | 250 |
| LEPROT | 202378_s_at | 0.334 | AGGCCTCTCATGACCCAGGAAGGCC | 251 |
| BTN3A2 BTN3A3 | 204820_s_at | 0.333 | TCATCACTATTATTGCTCACCACTG | 252 |
| INPP4B | 205376_at | 0.332 | AAGCTGACACCTAAGTTTACCAACA | 253 |
| DUSP1 | 201041_s_at | 0.331 | TAGGTGTCTGCCTTCACAAATGTCA | 254 |
| EVI2A | 204774_at | 0.33 | ATATTCCCTATGTAGCAACAGTGGT | 255 |
| TFPI | 213258_at | 0.33 | GATCATGCTGAAAACCACTCAAACG | 256 |
| EHD1 | 209037_s_at | 0.329 | AAGGTCCATAAAGACTGAGCGGATG | 257 |
| VEGFA | 210513_s_at | 0.329 | CTGAGGAGTCCAACATCACCATGCA | 258 |
| EPAS1 | 200878_at | 0.328 | GGACGACACCTCTGGTTTTTCAATA | 259 |
| IQGAP1 | 210840_s_at | 0.328 | TTCACTCCATCCCTATGGCAGAGGA | 260 |
| IL6ST | 212195_at | 0.327 | GAGATGCATTTAAGGCCGATAGTGA | 261 |
| CLIC3 | 219529_at | 0.327 | TCGTTACAGGGAGTCCAACACCGCC | 262 |
| TFPI | 210664_s_at | 0.326 | GATGGTCCGAATGGTTTCCAGGTGG | 263 |
| NACC2 | 212993_at | 0.326 | GTTTTTGTGCTGTTACTCGGTAGAG | 264 |
| TGFBI | 201506_at | 0.325 | GAGATGTGAGCCTTGTGCATGTGGG | 265 |
| ER3 | 201631_s_at | 0.325 | TGAGATCCGTGAGATCCTTCCATCT | 266 |
| MICA | 205904_at | 0.325 | TATTATTTTCTATGTCCGTTGTTGT | 267 |
| BTN3A2 | 212613_at | 0.325 | TACTGGGCAAGTGCTTGTCAAGTTC | 268 |
| IQGAP1 | 200791_s_at | 0.323 | GAGGATGCCCCAACAAACTCATGGC | 269 |
| CNN2 | 201605_x_at | 0.321 | TCTGAGTTGTTGGGGCTAAGCCTGA | 270 |
| TNFAIP8 | 208296_x_at | 0.321 | GAAAGGTAACAATCTTCATTCTACA | 271 |
| VEGFA | 211527_x_at | 0.321 | ATCGATACAGAAACCACGCTGCCGC | 272 |
| MBNL1 | 201152_s_at | 0.32 | ACTCTTGAGGGTTGATTATGCTGCA | 273 |
| ISG15 | 205483_s_at | 0.318 | CCCTGAGCACCGTGTTCATGAATCT | 274 |
| TNFAIP8 | 210260_s_at | 0.318 | GATTGAGTCATCGACATTCAGGATT | 275 |
| COPG1 | 217749_at | 0.318 | CACCCGGGACTACTTGCTGGTGACT | 276 |
| CD99 | 201028_s_at | 0.317 | TGGAGAAAATGACGACCCACGACCA | 277 |
| PSMB9 | 204279_at | 0.317 | GACAGCCTTTTGCCATTGGTGGCTC | 278 |
| ZFP36L1 | 211962_s_at | 0.317 | GGCCTTTCACAACTAGGACTGAGAA | 279 |
| IL6ST | 212196_at | 0.317 | TATGTAATGTACACCTGCCCTAAGG | 280 |
| SHC1 | 214853_s_at | 0.316 | GGGAGAGTTGACCGTTTTCATCCTG | 281 |
| GSTK1 | 217751_at | 0.316 | CATAAGGCACTGGGACTCGGATTTC | 282 |

TABLE 3-continued

Biomarkers of resistance to 2X-121. Dashes mean that the Affymetrix probeset has not been
mapped to a specific gene. Affymetrix IDs refer to the array type HG-U133_Plus_2.
All correlations are negative.

| Gene ID | Affymetrix ID | Correlation | Probe sequence | SEQ ID no |
|---------|---------------|-------------|----------------|-----------|
| CAV1 | 203065_s_at | 0.315 | GCACATCTGGGCAGTTGTACCATGC | 283 |
| HLA-F | 204806_x_at | 0.314 | CACTGACAGTGCCCAGGGCTCTGGG | 284 |
| KRT7 | 209016_s_at | 0.314 | GAGTGGGAGCCGTGAATATCTCTGT | 285 |
| TFPI | 209676_at | 0.314 | AAATTATCATACTACCGGCTACATC | 286 |
| SPTBN1 | 212071_s_at | 0.314 | TAATTTGCTTCATTTCCTTGCTATT | 287 |
| RHOG | 203175_at | 0.313 | AAGGTGAATGTACCCTAACCTGCTC | 288 |
| CDH11 | 207173_x_at | 0.313 | GAGCATCAATCTTGTTACTGCTGAT | 289 |
| ABCC3 | 208161_s_at | 0.313 | GATCCCCAAGTGGTGAATGACACGC | 290 |
| CAV1 | 212097_at | 0.313 | GTTACCTACTTTGACTTTTTGCATT | 291 |
| HLA-J | 217436_x_at | 0.313 | GAACGGGAAGGAGACGCTGCAGCGC | 292 |
| MYL12A | 201319_at | 0.312 | CAGACTGGAAACGGGACTTTCTATT | 293 |
| MRPS10 | 218106_s_at | 0.312 | AACCCCAGAGAAGTGCTTCATTTTC | 294 |
| RRAS | 212647_at | 0.309 | GACGAGGCTTTTGAGCAGCTGGTGC | 295 |
| TMEM2 | 218113_at | 0.309 | GCAAAATGCCTTTACGTTGTTCTAA | 296 |
| SIDT2 | 218765_at | 0.308 | GGGTCTGGATCTTTTCTCAGAGCGT | 297 |
| RAB11FIP1 | 219681_s_at | 0.308 | GGATTTCGTTTGCTGTGGCATTGGT | 298 |
| RTP4 | 219684_at | 0.308 | AACATCTGTGTCTTTATTTTGCTGC | 299 |
| LOC101928916 NNMT | 202238_s_at | 0.307 | TCCCCAGTGGTGACCTATGTGTGTG | 300 |
| SPTBN1 | 200671_s_at | 0.306 | ATGACAGTTTCACAACCTGCATTGA | 301 |
| TMEM189 TMEM189-UBE2V1 UBE2V1 UBE2V2 | 201003_x_at | 0.306 | GGGAACTTACTTCTCTATAGCCCAC | 302 |
| RPN2 | 213399_x_at | 0.305 | GCTCCTAGCACGATTATATTTCACC | 303 |
| ITGA5 | 201389_at | 0.304 | CACTAACTATGCATGGTGCCCCAGG | 304 |
| CDC42EP1 | 204693_at | 0.304 | GGCTTGCTCTGGGACTTTTATGCTC | 305 |
| BTN3A3 | 204821_at | 0.304 | GAGAATAACCTCATAGTACCAACAT | 306 |
| OSER1 | 209020_at | 0.304 | GGCTCCAGAACGAAGATCCACACTT | 307 |
| CHST15 | 203066_at | 0.303 | GGATTTTTCTTATGCACTCCTATGC | 308 |
| MDFIC | 211675_s_at | 0.303 | AAACATGTACTGGCACAATTGTGA | 309 |
| CAV2 | 203324_s_at | 0.302 | AAGGCAGACAGTTTTGCTTTAGTAC | 310 |
| CARD10 | 210026_s_at | 0.302 | ACGGGCCTTTTTCACTTAGAAGCTG | 311 |
| RAC2 | 213603_s_at | 0.302 | GAGTGTCTCAGAAGTGTGCTCCTCT | 312 |
| MLPH | 218211_s_at | 0.302 | GCTCTGTGCTTTCCACTATACACAG | 313 |
| F2R | 203989_x_at | 0.301 | GGTTGAAACATATCTCTTATCTTAC | 314 |
| ICAM3 | 204949_at | 0.301 | TGGTACTTATCAGTGCCAAGCGTCC | 315 |
| CRIM1 LOC101929500 | 202552_s_at | 0.3 | GTAAGAGAATTATCTGCAACTTGAT | 316 |
| IFI16 | 208966_x_at | 0.3 | TTCATAGTCACATCAAGGTCATCAA | 317 |
| EVI2B | 211742_s_at | 0.3 | GGAACTATCTGAAATCTGCTCAGAG | 318 |

TABLE 3-continued

Biomarkers of resistance to 2X-121. Dashes mean that the Affymetrix probeset has not been
mapped to a specific gene. Affymetrix IDs refer to the array type HG-U133_Plus_2.
All correlations are negative.

| Gene ID | Affymetrix ID | Correlation | Probe sequence | SEQ ID no |
|---------|---------------|-------------|----------------|-----------|
| PFKFB3 | 202464_s_at | 0.299 | GCAGTTGCCAGACCAATAAAATACC | 319 |
| MIR6513 TMBIM1 | 217730_at | 0.299 | GGGAGATACCGAAGCCTACTGTGGT | 320 |
| APOL3 | 221087_s_at | 0.299 | TGGAAGTGTATCTCAGTCAGCCAGT | 321 |
| CD55 | 201925_s_at | 0.298 | GATCTGTAATGTTATTTCCACTTAT | 322 |
| TRAM2 | 202369_s_at | 0.298 | TTTTCTACTCTAGCCTGTTCATATG | 323 |
| S100A4 | 203186_s_at | 0.297 | GGCTTCCCAGATAAGCAGCCCAGGA | 324 |
| SERPINB1 | 212268_at | 0.297 | GTGGACTAAACCTGAGAATCTCGAT | 325 |
| PIP4K2A | 212829_at | 0.297 | GTGGTTTGACCCAAGACCACAACCA | 326 |
| RPN2 | 213491_x_at | 0.297 | GGTGAGCTCAGATAGTCTCTTTCTC | 327 |
| ALDOA | 214687_x_at | 0.297 | TCGTCTCTAACCACGCCTATTAAGC | 328 |
| IFIT3 | 204747_at | 0.296 | GCATAGGCAGTATTTTCCTGTCAGC | 329 |
| PLAC8 | 219014_at | 0.296 | AATGAGGACTCTCTACAGGACCCGA | 330 |
| SDF4 | 221972_s_at | 0.296 | CAAGTACAGCGAGTTCTTCACGGGC | 331 |
| CAV2 | 203323_at | 0.294 | GATGGGACGCATAATCATTACCTTA | 332 |
| HLA-C | 216526_x_at | 0.294 | CGATCATCTTTCCTGTTCCAGAGAG | 333 |
| MVP | 202180_s_at | 0.292 | GAGCTCCAGAGGGTCCAGAAGGTCC | 334 |
| RNH1 | 206050_s_at | 0.292 | TCAGCAACAACTGCCTGGGGGACGC | 335 |
| EIF1 | 212225_at | 0.292 | AGGGGTGATAAATGCGTTCATGCTC | 336 |
| SERPINB1 | 213572_s_at | 0.292 | TGCGTAGATTCTTGACCATGTAGTA | 337 |
| ASL | 204608_at | 0.291 | AAGCTGTGTTCATGGCCGAGACCAA | 338 |
| CD99 | 201029_s_at | 0.29 | TGTTCACGGCGGATTCTTTGTTTTA | 339 |
| USP4 | 202682_s_at | 0.289 | GAACATCTTTGACACTCTGCAGACT | 340 |
| TACC1 | 200911_s_at | 0.288 | TTCCCACGGGTGCCATGAAGTGTGT | 341 |
| CD55 | 201926_s_at | 0.288 | GGTCCCACCAACAGTTCAGAAACCT | 342 |
| PDXK | 218019_s_at | 0.288 | GAGGCATCAAAGCACCTGTCGCCTC | 343 |
| BST2 | 201641_at | 0.287 | AACATTCCCTTGATCTCATCAGTTC | 344 |
| LOC101928916 NNMT | 202237_at | 0.287 | CAACAACGAAGGACTTTTCTCCCTG | 345 |
| DUSP5 | 209457_at | 0.287 | TGTGTAGACACCCTCTTGGGTCCAA | 346 |
| TNFSF13 | 210314_x_at | 0.287 | CCACAAGAAGCCTTATCCTACGTCC | 347 |
| COMT | 208818_s_at | 0.286 | TGAGTGCACACACTACCAATCGTTC | 348 |
| CYR61 | 210764_s_at | 0.286 | GATGCGGTTCCGCTGCGAAGATGGG | 349 |
| LY6E | 202145_at | 0.284 | GTCAGTAGGGATGTGTGCCTGGCTG | 350 |
| ACSL5 | 218322_s_at | 0.284 | CTCTCTAGTTAGATATCTGACTTGG | 351 |
| GBP2 | 202748_at | 0.283 | ACAGGGCCCAGTTAATGGCAGAGCA | 352 |
| TNFRSF1B | 203508_at | 0.283 | GAAGCGATGAATTTGGAGACTCTGT | 353 |
| PTRF | 208790_s_at | 0.283 | GGGTCCCAGAGGAACGCTGGAGCCA | 354 |

TABLE 3-continued

Biomarkers of resistance to 2X-121. Dashes mean that the Affymetrix probeset has not been
mapped to a specific gene. Affymetrix IDs refer to the array type HG-U133_Plus_2.
All correlations are negative.

| Gene ID | Affymetrix ID | Correlation | Probe sequence | SEQ ID no |
|---|---|---|---|---|
| CYR61 | 201289_at | 0.282 | GGAGCACATGTTACTGCTTCATTTT | 355 |
| BTN3A1 | 209770_at | 0.282 | ATCATTATTATTGCTCTCCACTGTA | 356 |
| PLEC | 201373_at | 0.281 | CATGGGAAGACGAGGCCCTCGGGCC | 357 |
| CTNND1 TMX2-CTNND1 | 208407_s_at | 0.281 | TACCAGGGACTATCTTTGCTGCAGA | 358 |
| TNFRSF14 | 209354_at | 0.281 | GTGAGGCCACAGTCATTGAGGCCCT | 359 |
| ABCC10 | 213485_s_at | 0.281 | GAGCCCACTTGCATTTTCATAGTTT | 360 |
| SELPLG | 209879_at | 0.28 | CACTGCACTGCCATTGTCTTTTGGT | 361 |
| GPX4 | 201106_at | 0.279 | GATCAAAGAGTTCGCCGCGGGCTAC | 362 |
| EDEM1 | 203279_at | 0.279 | AAGAAAATCCTGAGCTTTCCTGTCC | 363 |
| MIR6787 SLC16A3 | 202856_s_at | 0.278 | GATCGTCGCCCGATCAGTGTTTTGA | 364 |
| DMBT1 | 208250_s_at | 0.278 | GCTACCGAGGCTGTGTGTTGAGGTC | 365 |
| PSMB8 | 209040_s_at | 0.278 | TATCGGCCTAATCTTAGCCCTGAAG | 366 |
| FN1 | 214701_s_at | 0.278 | CGTCGACCAATGCCAGGATTCAGAG | 367 |
| COL1A1 | 202310_s_at | 0.277 | CAGACAAGCAACCCAAACTGAACCC | 368 |
| FOS | 209189_at | 0.277 | TCTCCTTAGTCTTCTCATAGCATTA | 369 |
| CYLD | 222142_at | 0.277 | TTCACCACCTGACTTTGAATTTGTC | 370 |
| ADAMTS1 | 222162_s_at | 0.276 | TGGTGAATGTCTGTTCAGCTCTTCT | 371 |
| ALDOA | 200966_x_at | 0.275 | TTCCCTCGTGACAGTGGTGTGTGGT | 372 |
| GATA6 | 210002_at | 0.275 | GACATTCTTATGCTTCTTTTACAAC | 373 |
| YWHAB | 217717_s_at | 0.275 | CCCCCTTTCCTACAGCAATATGTTC | 374 |
| CIB1 | 201953_at | 0.274 | AGACATCAAGTCCCATTATGCCTTC | 375 |
| OPTN | 202074_s_at | 0.273 | GAACAAGTGACTCTGACCAGCAGGC | 376 |
| IFI16 | 208965_s_at | 0.273 | GACCTGGCTGAAACTCTTAAAAAAG | 377 |
| CFLAR | 211316_x_at | 0.273 | TCTTCTGGAGCCTGTGTACTGCGGA | 378 |
| PTGER4 | 204897_at | 0.272 | GATTCCCAAACGTGGTTACATTAGC | 379 |
| CCND1 | 208712 at | 0.272 | AGCAAGCTGCCGAACCAAAGAATT | 380 |
| PDLIM5 | 212412 at | 0.271 | GGATTCTCAATGTATAAGTTGCCTT | 381 |
| HLA-F | 221875 x at | 0.271 | AGCTACTCTCAGGCTGCAGTGTGAG | 382 |
| CYP1B1 | 202437_s_at | 0.27 | TTAGCCTTTACCTGTGAAGTGTTAC | 383 |
| SVIL | 202565_s_at | 0.27 | GTTTGCTCTGCATTTTTGATGATGG | 384 |
| RNASET2 | 217983_s_at | 0.27 | GGCCTGACGTAATTCACTCGTTTCC | 385 |
| TAGLN2 | 200916 at | 0.269 | CTGCCTACCATGGTCTGGGGCTTGA | 386 |
| IFI27 | 202411 at | 0.267 | TCTGCCATTGCGGCTGTCATTGCGA | 387 |
| FLII | 212025_s_at | 0.267 | ATCAGACCCTGACGAAGCCAAGTTG | 388 |
| STAT6 | 201331_s_at | 0.266 | GAACATGTGTCTATCTGCTTTTGCC | 389 |
| WWP2 | 204022 at | 0.266 | TCAGGGTGCAAGCTGCTGGTGAGGT | 390 |
| FLNC | 207876_s at | 0.266 | CTGCGAGGCCAGGGAAGCCCTGAGT | 391 |

TABLE 3-continued

Biomarkers of resistance to 2X-121. Dashes mean that the Affymetrix probeset has not been
mapped to a specific gene. Affymetrix IDs refer to the array type HG-U133_Plus_2.
All correlations are negative.

| Gene ID | Affymetrix ID | Correlation | Probe sequence | SEQ ID no |
|---|---|---|---|---|
| PARP12 | 218543_s_at | 0.266 | TTGTCTCTGCAGTGATTCGGTTTCT | 392 |
| VPS13D | 220221_at | 0.266 | GACTGGCATTTTACTTCTGTGTTTT | 393 |
| IFITM2 | 201315_x_at | 0.265 | ATCATTGAGGCCAGGAGCTCTGCCC | 394 |
| CTSZ | 210042_s_at | 0.265 | ACTGGCTGCGAGTGTTCCTGAGAGT | 395 |
| C19orf10 | 221739_at | 0.265 | GTGAAGCTGAAGGGGCCTGTGTCCC | 396 |
| DAPK1 | 203139_at | 0.264 | TGATCAGTGTTGTTGCTCTAGGAAG | 397 |
| LOC101928189 RSRP1 | 209006_s_at | 0.264 | GTGCATGCTAGAATTTGGGACAGGC | 398 |
| MYOF | 211864_s_at | 0.263 | CTCTACTCTTTGCCGAACTATTTGT | 399 |
| ATP2B4 | 212135_s_at | 0.263 | CGCCCTTTCACTTAGTTCAGTGCCA | 400 |
| AXL | 202686_s_at | 0.262 | ATTGGTCCAAGATTCCGGATCCTAA | 401 |
| MIR6787 SLC16A3 | 202855_s_at | 0.262 | TGTTCGTGGTGAGCTACGCCAAGGA | 402 |
| LY96 | 206584_at | 0.262 | CAGTATTGGGTCTGCAACTCATCCG | 403 |
| FN1 | 212464_s_at | 0.262 | CTGTTCTGCTTCGAAGTATTCAATA | 404 |
| CREB3L1 | 213059_at | 0.261 | TTGTATTTTACAAATCTCCCTCTTC | 405 |
| TNFSF12-TNFSF13 TNFSF 13 | 209499_x_at | 0.26 | GTGTCATAATTCCCCGGGCAAGGGC | 406 |
| POFUT2 | 209578_s_at | 0.26 | GTTGCATTTTCCAGGCTGAGAGCTG | 407 |
| WDR1 | 200609_s_at | 0.259 | GTTGCCTGTCAGTGTTTACAAACTA | 408 |
| SLC7A7 | 204588_s_at | 0.259 | TAAAAGGGCCCACAATGCTCCAATT | 409 |
| MICB | 206247_at | 0.259 | ACCGTTATGCATTACTCTGTGTCTA | 410 |
| GATA3 | 209604_s_at | 0.258 | GTGTCTGTGTTCCAACCACTGAATC | 411 |
| LRRFIP1 | 211452_x_at | 0.257 | GAGCTATGATTGCACACTGTACTCT | 412 |
| RNASET2 | 217984_at | 0.256 | TAGATCGTGGCCCTTCAATTTAGAA | 413 |
| ITM2A | 202746_at | 0.255 | GCAAGCTCTTGTCAAATTTTAGTTT | 414 |

Tables 2 and 3 respectively list the biomarkers of sensitivity and the biomarkers of resistance to 2X-121. FIG. 1 shows protein-coding genes from Tables 2 and 3 associated with the known modes of action of 2x-121, namely PARP trapping, homologous repair and BRCA, base excision repair, and the Wnt/tankyrase pathway.

Example 2. Clinical Proof-of-Concept Study

Figure 2:
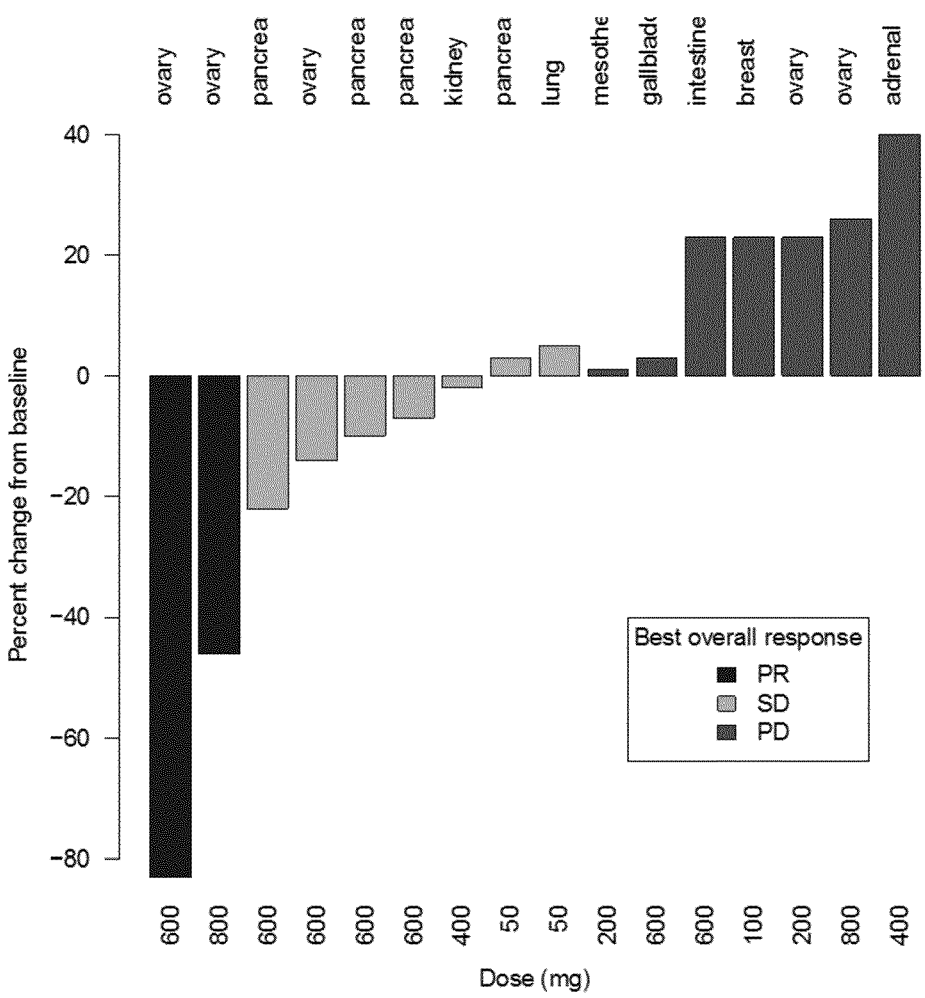
FIG. 2 is a waterfall plot showing change from baseline tumor diameter of 16 Phase I patients treated with 2X-121 for which biopsies were available. The plot shows patients with best overall response: partial response (PR), stable disease (SD), and progressive disease (PD).

A Phase I trial of 2X-121 was conducted in the UK (clinicaltrial.gov number NCT01618136). 2X-121 was administered as daily oral doses of 50-800 mg. Of 41 patients enrolled in the Phase I trial, 35 had response assessment. Of these, 2 had partial response (PR) (5% overall response rate (ORR)) and 13 had stable disease (SD). Biopsies and BRCA analysis were voluntary and available from 16, and 7 patients, respectively. FIG. 2 shows a waterfall plot of change from baseline tumor diameter of the 16 patients for which biopsies were received.

Of the 16 patients with biopsies, 13 passed our quality control (QC) in the lab and were assayed on the Affymetrix HG-U133Plus2 array. The 13 patients are shown in Table 4.

A statistical analysis plan was completed before initiation of blinded prediction of 2X-121 sensitivity on the 13 samples. In this analysis, the difference of the mean expression of genes in Table 3 were subtracted from the mean expression of genes in Table 2 for each patient to determine a difference score. This score was compared to a reference population of 819 breast cancer patients to convert the difference score to a percentile score. The percentile score is shown in Table 4 as "DRP score" and used for FIGS. 3 and 4, and Tables 5 and 6. Although, in this analysis, a DRP score was used to predict sensitivity to 2X-121, other analyses that do not use a DRP score, as discussed herein, are contemplated (e.g., an analysis based solely on the expression level of a biomarker(s) of sensitivity or a biomarker(s) of resistance without producing a difference score).

Figure 3:
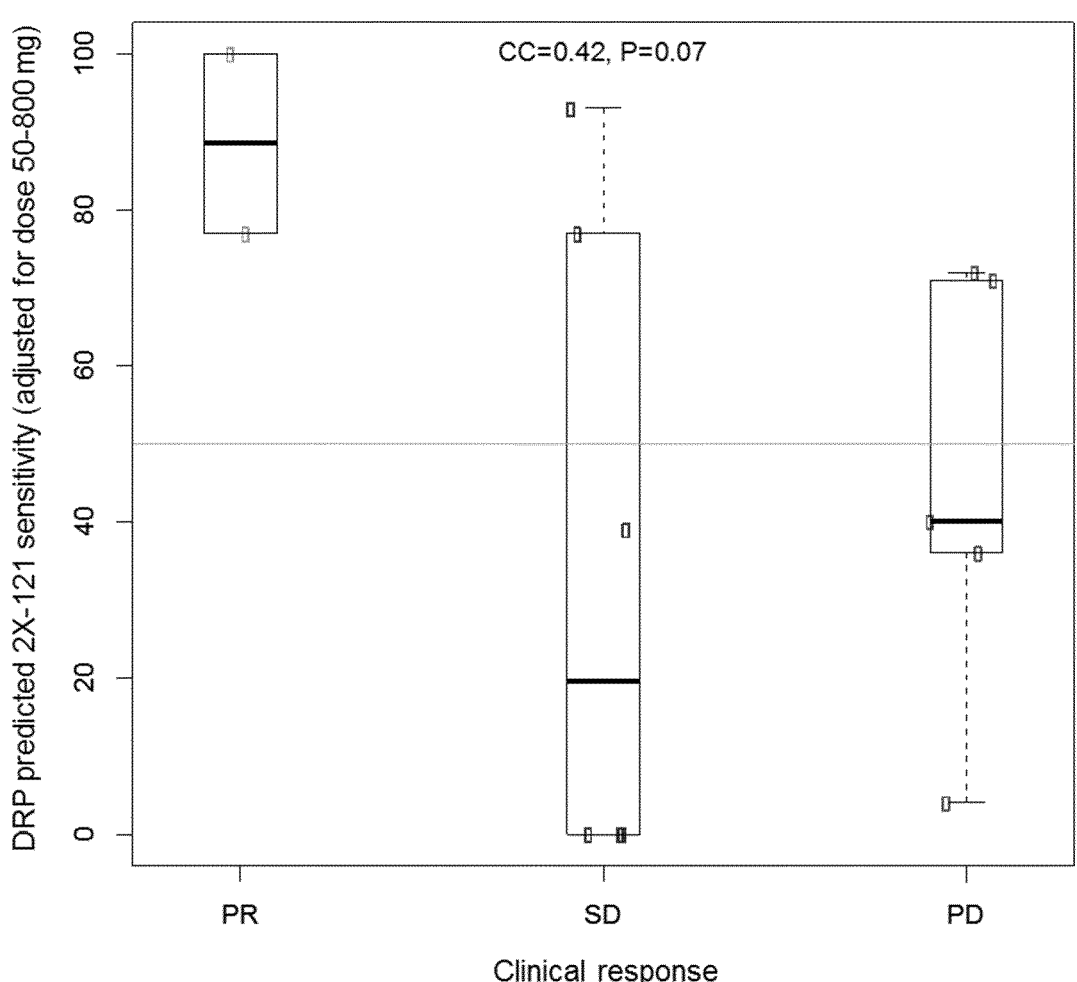
FIG. 3 is a graph depicting comparison of dose response predictor (DRP) predicted sensitivity to 2X-121 and clinical response to 2X-121. The cutoff is shown with a horizontal line.

FIG. 3 shows the unblinded comparison of dose-adjusted predicted sensitivity to 2X-121 and clinical response to 2X-121. The highest scoring SD patient was actually a long term progression-free pancreatic cancer survivor (still alive at last check at 406 days, and progression-free at last evaluation at 321 days, see Table 4). The prediction had been adjusted for dose as described in Table 4. The cutoff is shown with a horizontal line. A Pearson correlation test between adjusted score and change in tumor diameter shows a CC of 0.42 with a one-sided P-value of 0.07. Similar to FIG. 3, FIG. 4 also shows comparison of predicted sensitivity to 2X-121, and clinical response to 2X-121, but only in two response categories. A Pearson correlation test between dose-adjusted score and change in tumor diameter shows a CC of 0.42 with a one-sided P-value of 0.07. Tables 5 and 6 show the clinical performance of the DRP at the pre-specified cutoff of 50 (population median).

Figure 4:
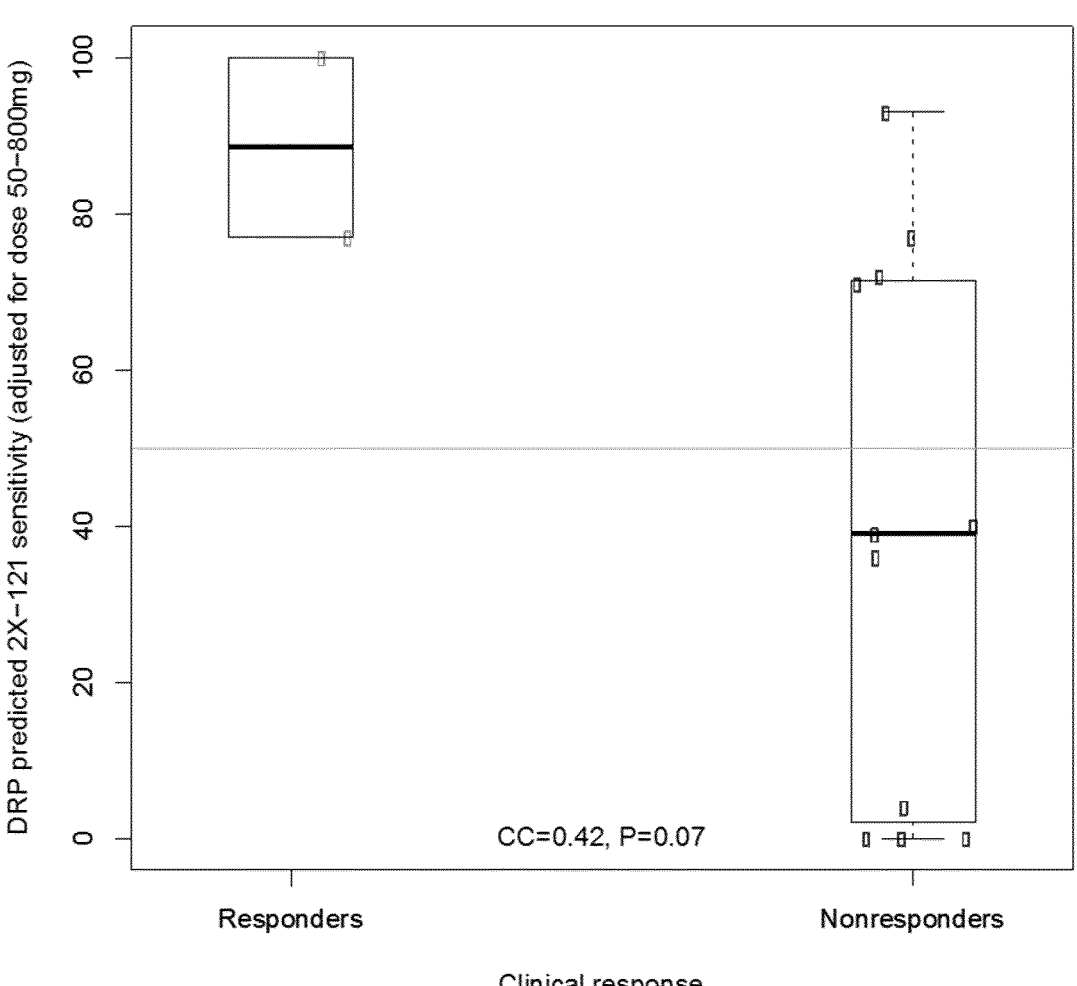
FIG. 4 is a graph comparing DRP predicted sensitivity to 2X-121 and clinical response to 2X-121, showing only two response categories. The cutoff is shown with a horizontal line.

If the score is adjusted for dose as was done in FIGS. 3 and 4, and Table 4, Table 6 remains unchanged, whereas the non-responder in Table 5 is predicted as responder, leading to worse statistics.

Thus the DRP can be performed with no dose adjustment. A dose adjustment was performed in the Phase I trial retrospective analysis because the trial was a dose-escalation trial where the highest dose was 16 times the lowest dose. All three ovarian cancer patients in Table 5 received a high dose of 600-800 mg (Table 4) making dose-adjustment for this subset unnecessary.

Figure 5:
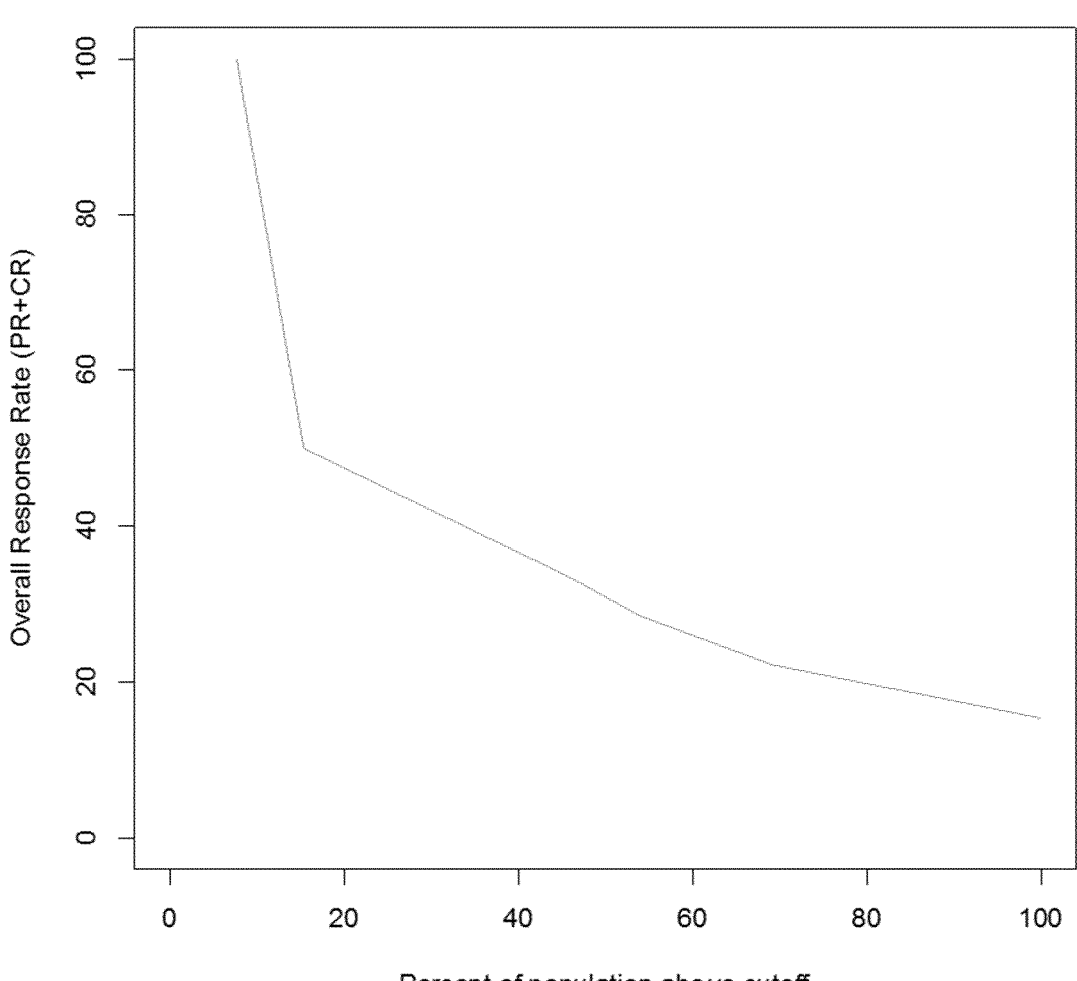
FIG. 5 is a graph showing response rate as a function of cutoff.

FIG. 5 shows how the choice of cutoff affects the response rate of patients above dose-adjusted cutoff. A cutoff of 0 on the y-axis of FIG. 4 corresponds to 100% of population above cutoff (x-axis in FIG. 5), and a response rate of

TABLE 4

| | | | | | | | | | | | | |
|---|---|---|---|---|---|---|---|---|---|---|---|---|
| | | | | | | | | | Description of 13 patients | | | |
| Patient | Tumor | 2X-121 dose (mg) | Diameter (%) | RECIST | TimeOS (days) | StatusOS | TimePFS (days) | StatusPFS | Platinum response | DRP | Score | BRCA |
| 1 | pancreas | 600 | −10 | SD | 208 | Death | 42 | censored | NA | 34 | 39 | BRCA2 |
| 2 | mesothelioma | 200 | 1 | PD | 167 | Death | 50 | Progression | SD | 10 | 4 | NA |
| 3 | pancreas | 600 | −22 | SD | 406 | censored | 321 | censored | NA | 80 | 93 | NA |
| 4 | intestine | 600 | 23 | PD | 120 | Death | 59 | Progression | SD | 62 | 72 | NA |
| 5 | ovary | 600 | −83 | PR | 379 | censored | 331 | Progression | NA | 86 | 100 | BRCA1 |
| 6 | lung | 50 | 5 | SD | 466 | censored | 155 | Progression | SD | 1 | 0 | NA |
| 7 | pancreas | 50 | 3 | SD | 335 | Death | 262 | censored | NA | 2 | 0 | NA |
| 8 | adrenal | 400 | 40 | PD | 190 | Death | 50 | Progression | PD | 52 | 40 | NA |
| 9 | kidney | 400 | −2 | SD | 865 | censored | 276 | Progression | PR | 100 | 77 | NA |
| 10 | ovary | 800 | 26 | PD | 301 | Death | 50 | Progression | PR-SD-PR | 46 | 71 | BRCA2 |
| 11 | ovary | 800 | −46 | PR | 715 | censored | 315 | Progression | PR-PD-PD | 50 | 77 | NA |
| 12 | pancreas | 600 | −7 | SD | 257 | Death | 189 | Progression | PR-SD-PR | 0 | 0 | NA |
| 13 | gallbladder | 600 | 3 | PD | 121 | Death | 41 | Progression | PD | 31 | 36 | NA |

DRP: DRP prediction
Score = DRP*doses/518 (DRP adjusted for differences in dose)
NA = not determined
Diameter = perscent change from baseline
SD = stable disease
PD = progressive disease
PR = partial response

TABLE 5

Clinical performance of DRP (ovarian samples only)

| Ovarian only (N = 3) | Responders (PR) | Non-responders (SD + PD) |
|---|---|---|
| DRP positive (top 50%) | 2 | 0 |
| DRP negative (bottom 50%) | 0 | 1 |

Overall precision: 100% correct prediction
Sensitivity: 100% of responders correctly predicted
Specificity: 100% of non-responders correctly predicted

TABLE 6

Clinical performance of DRP (all histologies)

| All histologies (N = 13) | Responders (PR) | Non-responders (SD + PD) |
|---|---|---|
| DRP positive (top 50%) | 2 | 4 |
| DRP negative (bottom 50%) | 0 | 7 |

Overall precision: 69% correct prediction
Sensitivity: 100% of responders correctly predicted
Specificity: 64% of non-responders correctly predicted 2/13=15%. A cutoff of 50 on the Y-axis of FIG. 4 corresponds to 50% of population above cutoff and a doubled response rate of 2/6=33%.

Figure 6:
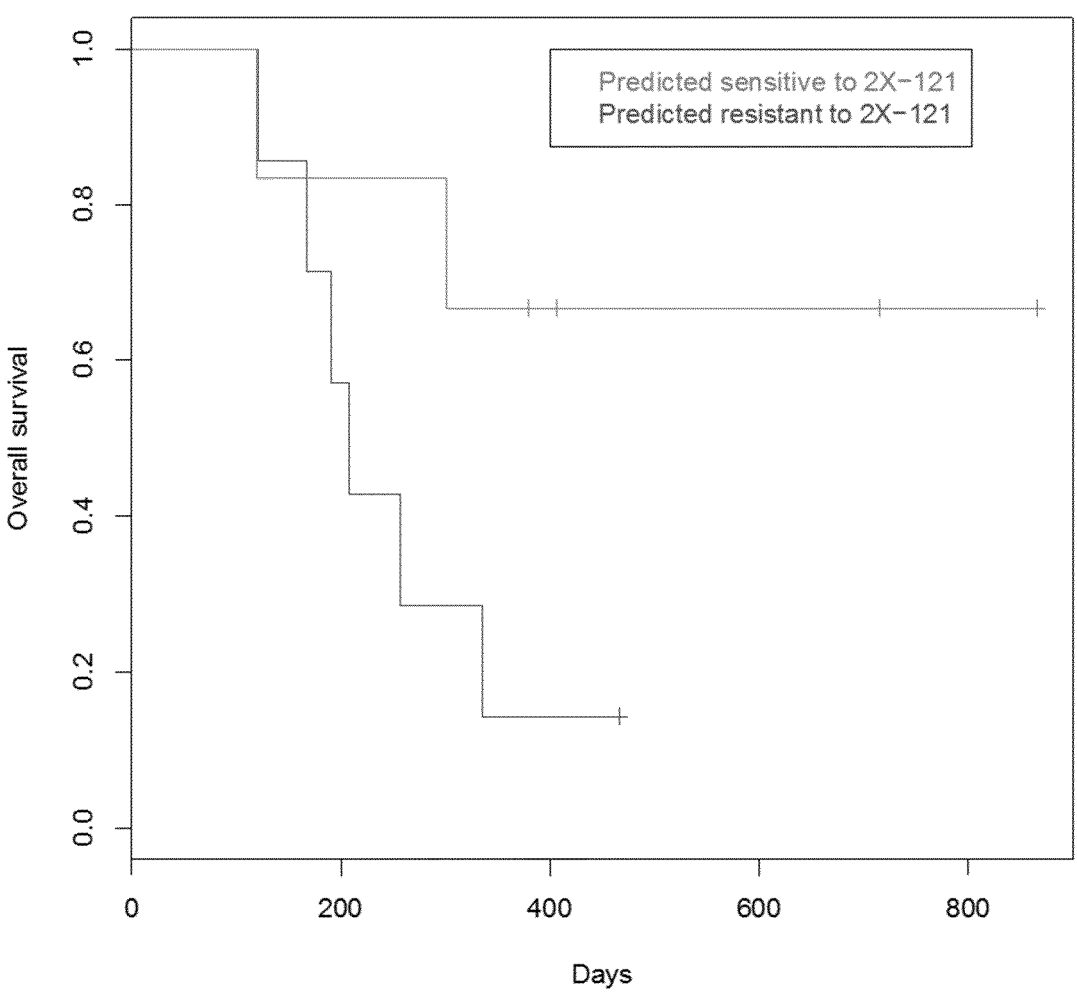
FIG. 6 depicts Kaplan-Meier curves of overall survival in two populations, those above a cutoff of 50 (N=6), and those below a cutoff of 50 (N=7).

FIG. 6 shows Kaplan-Meier curves of overall survival (OS) in two populations, those above a dose-adjusted cutoff of 50 (N=6), and those below a cutoff of 50 (N=7). The hazard ratio is 0.26 (P=0.04 one sided). The median survival in the predicted resistant group (below cutoff) is 208 days. More than half of the patients remained alive in the other group.

Figure 7:
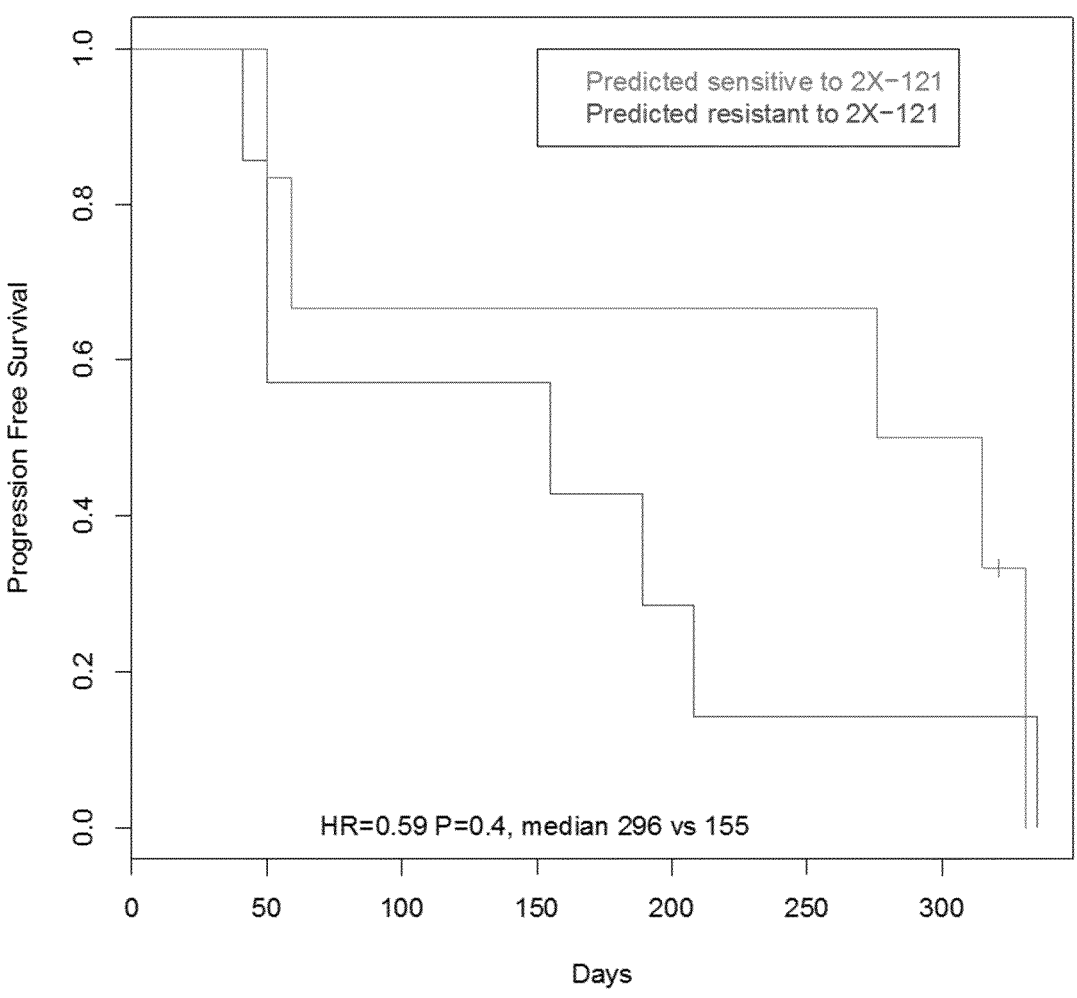
FIG. 7 depicts Kaplan-Meier curves of progression-free survival in two populations, those above a cutoff of 50 (N=6), and those below a cutoff of 50 (N=7).

FIG. 7 shows the Kaplan-Meier curves of progression-free survival (PFS) in the same two populations, those above a cutoff of 50 (N=6), and those below a cutoff of 50 (N=7). The hazard ratio is 0.59 (P=0.2 one-sided). The median PFS in the predicted resistant group (below cutoff) is 155 days versus 296 days in the predicted sensitive group.

Comparison to BRCA Mutation Status

BRCA mutation status was only available for 7 patients in the trial, of which 6 were BRCA mutated. Of these 6, 1 responded to 2X-121, giving a response rate of ⅙ or 16% in the BRCA mutated population. This equaled the response rate observed in the unselected 13 patients analyzed with DRP score. Thus, BRCA mutation may not be a predictor of 2X-121 response.

Comparison to Prior Platinum Response

Table 3 shows that one 2X-121 responder (Patient #11) had progressive disease (PD) response to prior carboplatin, while six 2X-121 non-responders in the entire trial, including patients not shown in Table 4, showed response to prior platinum (including Patients 9, 10, 12 in Table 4). Thus, prior platinum response may not be determinative of response to 2X-121.

CONCLUSION

The pre-specified statistical analysis plan called for a one-sided (the null hypothesis included significant association in the wrong direction) P-value below 0.1 in this small sample of 13 patients in either of the dose-adjusted analyses shown in FIG. 3, 5, or 6. FIGS. 3 and 6 both met these criteria, and the DRP certainly performed better than the trial BRCA and prior platinum as a biomarker in this trial.

Example 3. Predicting Responsiveness of Breast Cancer Patients to 2X-121 or a Pharmaceutically Acceptable Salt Thereof The diagnostic methods described herein can be used to predict the responsiveness of a breast cancer patient to treatment with 2X-121 or a pharmaceutically acceptable salt thereof. In particular, the breast cancer patient may be one that has not previously received any cancer treatment or one that has received a cancer treatment other than 2X-121 or a pharmaceutically acceptable salt thereof. Moreover, the patient may be one diagnosed with breast cancer or with recurrence of breast cancer.

A biological sample (e.g., a breast tissue sample, such as a breast tissue sample obtained by biopsy) may be obtained from the patient through methods well known in the art. The sample may be frozen and/or prepared, e.g., by formalin fixation and paraffin embedding. In particular, mRNA can be isolated from the sample and a gene expression profile can be determined, e.g., using a microarray platform, such as the Affymetrix HG-U133A, for one or more of the biomarkers shown in Table(s) 2 and/or 3. One or more of the biomarkers shown in Table(s) 2 and/or 3 can also be measured, e.g., by sequencing or PCR-based techniques, such as those described herein.

For example, the expression level of one or more biomarkers of sensitivity to 2X-121 or a pharmaceutically acceptable salt thereof can be determined in the sample from the patient, such as one or more biomarkers of SEQ ID NO: 1, SEQ ID NOs: 1-5, SEQ ID NOs: 1-10, SEQ ID NOs: 1-15, SEQ ID NOs: 1-20, or SEQ ID NOs: 1-25. In particular, the biomarker is SRSF7 (SEQ ID NO: 1). The expression level of one or more biomarkers of resistance to 2X-121 or a pharmaceutically acceptable salt thereof can also be determined in the sample from the patient, such as one or more of SEQ ID NO: 173 or 174 or 178, SEQ ID NOs: 173-179, SEQ ID NOs: 173-184; SEQ ID NOs: 173-189; SEQ ID NOs: 173-194; or SEQ ID NOs: 173-199. In particular, the biomarker is HLA-E (SEQ ID NO: 173 or 174 or 178).

The breast cancer patient may be responsive to 2X-121 or a pharmaceutically acceptable salt thereof if the expression level of the one or more biomarkers of sensitivity is similar to (e.g., substantially similar to) the expression level of the biomarkers of sensitivity in a cell or tissue known to be sensitive to 2X-121 or a pharmaceutically acceptable salt thereof. The breast cancer patient may also be responsive to 2X-121 or a pharmaceutically acceptable salt thereof if the expression level of one or more of the biomarkers of resistance is similar to (e.g., substantially similar to) the expression level of the biomarkers of resistance in a cell or tissue known to be sensitive to 2X-121 or a pharmaceutically acceptable salt thereof. Additionally, the breast cancer patient may be responsive to 2X-121 or a pharmaceutically acceptable salt thereof if the expression level of one or more of the biomarkers of sensitivity is dissimilar to (e.g., substantially dissimilar to) the expression level of the biomarkers of sensitivity in a cell or tissue known to be resistant to 2X-121 or a pharmaceutically acceptable salt thereof. The breast cancer patient may also be responsive to 2X-121 or a pharmaceutically acceptable salt thereof if the expression level of one or more of the biomarkers of resistance is dissimilar to (e.g., substantially dissimilar to) the expression level of the biomarkers of resistance in a cell or tissue known to be resistant to 2X-121 or a pharmaceutically acceptable salt thereof. If the patient is predicted to be responsive, then the patient can be administered 2X-121 or a pharmaceutically acceptable salt thereof, such as 2X-121 or a pharmaceutically acceptable salt thereof administered orally at a dose of about 5-5000 mg (e.g., about 50-800 mg). Conversely, if the patient is predicted to be non-responsive to 2X-121 or a pharmaceutically acceptable salt thereof treatment, then the patient can be administered one or more therapies other than 2X-121 or a pharmaceutically acceptable salt thereof, such as radiation or a therapeutic agent (e.g., doxorubicin, epirubicin, paclitaxel, docetaxel, 5-fluorouracil (5-FU), cyclophosphamide, carboplatin, cisplatin, vinorelbine, gemcitabine, mitoxantrone, ixabepilone, eribulin, irinotecan, capecitabine, tegafur, oxaliplatin, and/or another therapeutic agent described herein).

Example 4. Predicting Responsiveness of Ovarian Cancer Patients to 2X-121 or a Pharmaceutically Acceptable Salt Thereof The diagnostic methods of the present invention can be used to predict the responsiveness of an ovarian cancer patient to treatment with 2X-121 or a pharmaceutically acceptable salt thereof. In particular, the ovarian cancer patient may be one that has not previously received any cancer treatment or one that has received a cancer treatment other than 2X-121 or a pharmaceutically acceptable salt thereof. Moreover, the patient may be one diagnosed with ovarian cancer or with recurrence of ovarian cancer.

A biological sample (e.g., an ovarian tissue sample, such as an ovarian tissue sample obtained by biopsy) may be obtained from the patient through methods well known in the art. The sample may be frozen and/or prepared, e.g., by formalin fixation and paraffin embedding. In particular, mRNA can be isolated from the sample and a gene expression profile can be determined, e.g., using a microarray platform, such as the Affymetrix HG-U133A, for one or more of the biomarkers shown in Table(s) 2 and/or 3. One or more of the biomarkers shown in Table(s) 2 and/or 3 can also be measured, e.g., by sequencing or PCR-based techniques, such as those described herein.

For example, the expression level of one or more biomarkers of sensitivity to 2X-121 or a pharmaceutically acceptable salt thereof can be determined in the sample from the patient, such as one or more biomarkers of SEQ ID NO: 1, SEQ ID NOs: 1-5, SEQ ID NOs: 1-10, SEQ ID NOs: 1-15, SEQ ID NOs: 1-20, or SEQ ID NOs: 1-25. In particular, the biomarker is SRSF7 (SEQ ID NO: 1). The expression level of one or more biomarkers of resistance to 2X-121 or a pharmaceutically acceptable salt thereof can also be determined in the sample from the patient, such as one or more of SEQ ID NO: 173 or 174 or 178, SEQ ID NOs: 173-179, SEQ ID NOs: 173-184; SEQ ID NOs: 173-189; SEQ ID NOs: 173-194; or SEQ ID NOs: 173-199. In particular, the biomarker is HLA-E (SEQ ID NO: 173 or 174 or 178).

The ovarian cancer patient may be responsive to 2X-121 or a pharmaceutically acceptable salt thereof if the expression level of the one or more biomarkers of sensitivity is similar to (e.g., substantially similar to) the expression level of the biomarkers of sensitivity in a cell or tissue known to be sensitive to 2X-121 or a pharmaceutically acceptable salt thereof. The ovarian cancer patient may also be responsive to 2X-121 or a pharmaceutically acceptable salt thereof if the expression level of one or more of the biomarkers of resistance is similar to (e.g., substantially similar to) the expression level of the biomarkers of resistance in a cell or tissue known to be sensitive to 2X-121 or a pharmaceutically acceptable salt thereof. Additionally, the ovarian cancer patient may be responsive to 2X-121 or a pharmaceutically acceptable salt thereof if the expression level of one or more of the biomarkers of sensitivity is dissimilar to (e.g., substantially dissimilar to) the expression level of the biomarkers of sensitivity in a cell or tissue known to be resistant to 2X-121 or a pharmaceutically acceptable salt thereof. The ovarian cancer patient may also be responsive to 2X-121 or a pharmaceutically acceptable salt thereof if the expression level of one or more of the biomarkers of resistance is dissimilar to (e.g., substantially dissimilar to) the expression level of the biomarkers of resistance in a cell or tissue known to be resistant to 2X-121 or a pharmaceutically acceptable salt thereof. If the patient is predicted to be responsive, then the patient can be administered 2X-121 or a pharmaceutically acceptable salt thereof, such as 2X-121 or a pharmaceutically acceptable salt thereof administered orally at a dose of about 5-5000 mg (e.g., about 50-800 mg). Conversely, if the patient is predicted to be non-responsive to 2X-121 or a pharmaceutically acceptable salt thereof treatment, then the patient can be administered one or more therapies other than 2X-121 or a pharmaceutically acceptable salt thereof, such as radiation or a therapeutic agent (e.g., carboplatin, cisplatin, docetaxel, paclitaxel, and/or other therapeutic agents described herein).

Example 5. Treating Breast Cancer Patients with 2X-121 or a Pharmaceutically Acceptable Salt Thereof Breast cancer patients can be treated with 2X-121 or a pharmaceutically acceptable salt thereof after being predicted to be responsive to treatment with 2X-121 or a pharmaceutically acceptable salt thereof by the methods described herein. In particular, the breast cancer patient may be one that has not previously received any cancer treatment or one that has received a cancer treatment other than 2X-121 or a pharmaceutically acceptable salt thereof. Moreover, the patient may be one diagnosed with breast cancer or with recurrence of breast cancer.

The breast cancer patient can be determined to be responsive to 2X-121 or a pharmaceutically acceptable salt thereof following the methods exemplified in the aforementioned Example 3. Once the patient has been determined to be responsive to 2X-121 or a pharmaceutically acceptable salt thereof, according to the methods described herein, 2X-121 or a pharmaceutically acceptable salt thereof may be administered to the patient, for example, orally as a daily dose of 600 mg (e.g., the patient can be administered three hard gelatin capsules containing 200 mg each of 2X-121 or a pharmaceutically acceptable salt thereof). Alternative dosing regimens and forms of 2X-121 or a pharmaceutically acceptable salt thereof (e.g., hard gelatin capsules of 10 mg, 50 mg, or 200 mg) or film coated tablets (e.g., film coated tablets of 10 mg, 50 mg, or 200 mg) can also be administered.

2X-121 or a pharmaceutically acceptable salt thereof may be administered to the patient one or more times during a first treatment regimen (e.g., one or more times daily for up to six days or more). The patient can be administered a second treatment regimen of 2X-121 or a pharmaceutically acceptable salt thereof one week, two weeks, three weeks, four weeks, or five weeks after administration of the first treatment regimen of 2X-121 or a pharmaceutically acceptable salt thereof. The administration of 2X-121 or a pharmaceutically acceptable salt thereof can be repeated at such a frequency for a certain period of time, followed by a period without treatment. Such repeated administrations can occur over a course of therapy lasting a specified length of time (e.g., at least 1 week, 2 weeks, 3 weeks, 1 month, 2 months, 3 months, 6 months, or 1 year or more).

OTHER EMBODIMENTS

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. For example, it is anticipated that measuring the level of proteins, metabolites, identifying genetic mutations and DNA copy number variations, all will be useful in determining patient responsiveness.

SEQUENCE LISTING

```
<160> NUMBER OF SEQ ID NOS: 414

<210> SEQ ID NO 1
<211> LENGTH: 25
<212> TYPE: DNA
<213> ORGANISM: Homo sapiens

<400> SEQUENCE: 1
gatcaagatc tatctctctt cgtag                                          25
```

<210> SEQ ID NO 2
<211> LENGTH: 25
<212> TYPE: DNA
<213> ORGANISM: Homo sapiens

<400> SEQUENCE: 2
gagggacttt gctgatttcc cctct                                        25

<210> SEQ ID NO 3
<211> LENGTH: 25
<212> TYPE: DNA
<213> ORGANISM: Homo sapiens

<400> SEQUENCE: 3
tcagtgggca cagttcttca gctac                                        25

<210> SEQ ID NO 4
<211> LENGTH: 25
<212> TYPE: DNA
<213> ORGANISM: Homo sapiens

<400> SEQUENCE: 4
cctggagcaa tgcactgtac ctgcc                                        25

<210> SEQ ID NO 5
<211> LENGTH: 25
<212> TYPE: DNA
<213> ORGANISM: Homo sapiens

<400> SEQUENCE: 5
gtctgtgtct gacaatcgtc acgca                                        25

<210> SEQ ID NO 6
<211> LENGTH: 25
<212> TYPE: DNA
<213> ORGANISM: Homo sapiens

<400> SEQUENCE: 6
tccccgtaca cgcactggaa gcaga                                        25

<210> SEQ ID NO 7
<211> LENGTH: 25
<212> TYPE: DNA
<213> ORGANISM: Homo sapiens

<400> SEQUENCE: 7
ttgaagatcc ccgagatgca gctga                                        25

<210> SEQ ID NO 8
<211> LENGTH: 25
<212> TYPE: DNA
<213> ORGANISM: Homo sapiens

<400> SEQUENCE: 8
gcgtttctgg cgatgcagca attcc                                        25

<210> SEQ ID NO 9
<211> LENGTH: 25
<212> TYPE: DNA
<213> ORGANISM: Homo sapiens

<400> SEQUENCE: 9
aaccatgcct actaaatgta cagat                                        25

-continued

```
<210> SEQ ID NO 10
<211> LENGTH: 25
<212> TYPE: DNA
<213> ORGANISM: Homo sapiens

<400> SEQUENCE: 10
agatcattaa aatccgtgcc cagac                                         25

<210> SEQ ID NO 11
<211> LENGTH: 25
<212> TYPE: DNA
<213> ORGANISM: Homo sapiens

<400> SEQUENCE: 11
ttactcaagt tcaaacctcc agcct                                         25

<210> SEQ ID NO 12
<211> LENGTH: 25
<212> TYPE: DNA
<213> ORGANISM: Homo sapiens

<400> SEQUENCE: 12
tgttctagat ttcctgtagc tgtga                                         25

<210> SEQ ID NO 13
<211> LENGTH: 25
<212> TYPE: DNA
<213> ORGANISM: Homo sapiens

<400> SEQUENCE: 13
gtgctttagt tgctagtttg tactg                                         25

<210> SEQ ID NO 14
<211> LENGTH: 25
<212> TYPE: DNA
<213> ORGANISM: Homo sapiens

<400> SEQUENCE: 14
cctgcgagaa gtcatctgca cgtcc                                         25

<210> SEQ ID NO 15
<211> LENGTH: 25
<212> TYPE: DNA
<213> ORGANISM: Homo sapiens

<400> SEQUENCE: 15
gccattaaca gtgttttctt tccca                                         25

<210> SEQ ID NO 16
<211> LENGTH: 25
<212> TYPE: DNA
<213> ORGANISM: Homo sapiens

<400> SEQUENCE: 16
cgcagccacg ccgatggtta tacag                                         25

<210> SEQ ID NO 17
<211> LENGTH: 25
<212> TYPE: DNA
<213> ORGANISM: Homo sapiens

<400> SEQUENCE: 17
```

-continued tcttgctaaa accggcaatt ctccg                                                  25

<210> SEQ ID NO 18
<211> LENGTH: 25
<212> TYPE: DNA
<213> ORGANISM: Homo sapiens

<400> SEQUENCE: 18
tgactccatt tctgtaagct actct                                                  25

<210> SEQ ID NO 19
<211> LENGTH: 25
<212> TYPE: DNA
<213> ORGANISM: Homo sapiens

<400> SEQUENCE: 19
ggtggtcttt caggttatct tggca                                                  25

<210> SEQ ID NO 20
<211> LENGTH: 25
<212> TYPE: DNA
<213> ORGANISM: Homo sapiens

<400> SEQUENCE: 20
tgtgtcttag atcctcatta tttta                                                  25

<210> SEQ ID NO 21
<211> LENGTH: 25
<212> TYPE: DNA
<213> ORGANISM: Homo sapiens

<400> SEQUENCE: 21
ctgtactctt cgcatggact gggaa                                                  25

<210> SEQ ID NO 22
<211> LENGTH: 25
<212> TYPE: DNA
<213> ORGANISM: Homo sapiens

<400> SEQUENCE: 22
cggctctagc cactgagcgg ctaaa                                                  25

<210> SEQ ID NO 23
<211> LENGTH: 25
<212> TYPE: DNA
<213> ORGANISM: Homo sapiens

<400> SEQUENCE: 23
aagattggtg ctttttgcat gtttg                                                  25

<210> SEQ ID NO 24
<211> LENGTH: 25
<212> TYPE: DNA
<213> ORGANISM: Homo sapiens

<400> SEQUENCE: 24
gccgagagag cctgccggat gatga                                                  25

<210> SEQ ID NO 25
<211> LENGTH: 25
<212> TYPE: DNA
<213> ORGANISM: Homo sapiens

<400> SEQUENCE: 25

-continued ggagcaatct ccttggaagg attca                                                 25

<210> SEQ ID NO 26
<211> LENGTH: 25
<212> TYPE: DNA
<213> ORGANISM: Homo sapiens

<400> SEQUENCE: 26
gaaaagtcat ccctatttcc ttgtt                                                 25

<210> SEQ ID NO 27
<211> LENGTH: 25
<212> TYPE: DNA
<213> ORGANISM: Homo sapiens

<400> SEQUENCE: 27
agtgttgatg ggctctactt ctgat                                                 25

<210> SEQ ID NO 28
<211> LENGTH: 25
<212> TYPE: DNA
<213> ORGANISM: Homo sapiens

<400> SEQUENCE: 28
atttacctct aaatttccat atcct                                                 25

<210> SEQ ID NO 29
<211> LENGTH: 25
<212> TYPE: DNA
<213> ORGANISM: Homo sapiens

<400> SEQUENCE: 29
ggccttgtct aacttttgtg aagaa                                                 25

<210> SEQ ID NO 30
<211> LENGTH: 25
<212> TYPE: DNA
<213> ORGANISM: Homo sapiens

<400> SEQUENCE: 30
ccacagaaat ccagcatggc aactc                                                 25

<210> SEQ ID NO 31
<211> LENGTH: 25
<212> TYPE: DNA
<213> ORGANISM: Homo sapiens

<400> SEQUENCE: 31
aagatgaagc tctctttgct cttcc                                                 25

<210> SEQ ID NO 32
<211> LENGTH: 25
<212> TYPE: DNA
<213> ORGANISM: Homo sapiens

<400> SEQUENCE: 32 gaggggagg tttactctgc ggatc                                                  25

<210> SEQ ID NO 33
<211> LENGTH: 25
<212> TYPE: DNA
<213> ORGANISM: Homo sapiens -continued

```
<400> SEQUENCE: 33
atcgcatcat gccaacttgt gactt                                          25

<210> SEQ ID NO 34
<211> LENGTH: 25
<212> TYPE: DNA
<213> ORGANISM: Homo sapiens

<400> SEQUENCE: 34
ttttcctggc cgtggtagtt actca                                          25

<210> SEQ ID NO 35
<211> LENGTH: 25
<212> TYPE: DNA
<213> ORGANISM: Homo sapiens

<400> SEQUENCE: 35
tcatcctctt agaagcacct gtgaa                                          25

<210> SEQ ID NO 36
<211> LENGTH: 25
<212> TYPE: DNA
<213> ORGANISM: Homo sapiens

<400> SEQUENCE: 36
ggtagaggcg cttattgccc taacc                                          25

<210> SEQ ID NO 37
<211> LENGTH: 25
<212> TYPE: DNA
<213> ORGANISM: Homo sapiens

<400> SEQUENCE: 37
tctttccttc agctcctgat gttaa                                          25

<210> SEQ ID NO 38
<211> LENGTH: 25
<212> TYPE: DNA
<213> ORGANISM: Homo sapiens

<400> SEQUENCE: 38
catccaggac cgtgttcttt acgta                                          25

<210> SEQ ID NO 39
<211> LENGTH: 25
<212> TYPE: DNA
<213> ORGANISM: Homo sapiens

<400> SEQUENCE: 39
tattccggaa tgagaccctg gacgc                                          25

<210> SEQ ID NO 40
<211> LENGTH: 25
<212> TYPE: DNA
<213> ORGANISM: Homo sapiens

<400> SEQUENCE: 40
gctgcagctc tgacacaaca taatg                                          25

<210> SEQ ID NO 41
<211> LENGTH: 25
<212> TYPE: DNA
<213> ORGANISM: Homo sapiens
```

-continued

<400> SEQUENCE: 41
gaggatcttg ttcaatcgga aaccc                                        25

<210> SEQ ID NO 42
<211> LENGTH: 25
<212> TYPE: DNA
<213> ORGANISM: Homo sapiens

<400> SEQUENCE: 42
tgatgttctc aagcctcgga agtgg                                        25

<210> SEQ ID NO 43
<211> LENGTH: 25
<212> TYPE: DNA
<213> ORGANISM: Homo sapiens

<400> SEQUENCE: 43
ttaactacga catgcctgag gactc                                        25

<210> SEQ ID NO 44
<211> LENGTH: 25
<212> TYPE: DNA
<213> ORGANISM: Homo sapiens

<400> SEQUENCE: 44
ccagaggccg acgatctact atgtg                                        25

<210> SEQ ID NO 45
<211> LENGTH: 25
<212> TYPE: DNA
<213> ORGANISM: Homo sapiens

<400> SEQUENCE: 45
gctacataca acctagtaca cttga                                        25

<210> SEQ ID NO 46
<211> LENGTH: 25
<212> TYPE: DNA
<213> ORGANISM: Homo sapiens

<400> SEQUENCE: 46
aatgcggctg tagaacatgc tgaaa                                        25

<210> SEQ ID NO 47
<211> LENGTH: 25
<212> TYPE: DNA
<213> ORGANISM: Homo sapiens

<400> SEQUENCE: 47
ccttctcctt actatagtcg tggag                                        25

<210> SEQ ID NO 48
<211> LENGTH: 25
<212> TYPE: DNA
<213> ORGANISM: Homo sapiens

<400> SEQUENCE: 48
cacaggtccc ggggcatcag gagaa                                        25

<210> SEQ ID NO 49
<211> LENGTH: 25
<212> TYPE: DNA

-continued

```
<213> ORGANISM: Homo sapiens

<400> SEQUENCE: 49
ccaaggggtg ctgtatgctc taggc                                          25

<210> SEQ ID NO 50
<211> LENGTH: 25
<212> TYPE: DNA
<213> ORGANISM: Homo sapiens

<400> SEQUENCE: 50
cagtttccac gagagcacag aaggg                                          25

<210> SEQ ID NO 51
<211> LENGTH: 25
<212> TYPE: DNA
<213> ORGANISM: Homo sapiens

<400> SEQUENCE: 51
ggcgccaatg gcgagatctg cgtca                                          25

<210> SEQ ID NO 52
<211> LENGTH: 25
<212> TYPE: DNA
<213> ORGANISM: Homo sapiens

<400> SEQUENCE: 52
gagaaggagc ggaggatggc caaca                                          25

<210> SEQ ID NO 53
<211> LENGTH: 25
<212> TYPE: DNA
<213> ORGANISM: Homo sapiens

<400> SEQUENCE: 53
gggtcaatgc attttggggt gagct                                          25

<210> SEQ ID NO 54
<211> LENGTH: 25
<212> TYPE: DNA
<213> ORGANISM: Homo sapiens

<400> SEQUENCE: 54
caaacctttt cgttttactg atcat                                          25

<210> SEQ ID NO 55
<211> LENGTH: 25
<212> TYPE: DNA
<213> ORGANISM: Homo sapiens

<400> SEQUENCE: 55
ttggtcaagg ccattacctg tttcc                                          25

<210> SEQ ID NO 56
<211> LENGTH: 25
<212> TYPE: DNA
<213> ORGANISM: Homo sapiens

<400> SEQUENCE: 56
tatacccttt ctacagagtt gcctc                                          25

<210> SEQ ID NO 57
<211> LENGTH: 25
```

<212> TYPE: DNA
<213> ORGANISM: Homo sapiens

<400> SEQUENCE: 57
gctgaacagg cctatcttga acttt                                                          25

<210> SEQ ID NO 58
<211> LENGTH: 25
<212> TYPE: DNA
<213> ORGANISM: Homo sapiens

<400> SEQUENCE: 58
taatggccaa ggctgtttgc atccc                                                          25

<210> SEQ ID NO 59
<211> LENGTH: 25
<212> TYPE: DNA
<213> ORGANISM: Homo sapiens

<400> SEQUENCE: 59
agcgaaagtg cattcagtcc atcct                                                          25

<210> SEQ ID NO 60
<211> LENGTH: 25
<212> TYPE: DNA
<213> ORGANISM: Homo sapiens

<400> SEQUENCE: 60
actgattatg gctcaggcta cccca                                                          25

<210> SEQ ID NO 61
<211> LENGTH: 25
<212> TYPE: DNA
<213> ORGANISM: Homo sapiens

<400> SEQUENCE: 61
gtgatcgagg atgctcgaca cccac                                                          25

<210> SEQ ID NO 62
<211> LENGTH: 25
<212> TYPE: DNA
<213> ORGANISM: Homo sapiens

<400> SEQUENCE: 62
ggcaggcaat tctaagatct tccac                                                          25

<210> SEQ ID NO 63
<211> LENGTH: 25
<212> TYPE: DNA
<213> ORGANISM: Homo sapiens

<400> SEQUENCE: 63
gtgatcgtag tcatgcctca gaagc                                                          25

<210> SEQ ID NO 64
<211> LENGTH: 25
<212> TYPE: DNA
<213> ORGANISM: Homo sapiens

<400> SEQUENCE: 64
gatgggaagc gaaaggccaa ggacc                                                          25

<210> SEQ ID NO 65

<211> LENGTH: 25
<212> TYPE: DNA
<213> ORGANISM: Homo sapiens

<400> SEQUENCE: 65
acagacatca ccagttgact tctgc                                                25

<210> SEQ ID NO 66
<211> LENGTH: 25
<212> TYPE: DNA
<213> ORGANISM: Homo sapiens

<400> SEQUENCE: 66
gtaactaggt ttttgcttct ccagt                                                25

<210> SEQ ID NO 67
<211> LENGTH: 25
<212> TYPE: DNA
<213> ORGANISM: Homo sapiens

<400> SEQUENCE: 67
cacagcttcc tagccacagt gataa                                                25

<210> SEQ ID NO 68
<211> LENGTH: 25
<212> TYPE: DNA
<213> ORGANISM: Homo sapiens

<400> SEQUENCE: 68
cggcagcgca agatgagggt gaatg                                                25

<210> SEQ ID NO 69
<211> LENGTH: 25
<212> TYPE: DNA
<213> ORGANISM: Homo sapiens

<400> SEQUENCE: 69
agatactcag cactagacta acata                                                25

<210> SEQ ID NO 70
<211> LENGTH: 25
<212> TYPE: DNA
<213> ORGANISM: Homo sapiens

<400> SEQUENCE: 70
cattgctata tgtgtctgtt ctact                                                25

<210> SEQ ID NO 71
<211> LENGTH: 25
<212> TYPE: DNA
<213> ORGANISM: Homo sapiens

<400> SEQUENCE: 71
gagacagctg cattgttgtg gaatt                                                25

<210> SEQ ID NO 72
<211> LENGTH: 25
<212> TYPE: DNA
<213> ORGANISM: Homo sapiens

<400> SEQUENCE: 72
gcctgatggg cctggtagtt ttcca                                                25

<210> SEQ ID NO 73
<211> LENGTH: 25
<212> TYPE: DNA
<213> ORGANISM: Homo sapiens

<400> SEQUENCE: 73
gtaaccgtag caaaactgca ttggt                                    25

<210> SEQ ID NO 74
<211> LENGTH: 25
<212> TYPE: DNA
<213> ORGANISM: Homo sapiens

<400> SEQUENCE: 74
agatcggcat agtggagcca gtgct                                    25

<210> SEQ ID NO 75
<211> LENGTH: 25
<212> TYPE: DNA
<213> ORGANISM: Homo sapiens

<400> SEQUENCE: 75
tttgtaaaat gatgcttccc ccttc                                    25

<210> SEQ ID NO 76
<211> LENGTH: 25
<212> TYPE: DNA
<213> ORGANISM: Homo sapiens

<400> SEQUENCE: 76
aaggagatcg gcttgtggtt tcacc                                    25

<210> SEQ ID NO 77
<211> LENGTH: 25
<212> TYPE: DNA
<213> ORGANISM: Homo sapiens

<400> SEQUENCE: 77
acagcattgt acccagagtc tgtcc                                    25

<210> SEQ ID NO 78
<211> LENGTH: 25
<212> TYPE: DNA
<213> ORGANISM: Homo sapiens

<400> SEQUENCE: 78
tgcccaatcg gaagagctct gtgcc                                    25

<210> SEQ ID NO 79
<211> LENGTH: 25
<212> TYPE: DNA
<213> ORGANISM: Homo sapiens

<400> SEQUENCE: 79
aggtgccatt attctttcta gcctc                                    25

<210> SEQ ID NO 80
<211> LENGTH: 25
<212> TYPE: DNA
<213> ORGANISM: Homo sapiens

<400> SEQUENCE: 80
gaagctgtcc acgatgtctt ggatc                                    25

-continued

<210> SEQ ID NO 81
<211> LENGTH: 25
<212> TYPE: DNA
<213> ORGANISM: Homo sapiens

<400> SEQUENCE: 81
ggagcataaa agtgtaagac cgtaa                                          25

<210> SEQ ID NO 82
<211> LENGTH: 25
<212> TYPE: DNA
<213> ORGANISM: Homo sapiens

<400> SEQUENCE: 82
gatctttcag attttccatc tctag                                         25

<210> SEQ ID NO 83
<211> LENGTH: 25
<212> TYPE: DNA
<213> ORGANISM: Homo sapiens

<400> SEQUENCE: 83
atgaccactg ttagcccatt atatt                                         25

<210> SEQ ID NO 84
<211> LENGTH: 25
<212> TYPE: DNA
<213> ORGANISM: Homo sapiens

<400> SEQUENCE: 84
tagtatccag tccattgtac ctgct                                         25

<210> SEQ ID NO 85
<211> LENGTH: 25
<212> TYPE: DNA
<213> ORGANISM: Homo sapiens

<400> SEQUENCE: 85
agatggtctc atcggagtcg cattt                                         25

<210> SEQ ID NO 86
<211> LENGTH: 25
<212> TYPE: DNA
<213> ORGANISM: Homo sapiens

<400> SEQUENCE: 86
atatctatga ccactgttag cccat                                         25

<210> SEQ ID NO 87
<211> LENGTH: 25
<212> TYPE: DNA
<213> ORGANISM: Homo sapiens

<400> SEQUENCE: 87
taaagcctat tctaccagtt aaact                                         25

<210> SEQ ID NO 88
<211> LENGTH: 25
<212> TYPE: DNA
<213> ORGANISM: Homo sapiens

<400> SEQUENCE: 88
ggagcatcag ggttggcttg ggagc                                         25

<210> SEQ ID NO 89
<211> LENGTH: 25
<212> TYPE: DNA
<213> ORGANISM: Homo sapiens

<400> SEQUENCE: 89
cattgacctc gagggcaacg tctgc                                         25

<210> SEQ ID NO 90
<211> LENGTH: 25
<212> TYPE: DNA
<213> ORGANISM: Homo sapiens

<400> SEQUENCE: 90
ttatacgttt atatgctctg tctgc                                         25

<210> SEQ ID NO 91
<211> LENGTH: 25
<212> TYPE: DNA
<213> ORGANISM: Homo sapiens

<400> SEQUENCE: 91
gttggccaca acattatgat tattc                                         25

<210> SEQ ID NO 92
<211> LENGTH: 25
<212> TYPE: DNA
<213> ORGANISM: Homo sapiens

<400> SEQUENCE: 92
tcctgtgtgg tgtgtctact gtgag                                         25

<210> SEQ ID NO 93
<211> LENGTH: 25
<212> TYPE: DNA
<213> ORGANISM: Homo sapiens

<400> SEQUENCE: 93
agagctgggg ttaggatccg gttgg                                         25

<210> SEQ ID NO 94
<211> LENGTH: 25
<212> TYPE: DNA
<213> ORGANISM: Homo sapiens

<400> SEQUENCE: 94
tcctttctgt tttgcgagct tgtgt                                         25

<210> SEQ ID NO 95
<211> LENGTH: 25
<212> TYPE: DNA
<213> ORGANISM: Homo sapiens

<400> SEQUENCE: 95
aaaagcccag tgtgacagtg tcatg                                         25

<210> SEQ ID NO 96
<211> LENGTH: 25
<212> TYPE: DNA
<213> ORGANISM: Homo sapiens

<400> SEQUENCE: 96
cagtacaagc gctgcggtgt cacct                                                          25

<210> SEQ ID NO 97
<211> LENGTH: 25
<212> TYPE: DNA
<213> ORGANISM: Homo sapiens

<400> SEQUENCE: 97
gaaagccaac agacggtgct tcctc                                                          25

<210> SEQ ID NO 98
<211> LENGTH: 25
<212> TYPE: DNA
<213> ORGANISM: Homo sapiens

<400> SEQUENCE: 98
gtttacctct ggatacacta cttgt                                                          25

<210> SEQ ID NO 99
<211> LENGTH: 25
<212> TYPE: DNA
<213> ORGANISM: Homo sapiens

<400> SEQUENCE: 99
cgctctgccg agaccaggac gagct                                                          25

<210> SEQ ID NO 100
<211> LENGTH: 25
<212> TYPE: DNA
<213> ORGANISM: Homo sapiens

<400> SEQUENCE: 100
caccgacgtc agcaacttcg acgag                                                          25

<210> SEQ ID NO 101
<211> LENGTH: 25
<212> TYPE: DNA
<213> ORGANISM: Homo sapiens

<400> SEQUENCE: 101
aagcctacta gagccattgt atgtg                                                          25

<210> SEQ ID NO 102
<211> LENGTH: 25
<212> TYPE: DNA
<213> ORGANISM: Homo sapiens

<400> SEQUENCE: 102
cttcattact gaacaaaact acggt                                                          25

<210> SEQ ID NO 103
<211> LENGTH: 25
<212> TYPE: DNA
<213> ORGANISM: Homo sapiens

<400> SEQUENCE: 103
tgctcatcaa ctgccgcaac aataa                                                          25

<210> SEQ ID NO 104
<211> LENGTH: 25
<212> TYPE: DNA
<213> ORGANISM: Homo sapiens

<400> SEQUENCE: 104

-continued atcccacctg tgagaatatg aactt                                    25

<210> SEQ ID NO 105
<211> LENGTH: 25
<212> TYPE: DNA
<213> ORGANISM: Homo sapiens

<400> SEQUENCE: 105
agctaaacac caatttcttc ctgct                                    25

<210> SEQ ID NO 106
<211> LENGTH: 25
<212> TYPE: DNA
<213> ORGANISM: Homo sapiens

<400> SEQUENCE: 106
tagtgagctg cctgatgaga tagac                                    25

<210> SEQ ID NO 107
<211> LENGTH: 25
<212> TYPE: DNA
<213> ORGANISM: Homo sapiens

<400> SEQUENCE: 107
gcagctatct taccagactg tgcct                                    25

<210> SEQ ID NO 108
<211> LENGTH: 25
<212> TYPE: DNA
<213> ORGANISM: Homo sapiens

<400> SEQUENCE: 108
gaagttcatg gatcaacatc cggag                                    25

<210> SEQ ID NO 109
<211> LENGTH: 25
<212> TYPE: DNA
<213> ORGANISM: Homo sapiens

<400> SEQUENCE: 109
ggtgacataa accattcatt gctac                                    25

<210> SEQ ID NO 110
<211> LENGTH: 25
<212> TYPE: DNA
<213> ORGANISM: Homo sapiens

<400> SEQUENCE: 110
aagtgcccaa ataagtctga gtgct                                    25

<210> SEQ ID NO 111
<211> LENGTH: 25
<212> TYPE: DNA
<213> ORGANISM: Homo sapiens

<400> SEQUENCE: 111
tttgacaagg agactggctt tcaca                                    25

<210> SEQ ID NO 112
<211> LENGTH: 25
<212> TYPE: DNA
<213> ORGANISM: Homo sapiens -continued

```
<400> SEQUENCE: 112
aagtttgaat agcttctgtc cctct                                          25

<210> SEQ ID NO 113
<211> LENGTH: 25
<212> TYPE: DNA
<213> ORGANISM: Homo sapiens

<400> SEQUENCE: 113
tttggagttc tcttacgttt cctgg                                          25

<210> SEQ ID NO 114
<211> LENGTH: 25
<212> TYPE: DNA
<213> ORGANISM: Homo sapiens

<400> SEQUENCE: 114
tggcgagaga agcatgtccg gtcac                                          25

<210> SEQ ID NO 115
<211> LENGTH: 25
<212> TYPE: DNA
<213> ORGANISM: Homo sapiens

<400> SEQUENCE: 115
aataagtgcc gggagctttg tgaga                                          25

<210> SEQ ID NO 116
<211> LENGTH: 25
<212> TYPE: DNA
<213> ORGANISM: Homo sapiens

<400> SEQUENCE: 116
ggccagaaac cttgggtctt ttcat                                          25

<210> SEQ ID NO 117
<211> LENGTH: 25
<212> TYPE: DNA
<213> ORGANISM: Homo sapiens

<400> SEQUENCE: 117
ggatgtgggt ctgattgcaa ttcgg                                          25

<210> SEQ ID NO 118
<211> LENGTH: 25
<212> TYPE: DNA
<213> ORGANISM: Homo sapiens

<400> SEQUENCE: 118
tggaccatgg tctagcagta gcatc                                          25

<210> SEQ ID NO 119
<211> LENGTH: 25
<212> TYPE: DNA
<213> ORGANISM: Homo sapiens

<400> SEQUENCE: 119
gggcattcgc gtggtgaagg acctc                                          25

<210> SEQ ID NO 120
<211> LENGTH: 25
<212> TYPE: DNA
<213> ORGANISM: Homo sapiens
```

<400> SEQUENCE: 120
gctgtacccc aaggaagaca aggag                                          25

<210> SEQ ID NO 121
<211> LENGTH: 25
<212> TYPE: DNA
<213> ORGANISM: Homo sapiens

<400> SEQUENCE: 121
aaatctctga actgtgtggg ttttg                                          25

<210> SEQ ID NO 122
<211> LENGTH: 25
<212> TYPE: DNA
<213> ORGANISM: Homo sapiens

<400> SEQUENCE: 122
tgccctcaaa catacagaac ttcca                                          25

<210> SEQ ID NO 123
<211> LENGTH: 25
<212> TYPE: DNA
<213> ORGANISM: Homo sapiens

<400> SEQUENCE: 123
tcatctctag cagtatggca tcccc                                          25

<210> SEQ ID NO 124
<211> LENGTH: 25
<212> TYPE: DNA
<213> ORGANISM: Homo sapiens

<400> SEQUENCE: 124
gcaaggattg cggcgtgggt ttccg                                          25

<210> SEQ ID NO 125
<211> LENGTH: 25
<212> TYPE: DNA
<213> ORGANISM: Homo sapiens

<400> SEQUENCE: 125
tcaatggccg ctggtttgct ggccg                                          25

<210> SEQ ID NO 126
<211> LENGTH: 25
<212> TYPE: DNA
<213> ORGANISM: Homo sapiens

<400> SEQUENCE: 126
cacaccagct ctactcttta gtaaa                                          25

<210> SEQ ID NO 127
<211> LENGTH: 25
<212> TYPE: DNA
<213> ORGANISM: Homo sapiens

<400> SEQUENCE: 127
agaaactcac cctaaatctg aacgg                                          25

<210> SEQ ID NO 128
<211> LENGTH: 25
<212> TYPE: DNA

-continued

<213> ORGANISM: Homo sapiens

<400> SEQUENCE: 128
aagtggtaac aggactgatg ccgaa                                              25

<210> SEQ ID NO 129
<211> LENGTH: 25
<212> TYPE: DNA
<213> ORGANISM: Homo sapiens

<400> SEQUENCE: 129
tgtttataga tcactgccct ttttg                                             25

<210> SEQ ID NO 130
<211> LENGTH: 25
<212> TYPE: DNA
<213> ORGANISM: Homo sapiens

<400> SEQUENCE: 130
aagtcactca ggtcatgggc attgt                                             25

<210> SEQ ID NO 131
<211> LENGTH: 25
<212> TYPE: DNA
<213> ORGANISM: Homo sapiens

<400> SEQUENCE: 131
tgattactac ctcaggacca acctc                                             25

<210> SEQ ID NO 132
<211> LENGTH: 25
<212> TYPE: DNA
<213> ORGANISM: Homo sapiens

<400> SEQUENCE: 132
gtacttggat aggctggcta actcg                                             25

<210> SEQ ID NO 133
<211> LENGTH: 25
<212> TYPE: DNA
<213> ORGANISM: Homo sapiens

<400> SEQUENCE: 133
gaagctcgag agcccttaag ttctg                                             25

<210> SEQ ID NO 134
<211> LENGTH: 25
<212> TYPE: DNA
<213> ORGANISM: Homo sapiens

<400> SEQUENCE: 134
ccatcgacaa cacaaaccca gacgc                                             25

<210> SEQ ID NO 135
<211> LENGTH: 25
<212> TYPE: DNA
<213> ORGANISM: Homo sapiens

<400> SEQUENCE: 135
agcttgttgt tgatcagatt cactg                                             25

<210> SEQ ID NO 136
<211> LENGTH: 25

-continued

```
<212> TYPE: DNA
<213> ORGANISM: Homo sapiens

<400> SEQUENCE: 136
gcagagcatt cagtgccacg gttta                                          25

<210> SEQ ID NO 137
<211> LENGTH: 25
<212> TYPE: DNA
<213> ORGANISM: Homo sapiens

<400> SEQUENCE: 137
ctcttcagca gcatctactc taggc                                          25

<210> SEQ ID NO 138
<211> LENGTH: 25
<212> TYPE: DNA
<213> ORGANISM: Homo sapiens

<400> SEQUENCE: 138
ctgctgtaag gactggttcc agaat                                          25

<210> SEQ ID NO 139
<211> LENGTH: 25
<212> TYPE: DNA
<213> ORGANISM: Homo sapiens

<400> SEQUENCE: 139
gaacttgcca catacccagg tataa                                          25

<210> SEQ ID NO 140
<211> LENGTH: 25
<212> TYPE: DNA
<213> ORGANISM: Homo sapiens

<400> SEQUENCE: 140
catgaaggca cccttgaacc atcca                                          25

<210> SEQ ID NO 141
<211> LENGTH: 25
<212> TYPE: DNA
<213> ORGANISM: Homo sapiens

<400> SEQUENCE: 141
ggagccattg gctgtgaagc tgcag                                          25

<210> SEQ ID NO 142
<211> LENGTH: 25
<212> TYPE: DNA
<213> ORGANISM: Homo sapiens

<400> SEQUENCE: 142
aatctgaccc tatcggaaac tcaaa                                          25

<210> SEQ ID NO 143
<211> LENGTH: 25
<212> TYPE: DNA
<213> ORGANISM: Homo sapiens

<400> SEQUENCE: 143
atagcctcag gaacagtcca gactg                                          25

<210> SEQ ID NO 144
```

-continued

```
<211> LENGTH: 25
<212> TYPE: DNA
<213> ORGANISM: Homo sapiens

<400> SEQUENCE: 144
ggtggtgatc aaaactatag tggct                                            25

<210> SEQ ID NO 145
<211> LENGTH: 25
<212> TYPE: DNA
<213> ORGANISM: Homo sapiens

<400> SEQUENCE: 145
tgatcaccct gcaatcctat tatgt                                            25

<210> SEQ ID NO 146
<211> LENGTH: 25
<212> TYPE: DNA
<213> ORGANISM: Homo sapiens

<400> SEQUENCE: 146
acttagaatc catctcacta ccaat                                            25

<210> SEQ ID NO 147
<211> LENGTH: 25
<212> TYPE: DNA
<213> ORGANISM: Homo sapiens

<400> SEQUENCE: 147
tagagactat gtcgctttcc tgagc                                            25

<210> SEQ ID NO 148
<211> LENGTH: 25
<212> TYPE: DNA
<213> ORGANISM: Homo sapiens

<400> SEQUENCE: 148
tactgtgatg ggcagaacag ccttt                                            25

<210> SEQ ID NO 149
<211> LENGTH: 25
<212> TYPE: DNA
<213> ORGANISM: Homo sapiens

<400> SEQUENCE: 149
tctcatttag gactgggttc cccac                                            25

<210> SEQ ID NO 150
<211> LENGTH: 25
<212> TYPE: DNA
<213> ORGANISM: Homo sapiens

<400> SEQUENCE: 150
acagctttta acacagttcc ctgcc                                            25

<210> SEQ ID NO 151
<211> LENGTH: 25
<212> TYPE: DNA
<213> ORGANISM: Homo sapiens

<400> SEQUENCE: 151
gatgaaagat gagcccaagt ccacc                                            25
```

-continued

<210> SEQ ID NO 152
<211> LENGTH: 25
<212> TYPE: DNA
<213> ORGANISM: Homo sapiens

<400> SEQUENCE: 152
gatcctctta aaacgtttat attct                                        25

<210> SEQ ID NO 153
<211> LENGTH: 25
<212> TYPE: DNA
<213> ORGANISM: Homo sapiens

<400> SEQUENCE: 153
ccctggtcac atgtcatcgg gctgg                                        25

<210> SEQ ID NO 154
<211> LENGTH: 25
<212> TYPE: DNA
<213> ORGANISM: Homo sapiens

<400> SEQUENCE: 154
atccacatca gaatcccttg tagga                                        25

<210> SEQ ID NO 155
<211> LENGTH: 25
<212> TYPE: DNA
<213> ORGANISM: Homo sapiens

<400> SEQUENCE: 155
actgctttca agctggactg agcca                                        25

<210> SEQ ID NO 156
<211> LENGTH: 25
<212> TYPE: DNA
<213> ORGANISM: Homo sapiens

<400> SEQUENCE: 156
taaacattcc gtccctgttt gagac                                        25

<210> SEQ ID NO 157
<211> LENGTH: 25
<212> TYPE: DNA
<213> ORGANISM: Homo sapiens

<400> SEQUENCE: 157
gtgagatcaa agctcctcca aagcc                                        25

<210> SEQ ID NO 158
<211> LENGTH: 25
<212> TYPE: DNA
<213> ORGANISM: Homo sapiens

<400> SEQUENCE: 158
cctcggtggc cctgactgtc aggga                                        25

<210> SEQ ID NO 159
<211> LENGTH: 25
<212> TYPE: DNA
<213> ORGANISM: Homo sapiens

<400> SEQUENCE: 159
tcacgccgat gatggagctg aagcc                                        25

-continued

<210> SEQ ID NO 160
<211> LENGTH: 25
<212> TYPE: DNA
<213> ORGANISM: Homo sapiens

<400> SEQUENCE: 160
gagttctatt tgagacttcc agccc                                              25

<210> SEQ ID NO 161
<211> LENGTH: 25
<212> TYPE: DNA
<213> ORGANISM: Homo sapiens

<400> SEQUENCE: 161
ccaaaggagg cattatgctt ccaga                                             25

<210> SEQ ID NO 162
<211> LENGTH: 25
<212> TYPE: DNA
<213> ORGANISM: Homo sapiens

<400> SEQUENCE: 162
gaagtgtgct agtatgctcc ctagt                                             25

<210> SEQ ID NO 163
<211> LENGTH: 25
<212> TYPE: DNA
<213> ORGANISM: Homo sapiens

<400> SEQUENCE: 163
gttggggttg gagacgtgtg taata                                             25

<210> SEQ ID NO 164
<211> LENGTH: 25
<212> TYPE: DNA
<213> ORGANISM: Homo sapiens

<400> SEQUENCE: 164
ggaggctaag tattgctttc tacaa                                             25

<210> SEQ ID NO 165
<211> LENGTH: 25
<212> TYPE: DNA
<213> ORGANISM: Homo sapiens

<400> SEQUENCE: 165
tcattagctc tgcccttttt aatta                                             25

<210> SEQ ID NO 166
<211> LENGTH: 25
<212> TYPE: DNA
<213> ORGANISM: Homo sapiens

<400> SEQUENCE: 166
cacttctcct ttacgctgtg tagag                                             25

<210> SEQ ID NO 167
<211> LENGTH: 25
<212> TYPE: DNA
<213> ORGANISM: Homo sapiens

<400> SEQUENCE: 167
gtactttgat actgctcatg ctgac                                             25

<210> SEQ ID NO 168
<211> LENGTH: 25
<212> TYPE: DNA
<213> ORGANISM: Homo sapiens

<400> SEQUENCE: 168
caggggatgg cctgatcgag ctgcg                                          25

<210> SEQ ID NO 169
<211> LENGTH: 25
<212> TYPE: DNA
<213> ORGANISM: Homo sapiens

<400> SEQUENCE: 169
ccttattcca ttcttaactc tgcat                                          25

<210> SEQ ID NO 170
<211> LENGTH: 25
<212> TYPE: DNA
<213> ORGANISM: Homo sapiens

<400> SEQUENCE: 170
gcagtcactc tccctgaata agtaa                                          25

<210> SEQ ID NO 171
<211> LENGTH: 25
<212> TYPE: DNA
<213> ORGANISM: Homo sapiens

<400> SEQUENCE: 171
gaagaagaac tagccagtac tcccc                                          25

<210> SEQ ID NO 172
<211> LENGTH: 25
<212> TYPE: DNA
<213> ORGANISM: Homo sapiens

<400> SEQUENCE: 172
ggagtgccaa gtttgcaaac ctgca                                          25

<210> SEQ ID NO 173
<211> LENGTH: 25
<212> TYPE: DNA
<213> ORGANISM: Homo sapiens

<400> SEQUENCE: 173
aatgggttat cacaggaatg ggact                                          25

<210> SEQ ID NO 174
<211> LENGTH: 25
<212> TYPE: DNA
<213> ORGANISM: Homo sapiens

<400> SEQUENCE: 174
tgggcagagt gcggcagctc atgcc                                          25

<210> SEQ ID NO 175
<211> LENGTH: 25
<212> TYPE: DNA
<213> ORGANISM: Homo sapiens

<400> SEQUENCE: 175

-continued tggagtgaga ctgactgcaa gcccc                                                    25

<210> SEQ ID NO 176
<211> LENGTH: 25
<212> TYPE: DNA
<213> ORGANISM: Homo sapiens

<400> SEQUENCE: 176
tttttggatg gcaacgagct caccc                                                    25

<210> SEQ ID NO 177
<211> LENGTH: 25
<212> TYPE: DNA
<213> ORGANISM: Homo sapiens

<400> SEQUENCE: 177
ttattgctta atttctgcct ttccc                                                    25

<210> SEQ ID NO 178
<211> LENGTH: 25
<212> TYPE: DNA
<213> ORGANISM: Homo sapiens

<400> SEQUENCE: 178
gctgccttgt gtgcgactga gatgc                                                    25

<210> SEQ ID NO 179
<211> LENGTH: 25
<212> TYPE: DNA
<213> ORGANISM: Homo sapiens

<400> SEQUENCE: 179
ctacgatgag tttgagtact gctgg                                                    25

<210> SEQ ID NO 180
<211> LENGTH: 25
<212> TYPE: DNA
<213> ORGANISM: Homo sapiens

<400> SEQUENCE: 180
ctcctggact caatcatggc ttgtg                                                    25

<210> SEQ ID NO 181
<211> LENGTH: 25
<212> TYPE: DNA
<213> ORGANISM: Homo sapiens

<400> SEQUENCE: 181
tggagggcgc tcatcaagta gctgc                                                    25

<210> SEQ ID NO 182
<211> LENGTH: 25
<212> TYPE: DNA
<213> ORGANISM: Homo sapiens

<400> SEQUENCE: 182
tggtcccagc cagtttggtg ctgac                                                    25

<210> SEQ ID NO 183
<211> LENGTH: 25
<212> TYPE: DNA
<213> ORGANISM: Homo sapiens

<400> SEQUENCE: 183
gatcctttct gtaggctaat tcctc                                          25

<210> SEQ ID NO 184
<211> LENGTH: 25
<212> TYPE: DNA
<213> ORGANISM: Homo sapiens

<400> SEQUENCE: 184
ttcccagaag cggacctgag gaccc                                          25

<210> SEQ ID NO 185
<211> LENGTH: 25
<212> TYPE: DNA
<213> ORGANISM: Homo sapiens

<400> SEQUENCE: 185
gaccttcaag ggtcctcgtt ttgat                                          25

<210> SEQ ID NO 186
<211> LENGTH: 25
<212> TYPE: DNA
<213> ORGANISM: Homo sapiens

<400> SEQUENCE: 186
gacggtgctt ttcggtgcaa ggaaa                                          25

<210> SEQ ID NO 187
<211> LENGTH: 25
<212> TYPE: DNA
<213> ORGANISM: Homo sapiens

<400> SEQUENCE: 187
tgaacttgtt gagatccccg tgtta                                          25

<210> SEQ ID NO 188
<211> LENGTH: 25
<212> TYPE: DNA
<213> ORGANISM: Homo sapiens

<400> SEQUENCE: 188
ttctactcag gcacgggcta caagc                                          25

<210> SEQ ID NO 189
<211> LENGTH: 25
<212> TYPE: DNA
<213> ORGANISM: Homo sapiens

<400> SEQUENCE: 189
ccggtgtcct tgaccacatg aagaa                                          25

<210> SEQ ID NO 190
<211> LENGTH: 25
<212> TYPE: DNA
<213> ORGANISM: Homo sapiens

<400> SEQUENCE: 190
tgatgcactg attccatccc aggaa                                          25

<210> SEQ ID NO 191
<211> LENGTH: 25
<212> TYPE: DNA
<213> ORGANISM: Homo sapiens

<400> SEQUENCE: 191
tgacagtcac tagcttatct tgaac                                         25

<210> SEQ ID NO 192
<211> LENGTH: 25
<212> TYPE: DNA
<213> ORGANISM: Homo sapiens

<400> SEQUENCE: 192
ttgtgtgaag tggttcaccc ttgag                                         25

<210> SEQ ID NO 193
<211> LENGTH: 25
<212> TYPE: DNA
<213> ORGANISM: Homo sapiens

<400> SEQUENCE: 193
gacttccgga tcctgtcagg gtgtc                                         25

<210> SEQ ID NO 194
<211> LENGTH: 25
<212> TYPE: DNA
<213> ORGANISM: Homo sapiens

<400> SEQUENCE: 194
gacaaagatc ttgccttaca gactt                                         25

<210> SEQ ID NO 195
<211> LENGTH: 25
<212> TYPE: DNA
<213> ORGANISM: Homo sapiens

<400> SEQUENCE: 195
tggtcgcagc tgtgctgttc atcac                                         25

<210> SEQ ID NO 196
<211> LENGTH: 25
<212> TYPE: DNA
<213> ORGANISM: Homo sapiens

<400> SEQUENCE: 196
gtgacttcaa gagcctctgg catct                                         25

<210> SEQ ID NO 197
<211> LENGTH: 25
<212> TYPE: DNA
<213> ORGANISM: Homo sapiens

<400> SEQUENCE: 197
gagaacaaca gcattcattt ccatt                                         25

<210> SEQ ID NO 198
<211> LENGTH: 25
<212> TYPE: DNA
<213> ORGANISM: Homo sapiens

<400> SEQUENCE: 198
ccctcaccct gagatgggag ccgtc                                         25

<210> SEQ ID NO 199
<211> LENGTH: 25
<212> TYPE: DNA
<213> ORGANISM: Homo sapiens -continued

```
<400> SEQUENCE: 199
caccatcccc aacttgggca tcgtt                                    25

<210> SEQ ID NO 200
<211> LENGTH: 25
<212> TYPE: DNA
<213> ORGANISM: Homo sapiens

<400> SEQUENCE: 200
agtaaatgat tcctccttgt tctgt                                    25

<210> SEQ ID NO 201
<211> LENGTH: 25
<212> TYPE: DNA
<213> ORGANISM: Homo sapiens

<400> SEQUENCE: 201
caaaacgggc atcacccagt tgacc                                    25

<210> SEQ ID NO 202
<211> LENGTH: 25
<212> TYPE: DNA
<213> ORGANISM: Homo sapiens

<400> SEQUENCE: 202
aaggagggca cctctgtctg agttt                                    25

<210> SEQ ID NO 203
<211> LENGTH: 25
<212> TYPE: DNA
<213> ORGANISM: Homo sapiens

<400> SEQUENCE: 203
ttatttatac agtgccttgc tcggg                                    25

<210> SEQ ID NO 204
<211> LENGTH: 25
<212> TYPE: DNA
<213> ORGANISM: Homo sapiens

<400> SEQUENCE: 204
ttcggggaca atctggtcac ccgct                                    25

<210> SEQ ID NO 205
<211> LENGTH: 25
<212> TYPE: DNA
<213> ORGANISM: Homo sapiens

<400> SEQUENCE: 205
cctcattgag ttcggtgcat ctggc                                    25

<210> SEQ ID NO 206
<211> LENGTH: 25
<212> TYPE: DNA
<213> ORGANISM: Homo sapiens

<400> SEQUENCE: 206
tgcttgctac cgtgttcgga gtctc                                    25

<210> SEQ ID NO 207
<211> LENGTH: 25
<212> TYPE: DNA
```

<213> ORGANISM: Homo sapiens

<400> SEQUENCE: 207
ccctgcacat gaagaggcac ctctg                                                 25

<210> SEQ ID NO 208
<211> LENGTH: 25
<212> TYPE: DNA
<213> ORGANISM: Homo sapiens

<400> SEQUENCE: 208
ggctgtccta gcagttgtgg tcatc                                                 25

<210> SEQ ID NO 209
<211> LENGTH: 25
<212> TYPE: DNA
<213> ORGANISM: Homo sapiens

<400> SEQUENCE: 209
gtcacacacc agcactttat acact                                                 25

<210> SEQ ID NO 210
<211> LENGTH: 25
<212> TYPE: DNA
<213> ORGANISM: Homo sapiens

<400> SEQUENCE: 210
gaacactcta ctacatgtga ctggc                                                 25

<210> SEQ ID NO 211
<211> LENGTH: 25
<212> TYPE: DNA
<213> ORGANISM: Homo sapiens

<400> SEQUENCE: 211
gaggactact ctggatcagg cttcg                                                 25

<210> SEQ ID NO 212
<211> LENGTH: 25
<212> TYPE: DNA
<213> ORGANISM: Homo sapiens

<400> SEQUENCE: 212
gagctagtgg atgtgtttgt ctaca                                                 25

<210> SEQ ID NO 213
<211> LENGTH: 25
<212> TYPE: DNA
<213> ORGANISM: Homo sapiens

<400> SEQUENCE: 213
ttccttcctt atcactgaca caaaa                                                 25

<210> SEQ ID NO 214
<211> LENGTH: 25
<212> TYPE: DNA
<213> ORGANISM: Homo sapiens

<400> SEQUENCE: 214
ggactctatt ccatctatca agggg                                                 25

<210> SEQ ID NO 215
<211> LENGTH: 25

<212> TYPE: DNA
<213> ORGANISM: Homo sapiens

<400> SEQUENCE: 215
ccccatcgtg ggcattgttg ctggc                                                    25

<210> SEQ ID NO 216
<211> LENGTH: 25
<212> TYPE: DNA
<213> ORGANISM: Homo sapiens

<400> SEQUENCE: 216
gcggattctt cagcgagatc tcgca                                                    25

<210> SEQ ID NO 217
<211> LENGTH: 25
<212> TYPE: DNA
<213> ORGANISM: Homo sapiens

<400> SEQUENCE: 217
ctcaccagtg cttcatatac catga                                                    25

<210> SEQ ID NO 218
<211> LENGTH: 25
<212> TYPE: DNA
<213> ORGANISM: Homo sapiens

<400> SEQUENCE: 218
gcaagtttca tcagccctag ggaaa                                                    25

<210> SEQ ID NO 219
<211> LENGTH: 25
<212> TYPE: DNA
<213> ORGANISM: Homo sapiens

<400> SEQUENCE: 219
ctcagcttcc ctcttaagct aagac                                                    25

<210> SEQ ID NO 220
<211> LENGTH: 25
<212> TYPE: DNA
<213> ORGANISM: Homo sapiens

<400> SEQUENCE: 220
ccccatcgtg ggcattgttg ctggc                                                    25

<210> SEQ ID NO 221
<211> LENGTH: 25
<212> TYPE: DNA
<213> ORGANISM: Homo sapiens

<400> SEQUENCE: 221
gaatgttctc caagcagcaa tccaa                                                    25

<210> SEQ ID NO 222
<211> LENGTH: 25
<212> TYPE: DNA
<213> ORGANISM: Homo sapiens

<400> SEQUENCE: 222
atgtgcgtgt cgtcgctgtt tagac                                                    25

<210> SEQ ID NO 223

-continued

```
<211> LENGTH: 25
<212> TYPE: DNA
<213> ORGANISM: Homo sapiens

<400> SEQUENCE: 223
cacaagcccc tgaaccatat attgt                                           25

<210> SEQ ID NO 224
<211> LENGTH: 25
<212> TYPE: DNA
<213> ORGANISM: Homo sapiens

<400> SEQUENCE: 224
gatgtggacg ttcgggagct actgc                                           25

<210> SEQ ID NO 225
<211> LENGTH: 25
<212> TYPE: DNA
<213> ORGANISM: Homo sapiens

<400> SEQUENCE: 225
tcctgttgtt tgctgccatt ggcat                                           25

<210> SEQ ID NO 226
<211> LENGTH: 25
<212> TYPE: DNA
<213> ORGANISM: Homo sapiens

<400> SEQUENCE: 226
gtggccagca ctctgaaact gagaa                                           25

<210> SEQ ID NO 227
<211> LENGTH: 25
<212> TYPE: DNA
<213> ORGANISM: Homo sapiens

<400> SEQUENCE: 227
agttccgctt gtccaagatc tggtc                                           25

<210> SEQ ID NO 228
<211> LENGTH: 25
<212> TYPE: DNA
<213> ORGANISM: Homo sapiens

<400> SEQUENCE: 228
agagccccag tttgtaaatg aacct                                           25

<210> SEQ ID NO 229
<211> LENGTH: 25
<212> TYPE: DNA
<213> ORGANISM: Homo sapiens

<400> SEQUENCE: 229
gtccccaagt gtgcaagctc agtat                                           25

<210> SEQ ID NO 230
<211> LENGTH: 25
<212> TYPE: DNA
<213> ORGANISM: Homo sapiens

<400> SEQUENCE: 230
gacgtggagc tcgtggagac caggc                                           25
```

-continued

<210> SEQ ID NO 231
<211> LENGTH: 25
<212> TYPE: DNA
<213> ORGANISM: Homo sapiens

<400> SEQUENCE: 231
tttttgcttc aagctctgta gcagg                                    25

<210> SEQ ID NO 232
<211> LENGTH: 25
<212> TYPE: DNA
<213> ORGANISM: Homo sapiens

<400> SEQUENCE: 232
tccatttctg gcagcagcct ggagc                                    25

<210> SEQ ID NO 233
<211> LENGTH: 25
<212> TYPE: DNA
<213> ORGANISM: Homo sapiens

<400> SEQUENCE: 233
tctaccccag gtcagacgga cagaa                                    25

<210> SEQ ID NO 234
<211> LENGTH: 25
<212> TYPE: DNA
<213> ORGANISM: Homo sapiens

<400> SEQUENCE: 234
acgggctgtc cgtgtgcctc ctgtg                                    25

<210> SEQ ID NO 235
<211> LENGTH: 25
<212> TYPE: DNA
<213> ORGANISM: Homo sapiens

<400> SEQUENCE: 235
ggtggagtca gtgaccaggt cgtct                                    25

<210> SEQ ID NO 236
<211> LENGTH: 25
<212> TYPE: DNA
<213> ORGANISM: Homo sapiens

<400> SEQUENCE: 236
ctaacccacc ggcagagtat ttttg                                    25

<210> SEQ ID NO 237
<211> LENGTH: 25
<212> TYPE: DNA
<213> ORGANISM: Homo sapiens

<400> SEQUENCE: 237
gctttcgaag tggccagctg cggcc                                    25

<210> SEQ ID NO 238
<211> LENGTH: 25
<212> TYPE: DNA
<213> ORGANISM: Homo sapiens

<400> SEQUENCE: 238
gtgttagaag cagctgtggg ggtcc                                    25

-continued

<210> SEQ ID NO 239
<211> LENGTH: 25
<212> TYPE: DNA
<213> ORGANISM: Homo sapiens

<400> SEQUENCE: 239
gagtgaggcg atttgacctg ctcaa                                     25

<210> SEQ ID NO 240
<211> LENGTH: 25
<212> TYPE: DNA
<213> ORGANISM: Homo sapiens

<400> SEQUENCE: 240
taagggcttg attcctagcc ccgtt                                     25

<210> SEQ ID NO 241
<211> LENGTH: 25
<212> TYPE: DNA
<213> ORGANISM: Homo sapiens

<400> SEQUENCE: 241
aggggcctct gaacggaaca gtgtc                                     25

<210> SEQ ID NO 242
<211> LENGTH: 25
<212> TYPE: DNA
<213> ORGANISM: Homo sapiens

<400> SEQUENCE: 242
tgagcacgct cagttctact gtgtc                                     25

<210> SEQ ID NO 243
<211> LENGTH: 25
<212> TYPE: DNA
<213> ORGANISM: Homo sapiens

<400> SEQUENCE: 243
gtcttcgtcc gataccaata agtca                                     25

<210> SEQ ID NO 244
<211> LENGTH: 25
<212> TYPE: DNA
<213> ORGANISM: Homo sapiens

<400> SEQUENCE: 244
agctgagcca catcaagaca cggtc                                     25

<210> SEQ ID NO 245
<211> LENGTH: 25
<212> TYPE: DNA
<213> ORGANISM: Homo sapiens

<400> SEQUENCE: 245
cttatttacc ggaagcttct gttca                                     25

<210> SEQ ID NO 246
<211> LENGTH: 25
<212> TYPE: DNA
<213> ORGANISM: Homo sapiens

<400> SEQUENCE: 246
tgccttcatc ctaactgctg gggaa                                     25

-continued

```
<210> SEQ ID NO 247
<211> LENGTH: 25
<212> TYPE: DNA
<213> ORGANISM: Homo sapiens

<400> SEQUENCE: 247
gaggcaccac taaaagatcg cagtt                                         25

<210> SEQ ID NO 248
<211> LENGTH: 25
<212> TYPE: DNA
<213> ORGANISM: Homo sapiens

<400> SEQUENCE: 248
taccctgcgg agatcatact gacct                                         25

<210> SEQ ID NO 249
<211> LENGTH: 25
<212> TYPE: DNA
<213> ORGANISM: Homo sapiens

<400> SEQUENCE: 249
ggatgggaag tgttgcattg agcat                                         25

<210> SEQ ID NO 250
<211> LENGTH: 25
<212> TYPE: DNA
<213> ORGANISM: Homo sapiens

<400> SEQUENCE: 250
cttggagata tttccgtcct ccacc                                         25

<210> SEQ ID NO 251
<211> LENGTH: 25
<212> TYPE: DNA
<213> ORGANISM: Homo sapiens

<400> SEQUENCE: 251
aggcctctca tgacccagga aggcc                                         25

<210> SEQ ID NO 252
<211> LENGTH: 25
<212> TYPE: DNA
<213> ORGANISM: Homo sapiens

<400> SEQUENCE: 252
tcatcactat tattgctcac cactg                                         25

<210> SEQ ID NO 253
<211> LENGTH: 25
<212> TYPE: DNA
<213> ORGANISM: Homo sapiens

<400> SEQUENCE: 253
aagctgacac ctaagtttac caaca                                         25

<210> SEQ ID NO 254
<211> LENGTH: 25
<212> TYPE: DNA
<213> ORGANISM: Homo sapiens

<400> SEQUENCE: 254
```

357

358

-continued

```
taggtgtctg ccttcacaaa tgtca                                      25

<210> SEQ ID NO 255
<211> LENGTH: 25
<212> TYPE: DNA
<213> ORGANISM: Homo sapiens

<400> SEQUENCE: 255
atattcccta tgtagcaaca gtggt                                      25

<210> SEQ ID NO 256
<211> LENGTH: 25
<212> TYPE: DNA
<213> ORGANISM: Homo sapiens

<400> SEQUENCE: 256
gatcatgctg aaaaccactc aaacg                                      25

<210> SEQ ID NO 257
<211> LENGTH: 25
<212> TYPE: DNA
<213> ORGANISM: Homo sapiens

<400> SEQUENCE: 257
aaggtccata aagactgagc ggatg                                      25

<210> SEQ ID NO 258
<211> LENGTH: 25
<212> TYPE: DNA
<213> ORGANISM: Homo sapiens

<400> SEQUENCE: 258
ctgaggagtc caacatcacc atgca                                      25

<210> SEQ ID NO 259
<211> LENGTH: 25
<212> TYPE: DNA
<213> ORGANISM: Homo sapiens

<400> SEQUENCE: 259
ggacgacacc tctggttttt caata                                      25

<210> SEQ ID NO 260
<211> LENGTH: 25
<212> TYPE: DNA
<213> ORGANISM: Homo sapiens

<400> SEQUENCE: 260
ttcactccat ccctatggca gagga                                      25

<210> SEQ ID NO 261
<211> LENGTH: 25
<212> TYPE: DNA
<213> ORGANISM: Homo sapiens

<400> SEQUENCE: 261
gagatgcatt taaggccgat agtga                                      25

<210> SEQ ID NO 262
<211> LENGTH: 25
<212> TYPE: DNA
<213> ORGANISM: Homo sapiens

<400> SEQUENCE: 262
```

-continued

```
tcgttacagg gagtccaaca ccgcc                                    25

<210> SEQ ID NO 263
<211> LENGTH: 25
<212> TYPE: DNA
<213> ORGANISM: Homo sapiens

<400> SEQUENCE: 263
gatggtccga atggtttcca ggtgg                                    25

<210> SEQ ID NO 264
<211> LENGTH: 25
<212> TYPE: DNA
<213> ORGANISM: Homo sapiens

<400> SEQUENCE: 264
gtttttgtgc tgttactcgg tagag                                    25

<210> SEQ ID NO 265
<211> LENGTH: 25
<212> TYPE: DNA
<213> ORGANISM: Homo sapiens

<400> SEQUENCE: 265
gagatgtgag ccttgtgcat gtggg                                    25

<210> SEQ ID NO 266
<211> LENGTH: 25
<212> TYPE: DNA
<213> ORGANISM: Homo sapiens

<400> SEQUENCE: 266
tgagatccgt gagatccttc catct                                    25

<210> SEQ ID NO 267
<211> LENGTH: 25
<212> TYPE: DNA
<213> ORGANISM: Homo sapiens

<400> SEQUENCE: 267
tattattttc tatgtccgtt gttgt                                    25

<210> SEQ ID NO 268
<211> LENGTH: 25
<212> TYPE: DNA
<213> ORGANISM: Homo sapiens

<400> SEQUENCE: 268
tactgggcaa gtgcttgtca agttc                                    25

<210> SEQ ID NO 269
<211> LENGTH: 25
<212> TYPE: DNA
<213> ORGANISM: Homo sapiens

<400> SEQUENCE: 269
gaggatgccc caacaaactc atggc                                    25

<210> SEQ ID NO 270
<211> LENGTH: 25
<212> TYPE: DNA
<213> ORGANISM: Homo sapiens
```

-continued

```
<400> SEQUENCE: 270
tctgagttgt tggggctaag cctga                                    25

<210> SEQ ID NO 271
<211> LENGTH: 25
<212> TYPE: DNA
<213> ORGANISM: Homo sapiens

<400> SEQUENCE: 271
gaaaggtaac aatcttcatt ctaca                                    25

<210> SEQ ID NO 272
<211> LENGTH: 25
<212> TYPE: DNA
<213> ORGANISM: Homo sapiens

<400> SEQUENCE: 272
atcgatacag aaaccacgct gccgc                                    25

<210> SEQ ID NO 273
<211> LENGTH: 25
<212> TYPE: DNA
<213> ORGANISM: Homo sapiens

<400> SEQUENCE: 273
actcttgagg gttgattatg ctgca                                    25

<210> SEQ ID NO 274
<211> LENGTH: 25
<212> TYPE: DNA
<213> ORGANISM: Homo sapiens

<400> SEQUENCE: 274
ccctgagcac cgtgttcatg aatct                                    25

<210> SEQ ID NO 275
<211> LENGTH: 25
<212> TYPE: DNA
<213> ORGANISM: Homo sapiens

<400> SEQUENCE: 275
gattgagtca tcgacattca ggatt                                    25

<210> SEQ ID NO 276
<211> LENGTH: 25
<212> TYPE: DNA
<213> ORGANISM: Homo sapiens

<400> SEQUENCE: 276
cacccgggac tacttgctgg tgact                                    25

<210> SEQ ID NO 277
<211> LENGTH: 25
<212> TYPE: DNA
<213> ORGANISM: Homo sapiens

<400> SEQUENCE: 277
tggagaaaat gacgacccac gacca                                    25

<210> SEQ ID NO 278
<211> LENGTH: 25
<212> TYPE: DNA
<213> ORGANISM: Homo sapiens
```

<400> SEQUENCE: 278
gacagccttt tgccattggt ggctc                                              25

<210> SEQ ID NO 279
<211> LENGTH: 25
<212> TYPE: DNA
<213> ORGANISM: Homo sapiens

<400> SEQUENCE: 279
ggcctttcac aactaggact gagaa                                             25

<210> SEQ ID NO 280
<211> LENGTH: 25
<212> TYPE: DNA
<213> ORGANISM: Homo sapiens

<400> SEQUENCE: 280
tatgtaatgt acacctgccc taagg                                             25

<210> SEQ ID NO 281
<211> LENGTH: 25
<212> TYPE: DNA
<213> ORGANISM: Homo sapiens

<400> SEQUENCE: 281
gggagagttg accgttttca tcctg                                             25

<210> SEQ ID NO 282
<211> LENGTH: 25
<212> TYPE: DNA
<213> ORGANISM: Homo sapiens

<400> SEQUENCE: 282
cataaggcac tgggactcgg atttc                                             25

<210> SEQ ID NO 283
<211> LENGTH: 25
<212> TYPE: DNA
<213> ORGANISM: Homo sapiens

<400> SEQUENCE: 283
gcacatctgg gcagttgtac catgc                                             25

<210> SEQ ID NO 284
<211> LENGTH: 25
<212> TYPE: DNA
<213> ORGANISM: Homo sapiens

<400> SEQUENCE: 284
cactgacagt gcccagggct ctggg                                             25

<210> SEQ ID NO 285
<211> LENGTH: 25
<212> TYPE: DNA
<213> ORGANISM: Homo sapiens

<400> SEQUENCE: 285
gagtgggagc cgtgaatatc tctgt                                             25

<210> SEQ ID NO 286
<211> LENGTH: 25
<212> TYPE: DNA

-continued

<213> ORGANISM: Homo sapiens

<400> SEQUENCE: 286
aaattatcat actaccggct acatc                                          25

<210> SEQ ID NO 287
<211> LENGTH: 25
<212> TYPE: DNA
<213> ORGANISM: Homo sapiens

<400> SEQUENCE: 287
taatttgctt catttccttg ctatt                                          25

<210> SEQ ID NO 288
<211> LENGTH: 25
<212> TYPE: DNA
<213> ORGANISM: Homo sapiens

<400> SEQUENCE: 288
aaggtgaatg taccctaacc tgctc                                          25

<210> SEQ ID NO 289
<211> LENGTH: 25
<212> TYPE: DNA
<213> ORGANISM: Homo sapiens

<400> SEQUENCE: 289
gagcatcaat cttgttactg ctgat                                          25

<210> SEQ ID NO 290
<211> LENGTH: 25
<212> TYPE: DNA
<213> ORGANISM: Homo sapiens

<400> SEQUENCE: 290
gatccccaag tggtgaatga cacgc                                          25

<210> SEQ ID NO 291
<211> LENGTH: 25
<212> TYPE: DNA
<213> ORGANISM: Homo sapiens

<400> SEQUENCE: 291
gttacctact ttgacttttt gcatt                                          25

<210> SEQ ID NO 292
<211> LENGTH: 25
<212> TYPE: DNA
<213> ORGANISM: Homo sapiens

<400> SEQUENCE: 292
gaacgggaag gagacgctgc agcgc                                          25

<210> SEQ ID NO 293
<211> LENGTH: 25
<212> TYPE: DNA
<213> ORGANISM: Homo sapiens

<400> SEQUENCE: 293
cagactggaa acgggacttt ctatt                                          25

<210> SEQ ID NO 294
<211> LENGTH: 25

-continued

```
<212> TYPE: DNA
<213> ORGANISM: Homo sapiens

<400> SEQUENCE: 294
aaccccagag aagtgcttca ttttc                                         25

<210> SEQ ID NO 295
<211> LENGTH: 25
<212> TYPE: DNA
<213> ORGANISM: Homo sapiens

<400> SEQUENCE: 295
gacgaggctt ttgagcagct ggtgc                                         25

<210> SEQ ID NO 296
<211> LENGTH: 25
<212> TYPE: DNA
<213> ORGANISM: Homo sapiens

<400> SEQUENCE: 296
gcaaaatgcc tttacgttgt tctaa                                         25

<210> SEQ ID NO 297
<211> LENGTH: 25
<212> TYPE: DNA
<213> ORGANISM: Homo sapiens

<400> SEQUENCE: 297
gggtctggat cttttctcag agcgt                                         25

<210> SEQ ID NO 298
<211> LENGTH: 25
<212> TYPE: DNA
<213> ORGANISM: Homo sapiens

<400> SEQUENCE: 298
ggatttcgtt tgctgtggca ttggt                                         25

<210> SEQ ID NO 299
<211> LENGTH: 25
<212> TYPE: DNA
<213> ORGANISM: Homo sapiens

<400> SEQUENCE: 299
aacatctgtg tctttatttt gctgc                                         25

<210> SEQ ID NO 300
<211> LENGTH: 25
<212> TYPE: DNA
<213> ORGANISM: Homo sapiens

<400> SEQUENCE: 300
tccccagtgg tgacctatgt gtgtg                                         25

<210> SEQ ID NO 301
<211> LENGTH: 25
<212> TYPE: DNA
<213> ORGANISM: Homo sapiens

<400> SEQUENCE: 301
atgacagttt cacaacctgc attga                                         25

<210> SEQ ID NO 302
```

-continued

```
<211> LENGTH: 25
<212> TYPE: DNA
<213> ORGANISM: Homo sapiens

<400> SEQUENCE: 302
gggaacttac ttctctatag cccac                                          25

<210> SEQ ID NO 303
<211> LENGTH: 25
<212> TYPE: DNA
<213> ORGANISM: Homo sapiens

<400> SEQUENCE: 303
gctcctagca cgattatatt tcacc                                          25

<210> SEQ ID NO 304
<211> LENGTH: 25
<212> TYPE: DNA
<213> ORGANISM: Homo sapiens

<400> SEQUENCE: 304
cactaactat gcatggtgcc ccagg                                          25

<210> SEQ ID NO 305
<211> LENGTH: 25
<212> TYPE: DNA
<213> ORGANISM: Homo sapiens

<400> SEQUENCE: 305
ggcttgctct gggactttta tgctc                                          25

<210> SEQ ID NO 306
<211> LENGTH: 25
<212> TYPE: DNA
<213> ORGANISM: Homo sapiens

<400> SEQUENCE: 306
gagaataacc tcatagtacc aacat                                          25

<210> SEQ ID NO 307
<211> LENGTH: 25
<212> TYPE: DNA
<213> ORGANISM: Homo sapiens

<400> SEQUENCE: 307
ggctccagaa cgaagatcca cactt                                          25

<210> SEQ ID NO 308
<211> LENGTH: 25
<212> TYPE: DNA
<213> ORGANISM: Homo sapiens

<400> SEQUENCE: 308
ggatttttct tatgcactcc tatgc                                          25

<210> SEQ ID NO 309
<211> LENGTH: 25
<212> TYPE: DNA
<213> ORGANISM: Homo sapiens

<400> SEQUENCE: 309
aaacatgtac tggcacaatt tgtga                                          25
```

-continued

```
<210> SEQ ID NO 310
<211> LENGTH: 25
<212> TYPE: DNA
<213> ORGANISM: Homo sapiens

<400> SEQUENCE: 310
aaggcagaca gttttgcttt agtac                                          25

<210> SEQ ID NO 311
<211> LENGTH: 25
<212> TYPE: DNA
<213> ORGANISM: Homo sapiens

<400> SEQUENCE: 311
acgggccttt ttcacttaga agctg                                          25

<210> SEQ ID NO 312
<211> LENGTH: 25
<212> TYPE: DNA
<213> ORGANISM: Homo sapiens

<400> SEQUENCE: 312
gagtgtctca gaagtgtgct cctct                                          25

<210> SEQ ID NO 313
<211> LENGTH: 25
<212> TYPE: DNA
<213> ORGANISM: Homo sapiens

<400> SEQUENCE: 313
gctctgtgct ttccactata cacag                                          25

<210> SEQ ID NO 314
<211> LENGTH: 25
<212> TYPE: DNA
<213> ORGANISM: Homo sapiens

<400> SEQUENCE: 314
ggttgaaaca tatctcttat cttac                                          25

<210> SEQ ID NO 315
<211> LENGTH: 25
<212> TYPE: DNA
<213> ORGANISM: Homo sapiens

<400> SEQUENCE: 315 tggtactttat cagtgccaag cgtcc                                         25

<210> SEQ ID NO 316
<211> LENGTH: 25
<212> TYPE: DNA
<213> ORGANISM: Homo sapiens

<400> SEQUENCE: 316
gtaagagaat tatctgcaac ttgat                                          25

<210> SEQ ID NO 317
<211> LENGTH: 25
<212> TYPE: DNA
<213> ORGANISM: Homo sapiens

<400> SEQUENCE: 317
ttcatagtca catcaaggtc atcaa                                          25
```

-continued

```
<210> SEQ ID NO 318
<211> LENGTH: 25
<212> TYPE: DNA
<213> ORGANISM: Homo sapiens

<400> SEQUENCE: 318
ggaactatct gaaatctgct cagag                                     25

<210> SEQ ID NO 319
<211> LENGTH: 25
<212> TYPE: DNA
<213> ORGANISM: Homo sapiens

<400> SEQUENCE: 319
gcagttgcca gaccaataaa atacc                                     25

<210> SEQ ID NO 320
<211> LENGTH: 25
<212> TYPE: DNA
<213> ORGANISM: Homo sapiens

<400> SEQUENCE: 320
gggagatacc gaagcctact gtggt                                     25

<210> SEQ ID NO 321
<211> LENGTH: 25
<212> TYPE: DNA
<213> ORGANISM: Homo sapiens

<400> SEQUENCE: 321
tggaagtgta tctcagtcag ccagt                                     25

<210> SEQ ID NO 322
<211> LENGTH: 25
<212> TYPE: DNA
<213> ORGANISM: Homo sapiens

<400> SEQUENCE: 322
gatctgtaat gttatttcca cttat                                     25

<210> SEQ ID NO 323
<211> LENGTH: 25
<212> TYPE: DNA
<213> ORGANISM: Homo sapiens

<400> SEQUENCE: 323
ttttctactc tagcctgttc atatg                                     25

<210> SEQ ID NO 324
<211> LENGTH: 25
<212> TYPE: DNA
<213> ORGANISM: Homo sapiens

<400> SEQUENCE: 324
ggcttcccag ataagcagcc cagga                                     25

<210> SEQ ID NO 325
<211> LENGTH: 25
<212> TYPE: DNA
<213> ORGANISM: Homo sapiens

<400> SEQUENCE: 325
gtggactaaa cctgagaatc tcgat                                     25
```

-continued

```
<210> SEQ ID NO 326
<211> LENGTH: 25
<212> TYPE: DNA
<213> ORGANISM: Homo sapiens

<400> SEQUENCE: 326
gtggtttgac ccaagaccac aacca                                         25

<210> SEQ ID NO 327
<211> LENGTH: 25
<212> TYPE: DNA
<213> ORGANISM: Homo sapiens

<400> SEQUENCE: 327
ggtgagctca gatagtctct ttctc                                         25

<210> SEQ ID NO 328
<211> LENGTH: 25
<212> TYPE: DNA
<213> ORGANISM: Homo sapiens

<400> SEQUENCE: 328
tcgtctctaa ccacgcctat taagc                                         25

<210> SEQ ID NO 329
<211> LENGTH: 25
<212> TYPE: DNA
<213> ORGANISM: Homo sapiens

<400> SEQUENCE: 329
gcataggcag tattttcctg tcagc                                         25

<210> SEQ ID NO 330
<211> LENGTH: 25
<212> TYPE: DNA
<213> ORGANISM: Homo sapiens

<400> SEQUENCE: 330
aatgaggact ctctacagga cccga                                         25

<210> SEQ ID NO 331
<211> LENGTH: 25
<212> TYPE: DNA
<213> ORGANISM: Homo sapiens

<400> SEQUENCE: 331
caagtacagc gagttcttca cgggc                                         25

<210> SEQ ID NO 332
<211> LENGTH: 25
<212> TYPE: DNA
<213> ORGANISM: Homo sapiens

<400> SEQUENCE: 332
gatgggacgc ataatcatta cctta                                         25

<210> SEQ ID NO 333
<211> LENGTH: 25
<212> TYPE: DNA
<213> ORGANISM: Homo sapiens

<400> SEQUENCE: 333
```
cgatcatctt tcctgttcca gagag                                                25

<210> SEQ ID NO 334
<211> LENGTH: 25
<212> TYPE: DNA
<213> ORGANISM: Homo sapiens

<400> SEQUENCE: 334
gagctccaga gggtccagaa ggtcc                                                25

<210> SEQ ID NO 335
<211> LENGTH: 25
<212> TYPE: DNA
<213> ORGANISM: Homo sapiens

<400> SEQUENCE: 335
tcagcaacaa ctgcctgggg gacgc                                                25

<210> SEQ ID NO 336
<211> LENGTH: 25
<212> TYPE: DNA
<213> ORGANISM: Homo sapiens

<400> SEQUENCE: 336
aggggtgata aatgcgttca tgctc                                                25

<210> SEQ ID NO 337
<211> LENGTH: 25
<212> TYPE: DNA
<213> ORGANISM: Homo sapiens

<400> SEQUENCE: 337
tgcgtagatt cttgaccatg tagta                                                25

<210> SEQ ID NO 338
<211> LENGTH: 25
<212> TYPE: DNA
<213> ORGANISM: Homo sapiens

<400> SEQUENCE: 338
aagctgtgtt catggccgag accaa                                                25

<210> SEQ ID NO 339
<211> LENGTH: 25
<212> TYPE: DNA
<213> ORGANISM: Homo sapiens

<400> SEQUENCE: 339
tgttcacggc ggattctttg tttta                                                25

<210> SEQ ID NO 340
<211> LENGTH: 25
<212> TYPE: DNA
<213> ORGANISM: Homo sapiens

<400> SEQUENCE: 340
gaacatcttt gacactctgc agact                                                25

<210> SEQ ID NO 341
<211> LENGTH: 25
<212> TYPE: DNA
<213> ORGANISM: Homo sapiens

<400> SEQUENCE: 341

-continued

```
ttcccacggg tgccatgaag tgtgt                                    25

<210> SEQ ID NO 342
<211> LENGTH: 25
<212> TYPE: DNA
<213> ORGANISM: Homo sapiens

<400> SEQUENCE: 342
ggtcccacca acagttcaga aacct                                    25

<210> SEQ ID NO 343
<211> LENGTH: 25
<212> TYPE: DNA
<213> ORGANISM: Homo sapiens

<400> SEQUENCE: 343
gaggcatcaa agcacctgtc gcctc                                    25

<210> SEQ ID NO 344
<211> LENGTH: 25
<212> TYPE: DNA
<213> ORGANISM: Homo sapiens

<400> SEQUENCE: 344
aacattccct tgatctcatc agttc                                    25

<210> SEQ ID NO 345
<211> LENGTH: 25
<212> TYPE: DNA
<213> ORGANISM: Homo sapiens

<400> SEQUENCE: 345
caacaacgaa ggacttttct ccctg                                    25

<210> SEQ ID NO 346
<211> LENGTH: 25
<212> TYPE: DNA
<213> ORGANISM: Homo sapiens

<400> SEQUENCE: 346
tgtgtagaca ccctcttggg tccaa                                    25

<210> SEQ ID NO 347
<211> LENGTH: 25
<212> TYPE: DNA
<213> ORGANISM: Homo sapiens

<400> SEQUENCE: 347
ccacaagaag ccttatccta cgtcc                                    25

<210> SEQ ID NO 348
<211> LENGTH: 25
<212> TYPE: DNA
<213> ORGANISM: Homo sapiens

<400> SEQUENCE: 348
tgagtgcaca cactaccaat cgttc                                    25

<210> SEQ ID NO 349
<211> LENGTH: 25
<212> TYPE: DNA
<213> ORGANISM: Homo sapiens
```

-continued

<400> SEQUENCE: 349
gatgcggttc cgctgcgaag atggg                                    25

<210> SEQ ID NO 350
<211> LENGTH: 25
<212> TYPE: DNA
<213> ORGANISM: Homo sapiens

<400> SEQUENCE: 350
gtcagtaggg atgtgtgcct ggctg                                    25

<210> SEQ ID NO 351
<211> LENGTH: 25
<212> TYPE: DNA
<213> ORGANISM: Homo sapiens

<400> SEQUENCE: 351
ctctctagtt agatatctga cttgg                                    25

<210> SEQ ID NO 352
<211> LENGTH: 25
<212> TYPE: DNA
<213> ORGANISM: Homo sapiens

<400> SEQUENCE: 352
acagggccca gttaatggca gagca                                    25

<210> SEQ ID NO 353
<211> LENGTH: 25
<212> TYPE: DNA
<213> ORGANISM: Homo sapiens

<400> SEQUENCE: 353
gaagcgatga atttggagac tctgt                                    25

<210> SEQ ID NO 354
<211> LENGTH: 25
<212> TYPE: DNA
<213> ORGANISM: Homo sapiens

<400> SEQUENCE: 354
gggtcccaga ggaacgctgg agcca                                    25

<210> SEQ ID NO 355
<211> LENGTH: 25
<212> TYPE: DNA
<213> ORGANISM: Homo sapiens

<400> SEQUENCE: 355
ggagcacatg ttactgcttc atttt                                    25

<210> SEQ ID NO 356
<211> LENGTH: 25
<212> TYPE: DNA
<213> ORGANISM: Homo sapiens

<400> SEQUENCE: 356
atcattatta ttgctctcca ctgta                                    25

<210> SEQ ID NO 357
<211> LENGTH: 25
<212> TYPE: DNA
<213> ORGANISM: Homo sapiens -continued

<400> SEQUENCE: 357
catgggaaga cgaggccctc gggcc                                    25

<210> SEQ ID NO 358
<211> LENGTH: 25
<212> TYPE: DNA
<213> ORGANISM: Homo sapiens

<400> SEQUENCE: 358
taccagggac tatctttgct gcaga                                    25

<210> SEQ ID NO 359
<211> LENGTH: 25
<212> TYPE: DNA
<213> ORGANISM: Homo sapiens

<400> SEQUENCE: 359
gtgaggccac agtcattgag gccct                                    25

<210> SEQ ID NO 360
<211> LENGTH: 25
<212> TYPE: DNA
<213> ORGANISM: Homo sapiens

<400> SEQUENCE: 360
gagcccactt gcattttcat agttt                                    25

<210> SEQ ID NO 361
<211> LENGTH: 25
<212> TYPE: DNA
<213> ORGANISM: Homo sapiens

<400> SEQUENCE: 361
cactgcactg ccattgtctt ttggt                                    25

<210> SEQ ID NO 362
<211> LENGTH: 25
<212> TYPE: DNA
<213> ORGANISM: Homo sapiens

<400> SEQUENCE: 362
gatcaaagag ttcgccgcgg gctac                                    25

<210> SEQ ID NO 363
<211> LENGTH: 25
<212> TYPE: DNA
<213> ORGANISM: Homo sapiens

<400> SEQUENCE: 363
aagaaaatcc tgagctttcc tgtcc                                    25

<210> SEQ ID NO 364
<211> LENGTH: 25
<212> TYPE: DNA
<213> ORGANISM: Homo sapiens

<400> SEQUENCE: 364
gatcgtcgcc cgatcagtgt tttga                                    25

<210> SEQ ID NO 365
<211> LENGTH: 25
<212> TYPE: DNA

-continued

```
<213> ORGANISM: Homo sapiens

<400> SEQUENCE: 365
gctaccgagg ctgtgtgttg aggtc                                      25

<210> SEQ ID NO 366
<211> LENGTH: 25
<212> TYPE: DNA
<213> ORGANISM: Homo sapiens

<400> SEQUENCE: 366
tatcggccta atcttagccc tgaag                                      25

<210> SEQ ID NO 367
<211> LENGTH: 25
<212> TYPE: DNA
<213> ORGANISM: Homo sapiens

<400> SEQUENCE: 367
cgtcgaccaa tgccaggatt cagag                                      25

<210> SEQ ID NO 368
<211> LENGTH: 25
<212> TYPE: DNA
<213> ORGANISM: Homo sapiens

<400> SEQUENCE: 368
cagacaagca acccaaactg aaccc                                      25

<210> SEQ ID NO 369
<211> LENGTH: 25
<212> TYPE: DNA
<213> ORGANISM: Homo sapiens

<400> SEQUENCE: 369
tctccttagt cttctcatag catta                                      25

<210> SEQ ID NO 370
<211> LENGTH: 25
<212> TYPE: DNA
<213> ORGANISM: Homo sapiens

<400> SEQUENCE: 370
ttcaccacct gactttgaat ttgtc                                      25

<210> SEQ ID NO 371
<211> LENGTH: 25
<212> TYPE: DNA
<213> ORGANISM: Homo sapiens

<400> SEQUENCE: 371
tggtgaatgt ctgttcagct cttct                                      25

<210> SEQ ID NO 372
<211> LENGTH: 25
<212> TYPE: DNA
<213> ORGANISM: Homo sapiens

<400> SEQUENCE: 372
ttccctcgtg acagtggtgt gtggt                                      25

<210> SEQ ID NO 373
<211> LENGTH: 25
```

```
<212> TYPE: DNA
<213> ORGANISM: Homo sapiens

<400> SEQUENCE: 373
gacattctta tgcttctttt acaac                                          25

<210> SEQ ID NO 374
<211> LENGTH: 25
<212> TYPE: DNA
<213> ORGANISM: Homo sapiens

<400> SEQUENCE: 374
ccccctttcc tacagcaata tgttc                                          25

<210> SEQ ID NO 375
<211> LENGTH: 25
<212> TYPE: DNA
<213> ORGANISM: Homo sapiens

<400> SEQUENCE: 375
agacatcaag tcccattatg ccttc                                          25

<210> SEQ ID NO 376
<211> LENGTH: 25
<212> TYPE: DNA
<213> ORGANISM: Homo sapiens

<400> SEQUENCE: 376
gaacaagtga ctctgaccag caggc                                          25

<210> SEQ ID NO 377
<211> LENGTH: 25
<212> TYPE: DNA
<213> ORGANISM: Homo sapiens

<400> SEQUENCE: 377
gacctggctg aaactcttaa aaaag                                          25

<210> SEQ ID NO 378
<211> LENGTH: 25
<212> TYPE: DNA
<213> ORGANISM: Homo sapiens

<400> SEQUENCE: 378
tcttctggag cctgtgtact gcgga                                          25

<210> SEQ ID NO 379
<211> LENGTH: 25
<212> TYPE: DNA
<213> ORGANISM: Homo sapiens

<400> SEQUENCE: 379
gattcccaaa cgtggttaca ttagc                                          25

<210> SEQ ID NO 380
<211> LENGTH: 25
<212> TYPE: DNA
<213> ORGANISM: Homo sapiens

<400> SEQUENCE: 380
agcaagctgc cgaaccaaaa gaatt                                          25

<210> SEQ ID NO 381
```

-continued

```
<211> LENGTH: 25
<212> TYPE: DNA
<213> ORGANISM: Homo sapiens

<400> SEQUENCE: 381
ggattctcaa tgtataagtt gcctt                                              25

<210> SEQ ID NO 382
<211> LENGTH: 25
<212> TYPE: DNA
<213> ORGANISM: Homo sapiens

<400> SEQUENCE: 382
agctactctc aggctgcagt gtgag                                              25

<210> SEQ ID NO 383
<211> LENGTH: 25
<212> TYPE: DNA
<213> ORGANISM: Homo sapiens

<400> SEQUENCE: 383
ttagccttta cctgtgaagt gttac                                              25

<210> SEQ ID NO 384
<211> LENGTH: 25
<212> TYPE: DNA
<213> ORGANISM: Homo sapiens

<400> SEQUENCE: 384
gtttgctctg catttttgat gatgg                                              25

<210> SEQ ID NO 385
<211> LENGTH: 25
<212> TYPE: DNA
<213> ORGANISM: Homo sapiens

<400> SEQUENCE: 385
ggcctgacgt aattcactcg tttcc                                              25

<210> SEQ ID NO 386
<211> LENGTH: 25
<212> TYPE: DNA
<213> ORGANISM: Homo sapiens

<400> SEQUENCE: 386
ctgcctacca tggtctgggg cttga                                              25

<210> SEQ ID NO 387
<211> LENGTH: 25
<212> TYPE: DNA
<213> ORGANISM: Homo sapiens

<400> SEQUENCE: 387
tctgccattg cggctgtcat tgcga                                              25

<210> SEQ ID NO 388
<211> LENGTH: 25
<212> TYPE: DNA
<213> ORGANISM: Homo sapiens

<400> SEQUENCE: 388
atcagaccct gacgaagcca agttg                                              25
```

-continued

```
<210> SEQ ID NO 389
<211> LENGTH: 25
<212> TYPE: DNA
<213> ORGANISM: Homo sapiens

<400> SEQUENCE: 389
gaacatgtgt ctatctgctt ttgcc                                           25

<210> SEQ ID NO 390
<211> LENGTH: 25
<212> TYPE: DNA
<213> ORGANISM: Homo sapiens

<400> SEQUENCE: 390
tcagggtgca agctgctggt gaggt                                           25

<210> SEQ ID NO 391
<211> LENGTH: 25
<212> TYPE: DNA
<213> ORGANISM: Homo sapiens

<400> SEQUENCE: 391
ctgcgaggcc agggaagccc tgagt                                           25

<210> SEQ ID NO 392
<211> LENGTH: 25
<212> TYPE: DNA
<213> ORGANISM: Homo sapiens

<400> SEQUENCE: 392
ttgtctctgc agtgattcgg tttct                                           25

<210> SEQ ID NO 393
<211> LENGTH: 25
<212> TYPE: DNA
<213> ORGANISM: Homo sapiens

<400> SEQUENCE: 393
gactggcatt ttacttctgt gtttt                                           25

<210> SEQ ID NO 394
<211> LENGTH: 25
<212> TYPE: DNA
<213> ORGANISM: Homo sapiens

<400> SEQUENCE: 394
atcattgagg ccaggagctc tgccc                                           25

<210> SEQ ID NO 395
<211> LENGTH: 25
<212> TYPE: DNA
<213> ORGANISM: Homo sapiens

<400> SEQUENCE: 395
actggctgcg agtgttcctg agagt                                           25

<210> SEQ ID NO 396
<211> LENGTH: 25
<212> TYPE: DNA
<213> ORGANISM: Homo sapiens

<400> SEQUENCE: 396
gtgaagctga aggggcctgt gtccc                                           25
```

```
<210> SEQ ID NO 397
<211> LENGTH: 25
<212> TYPE: DNA
<213> ORGANISM: Homo sapiens

<400> SEQUENCE: 397
tgatcagtgt tgttgctcta ggaag                                 25

<210> SEQ ID NO 398
<211> LENGTH: 25
<212> TYPE: DNA
<213> ORGANISM: Homo sapiens

<400> SEQUENCE: 398
gtgcatgcta gaatttggga caggc                                 25

<210> SEQ ID NO 399
<211> LENGTH: 25
<212> TYPE: DNA
<213> ORGANISM: Homo sapiens

<400> SEQUENCE: 399
ctctactctt tgccgaacta tttgt                                 25

<210> SEQ ID NO 400
<211> LENGTH: 25
<212> TYPE: DNA
<213> ORGANISM: Homo sapiens

<400> SEQUENCE: 400
cgccctttca cttagttcag tgcca                                 25

<210> SEQ ID NO 401
<211> LENGTH: 25
<212> TYPE: DNA
<213> ORGANISM: Homo sapiens

<400> SEQUENCE: 401
attggtccaa gattccggat cctaa                                 25

<210> SEQ ID NO 402
<211> LENGTH: 25
<212> TYPE: DNA
<213> ORGANISM: Homo sapiens

<400> SEQUENCE: 402
tgttcgtggt gagctacgcc aagga                                 25

<210> SEQ ID NO 403
<211> LENGTH: 25
<212> TYPE: DNA
<213> ORGANISM: Homo sapiens

<400> SEQUENCE: 403
cagtattggg tctgcaactc atccg                                 25

<210> SEQ ID NO 404
<211> LENGTH: 25
<212> TYPE: DNA
<213> ORGANISM: Homo sapiens

<400> SEQUENCE: 404
ctgttctgct tcgaagtatt caata                                 25
```

-continued

<210> SEQ ID NO 405
<211> LENGTH: 25
<212> TYPE: DNA
<213> ORGANISM: Homo sapiens

<400> SEQUENCE: 405
ttgtatttta caaatctccc tcttc                                      25

<210> SEQ ID NO 406
<211> LENGTH: 25
<212> TYPE: DNA
<213> ORGANISM: Homo sapiens

<400> SEQUENCE: 406
gtgtcataat tccccgggca agggc                                      25

<210> SEQ ID NO 407
<211> LENGTH: 25
<212> TYPE: DNA
<213> ORGANISM: Homo sapiens

<400> SEQUENCE: 407
gttgcatttt ccaggctgag agctg                                      25

<210> SEQ ID NO 408
<211> LENGTH: 25
<212> TYPE: DNA
<213> ORGANISM: Homo sapiens

<400> SEQUENCE: 408
gttgcctgtc agtgtttaca aacta                                      25

<210> SEQ ID NO 409
<211> LENGTH: 25
<212> TYPE: DNA
<213> ORGANISM: Homo sapiens

<400> SEQUENCE: 409
taaaagggcc cacaatgctc caatt                                      25

<210> SEQ ID NO 410
<211> LENGTH: 25
<212> TYPE: DNA
<213> ORGANISM: Homo sapiens

<400> SEQUENCE: 410
accgttatgc attactctgt gtcta                                      25

<210> SEQ ID NO 411
<211> LENGTH: 25
<212> TYPE: DNA
<213> ORGANISM: Homo sapiens

<400> SEQUENCE: 411
gtgtctgtgt tccaaccact gaatc                                      25

<210> SEQ ID NO 412
<211> LENGTH: 25
<212> TYPE: DNA
<213> ORGANISM: Homo sapiens

<400> SEQUENCE: 412

-continued

The invention claimed is:

1. A method of treating a cancer in a human subject in need thereof comprising orally administering 2X-121 or a pharmaceutically acceptable salt thereof to the subject with a difference score determined from a tumor sample from the subject that is above a cutoff value of the 50th percentile or greater of the difference score in a reference population with the same diagnosis as the subject, wherein the difference score is a level of mRNA expression of HLA-E determined from the tumor sample subtracted from a level of mRNA expression of SRSF7 determined from the tumor sample.

2. The method of claim 1, wherein the difference score is determined by subtracting a mean score of a level of mRNA expression of biomarkers of resistance from a mean score of a level of mRNA expression of biomarkers of sensitivity, wherein:

(i) the mean score of the level of mRNA expression of the biomarkers of resistance is the mean of the level of mRNA expression of HLA-E and the level of mRNA expression of one or more biomarkers of resistance selected from the group consisting of GADD45B, CLIC1, LASP1, APOBEC3B, LGALS1, TAPBP, AHNAK, BHLHE40, S100A11, LITAF, ZBTB38, TCIRG1, S100A11P1, CTSA, FXYD5, YPEL5, HLA-C, STOM, PLIN3, IRF1, LMNA, NPC2, P4HB, KLF6, RHOC, SRGN, STAT1, PIEZO1, LGALS3, CD97, HLA-B, FNDC3B/LOC101928615, CKLF/CKLF-CMTM1, IFI35, TIPARP, TAP1, MICALL2, RRBP1, ZFP36, TNIP1, CD59, LDLRAP1, FLNB, PSG6, CBX7, RARRES3, CFLAR, SUN2, EHD2, MAP3K5, NOL12/TRIOBP, ARPC1B, TNFSF10, HLA-G, RP11-395B7.7, LEPROT, BTN3A2/BTN3A3, INPP4B, DUSP1, EVI2A, EHD1, EPAS1, IQGAP1, CLIC3, NACC2, TGFBI, IER3, MICA, CNN2, VEGFA, MBNL1, ISG15, TNFAIP8, COPG1, PSMB9, ZFP36L1, IL6ST, SHC1, GSTK1, CAV1, KRT7, TFPI, RHOG, CDH11, ABCC3, HLA-J, MYL12A, MRPS10, RRAS, TMEM2, SIDT2, RAB11FIP1, RTP4, SPTBN1, TMEM189/TMEM189-UBE2V1/UBE2V1/ UBE2V2, ITGA5, CDC42EP1, OSER1, CHST15, MDFIC, CAV2, CARD10, RAC2, MLPH, F2R, ICAM3, CRIM1/LOC101929500, EVI2B, PFKFB3, MIR6513/TMBIM1, APOL3, CD55, TRAM2, S100A4, PIP4K2A, RPN2, IFIT3, PLAC8, SDF4, MVP, RNH1, EIF1, SERPINB1, ASL, CD99, USP4, TACC1, PDXK, BST2, LOC101928916/NNMT, DUSP5, COMT, LY6E, ACSL5, GBP2, TNFRSF1B, PTRF, CYR61, BTN3A1, PLEC, CTNND1/TMX2-CTNND1, TNFRSF14, ABCC10, SELPLG, GPX4, EDEM1, MIR6787/SLC16A3, DMBT1, PSMB8, COL1A1, FOS, CYLD, ADAMTS1, ALDOA, GATA6, YWHAB, CIB1, OPTN, IFI16, PTGER4, CCND1, PDLIM5, HLA-F, CYP1B1, SVIL, TAGLN2, IFI27, FLII, STAT6, WWP2, FLNC, PARP12, VPS13D, IFITM2, CTSZ, C19orf10, DAPK1, LOC101928189/ RSRP1, MYOF, ATP2B4, AXL, LY96, FN1, CREB3L1, TNFSF12-TNFSF13/TNFSF13, POFUT2, WDR1, SLC7A7, MICB, GATA3, LRRFIP1, RNA-SET2, and ITM2A, and the mean score of the level of mRNA expression of biomarkers of sensitivity is the mean of the level of mRNA expression of SRSF7 and the level of mRNA expression of one or more biomarkers of sensitivity selected from the group consisting of UCHL1, MLLT11, ADD2, PRMT1, SRSF3, PRMT5, COCH, RUVBL1, MARCKSL1, CHERP, MTSS1, LSM4, RAPGEF5, PRPF4, DESI2, RNPS1, SNX10, CUL3, CHD4, MSH2, HNRNPM, SRSF1, NELL2, PAICS, HOXA10, BUB1B, E2F5, MAGED4/MAGED4B/ SNORA11D/SNORA11E, PRPF8, SORD, HNRNPU, PEX5, HYPK/MIR1282/SERF2/SERF2-C15ORF63, STRAP, NDUFAB1, FARSA, STOML2, ERH, HSBP1, DDX39A, ODC1, TAF5, TBC1D31, TRA2B, NUDC, DDX23, PRPF31, UBE2S, TCF4, MLF2, CCDC181, RPF1, PASK, NUP88, RNASEH2A, FBL, LOC101928747/RBMX/SNORD61, NXF1, PLEKHO1, GAR1, RPA1, ZNF24, BOP1 MIR7112, RAB3B, SLC35G2, DKC1/MIR664B/SNORA56, PSMC3IP, DNAJC7, RRP1B, NME1, SNRPA, DBN1, KIAA0020, SUPV3L1, ZNF573, FAM134B, TOX3, HSPD1, ACLY, MSANTD3-TMEFF1/TMEFF1, AKI-RIN1, UBE2M, MTF2, EWSR1, SKP2, TMEM97, HNRNPD, ILKAP, NASP, SNRPD1, TIMM44, PKN1, STAU2, DNAAF2, SNRPD2, FUS, ATP6V1G2-DDX39B/DDX39B/SNORD84, PDSS1, TPGS2, SLIRP, NCL, ANP32A, SAFB, STIP1, CEP68, C8orf33, MRPL11, POLR21, MCAM/MIR6756, ECSIT, MDK, PUF60, PFN2, SYNCRIP, TSPAN3, SLC16A1, POLR2H, MAP3K7, CSRP2, BCL11A, PNKP, DNAJC6, FDFT1, FADS1/MIR1908, RPARP- AS1, DHRS7, CCNB1IP1, CCT3/LOC101927137, DDX18, AARSD1/PTGES3L/PTGES3L-AARSD1, HNRNPDL, ATXN7L3B, MRPS14, SOX4, ELOVL2, KCNJ8, TRIAP1, EIF2B1, FBXL14, MAPRE2, ORC4, MDN1, KNOP1, KBTBD11, FADS2, RANBP1, PLEKHB1, HSPE1, ITFG2/LOC100507424, SFPQ, RFC3, SDR39U1, PBK, PHB, KHDRBS1, PDAP1, SSRP1, and B3GALT2.

3. The method of claim 2, wherein the biomarkers of sensitivity are selected from:

(a) one or more of SEQ ID NOs: 2-25;

(b) one or more of SEQ ID NOs: 26-50;

(c) one or more of SEQ ID NOs: 51-75;

(d) one or more of SEQ ID NOs: 76-100;

(e) one or more of SEQ ID NOs: 101-125;

(f) one or more of SEQ ID NOs: 126-150; and/or (g) one or more of SEQ ID NOs: 151-172.

4. The method of claim 2, wherein the biomarkers of resistance are selected from:

(a) one or more of SEQ ID NOs: 175-177 and 179-200;

(b) one or more of SEQ ID NOs: 201-225;

(c) one or more of SEQ ID NOs: 226-250;

(d) one or more of SEQ ID NOs: 251-275;

(e) one or more of SEQ ID NOs: 276-300;

(f) one or more of SEQ ID NOs: 301-325;

(g) one or more of SEQ ID NOs: 326-350;

(h) one or more of SEQ ID NOs: 351-375;

(i) one or more of SEQ ID NOs: 376-400; and/or (j) one or more of SEQ ID NOs: 401-414.

5. The method of claim 2, wherein:

(i) the biomarkers of sensitivity are selected from at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, or at least 171 of SEQ ID NOs: 2-172; and/or (ii) the biomarkers of resistance are selected from at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, or at least 240 of SEQ ID NOs: 175-177 and 179-414.

6. The method of claim 1, further comprising administering one or more additional therapies to the subject prior to, concurrently, or after administration of 2X-121 or the pharmaceutically acceptable salt thereof.

7. The method of claim 6, wherein the one or more additional therapies comprises surgery, radiation, or a therapeutic agent.

8. The method of claim 7, wherein the therapeutic agent is administered intravenously, intramuscularly, transdermally, intradermally, intra-arterially, intracranially, subcutaneously, intraorbitally, intraventricularly, intraspinally, intraperitoneally, or intranasally.

9. The method of claim 1, comprising administering 2X-121 or the pharmaceutically acceptable salt thereof to the subject two or more times.

10. The method of claim 1, comprising administering 2X-121 or the pharmaceutically acceptable salt thereof to the subject one or more times daily, weekly, every two weeks, every three weeks, or monthly.

11. The method of claim 10, comprising administering 2X-121 or the pharmaceutically acceptable salt thereof to the subject one or more times daily.

12. The method of claim 11, wherein about 600 mg of 2X-121 or the pharmaceutically acceptable salt thereof is administered to the subject daily.

13. The method of claim 1, comprising administering a second dose of 2X-121 or the pharmaceutically acceptable salt thereof to the subject two weeks, three weeks, four weeks, or five weeks after administration of a first dose of 2X-121 or the pharmaceutically acceptable salt thereof.

14. The method of claim 1, wherein 2X-121 or the pharmaceutically acceptable salt thereof is administered in a dosage form.

15. The method of claim 14, wherein 2X-121 or the pharmaceutically acceptable salt thereof is administered to the subject at a dose of about 5-5000 mg.

16. The method of claim 15, wherein 2X-121 or the pharmaceutically acceptable salt thereof is administered to the subject at a dose of about 10 mg, 50 mg, or 200 mg.

17. The method of claim 15, wherein 2X-121 or the pharmaceutically acceptable salt thereof is administered to the subject at a dose of about 50-800 mg.

18. The method of claim 1, wherein the cutoff value is a $60^{th}$ percentile, 70th percentile, $80^{th}$ percentile, or greater of the difference score in the reference population with the same diagnosis as the subject.

19. The method of claim 1, wherein:

(a) the cancer is selected from a solid tumor cancer and a hematological cancer; or (b) the cancer is selected from the group consisting of multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, estrogen receptor-positive (ERpos) breast cancer, lung cancer, non-small cell lung carcinoma (NSCLC), mesothelioma, intestinal cancer, colon cancer, bladder cancer, adrenal cancer, gallbladder cancer, and squamous cell carcinoma of the head and neck (SCCHN).

20. The method of claim 19, wherein the cancer is breast cancer.

21. The method of claim 20, wherein the breast cancer is estrogen receptor-positive (ER pos) breast cancer or is a metastatic form of breast cancer.

22. The method of claim 19, wherein the cancer is ovarian cancer.

23. The method of claim 19, wherein the cancer is pancreatic cancer.

24. The method of claim 1, wherein the subject has recurrence of cancer.

25. A method of treating cancer in a human subject in need thereof comprising:

(a) determining a level of mRNA expression of SRSF7 and a level of mRNA expression of HLA-E in a tumor sample from the subject;

(b) calculating a difference score for the subject by subtracting the level of mRNA expression of HLA-E from the level of mRNA expression of SRSF7, wherein the difference score of the subject is above a cutoff value of a difference score in a reference population with the same diagnosis as the subject, thereby identifying the subject as responsive to 2X-121 or a pharmaceutically acceptable salt thereof, and wherein the cutoff value is a 50th percentile of the difference score in the reference population with the same diagnosis as the subject; and (c) orally administering 2X-121 or a pharmaceutically acceptable salt thereof to the subject.

26. The method of claim 25, wherein the cutoff value is a 60th percentile, $70^{th}$ percentile, $80^{th}$ percentile, or greater of the difference score in a reference population with the same diagnosis as the subject.

27. The method of claim 25, wherein the level of mRNA expression of SRSF7 and the level of mRNA expression of HLA-E are determined using a device.

28. The method of claim 27, wherein the device is a microarray.

29. The method of claim 28, wherein the microarray is a deoxyribonucleic acid (DNA)-based platform.

30. The method of claim 25, wherein the level of mRNA expression of SRSF7 and the level of mRNA expression of HLA-E are determined by microarray analysis, a nucleic acid amplification method, pyrosequencing, nanopore sequencing, sequencing by synthesis, sequencing by expansion, single molecule real time technology, sequencing by ligation, microfluidics, infrared fluorescence, or a ribonucleic acid (RNA) sequencing technique (RNA-Seq).

31. The method of claim 25, wherein step (a) of the method further comprises:

(i) determining a level of mRNA expression of one or more biomarkers of sensitivity selected from the group consisting of UCHL1, MLLT11, ADD2, PRMT1, SRSF3, PRMT5, COCH, RUVBL1, MARCKSL1, CHERP, MTSS1, LSM4, RAPGEF5, PRPF4, DESI2, RNPS1, SNX10, CUL3, CHD4, MSH2, HNRNPM, SRSF1, NELL2, PAICS, HOXA10, BUB1B, E2F5, MAGED4/MAGED4B/SNORA11D/SNORA11E, PRPF8, SORD, HNRNPU, PEX5, HYPK/MIR1282/SERF2/SERF2-C15ORF63, STRAP, NDUFAB1, FARSA, STOML2, ERH, HSBP1, DDX39A, ODC1, TAF5, TBC1D31, TRA2B, NUDC, DDX23, PRPF31, UBE2S, TCF4, MLF2, CCDC181, RPF1, PASK, NUP88, RNASEH2A, FBL, LOC101928747/RBMX/SNORD61, NXF1, PLEKHO1, GAR1, RPA1, ZNF24, BOP1 MIR7112, RAB3B, SLC35G2, DKC1/MIR664B/SNORA56, PSMC3IP, DNAJC7, RRP1B, NME1, SNRPA, DBN1, KIAA0020, SUPV3L1, ZNF573, FAM134B, TOX3, HSPD1, ACLY, MSANTD3-TMEFF1/TMEFF1, AKIRIN1, UBE2M, MTF2, EWSR1, SKP2, TMEM97, HNRNPD, ILKAP, NASP, SNRPD1, TIMM44, PKN1, STAU2, DNAAF2, SNRPD2, FUS, ATP6V1G2-DDX39B/DDX39B/SNORD84, PDSS1, NUDG, TPGS2, SLIRP, NCL, ANP32A, SAFB, STIP1, CEP68, C8orf33, MRPL11, POLR21, MCAM/MIR6756, ECSIT, MDK, PUF60, PFN2, SYNCRIP, TSPAN3, SLC16A1, POLR2H, MAP3K7, CSRP2, BCL11A, PNKP, DNAJC6, FDFT1, FADS1/MIR1908, RPARP-AS1, DHRS7, CCNB1IP1, CCT3/LOC101927137, DDX18, AARSD1/PTGES3L/PTGES3L-AARSD1, HNRNPDL, ATXN7L3B, MRPS14, SOX4, ELOVL2, KCNJ8, TRIAP1, EIF2B1, FBXL14, MAPRE2, ORC4, MDN1, KNOP1, KBTBD11, FADS2, RANBP1, PLEKHB1, HSPE1, ITFG2/LOC100507424, SFPQ, RFC3, SDR39U1, PBK, PHB, KHDRBS1, PDAP1, SSRP1, and B3GALT2; and (ii) determining a level of mRNA expression of one or more biomarkers of resistance selected from the group consisting of GADD45B, CLIC1, LASP1, APOBEC3B, LGALS1, TAPBP, AHNAK, BHLHE40, S100A11, LITAF, ZBTB38, TCIRG1, S100A11P1, CTSA, FXYD5, YPEL5, HLA-C, STOM, PLIN3, IRF1, LMNA, NPC2, P4HB, KLF6, RHOC, SRGN, STAT1, PIEZO1, LGALS3, CD97, HLA-B, FNDC3B/LOC101928615, CKLF/CKLF-CMTM1, IFI35, TIPARP, TAP1, MICALL2, RRBP1, ZFP36, TNIP1, CD59, LDLRAP1, FLNB, PSG6, CBX7, RARRES3, CFLAR, SUN2, EHD2, MAP3K5, NOL12/TRIOBP, CKLE, ARPC1B, TNFSF10, HLA-G, RP11-395B7.7, LEPROT, BTN3A2/BTN3A3, INPP4B, DUSP1, EVI2A, EHD1, EPAS1, IQGAP1, CLIC3, NACC2, TGFBI, IER3, MICA, CNN2, VEGFA, MBNL1, ISG15, TNFAIP8, COPG1, PSMB9, ZFP36L1, IL6ST, SHC1, GSTK1, CAV1, KRT7, TFPI, RHOG, CDH11, ABCC3, HLA-J, MYL12A, MRPS10, RRAS, TMEM2, SIDT2, RAB11FIP1, RTP4, SPTBN1, TMEM189/TMEM189-UBE2V1/UBE2V1/UBE2V2, ITGA5, CDC42EP1, OSER1, CHST15, MDFIC, CAV2, CARD10, RAC2, MLPH, F2R, ICAM3, CRIM1/LOC101929500, EVI2B, PFKFB3, MIR6513/TMBIM1, APOL3, CD55, TRAM2, S100A4, PIP4K2A, RPN2, IFIT3, PLAC8, SDF4, MVP, RNH1, EIF1, SERPINB1, ASL, CD99, USP4, TACC1, PDXK, BST2, LOC101928916/NNMT, DUSP5, COMT, LY6E, ACSL5, GBP2, TNFRSF1B, PTRF, CYR61, BTN3A1, PLEC, CTNND1/TMX2-CTNND1, TNFRSF14, ABCC10, SELPLG, GPX4, EDEM1, MIR6787/SLC16A3, DMBT1, PSMB8, COL1A1, FOS, CYLD, ADAMTS1, ALDOA, GATA6, YWHAB, CIB1, OPTN, IFI16, PTGER4, CCND1, PDLIM5, HLA-F, CYP1B1, SVIL, TAGLN2, IFI27, FLII, STAT6, WWP2, FLNC, PARP12, VPS13D, IFITM2, CTSZ, C19orf10, DAPK1, LOC101928189/RSRP1, MYOF, ATP2B4, AXL, LY96, FN1, CREB3L1, TNFSF12-TNFSF13/TNFSF13, POFUT2, WDR1, SLC7A7, MICB, GATA3, LRRFIP1, RNASET2, and ITM2A.

32. The method of claim 31, wherein the level of mRNA expression of SRSF7 and the level of mRNA expression of the one or more biomarkers of sensitivity and/or the level of mRNA expression of HLA-E and the level of mRNA expression of the one or more biomarkers of resistance are determined using a device.

33. The method of claim 32, wherein the device comprises (i) single-stranded nucleic acid molecules capable of specifically hybridizing with nucleotides of SRSF7 and single-stranded nucleic acid molecules capable of specifically hybridizing with the one or more biomarkers of sensitivity and/or (ii) single-stranded nucleic acid molecules capable of specifically hybridizing with nucleotides of HLA-E and single-stranded nucleic acid molecules capable of specifically hybridizing with the one or more biomarkers of resistance.

34. The method of claim 33, wherein the single-stranded nucleic acid molecules of the device have a length in the range of 10-100 nucleotides.

35. The method of claim 34, wherein the single-stranded nucleic acid molecules have a length in the range of 20-60 nucleotides.

36. The method of claim 31, wherein step (a) of the method further comprises converting the level of mRNA expression of SRSF7 and the level of mRNA expression of the one or more biomarkers of sensitivity and the level of mRNA expression of HLA-E and the level of mRNA expression of the one or more biomarkers of resistance into a mean score.

37. The method of claim 36, wherein step (b) of the method further comprises subtracting the mean score for the level of mRNA expression of HLA-E and the level of mRNA expression of the one or more biomarkers of resistance from the mean score for the level of mRNA expression of SRSF7 and the level of mRNA expression of the one or more biomarkers of sensitivity to obtain the difference score.

38. The method of claim 37, wherein the cutoff value is a 60th percentile, 70th percentile, 80th percentile, or greater of the difference score in the reference population with the same diagnosis as the subject.

* * * * *